US012331051B2

(12) United States Patent
Sheshbaradaran et al.

(10) Patent No.: US 12,331,051 B2
(45) Date of Patent: *Jun. 17, 2025

(54) LSD DERIVATIVES, SYNTHESIS AND METHOD FOR TREATMENT OF DISEASES AND DISORDERS

(71) Applicant: BETTERLIFE PHARMA INC., Vancouver (CA)

(72) Inventors: Hooshmand Sheshbaradaran, Toronto (CA); Scott Rudge, Boulder, CO (US); Abdi Ghaffari, Kingston (CA); Stefan Soderman, Drayton (CA); Petar Duspara, Mississauga (CA)

(73) Assignee: BETTERLIFE PHARMA INC., Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/214,327

(22) Filed: Jun. 26, 2023

(65) Prior Publication Data

US 2023/0357243 A1    Nov. 9, 2023

Related U.S. Application Data

(63) Continuation of application No. 17/949,183, filed on Sep. 20, 2022.

(60) Provisional application No. 63/341,388, filed on May 12, 2022, provisional application No. 63/246,290, filed on Sep. 20, 2021.

(51) Int. Cl.
*C07D 471/06*    (2006.01)

(52) U.S. Cl.
CPC ........ *C07D 471/06* (2013.01); *C07B 2200/07* (2013.01); *C07B 2200/13* (2013.01)

(58) Field of Classification Search
CPC ............... C07D 471/06; C07D 457/06; C07B 2200/07; C07B 2200/13
See application file for complete search history.

(56) References Cited

U.S. PATENT DOCUMENTS

| 4,524,072 | A  | 6/1985  | Zivin |
| 9,868,732 | B2 | 1/2018  | Kirkland |
| 10,377,752 | B2 | 8/2019  | Kirland |
| 2009/0264456 | A1 | 10/2009 | Sewell |
| 2016/0237080 | A1 | 8/2016  | Kirkland |
| 2023/0219955 | A1 | 7/2023  | Sheshbaradaran et al. |

FOREIGN PATENT DOCUMENTS

| EP | 0082805 | A2 | 6/1983 |
| EP | 0411494 | A2 | 2/1991 |
| EP | 0205068 | B1 | 1/1992 |
| EP | 2331100 | B1 | 7/2014 |
| WO | 2018/064465 | A1 | 4/2018 |
| WO | 2021/195427 | A1 | 9/2021 |
| WO | 2022/115405 | A1 | 6/2022 |
| WO | 2022232093 | A1 | 11/2022 |

OTHER PUBLICATIONS

Rougeot et al. (Organic Process Research & Development, 2015, 19, pp. 1809-1819).*
Bhattacharya et al. (Brittain, ed. Polymorphism in Pharmaceutical Solids, 2009, p. 334.*
International Search Report (ISR) for PCT/CA2022/051396 mailed Dec. 23, 2022 (9 pages).
Troxler, F. et al., "Egot alkaloids, XLV. Substitution in the ring system of lysergic acid. 3. Halogenation." Helvetica Chimica Acta, Jan. 1, 1957, vol. 4, p. 2160-2170.
G. Maurer et al., "Fate and disposition of bromocriptine in animals and man. II Absorption, elimination and metabolism" European Journal of Drug Metabolism and Pharmacokinetics, Jan. 1, 1983, vol. 8(1), p. 51-62.
M.R. Whipple et al., "Inhibition of synaptosomal neurotransmitter uptake hallucinogens" Journal of Neurochemisty, Apr. 1, 1983, vol. 40(4), p. 1185-1188.
M. Karst et al., "The non-hallucinogen 2-bromo-lysergic acid diethylamide as preventative treatment for cluster headache: An open, non-randomized case series", Cephalagia, Mar. 26, 2010, vol. 30 p. 1140-1144.
Betterlife Pharma, "Life Science Company With an Evolving Portfolio of Novel Psychedelic and Anti-Viral Drugs". Investor Presentation. May 26, 2021, p. 1-27.

(Continued)

*Primary Examiner* — Susanna Moore
(74) *Attorney, Agent, or Firm* — Shumaker, Loop & Kendrick, LLP

(57) ABSTRACT

LSD derivative compounds and polymorphs thereof, methods for their synthesis, compositions and treatment of diseases and disorders are described herein, the compounds having the structure of Formula I:

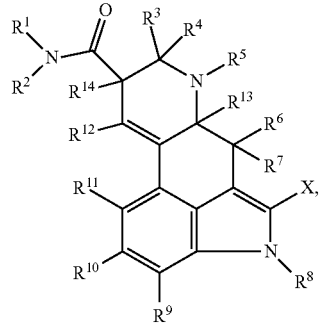

Formula I including pharmaceutically acceptable salts, hydrates, solvates, tautomers, enantiomers, diastereomers, racemates, polymorphs or combinations thereof; wherein: $R^1$ to $R^{14}$ are each independently selected from H, or a substituted or unsubstituted hydrocarbon group and X is selected from a halo group.

19 Claims, 32 Drawing Sheets

(56) References Cited

OTHER PUBLICATIONS

Transcend Biodynamics, "Optimizing the Human Condition", Corporate Presentation, Nov. 1, 2020.
Caira, "Crystalline Polymorphism of Organic Compounds" Topics in Current Chemistry, Jan. 1, 1998, vol. 198, p. 162-208.
Bavin, "Polymorphism in Process Development" Chemistry and Industry, Aug. 21, 1989, vol. 16, p. 527-529.
Depoortere et al., "Alterations in the sleep/wakefulness cycle in rats after administraiton of (−)-LSD or BOL-148. A comparision with (+)-LSD", British Journal of Pharmacological Society, Feb. 1, 1972, vol. 44(2), p. 354-355.
Non-Final Office Action (NFOA) issued for U.S. Appl. No. 17/949,813, mailed Oct. 18, 2024 (19 pages).
Recrystallization ((filed://C:/Users/smoore2/Downloads/Recrystallization%20(1).pdf, downloaded Apr. 24, 2021, pp. 1-18).
Non-Final Office Action (NFOA) issued for U.S. Appl. No. 17/949,813, mailed Nov. 22, 2024 (20 pages).
Hardwood et al. (Experimental Organic Chemistry, Standard and Microscale, 2nd Edition, Wiley-Blackwell Publisher, 1998, pp. 131-143).
Perrin et al. (Purification of Laboratory Chemicals, 3rd Edition, Pergamon Publisher, 1988, pp. 12-41).

\* cited by examiner

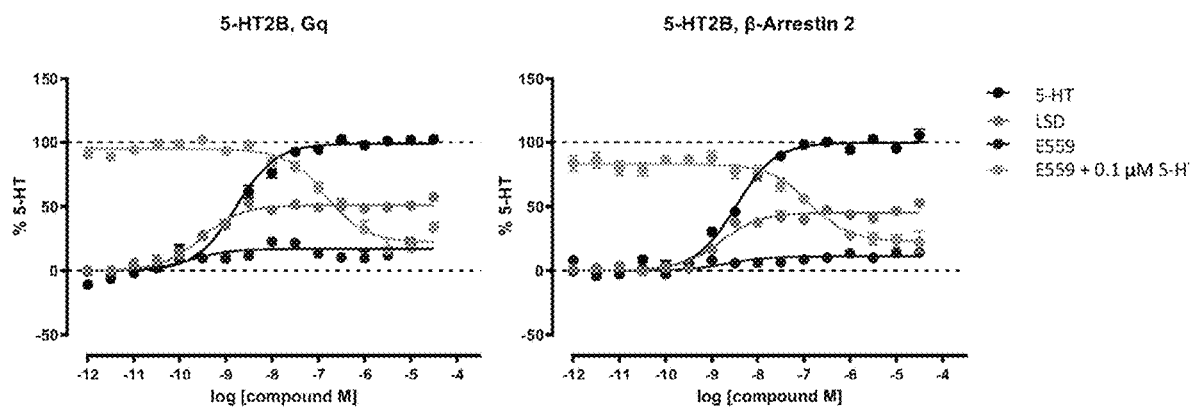
FIG. 14A  FIG. 14B
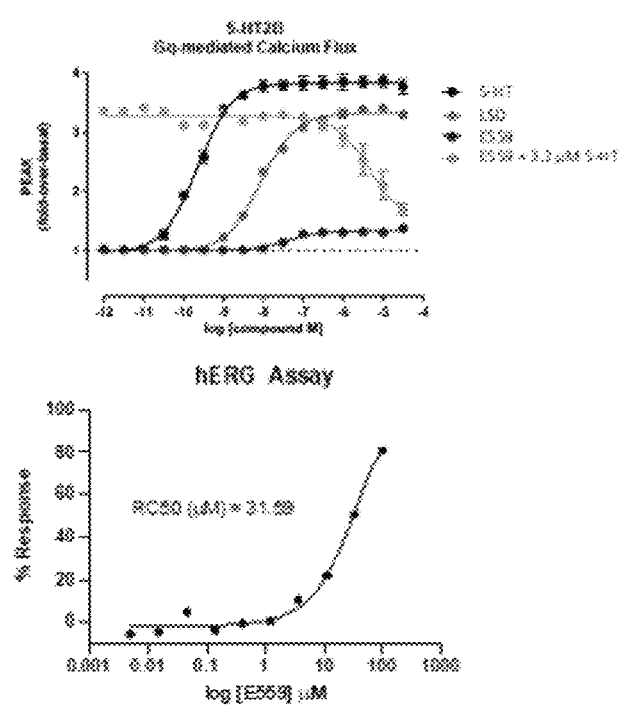
FIG. 14C/D

Sholl Analysis: To generates measures of neuron arbor complexity by measuring A) number of times neuron processes are crossed, B) total length of neurons, and C) number of nodes and end points.

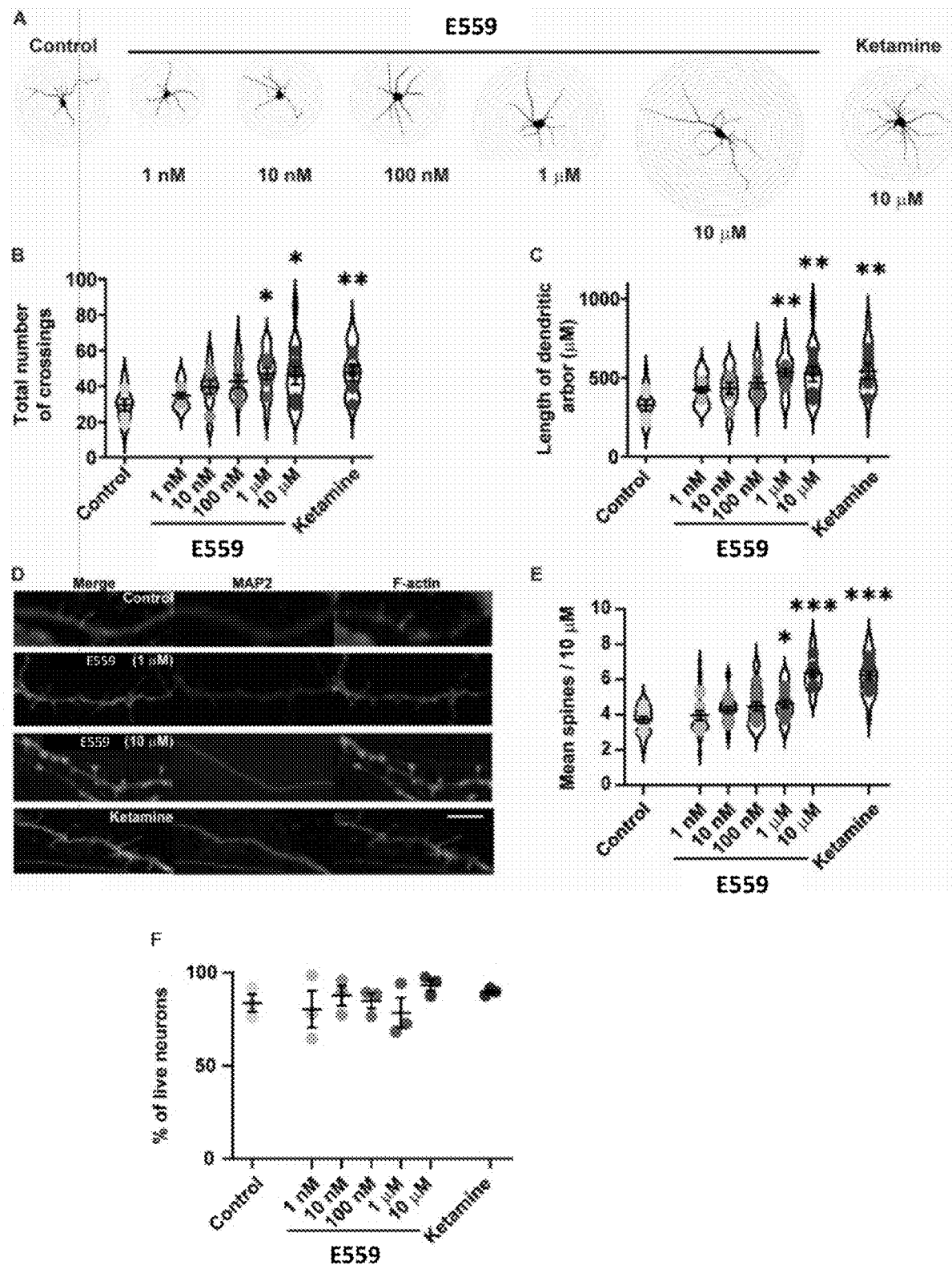
FIG. 19A-F

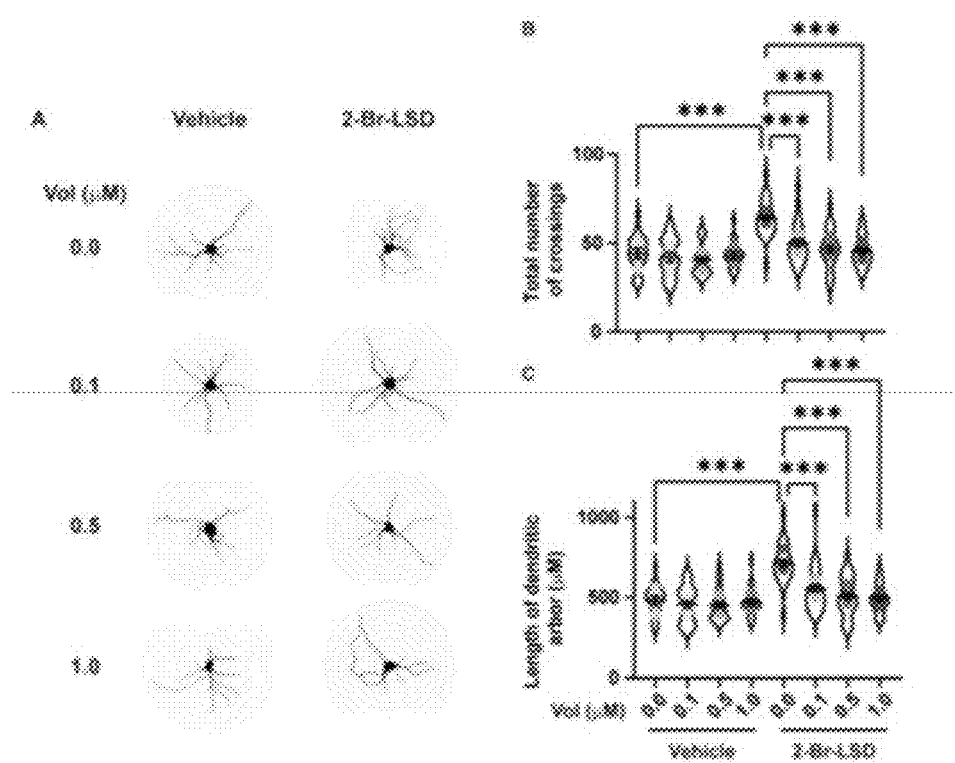
FIG. 20A-C

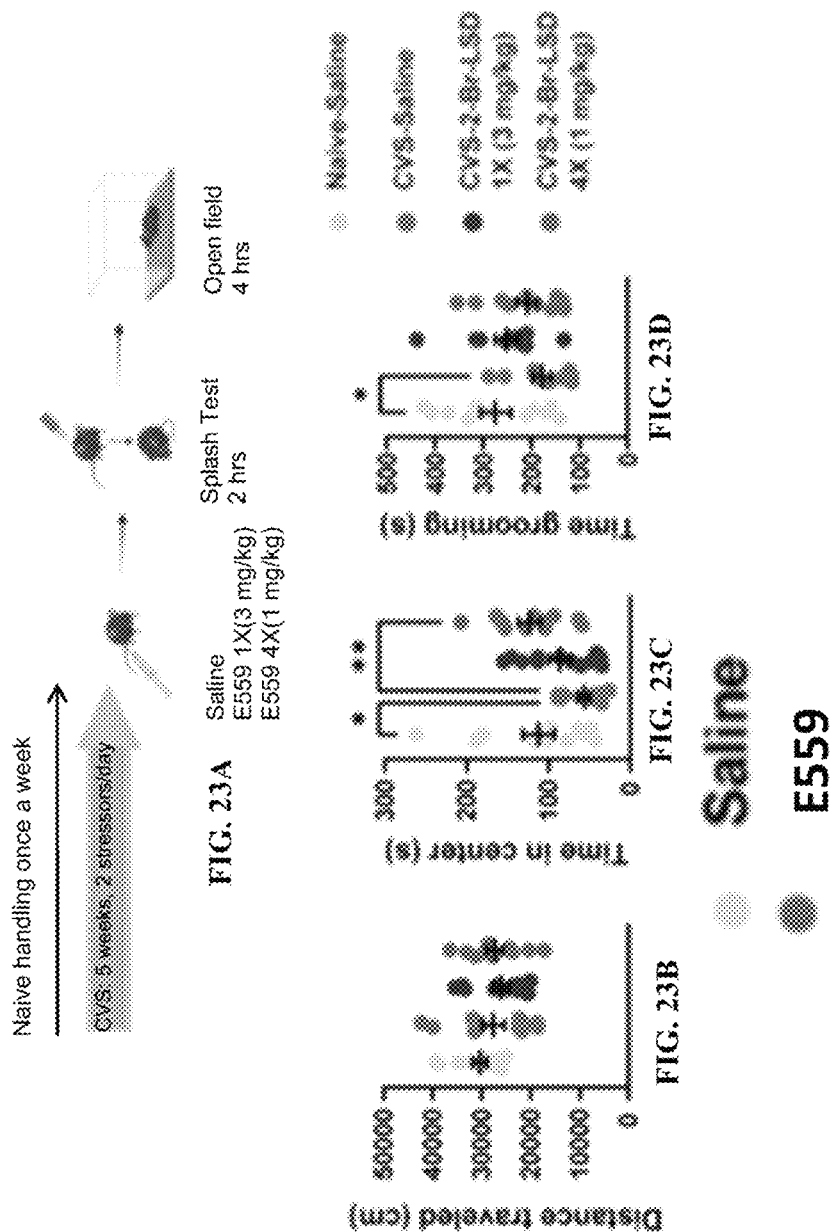

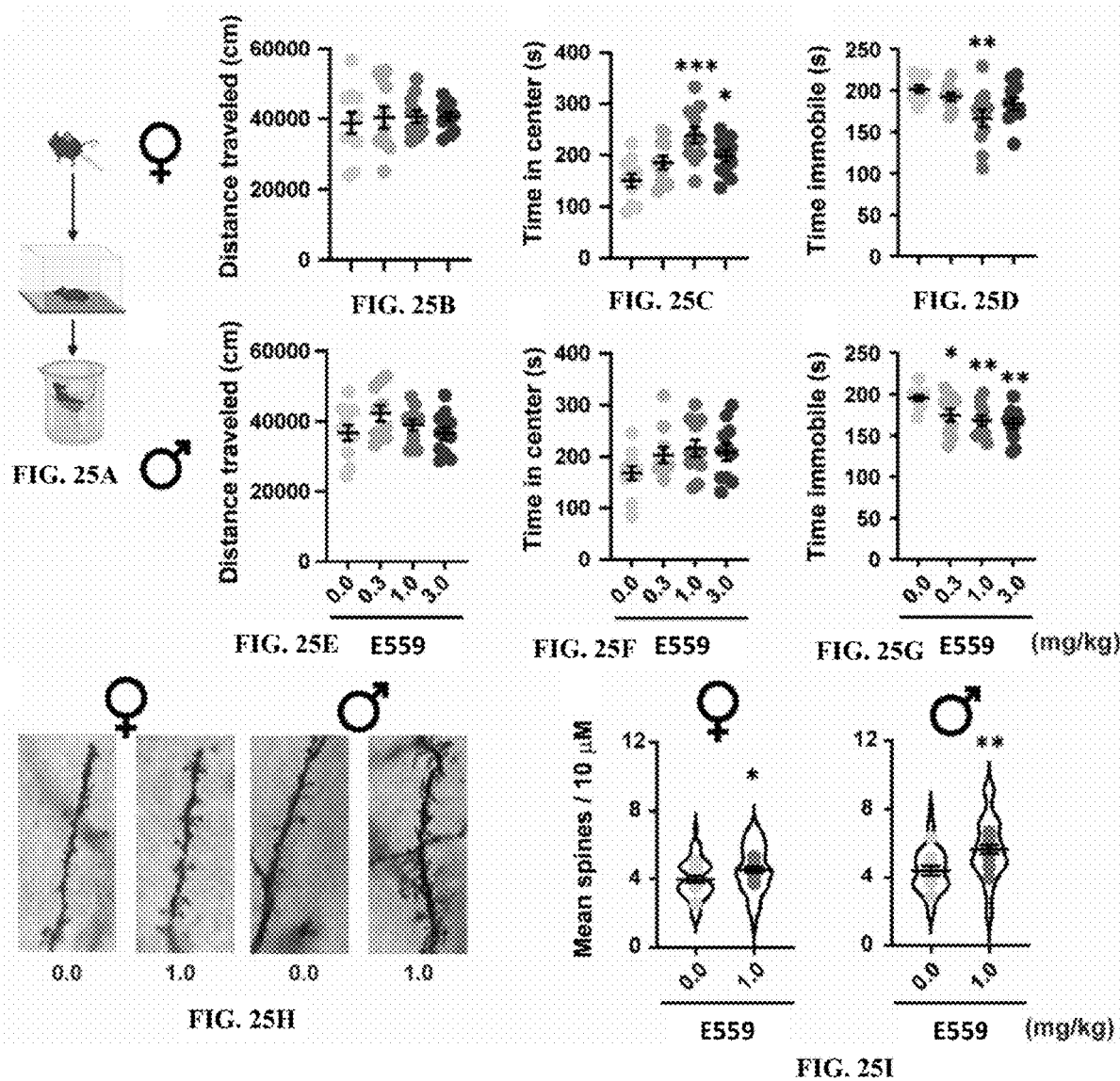

LSD DERIVATIVES, SYNTHESIS AND METHOD FOR TREATMENT OF DISEASES AND DISORDERS

FIELD

This application generally relates to novel LSD derivatives and polymorphs thereof, compositions thereof, method of synthesis and therapeutic uses thereof.

BACKGROUND OF INVENTION

LSD, commonly known as acid, scientifically known as lysergic acid diethylamide, is a potent semi-synthetic psychedelic substance causing a wide variety of effects from wild sensory distortions and intense open-eyed hallucinations to feelings of spirituality and connectedness to everything. LSD can induce a dissociative state in users and, at times, send them off into a full-blown panic attack.

LSD is classified as a strictly controlled substance by regulatory agencies and thus illegal in most parts of the world. LSD, however, has upsides as it has no addictive properties and has been demonstrated to promote neural cell growth.

It would be beneficial to provide non-hallucinogenic forms of LSD that retain at least one beneficial property.

SUMMARY OF INVENTION

The disclosure describes Lysergic Acid Diethylamide (LSD) derivatives and crystalline polymorphs thereof for general use and use in medicine.

The present disclosure generally relates to a compound having the structure of Formula I.

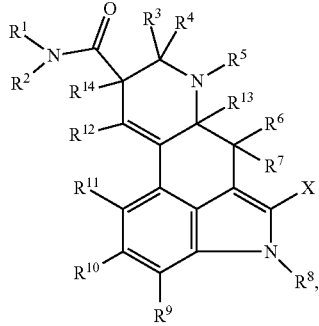

Formula I a pharmaceutically acceptable salt, hydrate, solvate, tautomer, enantiomer, diastereomer, racemate, polymorph or combination thereof; wherein: $R^1$ to $R^{14}$ are each independently selected from H, or a substituted or unsubstituted hydrocarbon group and X is selected from a halo group.

According to an aspect of the invention are novel compounds of Formula I. In aspects, these are substantially non-hallucinogenic, and in further aspects surprisingly do not induce tolerance as known to occur with LSD.

According to an aspect of the invention are novel polymorph compounds of Formula I. In aspects, these are substantially non-hallucinogenic, and in further aspects surprisingly do not induce tolerance as known to occur with LSD.

The LSD derivative(s) compounds and polymorph(s) thereof of Formula I encompass a crystalline form, optionally, an isolated crystalline form. In aspects, the present invention encompasses a polymorph, optionally, an isolated polymorph. In aspects, the present invention encompasses substantially one crystalline form. In aspects, the present invention encompasses substantially one polymorph. In aspects, the present invention encompasses one or more polymorphs thereof which are substantially free of solvate. In a presently preferred embodiment, the polymorphs are substantially free of water. In aspects the compound is (5R,8R) 2-bromo-LSD hemi-D-tartrate salt.

In aspects the compound is an isolated polymorph of (5R,8R) 2-bromo-LSD hemi-D-tartrate salt. In further aspects the isolated polymorph of (5R,8R) 2-bromo-LSD hemi-D-tartrate salt (E559) is formulated as a composition or formulation.

Another embodiment of the present invention encompasses pharmaceutical compositions comprising compounds of Formula I which are substantially free of solvate, and a pharmaceutically acceptable carrier, diluent or excipient therefor. In other embodiments, pharmaceutical compositions contemplated herein further comprise additional forms of Formula I in a crystalline, solvate or amorphous form.

According to a further aspect are compositions and formulations of non-hallucinogenic LSD derivative(s), including polymorph(s) thereof.

Compositions and formulations comprise LSD derivative(s) and polymorph(s) thereof represented by Formula I; Formula I'; Formula Ia, Ib, Ic, Id; Formula Ia', Ib', Ic', Id'; Formula Ia", Ib", Ic", Id"; Formula IA, IB, Ic, Id; Formula IAA, IBB, ICC, IDD; Formula IAA', IBB', ICC', IDD'; Formula IAA", IBB", ICC", IDD"; Formula IAA''', IBB''', ICC''', IDD'''; and any mixture thereof.

According to a further aspect use of the LSD derivative and polymorph compounds/compositions/formulations disclosed herein for treating one or more of: depressive disorders; bipolar and related disorders; schizophrenia spectrum and other psychotic disorders; personality disorders; anxiety disorders; trauma and stressor-related disorders; obsessive-compulsive and related disorders; disruptive disorders, impulse-control and conduct disorders; feeding and eating disorders; dissociative disorders; somatic symptom and related disorders; neurodevelopmental disorders; sleep-wake disorders; substance-related and addictive disorders; headache disorders; pain disorders; spasticity; nerve injury disorders; fatigue; neuro-degenerative disorders; sexual dysfunctions and gender dysphoria disorders; neurocognitive disorders; neurological—viral infection; counteracting other drug's side effects; and general well-being.

In embodiments, the novel LSD derivative and polymorph compounds/compositions/formulations disclosed herein are for reducing at one or more signs or symptoms of any one or more of: depressive disorders; bipolar and related disorders; schizophrenia spectrum and other psychotic disorders; personality disorders; anxiety disorders; trauma and stressor-related disorders; obsessive-compulsive and related disorders; disruptive disorders, impulse-control and conduct disorders; feeding and eating disorders; dissociative disorders; somatic symptom and related disorders; neurodevelopmental disorders; sleep-wake disorders; substance-related and addictive disorders; headache disorders; pain disorders; spasticity; nerve injury disorders; fatigue; neuro-degenerative disorders; sexual dysfunctions and gender dysphoria disorders; neurocognitive disorders; and neurological—viral infection.

In some aspects, the compounds of the invention are alternatively not used for treatment of recurrent cluster headache disorder, wherein the subject has a recurrent cluster headache disorder, in aspects that is refractory to one or more, prophylactic therapies. In aspects the compounds of the invention may alternatively not be used for treatment of a disorder that is trigeminal autonomic cephalagia, byenteral, sublingual or parenteral administration.

The compounds of the present disclosure can be described as embodiments in any of the following enumerated clauses. It will be understood that any of the embodiments described herein can be used in connection with any other embodiments described herein to the extent that the embodiments do not contradict one another.

Disclosed herein are non-hallucinogenic LSD-derivatives and their methods of use. In certain aspects, a compound having the structure of Formula I:

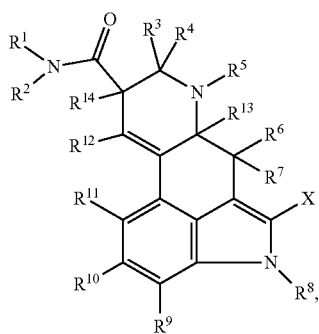

Formula I a pharmaceutically acceptable salt, hydrate, solvate, tautomer, enantiomer, diastereomer, racemate, polymorph or combination thereof is disclosed. $R^1$ to $R^{14}$ are each independently selected from H, or a substituted or unsubstituted hydrocarbon group and X is selected from a halo group.

In certain aspects, the compound is crystalline. In certain aspects, the compound is an isolated crystalline form. In certain aspects, the compound includes polymorphs thereof. The compound may include a single polymorph. Additionally, or alternatively, the compound may include an isolated polymorph.

In certain aspects, (i) the compound is one or more polymorphs thereof; (ii) the compound comprises one or more compounds, each having two stereocenters, independently selected from 5S,8R; 5R,8R; 5R,8S; or 5S,8S; (iii) the compound comprises one or more compounds, each having two stereocenters, independently selected from 5R,8S; 5R,8R; or 5S,8R; (iv) the compound comprises one or more compounds, each having two stereocenters, independently selected from 5R,8S or 5R,8R; (v) the compound has two stereocenters, which are 5R,8R; (vi) the compound has two stereocenters, which are 5R,8S; and (vii) any one or more of (i) to (vi).

In certain aspects, the compound has stereocenters 5S,8R; 5R,8R; 5R,8S; or 5S,8S. In certain aspects, the compound has stereocenters 5S,8R; 5R,8R; or 5R,8S. In certain aspects, the compound has stereocenters selected from 5R,8S or 5R,8R.

In certain aspects, the compound is a pharmaceutically acceptable salt, hydrate and/or solvate of formula (I). In certain aspects, the compound is an acid salt. In certain aspects, the acid of the acid salt is selected from hydrochloric acid, hydrobromic acid, nitric acid, carbonic acid, monohydrogencarbonic acid, phosphoric acid, monohydrogenphosphoric acid, dihydrogenphosphoric acid, sulfuric acid, monohydrogensulfuric acid, hydriodic acid, ethanedisulfonic acid, phosphorous acid, acetic acid, propionic acid, isobutyric acid, butyric acid, maleic acid, mandelic acid (D or L), ethane-1,2-disulfonic acid (dihydrate), toluene sulfonic acid (e.g. monohydrate), p-toluene sulfonic acid (e.g. monohydrate), 10-camphorsulfonic acid (e.g. (−)-10-camphorsulfonic acid), malic acid, malonic acid, benzoic acid, succinic acid, suberic acid, fumaric acid, lactic acid, mandelic acid, phthalic acid, benzenesulfonic acid, p-tolylsulfonic acid, citric acid, tartaric acid (L-tartaric acid or D-tartaric acid), mesotartaric acid (or erythraric acid), methanesulfonic acid, glutamic acid (L-glutamic acid or D-glutamic acid), ascorbic acid (L-ascorbic acid or D-ascorbic acid), isoascorbic acid (L-isoascorbic acid or D-isoascorbic acid), or a combination thereof.

In certain aspects, the acid of the acid salt is selected from hydrochloric acid, tartaric acid (L-tartaric acid or D-tartaric acid), mesotartaric acid (or erythraric acid), methanesulfonic acid, glutamic acid (L-glutamic acid or D-glutamic acid), ascorbic acid (L-ascorbic acid or D-ascorbic acid), isoascorbic acid (L-isoascorbic acid or D-isoascorbic acid), or a combination thereof.

In certain aspects, the acid of the acid salt is selected from tartaric acid (L-tartaric acid or D-tartaric acid), mesotartaric acid (or erythraric acid), glutamic acid (L-glutamic acid or D-glutamic acid), ascorbic acid (L-ascorbic acid or D-ascorbic acid), isoascorbic acid (L-isoascorbic acid or D-isoascorbic acid), or a combination thereof.

In certain aspects, $R^1$ to $R^{14}$ are each independently selected from H, substituted or unsubstituted alkyl group, substituted or unsubstituted alkenyl group, or substituted or unsubstituted alkynyl group. In certain aspects, $R^1$ to $R^{14}$ are each independently selected from H, substituted or unsubstituted $C_1$-$C_6$ alkyl group, substituted or unsubstituted $C_2$-$C_6$ alkenyl group, or substituted or unsubstituted $C_2$-$C_6$ alkynyl group. In certain aspects, $R^1$ to $R^{14}$ are each independently selected from H, or substituted or unsubstituted $C_1$-$C_6$ alkyl group. In certain aspects, $R^1$ to $R^{14}$ are each independently selected from H, a methyl group or an ethyl group. In certain aspects, $R^1$ and $R^2$ are each independently selected from H, a methyl group or an ethyl group; $R^3$, $R^4$, and $R^6$ to $R^{14}$ are each H, and $R^5$ is a methyl group. In certain aspects, $R^1$ and $R^2$ are each independently selected from a methyl group or an ethyl group; $R^3$, $R^4$, and $R^6$ to $R^{14}$ are each H; and $R^5$ is a methyl group. In certain aspects, $R^1$ and $R^2$ are each ethyl groups; $R^3$, $R^4$, and $R^6$ to $R^{14}$ are each H; and $R^5$ is a methyl group.

In certain aspects, X is selected from bromo, chloro, fluoro or iodo. In certain aspects, X is selected from bromo, chloro, or fluoro. In certain aspects, X is selected from bromo or chloro. In certain aspects, X is bromo.

In certain aspects, the compound has the structure of Formula I':

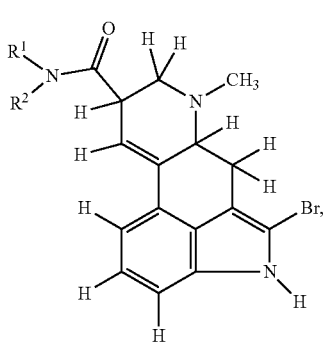

Formula I' a pharmaceutically acceptable salt, hydrate, solvate, tautomer, enantiomer, diastereomer, racemate, polymorph, or combination thereof; wherein: $R^1$ and $R^2$ are each independently selected from H, or a substituted or unsubstituted hydrocarbon group.

In certain aspects, the compound is crystalline. In creatin aspects, the compound is an isolated crystalline form.

In certain aspects, the compound comprises polymorphs thereof. In certain aspects, the compound comprises a single polymorph thereof. Additionally, or alternatively, the compound comprises an isolated polymorph thereof.

In certain aspects, i) the compound is one or more polymorphs thereof; and/or ii) the compound comprises one or more compounds, each having two stereocenters, independently selected from 5S,8R; 5R,8R; 5R,8S; or 5S,8S; iii) the compound comprises one or more compounds, each having two stereocenters, independently selected from 5R,8S; 5R,8R; or 5S,8R; iv) the compound comprises one or more compounds, each having two stereocenters, independently selected from 5R,8S or 5R,8R; v) the compound has two stereocenters, which are 5R,8R; or vi) the compound has two stereocenters, which are 5R,8S.

In certain aspects, the compound has stereocenters selected from 5S,8R; 5R,8R; 5R,8S; or 5S,8S. In certain aspects, the compound has stereocenters selected from 5S,8R; 5R,8R; or 5R,8S. In certain aspects, the compound has stereocenters selected from 5R,8S or 5R,8R.

In certain aspects, the compound is a pharmaceutically acceptable salt, hydrate and/or solvate thereof. In certain aspects, the compound is an acid salt. In certain aspects, the acid of the acid salt is selected from hydrochloric acid, hydrobromic acid, nitric acid, carbonic acid, monohydrogencarbonic acid, phosphoric acid, monohydrogenphosphoric acid, dihydrogenphosphoric acid, sulfuric acid, monohydrogensulfuric acid, hydriodic acid, ethanedisulfonic acid, phosphorous acid, acetic acid, propionic acid, isobutyric acid, butyric acid, maleic acid, mandelic acid (D or L), ethane-1,2-disulfonic acid (dihydrate), toluene sulfonic acid (e.g. monohydrate), p-toluene sulfonic acid (e.g. monohydrate), 10-camphorsulfonic acid (e.g. (−)-10-camphorsulfonic acid), malic acid, malonic acid, benzoic acid, succinic acid, suberic acid, fumaric acid, lactic acid, mandelic acid, phthalic acid, benzenesulfonic acid, p-tolylsulfonic acid, citric acid, tartaric acid (L-tartaric acid or D-tartaric acid), mesotartaric acid (or erythraric acid), methanesulfonic acid, glutamic acid (L-glutamic acid or D-glutamic acid), ascorbic acid (L-ascorbic acid or D-ascorbic acid), isoascorbic acid (L-isoascorbic acid or D-isoascorbic acid), or a combination thereof.

In certain aspects, the acid of the acid salt is selected from hydrochloric acid, tartaric acid (L-tartaric acid or D-tartaric acid), mesotartaric acid (or erythraric acid), methanesulfonic acid, glutamic acid (L-glutamic acid or D-glutamic acid), ascorbic acid (L-ascorbic acid or D-ascorbic acid), isoascorbic acid (L-isoascorbic acid or D-isoascorbic acid), or a combination thereof.

In certain aspects, the acid of the acid salt is selected from tartaric acid (L-tartaric acid or D-tartaric acid), mesotartaric acid (or erythraric acid), glutamic acid (L-glutamic acid or D-glutamic acid), ascorbic acid (L-ascorbic acid or D-ascorbic acid), isoascorbic acid (L-isoascorbic acid or D-isoascorbic acid), or a combination thereof.

In certain aspects, $R^1$ and $R^2$ are each independently selected from H, substituted or unsubstituted alkyl group, substituted or unsubstituted alkenyl group, or substituted or unsubstituted alkynyl group. In certain aspects, $R^1$ and $R^2$ are each independently selected from H, substituted or unsubstituted $C_1$-$C_6$ alkyl group, substituted or unsubstituted $C_2$-$C_6$ alkenyl group, or substituted or unsubstituted $C_2$-$C_6$ alkynyl group. In certain aspects, $R^1$ and $R^2$ are each independently selected from H, or substituted or unsubstituted $C_1$-$C_6$ alkyl group. In certain aspects, $R^1$ and $R^2$ are each independently selected from H, a methyl group or an ethyl group. In certain aspects, $R^1$ and $R^2$ are each independently selected from a methyl group or an ethyl group. In certain aspects, $R^1$ and $R^2$ are each ethyl groups.

In certain aspects, the compound has the structure of Formula I' selected from:

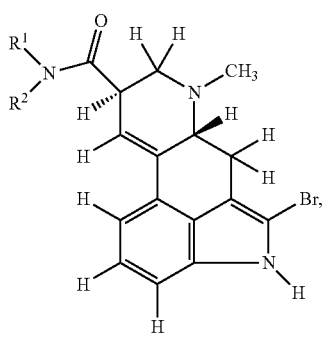

Formula Ia

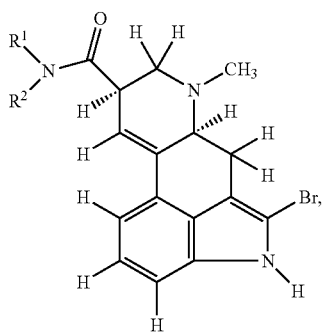

Formula Ib

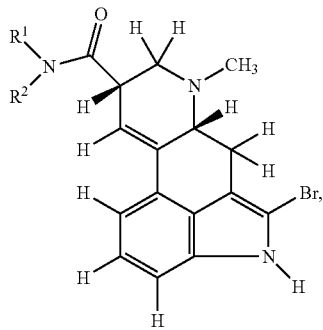

Formula Ic

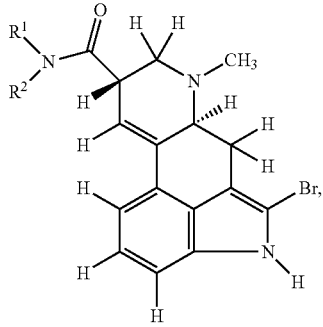

Formula Id a pharmaceutically acceptable salt, hydrate, solvate, tautomer, enantiomer, diastereomer, racemate, polymorph, or combination thereof; wherein: $R^1$ and $R^2$ are each independently selected from H, or a substituted or unsubstituted hydrocarbon group.

In certain aspects, the compound is crystalline. In certain aspects, the compound is an isolated crystalline form.

In certain aspects, the compound comprises polymorphs thereof. In certain aspects, the compound comprises a single polymorph thereof. In certain aspects, the compound comprises an isolated polymorph thereof.

In certain aspects, i) the compound is one or more polymorphs thereof; and/or ii) the compound comprises one or more compounds, each having two stereocenters, independently selected from 5S,8R; 5R,8R; 5R,8S; or 5S,8S; iii) the compound comprises one or more compounds, each having two stereocenters, independently selected from 5R,8S; 5R,8R; or 5S,8R; iv) the compound comprises one or more compounds, each having two stereocenters, independently selected from 5R,8S or 5R,8R; v) the compound has two stereocenters, which are 5R,8R; or vi) the compound has two stereocenters, which are 5R,8S.

In certain aspects, Formula I' is selected from Formula Ia; Ib; or Id. In certain aspects, Formula I' is Formula Ib or Id. In certain aspects, the compound is a pharmaceutically acceptable salt, hydrate and/or solvate thereof.

In certain aspects, the compound is an acid salt. In certain aspects, the acid of the acid salt is selected from hydrochloric acid, hydrobromic acid, nitric acid, carbonic acid, monohydrogencarbonic acid, phosphoric acid, monohydrogenphosphoric acid, dihydrogenphosphoric acid, sulfuric acid, monohydrogensulfuric acid, hydriodic acid, ethanedisulfonic acid, phosphorous acid, acetic acid, propionic acid, isobutyric acid, butyric acid, maleic acid, mandelic acid (D or L), ethane-1,2-disulfonic acid (dihydrate), toluene sulfonic acid (e.g. monohydrate), p-toluene sulfonic acid (e.g. monohydrate), 10-camphorsulfonic acid (e.g. (−)-10-camphorsulfonic acid), malic acid, malonic acid, benzoic acid, succinic acid, suberic acid, fumaric acid, lactic acid, mandelic acid, phthalic acid, benzenesulfonic acid, p-tolylsulfonic acid, citric acid, tartaric acid (L-tartaric acid or D-tartaric acid), mesotartaric acid (or erythraric acid), methanesulfonic acid, glutamic acid (L-glutamic acid or D-glutamic acid), ascorbic acid (L-ascorbic acid or D-ascorbic acid), isoascorbic acid (L-isoascorbic acid or D-isoascorbic acid), or a combination thereof. In certain aspects, the acid of the acid salt is selected from hydrochloric acid, tartaric acid (L-tartaric acid or D-tartaric acid), mesotartaric acid (or erythraric acid), methanesulfonic acid, glutamic acid (L-glutamic acid or D-glutamic acid), ascorbic acid (L-ascorbic acid or D-ascorbic acid), isoascorbic acid (L-isoascorbic acid or D-isoascorbic acid), or a combination thereof. In certain aspects, the acid of the acid salt is selected from tartaric acid (L-tartaric acid or D-tartaric acid), mesotartaric acid (or erythraric acid), glutamic acid (L-glutamic acid or D-glutamic acid), ascorbic acid (L-ascorbic acid or D-ascorbic acid), isoascorbic acid (L-isoascorbic acid or D-isoascorbic acid), or a combination thereof.

In certain aspects, $R^1$ and $R^2$ are each independently selected from H, substituted or unsubstituted alkyl group, substituted or unsubstituted alkenyl group, or substituted or unsubstituted alkynyl group. In certain aspects, $R^1$ and $R^2$ are each independently selected from H, substituted or unsubstituted $C_1$-$C_6$ alkyl group, substituted or unsubstituted $C_2$-$C_6$ alkenyl group, or substituted or unsubstituted $C_2$-$C_6$ alkynyl group. In certain aspects, $R^1$ and $R^2$ are each independently selected from H, or substituted or unsubstituted $C_1$-$C_6$ alkyl group. In certain aspects, $R^1$ and $R^2$ are each independently selected from H, a methyl group or an ethyl group. In certain aspects, $R^1$ and $R^2$ are each independently selected from a methyl group or an ethyl group. In certain aspects, $R^1$ and $R^2$ are each ethyl groups.

In certain aspects, the compound has the structure of Formula I' selected from:

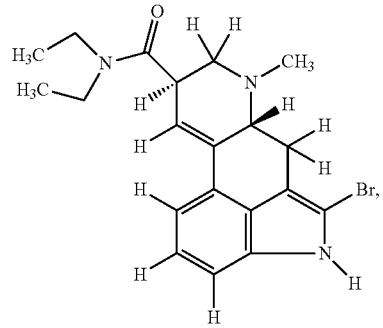

Formula Ia'

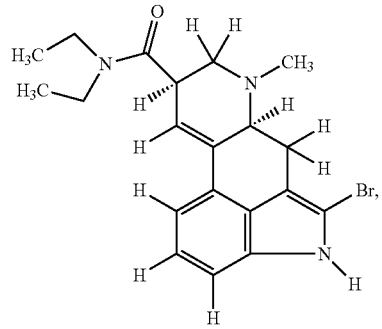

Formula Ib'

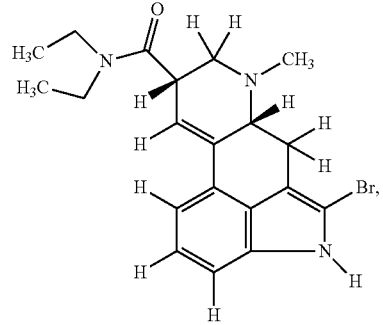

Formula Ic'

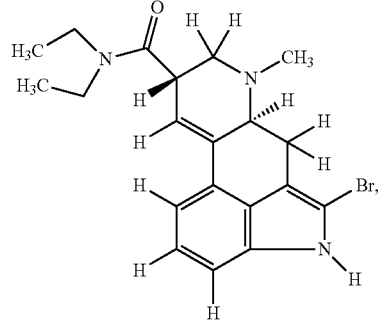

Formula Id' a pharmaceutically acceptable salt, hydrate, solvate, tautomer, polymorph or combination thereof.

In certain aspects, the compound is crystalline.

In certain aspects, the compound is an isolated crystalline form.

In certain aspects, the compound comprises polymorphs thereof.

In certain aspects, the compound comprises a single polymorph thereof.

In certain aspects, ein the compound comprises an isolated polymorph thereof.

In certain aspects, the compound is one or more polymorphs thereof; and/or ii) the compound comprises one or more compounds, each having two stereocenters, independently selected from 5S,8R; 5R,8R; 5R,8S; or 5S,8S; iii) the compound comprises one or more compounds, each having two stereocenters, independently selected from 5R,8S; 5R,8R; or 5S,8R; iv) the compound comprises one or more compounds, each having two stereocenters, independently selected from 5R,8S or 5R,8R; v) the compound has two stereocenters, which are 5R,8R; or vi) the compound has two stereocenters, which are 5R,8S.

In certain aspects, Formula I' is selected from Formula Ia'; Ib'; or Id'.

In certain aspects, Formula I' is Formula Ib' or Id'.

In certain aspects, the compound is a pharmaceutically acceptable salt, hydrate and/or solvate thereof.

In certain aspects, the compound is an acid salt.

In certain aspects, the acid of the acid salt is selected from hydrochloric acid, hydrobromic acid, nitric acid, carbonic acid, monohydrogencarbonic acid, phosphoric acid, monohydrogenphosphoric acid, dihydrogenphosphoric acid, sulfuric acid, monohydrogensulfuric acid, hydriodic acid, ethanedisulfonic acid, phosphorous acid, acetic acid, propionic acid, isobutyric acid, butyric acid, maleic acid, mandelic acid (D or L), ethane-1,2-disulfonic acid (dihydrate), toluene sulfonic acid (e.g. monohydrate), p-toluene sulfonic acid (e.g. monohydrate), 10-camphorsulfonic acid (e.g. (–)-10-camphorsulfonic acid), malic acid, malonic acid, benzoic acid, succinic acid, suberic acid, fumaric acid, lactic acid, mandelic acid, phthalic acid, benzenesulfonic acid, p-tolylsulfonic acid, citric acid, tartaric acid (L-tartaric acid or D-tartaric acid), mesotartaric acid (or erythraric acid), methanesulfonic acid, glutamic acid (L-glutamic acid or D-glutamic acid), ascorbic acid (L-ascorbic acid or D-ascorbic acid), isoascorbic acid (L-isoascorbic acid or D-isoascorbic acid), or a combination thereof.

In certain aspects, the acid of the acid salt is selected from hydrochloric acid, tartaric acid (L-tartaric acid or D-tartaric acid), mesotartaric acid (or erythraric acid), methanesulfonic acid, glutamic acid (L-glutamic acid or D-glutamic acid), ascorbic acid (L-ascorbic acid or D-ascorbic acid), isoascorbic acid (L-isoascorbic acid or D-isoascorbic acid), or a combination thereof.

In certain aspects, the acid of the acid salt is selected from tartaric acid (L-tartaric acid or D-tartaric acid), mesotartaric acid (or erythraric acid), glutamic acid (L-glutamic acid or D-glutamic acid), ascorbic acid (L-ascorbic acid or D-ascorbic acid), isoascorbic acid (L-isoascorbic acid or D-isoascorbic acid), or a combination thereof.

In certain aspects, the compound has the structure of Formula I' selected from:

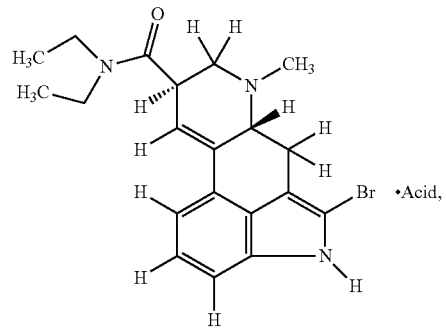

Formula Ia″

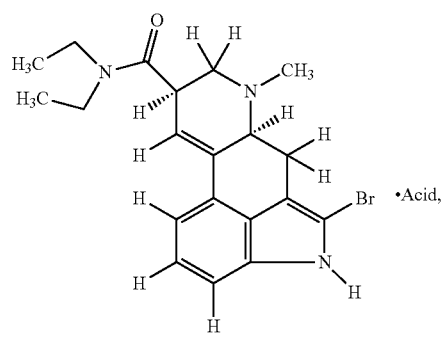

Formula Ib″

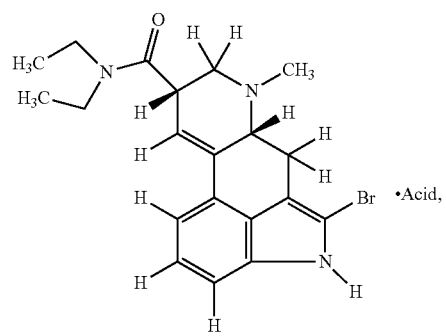

Formula Ic″

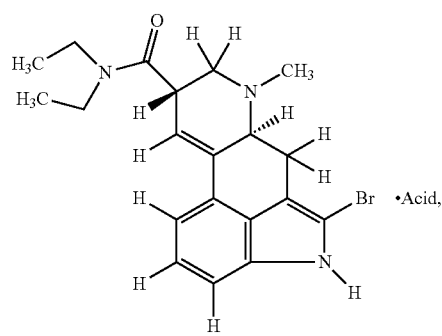

Formula Id″ or combination thereof.

In certain aspects, the compound is crystalline.

In certain aspects, the compound is an isolated crystalline form.

In certain aspects, the compound comprises polymorphs thereof.

In certain aspects, the compound comprises an isolated polymorph thereof.

In certain aspects, i) the compound is one or more polymorphs thereof; and/or ii) the compound comprises one or more compounds, each having two stereocenters, independently selected from 5S,8R; 5R,8R; 5R,8S; or 5S,8S; iii) the compound comprises one or more compounds, each having two stereocenters, independently selected from 5R,8S; 5R,8R; or 5S,8R; iv) the compound comprises one or more compounds, each having two stereocenters, independently selected from 5R,8S or 5R,8R; v) the compound has two stereocenters, which are 5R,8R; or vi) the compound has two stereocenters, which are 5R,8S.

In certain aspects, Formula I' is selected from Formula Ia"; Ib"; or Id".

8 In certain aspects, Formula I' is Formula Ib' or Id'.

In certain aspects, the compound is a pharmaceutically acceptable salt, hydrate and/or solvate thereof.

In certain aspects, the compound is an acid salt.

In certain aspects, the acid of the acid salt is selected from hydrochloric acid, hydrobromic acid, nitric acid, carbonic acid, monohydrogencarbonic acid, phosphoric acid, monohydrogenphosphoric acid, dihydrogenphosphoric acid, sulfuric acid, monohydrogensulfuric acid, hydriodic acid, ethanedisulfonic acid, phosphorous acid, acetic acid, propionic acid, isobutyric acid, butyric acid, maleic acid, mandelic acid (D or L), ethane-1,2-disulfonic acid (dihydrate), toluene sulfonic acid (e.g. monohydrate), p-toluene sulfonic acid (e.g. monohydrate), 10-camphorsulfonic acid (e.g. (−)-10-camphorsulfonic acid), malic acid, malonic acid, benzoic acid, succinic acid, suberic acid, fumaric acid, lactic acid, mandelic acid, phthalic acid, benzenesulfonic acid, p-tolylsulfonic acid, citric acid, tartaric acid (L-tartaric acid or D-tartaric acid), mesotartaric acid (or erythraric acid), methanesulfonic acid, glutamic acid (L-glutamic acid or D-glutamic acid), ascorbic acid (L-ascorbic acid or D-ascorbic acid), isoascorbic acid (L-isoascorbic acid or D-isoascorbic acid), or a combination thereof.

In certain aspects, the acid of the acid salt is selected from hydrochloric acid, tartaric acid (L-tartaric acid or D-tartaric acid), mesotartaric acid (or erythraric acid), methanesulfonic acid, glutamic acid (L-glutamic acid or D-glutamic acid), ascorbic acid (L-ascorbic acid or D-ascorbic acid), isoascorbic acid (L-isoascorbic acid or D-isoascorbic acid), or a combination thereof.

In certain aspects, the acid of the acid salt is selected from tartaric acid (L-tartaric acid or D-tartaric acid), mesotartaric acid (or erythraric acid), glutamic acid (L-glutamic acid or D-glutamic acid), ascorbic acid (L-ascorbic acid or D-ascorbic acid), isoascorbic acid (L-isoascorbic acid or D-isoascorbic acid), or a combination thereof.

In certain aspects, the compound is selected from:

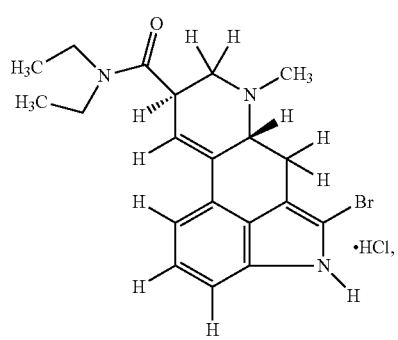

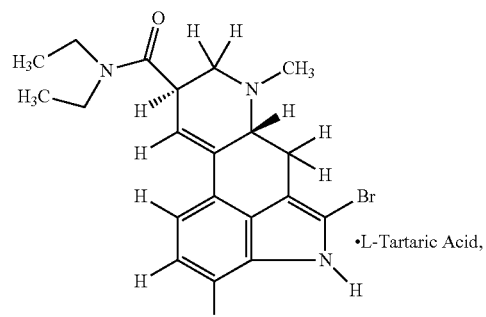

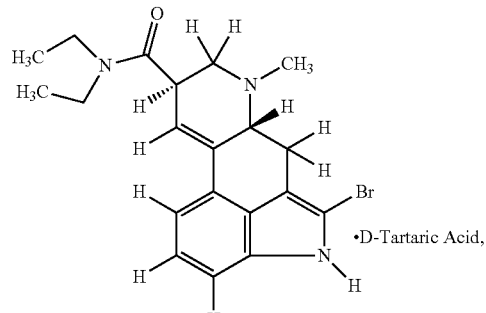

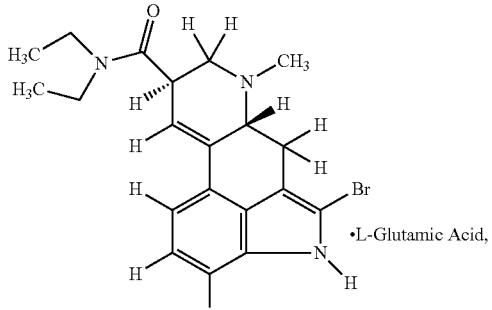

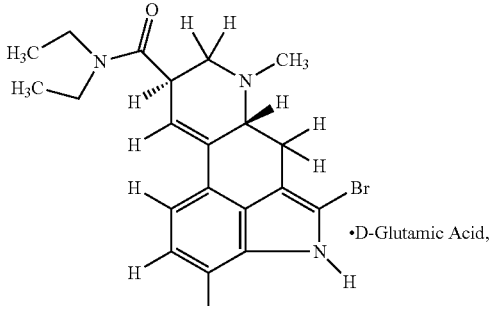

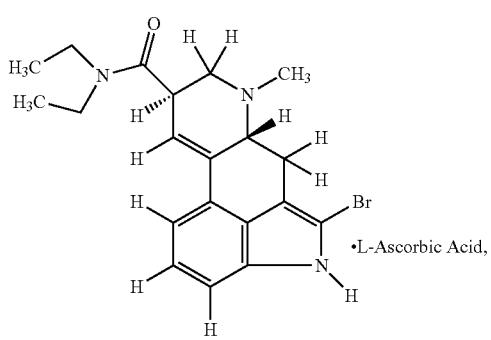

-continued
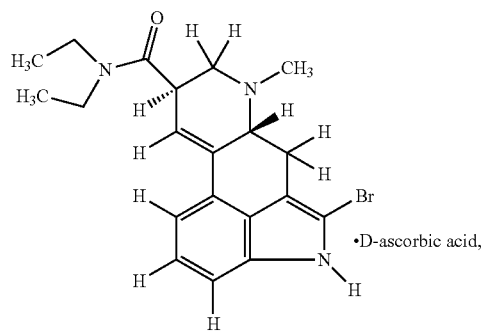
•D-ascorbic acid,
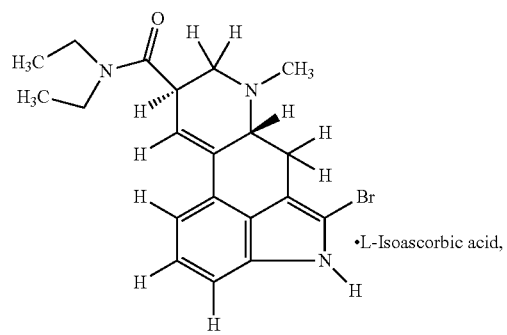
•L-Isoascorbic acid,
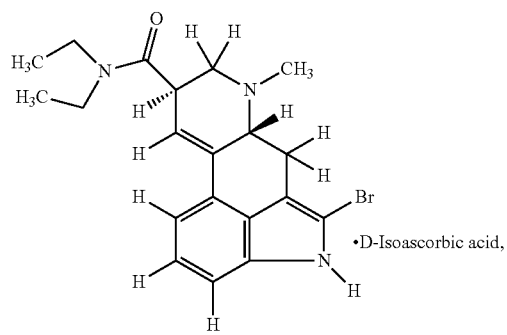
•D-Isoascorbic acid,
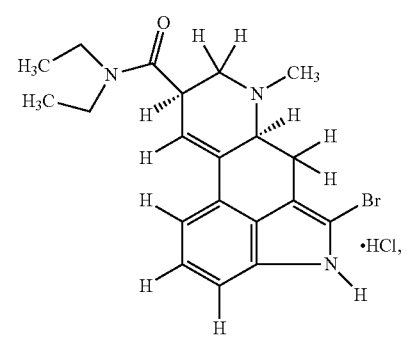
•HCl,
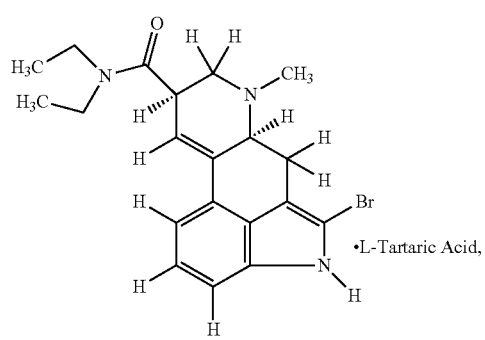
•L-Tartaric Acid,
-continued
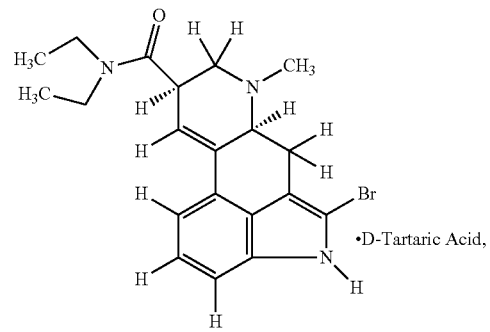
•D-Tartaric Acid,
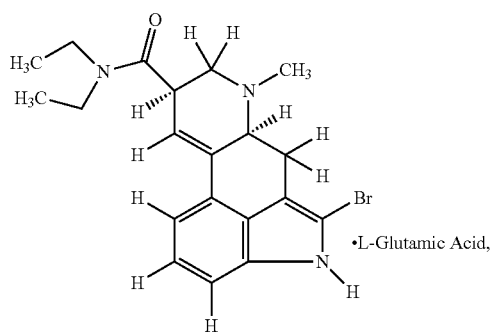
•L-Glutamic Acid,
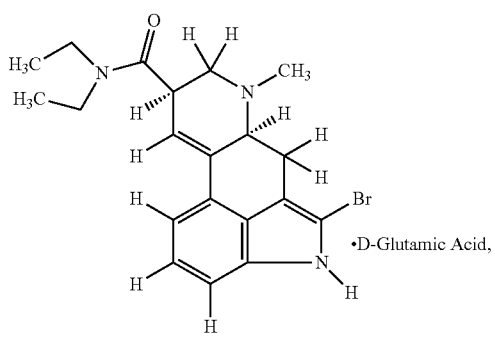
•D-Glutamic Acid,
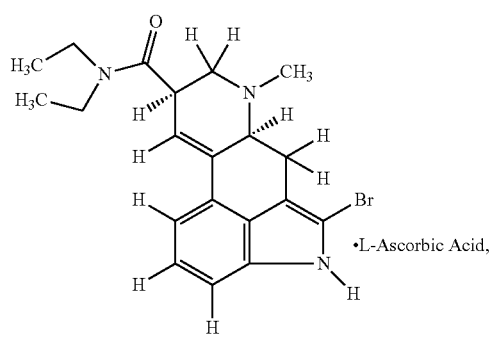
•L-Ascorbic Acid,
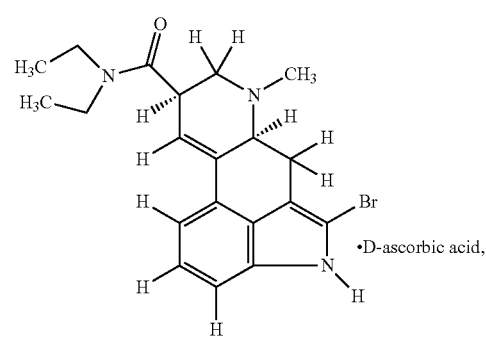
•D-ascorbic acid, -continued
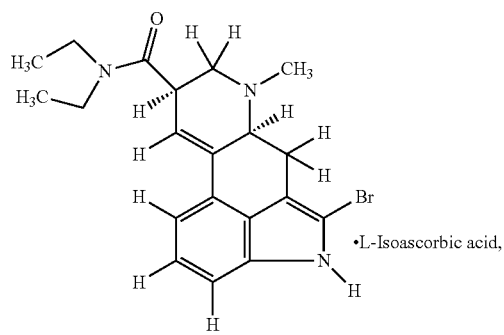
•L-Isoascorbic acid,
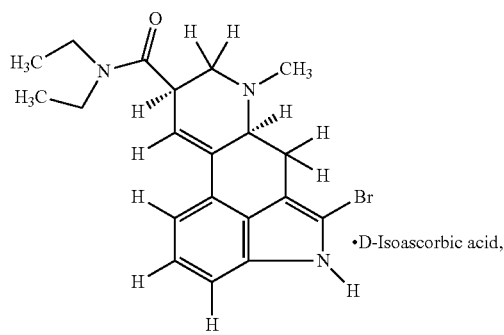
•D-Isoascorbic acid,
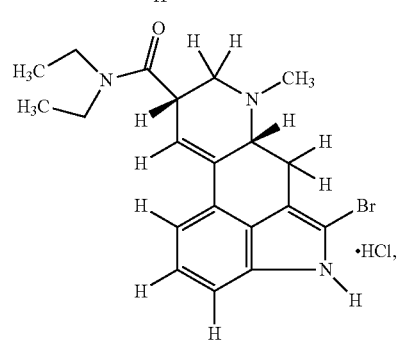
•HCl,
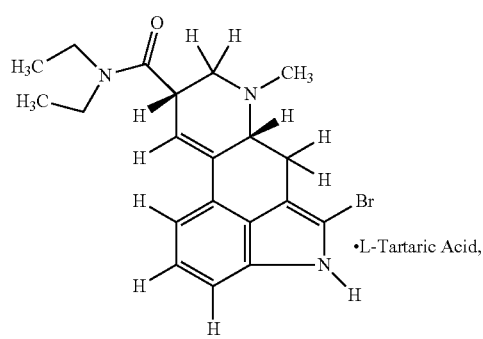
•L-Tartaric Acid,
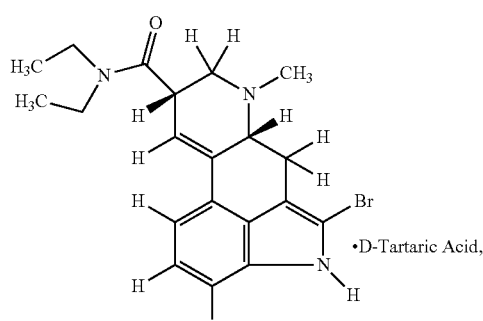
•D-Tartaric Acid,
-continued
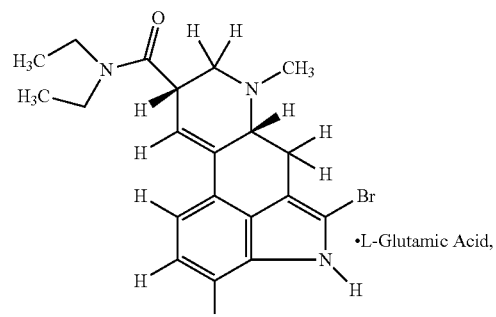
•L-Glutamic Acid,
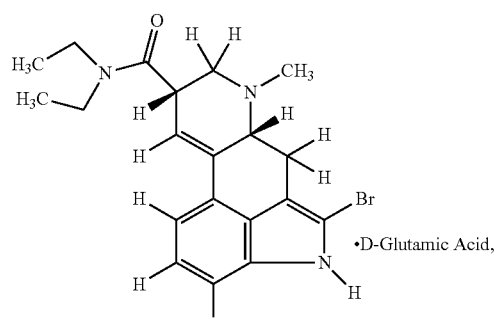
•D-Glutamic Acid,
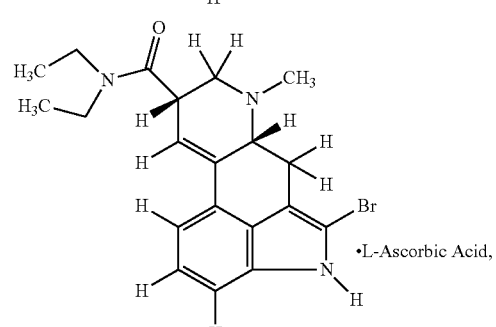
•L-Ascorbic Acid,
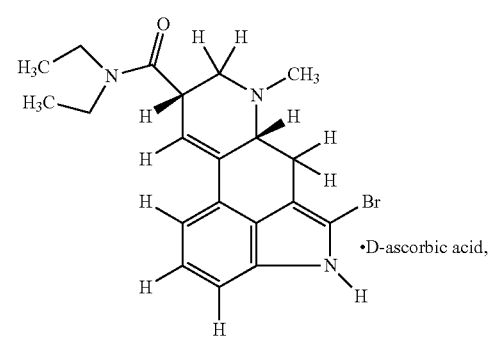
•D-ascorbic acid,
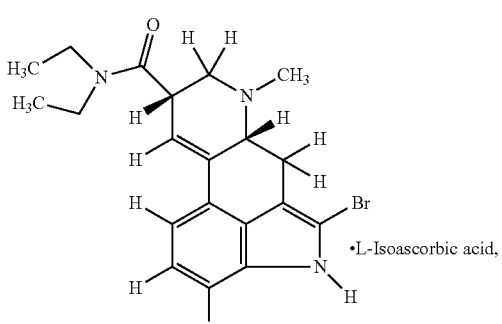
•L-Isoascorbic acid,

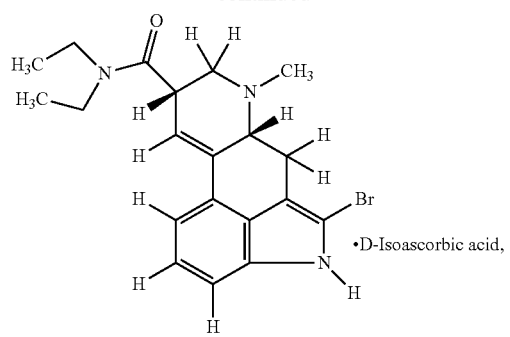
•D-Isoascorbic acid,
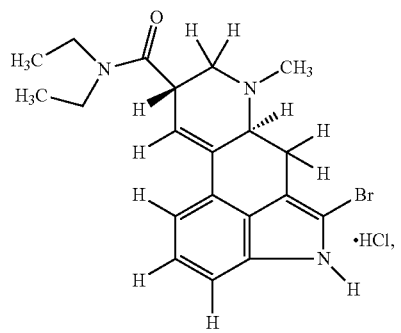
•HCl,
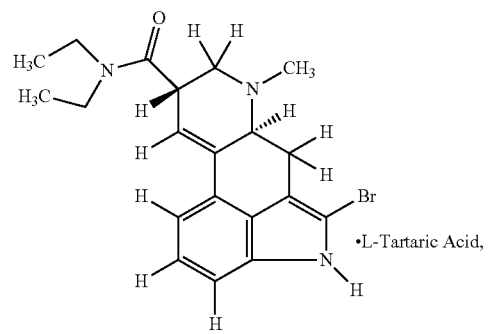
•L-Tartaric Acid,
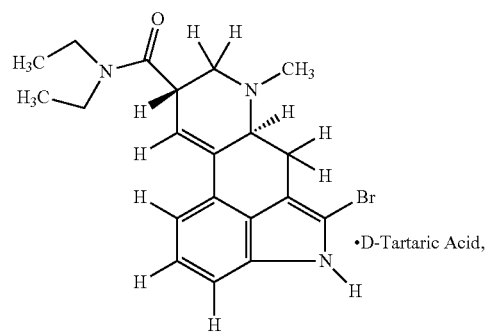
•D-Tartaric Acid,
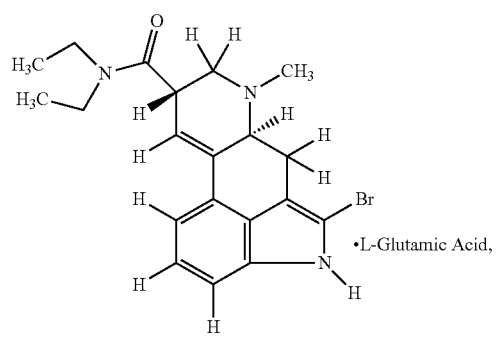
•L-Glutamic Acid,
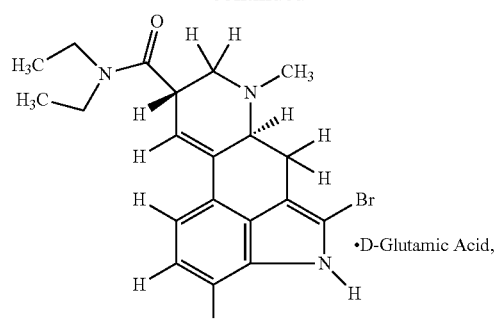
•D-Glutamic Acid,
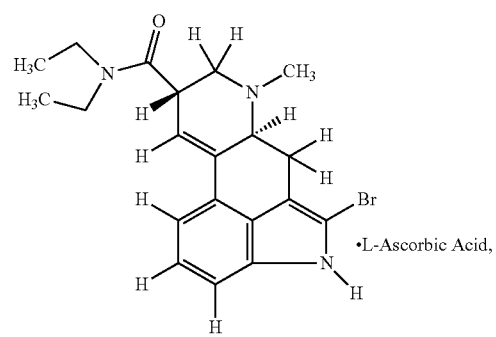
•L-Ascorbic Acid,
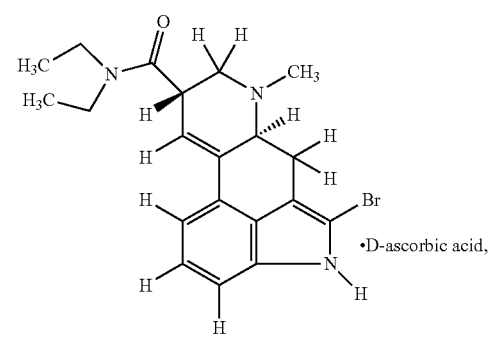
•D-ascorbic acid,
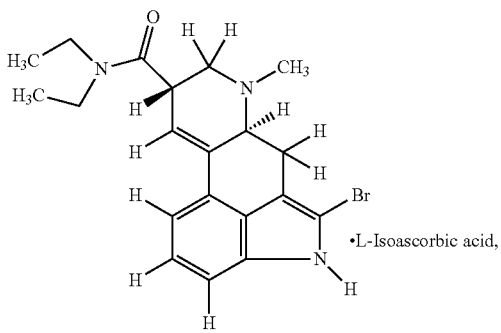
•L-Isoascorbic acid,
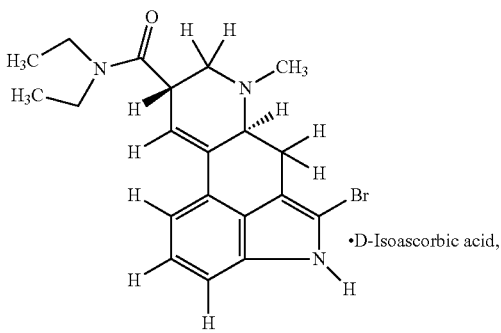
•D-Isoascorbic acid,
or combination thereof.

In certain aspects, the compound is crystalline.

In certain aspects, the compound is an isolated crystalline form.

In certain aspects, the compound comprises polymorphs thereof.

In certain aspects, the compound comprises a single polymorph thereof.

In certain aspects, the compound comprises an isolated polymorph thereof.

In certain aspects, i) the compound is one or more polymorphs thereof; and/or ii) the compound comprises one or more compounds, each having two stereocenters, independently selected from 5S,8R; 5R,8R; 5R,8S; or 5S,8S; iii) the compound comprises one or more compounds, each having two stereocenters, independently selected from 5R,8S; 5R,8R; or 5S,8R; iv) the compound comprises one or more compounds, each having two stereocenters, independently selected from 5R,8S or 5R,8R; v) the compound has two stereocenters, which are 5R,8R; or vi) the compound has two stereocenters, which are 5R,8S.

In certain aspects, the compound comprises 2-bromoLSD tartrate salt (about 1:about 0.5) and/or (about 1:about 1), i) the compound is one or more polymorphs thereof; and/or ii) the compound comprises one or more compounds, each having two stereocenters, independently selected from 5S,8R; 5R,8R; 5R,8S; or 5S,8S; iii) the compound comprises one or more compounds, each having two stereocenters, independently selected from 5R,8S; 5R,8R; or 5S,8R; iv) the compound comprises one or more compounds, each having two stereocenters, independently selected from 5R,8S or 5R,8R; v) the compound has two stereocenters, which are 5R,8R; or vi) the compound has two stereocenters, which are 5R,8S.

In certain aspects, the ratio of the compound of Formula I, I', Ia, Ib, Ic, Id, Ia', Ib', Ic', or Id' to the acid is from about 0.5:1 to about 2:1.

In certain aspects, the compound is (5R,8R) 2-bromo-LSD hemi-D-tartrate salt.

In certain aspects, the compound is an isolated polymorph of (5R,8R) 2-bromo-LSD hemi-D-tartrate salt.

In certain aspects, the compound has a Powder X-ray Diffraction (PXRD) pattern comprising a peak at about 10.3° (2θ).

In certain aspects, the compound has an X-ray powder diffraction (PXRD) pattern comprising a peak at about 4.7° (2θ), about 9.4° (2θ), and about 10.3° (2θ).

In certain aspects, the compound has an X-ray powder diffraction (PXRD) pattern comprising a peak at about 4.7° (2θ), about 9.4° (2θ), about 10.30 (2θ), and about 20.10 (2θ).

In certain aspects, the compound has a Powder X-ray Diffraction (PXRD) pattern comprising a peak at about 10.30 (2θ) and d value of about 8.6 Å.

In certain aspects, the compound has an X-ray powder diffraction (PXRD) pattern comprising a peak at about 4.7° (2θ) and d value of about 18.8 Å, about 9.4° (2θ) and d value of about 9.4 Å, and about 10.3° (2θ) and d value of about 8.6 Å.

In certain aspects, the compound has an X-ray powder diffraction (PXRD) pattern comprising a peak at about 4.7° (2θ) and d value of about 18.8 Å, about 9.4° (2θ) and d value of about 9.4 Å, about 10.3° (2θ) and d value of about 8.6 Å, and about 20.10 (2θ) and d value of about 4.4 Å.

In certain aspects, the compound has a Powder X-ray Diffraction (PXRD) pattern comprising a peak at 10.3°±0.2° (2θ).

In certain aspects, the compound has an X-ray powder diffraction (PXRD) pattern comprising a peak at 4.7°±0.2° (2θ), 9.4°±0.2° (2θ), and 10.3°±0.2° (2θ).

114 In certain aspects, the compound has an X-ray powder diffraction (PXRD) pattern comprising a peak at 4.7°±0.2° (2θ), 9.4°±0.2° (2θ), 10.3°±0.2° (2θ), and 20.1°±0.2° (2θ).

In certain aspects, the optical rotation is about 0.30° to about 0.40°; optionally, about 0.30° to about 0.35°.

In certain aspects, the compound or polymorph thereof is non-hallucinogenic.

In certain aspects, the compound or polymorph thereof is substantially non-hallucinogenic.

In certain aspects, the compound does not induce tolerance in a subject,

In certain aspects, the compound is a moderate to potent pan-agonist across all 5-HT1 receptor subtypes.

In certain aspects, the compound is a potent 5-HT6 receptor partial agonist.

In certain aspects, the compound is a partial agonist at 5-HT2A and 5-HT1A receptor subtypes.

In certain aspects, the compound exhibits agonism at D2-like receptors including D2 and D4.

In certain aspects, the compound promotes neural plasticity in neurons, for example in cortical neurons.

In certain aspects, the present invention includes a composition comprising a compound described above.

In certain aspects, the composition further comprises a pharmaceutically acceptable carrier, adjuvant or vehicle.

In certain aspects, the composition further comprises a second therapeutic agent.

In certain aspects, the composition is a pharmaceutical composition.

In certain aspects, the present invention includes a formulation comprising a composition described above and/or the pharmaceutical composition described above.

In certain aspects, the formulation is a liquid or solid, optionally where the solid is a powder, tablet or pill.

In certain aspects, the formulation comprises an established amount of the compound, optionally wherein the formulation is for oral or parenteral administration.

In certain aspects, the formation is to make a medicament for the treatment of one or more of: depressive disorders; bipolar and related disorders; schizophrenia spectrum and other psychotic disorders; personality disorders; anxiety disorders; trauma and stressor-related disorders; obsessive-compulsive and related disorders; disruptive disorders, impulse-control and conduct disorders; feeding and eating disorders; dissociative disorders; somatic symptom and related disorders; neurodevelopmental disorders; sleep-wake disorders; substance-related and addictive disorders; headache disorders; pain disorders; spasticity; nerve injury disorders; fatigue; neuro-degenerative disorders; sexual dysfunctions and gender dysphoria disorders; neurocognitive disorders; neurological—viral infection; counteracting other drug's side effects; and general well-being.

In certain aspects, the formation is for the treatment of one or more of: depressive disorders; bipolar and related disorders; schizophrenia spectrum and other psychotic disorders; personality disorders; anxiety disorders; trauma and stressor-related disorders; obsessive-compulsive and related disorders; disruptive disorders, impulse-control and conduct disorders; feeding and eating disorders; dissociative disorders; somatic symptom and related disorders; neurodevelopmental disorders; sleep-wake disorders; substance-related and addictive disorders; headache disorders; pain disorders; spasticity; nerve injury disorders; fatigue; neuro-degenerative disorders; sexual dysfunctions and gender dysphoria disorders; neurocognitive disorders; neurological—viral infection; counteracting other drug's side effects; and general well-being.

In certain aspects, the formation is for reducing at one or more signs or symptoms of any one or more of: depressive disorders; bipolar and related disorders; schizophrenia spectrum and other psychotic disorders; personality disorders; anxiety disorders; trauma and stressor-related disorders; obsessive-compulsive and related disorders; disruptive disorders, impulse-control and conduct disorders; feeding and eating disorders; dissociative disorders; somatic symptom and related disorders; neurodevelopmental disorders; sleep-wake disorders; substance-related and addictive disorders; headache disorders; pain disorders; spasticity; nerve injury disorders; fatigue; neuro-degenerative disorders; sexual dysfunctions and gender dysphoria disorders; neurocognitive disorders; and neurological—viral infection.

In certain aspects, the present invention includes a method of making any one of the compounds described above, wherein the method comprises:

a) hydrolyzing a compound of Formula IA to form an intermediate of Formula IB:

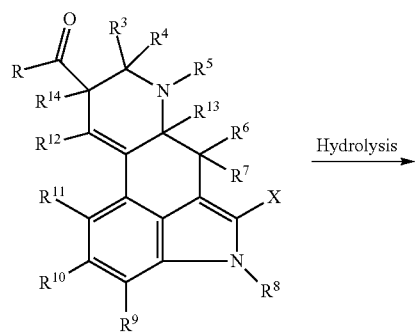

Formula IA

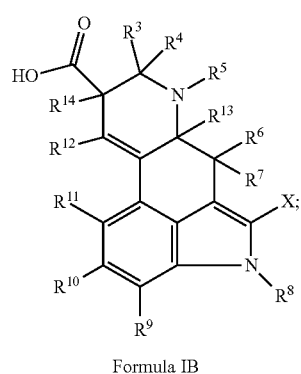

Formula IB b) reacting the intermediate of Formula IB with $R^1$—NH—$R^2$ to form a compound of Formula IC

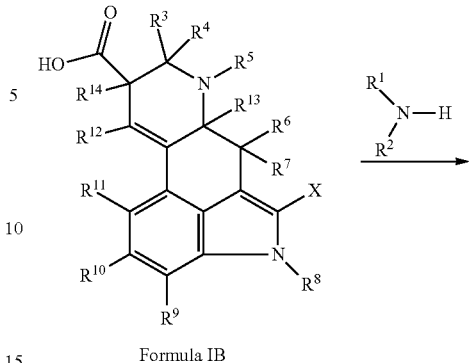

Formula IB

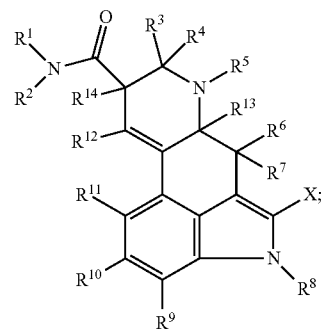

Formula IC c) converting a compound of Formula IC to a salt or hydrate using an organic or inorganic acid, wherein R is selected from —$OR_1$ or —$NR_1R_2$, $R_1$ and $R_2$ each being independently selected from H, halo group, hydroxyl group, amino group, a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic, optionally, $R_1$ and $R_2$ are each independently selected from H, a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic.

In certain aspects, the method of making does not use LSD as a substrate and/or other schedule I substances.

In certain aspects, the hydrolysis is acid or base hydrolysis, optionally, the acid is selected from hydrochloric acid, sulfuric acid, trifluoroacetic acid, formic acid, hydrofluoric acid, and/or nitric acid or the base is selected from potassium hydroxide, sodium hydroxide, potassium t-butoxide, barium hydroxide, lithium hydroxide, and/or tetrabutylammoniun hydroxide.

In certain aspects, the method further comprises using water-miscible solvents, optionally, alcohols (e.g. methanol, ethanol, isopropyl alcohol (IPA), etc.), acetonitrile, acetone, isopropyl acetate, THF, 2-methyl-THF, or a combination thereof.

In certain aspects, the method comprises heating in a), b), and/or c) from about 50° C. to about 95° C.

In certain aspects, b) further comprises converting the hydroxyl group of the carboxylic acid to a better leaving group (LG) such as halides (e.g., Cl, Br, I), tosylates, mesylates, or perfluoroalkylsulfonates, optionally, converting to acid chlorides using phosphoryl chloride or thionyl chloride.

In certain aspects, b) further comprises base catalyzed amide bond formation, optionally, using a base and a coupling agent.

In certain aspects, the coupling agent is selected from carbonyldiimidazole (CDI), 2-chloro-4,6-dimethoxy-1,3,5 triazine (CDMT), 1-hydroxybenzotriazole (HOBt), hexafluorophosphate azabenzotriazole tetramethyl uronium (HATU), propylphosphonic anhydride (T3P), phosphorous oxychloride ($POCl_3$), ethyl 2-cyano-2-(hydroxyamino) acetate (OxymaPure), benzotriazome-1-yl-oxy-tris-(dimethylamino)-phosphonium hexafluorophosphate (BOP), 1-[(1-(cyano-2-ethoxy-2-oxoethylindeneaminooxy) dimethylaminomorpholino)] uranium hexafluorphosphate (COMU), 2-(1H-benzotriazole-1-yl)-1,1,3,3-tetramethyluronium hexafluorophosphate (HBTU), O-(1H-6-chlorobenzotriazole-1-yl)-1,1,3,3-tetramethyluronium hexafluorophosphate (HCTU), (3-Hydroxy-3H-1,2,3-triazolo[4,5-b]pyridinato-O)tri-1-pyrrolidinyl-phosphorus hexafluorophosphate (PyAOP), (1H-benzotriazol-1-yloxy)(tri-1-pyrrolidinyl) phosphonium hexafluorophosphate (PyBOP), 6-chloro-benzotriazole-1-yloxy-tris-pyrrolidinophosphonium hexafluorophosphate (PyClock), (E)-(ethyl cyano({[tris(pyrrolidin-1-yl)phosphaniumyl]oxy}imino)formate) (PyOxim), and (5E)-6-cyano-N,N,2-trimethyl-7-oxo-4,8-dioxa-2,5-diazadec-5-en-3-iminium tetrafluoroborate (TOTU), or a combination thereof.

In certain aspects, the coupling agent is selected from carbonyldiimidazole (CDI), 2-chloro-4,6-dimethoxy-1,3,5 triazine (CDMT), 1-hydroxybenzotriazole (HOBt), hexafluorophosphate azabenzotriazole tetrameth25raniumium (HATU), propylphosphonic anhydride (T3P), phosphorous oxychloride ($POCl_3$), or a combination thereof.

In certain aspects, b) further comprises base catalyzed amide bond formation, optionally, using N-methylmorpholine (NMM) and 1,1'-carbonyldiimidazole (CDI).

In certain aspects, in a) and/or b) the acidity of the intermediates of Formulae IB and IC were adjusted to form a precipitate; optionally, adjusting the pH from about 6 to about 8 with an acid.

In certain aspects, in c), converting a compound of Formula IC to a salt or hydrate thereof using an organic or inorganic acid, in-situ with (b) or in a separate step.

In certain aspects, the acid is selected from hydrochloric acid, hydrobromic acid, nitric acid, carbonic acid, monohydrogencarbonic acid, phosphoric acid, monohydrogenphosphoric acid, dihydrogenphosphoric acid, sulfuric acid, monohydrogensulfuric acid, hydriodic acid, ethanedisulfonic acid, phosphorous acid, acetic acid, propionic acid, isobutyric acid, butyric acid, maleic acid, mandelic acid (D or L), ethane-1,2-disulfonic acid (dihydrate), toluene sulfonic acid (e.g. monohydrate), p-toluene sulfonic acid (e.g. monohydrate), 10-camphorsulfonic acid (e.g. (−)-10-camphorsulfonic acid), malic acid, malonic acid, benzoic acid, succinic acid, suberic acid, fumaric acid, lactic acid, mandelic acid, phthalic acid, benzenesulfonic acid, p-tolylsulfonic acid, citric acid, tartaric acid (L-tartaric acid or D-tartaric acid), mesotartaric acid (or erythraric acid), methanesulfonic acid, glutamic acid (L-glutamic acid or D-glutamic acid), ascorbic acid (L-ascorbic acid or D-ascorbic acid), isoascorbic acid (L-isoascorbic acid or D-isoascorbic acid), or a combination thereof.

In certain aspects, c) comprises heating the compound of Formula IC with the organic or inorganic acid in a water immiscible solvent, optionally, alcohols (e.g. methanol, ethanol, isopropyl alcohol (IPA), etc.), acetonitrile, acetone, isopropyl acetate, THF, 2-methyl-THF, etc.) or a combination thereof.

In certain aspects, c) comprises heating at a temperature of from about 60° C. to about 80° C., optionally, from about 60° C. to about 70° C.

In certain aspects, the water-miscible solvent is selected from methanol, ethanol, isopropyl alcohol (IPA) or a combination thereof; optionally, wherein the water-miscible solvent is selected from ethanol, isopropyl alcohol (IPA) or a combination thereof; optionally, ethanol or isopropyl alcohol (IPA).

In certain aspects, heating the compound of Formula IC with the organic or inorganic acid is heated for about 30 minutes to about 1 hour.

In certain aspects, cooling the compound in solution to about 0 to about 10° C., optionally, about 3 to about 7° C., optionally about 5° C., and optionally for about 30 minutes to about 2 h.

In certain aspects, the salt or hydrate of the compound of Formula IC is recrystallized to form a crystalline compound.

In certain aspects, the salt or hydrate of the compound of Formula IC is an isolated crystalline form.

In certain aspects, the salt or hydrate of the compound of Formula IC comprises polymorphs thereof.

In certain aspects, the salt or hydrate of the compound of Formula IC comprises a single polymorph thereof.

In certain aspects, the salt or hydrate of the compound of Formula IC comprises an isolated polymorph thereof.

In certain aspects, the salt or hydrate of the compound of Formula IC is recrystallized using water-miscible solvents, optionally, alcohols (e.g. methanol, ethanol, isopropyl alcohol (IPA), etc.), acetonitrile, acetone, isopropyl acetate, THF, 2-methyl-THF, etc.) or a combination thereof.

In certain aspects, the water-miscible solvent is selected from methanol, ethanol, isopropyl alcohol (IPA) or a combination thereof; optionally, wherein the water-miscible solvent is selected from ethanol, isopropyl alcohol (IPA) or a combination thereof; optionally, ethanol or isopropyl alcohol (IPA).

In certain aspects, recrystallization comprises heating the salt or hydrate of the compound of Formula IC in the solvent to a suitable temperature for a suitable time period and cooling to form anyone of the compounds described herein.

In certain aspects, recrystallization comprises heating the salt or hydrate of the compound of Formula IC in the solvent of from about 60° C. to about 80° C., optionally, from about 60° C. to about 70° C.

In certain aspects, recrystallization comprises heating the salt or hydrate of the compound of Formula IC in the solvent of from about 60° C. to about 80° C., optionally, from about 60° C. to about 70° C., for about 1 h to about 2 h.

In certain aspects, recrystallization comprises heating the salt or hydrate of the compound of Formula IC in the solvent of from about 60° C. to about 80° C., optionally, from about 60° C. to about 70° C., for about 1 h to about 2 h, and cooling the compound in solution to about 0 to about 10° C., optionally, about 3 to about 7° C., optionally about 5° C., and optionally for about 1 h to about 2 h.

In certain aspects, the recrystallized compound is about 99% to about 99.9% purity, optionally, about 99.5% to about 99.9% purity.

In certain aspects, the method comprises:
a) hydrolyzing a compound of Formula IAA (5S,8R) to form an intermediate of Formula IBB:

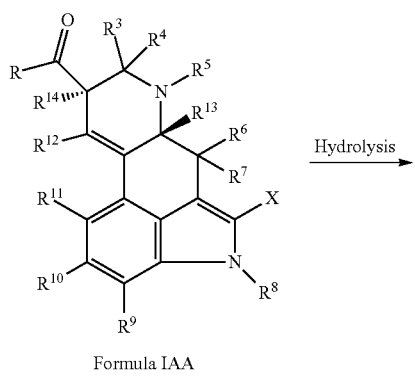

Formula IAA

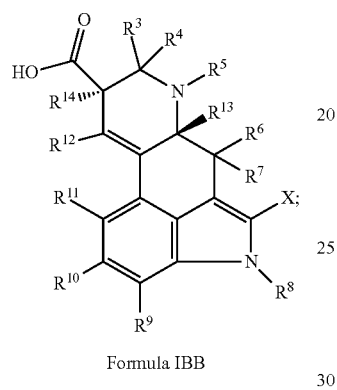

Formula IBB b) reacting the intermediate of Formula IBB with R¹—NH—R² to form Formula ICC

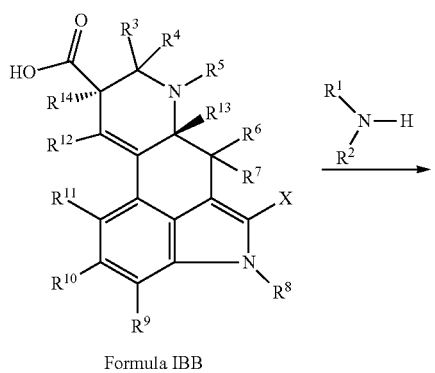

Formula IBB

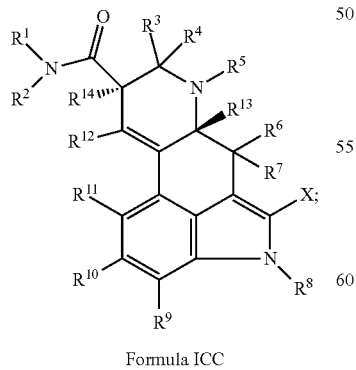

Formula ICC c) converting a compound of Formula ICC to a salt or hydrate using an organic or inorganic acid.

In certain aspects, the method comprises:
a) hydrolyzing a compound of Formula IAA' (5R,8R) is hydrolyzed to form an intermediate of Formula IBB':

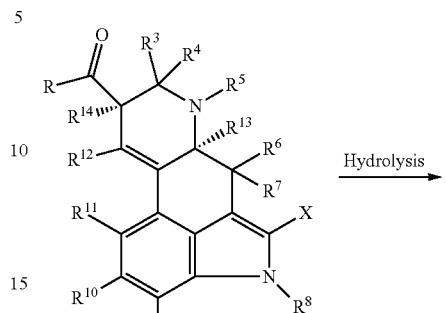

Formula IAA'

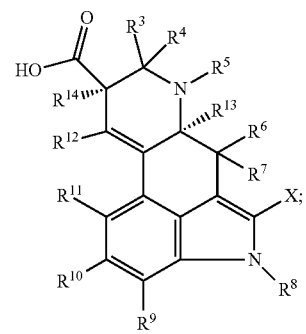

Formula IBB' b) reacting the intermediate of Formula IBB' with R¹—NH—R² to form Formula

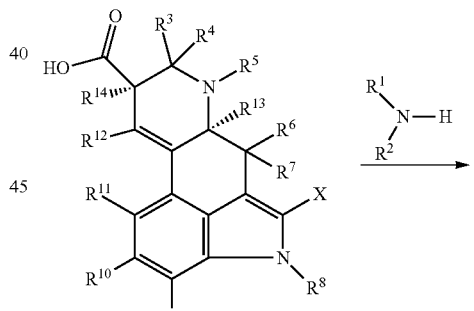

Formula IBB'

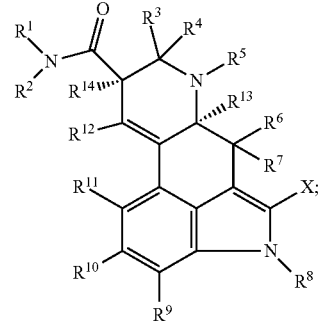

Formula ICC' c) converting a compound of Formula ICC' to a salt or hydrate using an organic or inorganic acid.

In certain aspects, the method comprises:

a) hydrolyzing a) a compound of Formula IAA" (5R,8S) is hydrolyzed to form an intermediate of Formula IBB":

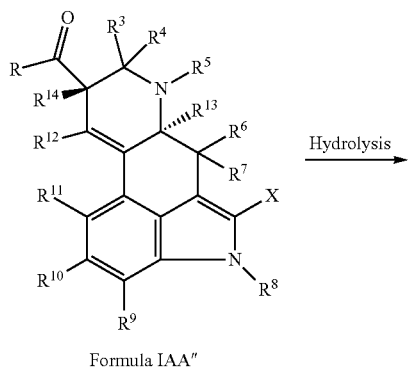

Formula IAA"

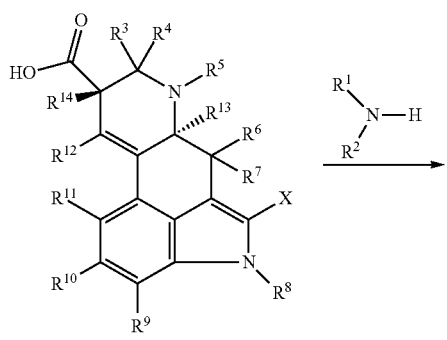

Formula IBB"

b) reacting the intermediate of Formula IBB" with $R^1$—NH—$R^2$ to form Formula

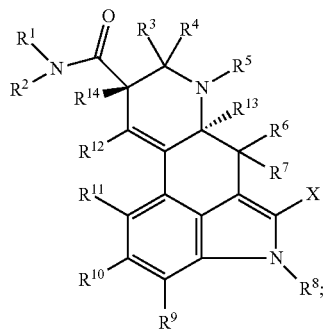

Formula ICC"

c) converting a compound of Formula ICC" to a salt or hydrate using an organic or inorganic acid.

In certain aspects, the method comprises:

a) hydrolyzing a compound of Formula IAA'"(5S,8S) is hydrolyzed to form an intermediate of Formula IBB'":

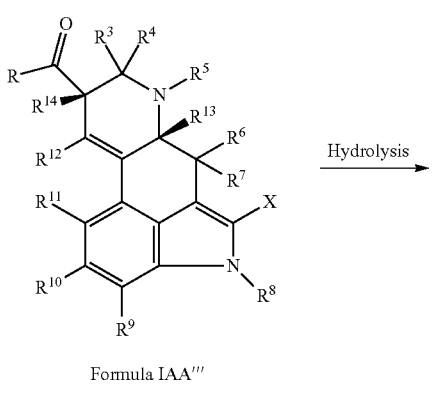

Formula IAA'"

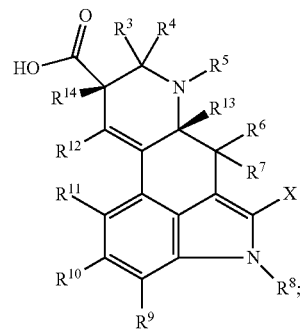

Formula IBB'"

b) reacting the intermediate of Formula IBB'" with $R^1$—NH—$R^2$ to form Formula ICC'"

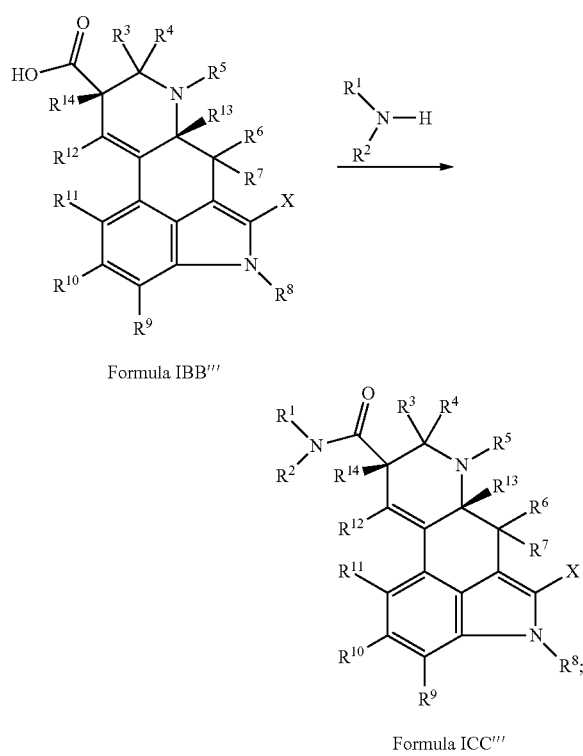

Formula IBB'''

Formula ICC''';

c) converting a compound of Formula ICC''' to a salt or hydrate using an organic or inorganic acid.

In certain aspects, the compound of Formula IA, IAA, IAA', IAA'', or IAA''' is a bromine-containing ergoline derivative such as bromocriptine mesylate.

In certain aspects, the compound of Formula IA, IAA, IAA', IAA'', or IAA''' is

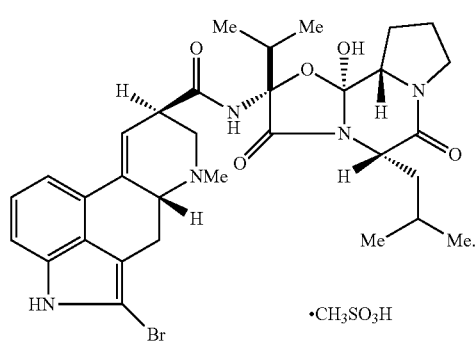

·CH₃SO₃H

In certain aspects, the method comprises heating 2-bromolysergicdiamide and IPA, combining D-tartaric acid and IPA with 2-bromolysergicdiamide and IPA, wherein the combined solution became clear, heating the combined solution for a predetermined time, allowing the mixture to cool to about room temperature, cooling further to provide a solid comprising a major amount of (5R,8R) 2-bromo-LSD hemi-D-tartrate salt and a minor amount of (5R,8S) 2-bromo-LSD hemi-D-tartrate salt.

In certain aspects, the method comprises heating 2-bromolysergicdiamide and IPA to about 65° C., combining D-tartaric acid and IPA with 2-bromolysergicdiamide and IPA, wherein the combined solution became clear, heating the combined solution to about 65° C. for a predetermined time, allowing the mixture to cool to about room temperature, cooling to about 5° C. to provide a solid comprising a major amount of (5R,8R) 2-bromo-LSD hemi-D-tartrate salt and a minor amount of (5R,8S) 2-bromo-LSD hemi-D-tartrate salt.

In certain aspects, the predetermined time is about 30 minutes.

In certain aspects, the ratio of (5R,8R) 2-bromo-LSD hemi-D-tartrate salt to (5R,8S) 2-bromo-LSD hemi-D-tartrate salt is about 87 to about 13.

In certain aspects, the solid is recrystallized to obtain (5R,8R) 2-bromo-LSD hemi-D-tartrate salt; optionally, using ethanol.

In certain aspects, the solid is recrystallized to obtain (5R,8R) 2-bromo-LSD hemi-D-tartrate salt having about 99% to about 99.9% purity, optionally, about 99.5% to about 99.9% purity.

In certain aspects, the solid is a polymorph.

In certain aspects, the present invention includes a method for treating a depressive disorder, wherein the method comprises administration of the compound of any one the compounds, compositions, and/or formulations described above to a subject in need thereof.

In certain aspects, the depressive disorder is: depression, major depressive disorder (including major depressive episode), disruptive mood dysregulation disorder, atypical depression, psychotic major depression, catatonic depression, post-partum depression, premenstrual dysphoric disorder, seasonal affective disorder, substance/medication-induced depressive disorder, double depression, depressive personality disorder, persistent depressive disorder (dysthymia), recurrent brief depression, minor depressive disorder, depressive disorder due to a medical condition, a depressive disorder not otherwise specified, or a depressive disorder that is resistant to treatment.

In certain aspects, the depressive disorder is major depressive disorder.

In certain aspects, the major depressive disorder is dysthymia.

In certain aspects, the depressive disorder is atypical depression.

In certain aspects, the depressive disorder is catatonic depression.

In certain aspects, the depressive disorder is due to a medical condition.

In certain aspects, the depressive disorder is postpartum depression.

In certain aspects, the depressive disorder is premenstrual dysphoric disorder.

In certain aspects, the depressive disorder is seasonal affective disorder.

In certain aspects, an amount of the compound for administration to said subject is a range selected from about 25 to 500 µg/kg/bodyweight/day; or about 50 to about 2000 µg/kg/bodyweight/day; or about 10 to about 500 µg/kg/bodyweight/day.

In certain aspects, the present invention includes a method for treating a bipolar and related disorder, wherein the method comprises administration of any one the compounds, compositions, and/or formulations described above to a subject in need thereof.

In certain aspects, the bipolar and related disorders are bipolar I disorder, bipolar II disorder, cyclothymic disorder, substance/medication-induced bipolar and related disorders, and bipolar disorder not otherwise specified.

In certain aspects, an amount of the compound for administration to said subject is a range selected from about 25 to about 1000 μg/kg/bodyweight/day In certain aspects, the present invention includes a method for treating schizophrenia spectrum and other psychotic disorders, wherein the method comprises administration of any one the compounds, compositions, and/or formulations described above to a subject in need thereof.

In certain aspects, the schizophrenia spectrum and other psychotic disorders is: delusional disorder, brief psychotic disorder, schizophrenia, schizophreniform disorder, schizoaffective disorder, substance/medication-induced psychotic disorder, schizotypal (personality) disorders, psychotic disorders due to another medical condition, catatonia associated with another mental disorder, and other specified or unspecified schizophrenia spectrum and other psychotric disorders.

In certain aspects, an amount of the compound for administration to said subject is a range from about 50 to about 2000 μg/kg/bodyweight/day.

In certain aspects, the present invention includes a method for treating personality disorders are classified by the DSM-5, wherein the method comprises administration of any one the compounds, compositions, and/or formulations described above to a subject in need thereof.

In certain aspects, the personality disorders are: paranoid personality disorder; schizoid personality disorder; schizotypal personality disorder; antisocial personality disorder; borderline personality disorder; histrionic personality disorder; narcissistic personality disorder; avoidant personality disorder; dependent personality disorder; obsessive-compulsive personality disorder; personality change due to another medical condition; other specified personality disorder and unspecified personality disorder.

In certain aspects, the method comprises administration of any one the compounds, compositions, and/or formulations described above to a subject in need thereof.

In certain aspects, the anxiety disorders include generalized anxiety disorder, separation anxiety disorder, panic disorder, selective mutism, specific phobia (animal, natural environment, fear of blood/injection/injury, situational, other), social anxiety disorder, panic disorder, panic attack specifier, agoraphobia, substance/medication-induced anxiety disorder, anxiety disorder due to other medical conditions, and other specified or unspecified anxiety disorders.

In certain aspects, an amount of the compound for administration to said subject is a range of about 10 to about 1000 μg/kg/bodyweight/day.

In certain aspects, the present invention includes a method for treating trauma- and stressor-related disorders, wherein the method comprises administration of any one the compounds, compositions, and/or formulations described above to a subject in need thereof.

In certain aspects, the trauma- and stressor-related disorders include attachment disorder, disinhibited social engagement disorder, posttraumatic stress disorder (PTSD), acute stress disorder, adjustment disorders, other specified or unspecified trauma- and stressor-related disorders.

In certain aspects, an amount of the compound for administration to said subject is a range of about 10 to about 1000 μg/kg/bodyweight/day.

In certain aspects, the present invention includes a method for treating obsessive-compulsive and related disorders, wherein the method comprises administration of any one the compounds, compositions, and/or formulations described above to a subject in need thereof.

In certain aspects, the obsessive-compulsive and related disorders include: obsessive-compulsive disorder (OCD), body dysmorphic disorder, hoarding disorder, trichotillomania (hair-pulling disorder), excoriation (skin-picking) disorder, substance/medication-induced obsessive-compulsive and related disorder, obsessive-compulsive and related disorder due to another medical condition, and other specified and unspecified obsessive-compulsive and related disorders (e.g., body-focused repetitive behavior disorder, obsessional jealousy).

In certain aspects, an amount of the compound for administration to said subject is a range of about 10 to about 1000 μg/kg/bodyweight/day.

In certain aspects, the present invention includes a method for treating disruptive, impulse-control, and conduct disorders, wherein the method comprises administration of any one the compounds, compositions, and/or formulations described above to a subject in need thereof.

In certain aspects, the disruptive, impulse-control, and conduct disorders include: oppositional defiant disorder, intermittent explosive disorder, conduct disorder, antisocial personality disorder, pyromania, kleptomania, trichotillomania, and other specific and unspecified disruptive, impulse-control, and conduct disorders.

In certain aspects, the present invention includes a method for treating feeding and eating disorders, wherein the method comprises administration of any one the compounds, compositions, and/or formulations described above to a subject in need thereof.

In certain aspects, the feeding and eating disorders include: pica, rumination disorder, avoidant/restrictive food intake disorder, anorexia nervosa, binge-eating disorder, bulimia nervosa, polyphagia or over-eating disorders, diabetic hyperphagia, Prader-Willi Syndrome, and hypothalamic obesity, body dismorphic disorders, and other specified and unspecified feeding or eating disorders.

In certain aspects, the present invention includes a method for treating dissociative disorders, wherein the method comprises administration of any one the compounds, compositions, and/or formulations described above to a subject in need thereof.

In certain aspects, the dissociative disorders include dissociative identity disorder, dissociative amnesia, depersonalization/derealization disorders, and other specified and unspecified dissociative disorders.

In certain aspects, the present invention includes a method for treating neurodevelopmental disorders, wherein the method comprises administration of any one the compounds, compositions, and/or formulations described above to a subject in need thereof.

In certain aspects, the neurodevelopmental disorders include: intellectual disability (intellectual developmental disorder), global developmental delay, communication (language, speech/sound, childhood-onset fluency or stuttering, social, unspecified) disorders, autism spectrum disorders, attention-deficit disorder (ADD), attention-deficit hyperactivity disorder (ADHD), specific learning disorders, motor disorders (developmental coordination, stereotypic movement, tourette's disorder, persistent/chronic motor or vocal tic disorder, provisional tic disorder), and other specified or unspecified neurodevelopmental disorders.

In certain aspects, the present invention includes a method for treating a disorder, wherein the method comprises administration of any one the compounds, compositions, and/or formulations described above to a subject in need thereof, wherein the disorder includes: seizures (including generalized seizures, focal seizures, unknown onset seizures, and focal to bilateral seizures) and epilepsy (including generalized epilepsy, focal epilepsy, generalized and focal epilepsy, Dravet syndrome, and unknown onset epilepsy).

In certain aspects, the present invention includes a method for treating sleep-wake disorders, wherein the method comprises administration of any one the compounds, compositions, and/or formulations described above to a subject in need thereof.

In certain aspects, the sleep-wake disorder include: insomnia disorder, hypersomnolence disorder, narcolepsy, breathing-related sleep disorders (e.g., obstructive sleep apnea hypopnea, central sleep apnea, idiopathic central sleep apnea, sleep-related hypoventilation), circadian rhythm sleep-wake disorders, non-rapid eye movement (NREM) sleep arousal disorders, nightmare disorder, rapid eye movement (REM) sleep behavior disorder, restless legs syndrome, substance/medication-induced sleep disorder, and other specified and unspecified sleep-wake disorders.

In certain aspects, the present invention includes a method for treating substance-related disorders (SRD) and addictive disorders, wherein the method comprises administration of any one the compounds, compositions, and/or formulations described above to a subject in need thereof.

In certain aspects, the substance-related disorders (SRD) and addictive disorders including, but not limited to, the following class of drugs: alcohol, nicotine, cannabis, hallucinogens, inhalants, opioids, sedatives, hypnotics, anxiolytics, stimulants (amphetamine-type substances, cocaine, and other stimulants), and pharmaceutical drugs, and other specified or unspefied substance-induced disorders.

In certain aspects, the present invention includes a method for treating non-substance-related disorders, wherein the method comprises administration of any one the compounds, compositions, and/or formulations described above to a subject in need thereof.

In certain aspects, the non-substance-related disorder is a gambling disorder.

In certain aspects, the present invention includes a method for treating headache disorders, wherein the method comprises administration of any one the compounds, compositions, and/or formulations described above to a subject in need thereof.

In certain aspects, the headache disorder is classified in Headache Classification Committee of the International Headache Society (IHS) and includes: primary headaches which include migraines (including migraines without aura, migraines with aura, and chronic migraines), tension-type headaches (including infrequent episodic-, frequent episodic-, and chronic tension-type headache), trigeminal autonomic cephalgias (including cluster headaches, paroxysmal hemicrania, short-lasting unilateral neuraligiform headache attacks, and hemicrania continua), and other primary headache disorders.

In certain aspects, the headache disorder is a Trigeminal autonomic cephalgia (TAC) including cluster headaches (familial cluster headaches, histamine cephalgia or vasogenic facial pain), episodic cluster headaches, recurrent or chronic cluster headaches, short-lasting unilateral neuralgiform headache attacks (SUNHA), short-lasting unilateral neuralgiform headache attacks with conjunctival injection and tearing (SUNCT) and short-lasting unilateral neuralgiform headache attacks with cranial autonomic symptoms.

In certain aspects, the headache disorder is a secondary headaches which includes headaches attributed to trauma or injury to the head and/or neck, headaches attributed to cranial and/or cervical vascular disorder, headaches attributed to non-vascular intracranial disorder, headaches attributed to a substance or its withdrawal, headaches attributed to infection, headaches attributed to disorder of homeostasis, headaches or facial pain attributed to disorder of the cranium, neck, eyes, ears, nose, sinuses, teeth, mouth or other facial or cervical structure, headaches attributed to psychiatric disorder, and the headached category of painful lesions of the cranial nerve and other facial pain which includes pain attributed to lesion or disease of the trigeminal nerve.

In certain aspects, the present invention includes a method for treating pain, wherein the method comprises administration of any one the compounds, compositions, and/or formulations described above to a subject in need thereof.

In certain aspects, the pain is caused by conditions including inflammation (e.g. rheumatoid arthritis, lupus, Behcet's disease), genetic factors (e.g. erythromelalgia), neuropathic factors which include conditions causing nerve damage leading to pain such as in diabetes, cancer and cancer treatments such as chemotherapy, neurological conditions such as multiple sclerosis (MS), neurodegenerative conditions such as Parkinson's disease, stroke, shingles, HIV, leprosy, Guillain-Barre syndrome, blood vessel disease, vascular malformations and autoimmune conditions, all neuropathies including peripherial neuropathy, autonomic neuropathy, focal neuropathy, proximal neuropathy, diabetic neuropathy and compression mononeuropathy, phantom limb pain, residual limb pain, and complex regional pain syndrome (CRPS), trigeminal neuralgia, postherpetic neuralgia, radicular pain, radiculitis and all radiculopathies including thoracic or lumbar radiculopathy, nociceptive pain (e.g. injury-induced pain, cancer pain), high prevalence of somatization or nociplastic pain (e.g. chronic widespread pain, fibromyalgia, chronic temporomandibular joint disorders, chronic low back pain of unknown causes, irritable bowel syndrome, chronic primary bladder pain syndrome, chronic primary pelvic pain syndromes), and various other forms of chronic pain regardless of etiology (e.g. chronic lower back pain).

In certain aspects, the pain is chronic pain that includes: chronic primary pain (which includes fibromyalgia, chronic pelvic pain, non-specific back pain, and chronic primary pain not otherwise specified); chronic cancer pain (which includes pain due to cancer and metastases, chemotherapy-induced pain, pain due to radiotherapy, pain due to cancer surgery, and other chronic pain related to cancer); chronic post-surgical and post-traumatic pain (which includes all post-surgical and post-traumatic pain, and the post-surgical/traumatic pain not otherwise specified); chronic neuropathic pain (which includes peripheral neuropathic pain, central neuropathic pain, and other neuropathic pain and neuropathic pain not otherwise specified); chronic headache and orofacial pain (which includes chronic primary headaches, chronic secondary headaches, chronic orofacial pain, and headache and orofacial pain not otherwise specified); chronic visceral pain (which includes chronic visceral pain from persistent inflammation, and/or vascular mechanisms, and/or obstruction/distension, and/or traction/compression, and/or combined mechanisms, or chronic visceral pain referred from other locations, from cancer, or functional or unexplained chronic pain); and chronic musculoskeletal pain (which includes chronic muscloskeletal pain from persistent inflammation, and/or structural osteoarticular changes, and/or chronic musculoskeletal pain originating from diseases of the nervous system such as spastic pain, and chronic non-specific musculoskeletal pain and related pain syndromes).

In certain aspects, the pain is acute pain includes pain that lasts for short period, from some hours or days or up to 3 months, regardless of type of pain and including inflammatory, nociceptive, neuropathic, nociplastic and other kinds of pain, and which includes acute pain from tissue injury including those arising from any kind of surgery, dental work, labor and childbirth, cuts, burns, broken bones and other accidents or trauma, acute pain arising from any disease state, acute pain arising from any kind of trauma, and acute pain arising from undetermined causes.

In certain aspects, the present invention includes a method for treating spasticity, wherein the method comprises administration of any one the compounds, compositions, and/or formulations described above to a subject in need thereof.

In certain aspects, the spasticity is with or without neuropathic pain, and includes: cerebral palsy, stroke, multiple sclerosis (MS), traumatic brain injury (TBI), amyotrophic lateral sclerosis (ALS), hereditary spastic paraplegias, adrenoleukodystrophy (ALD), phenylketonuria, krabbe disease, and spinal cord injury.

In certain aspects, the present invention includes a method for treating disorders and diseases associated with nerve injury or trauma, wherein the method comprises administration of any one the compounds, compositions, and/or formulations described above to a subject in need thereof.

In certain aspects, the disorders and diseases are associated with nerve injury or trauma from: peripheral nerve injury or trauma regardless of cause and/or central nervous system (brain and spinal cord) nerve injury or trauma regardless of cause; disorders and diseases arising from external physical factors such as accidents, sports injury, fall, gunshots or an explosive blaststroke; or internal factors such as stroke, ruptured brain aneurysm, lack of oxygen, infection (viral, bacterial, prion, or other), autoimmune diseases; other nerve injury or trauma caused directly or indirectly by external factors, and/or nerve injury or trauma that arise directly or indirectly from disease states.

In certain aspects, the present invention includes a method for treating fatigue, wherein the method comprises administration of any one the compounds, compositions, and/or formulations described above to a subject in need thereof.

In certain aspects, the fatigue is chronic fatigue (e.g. physical fatigue, psychological fatigue or mental fatigue) from traumatic brain injury (TBI), chronic fatigue syndrome (CFS), and related conditions, and other diseases and/or disorders causing chronic fatigue.

In certain aspects, the present invention includes a method for treating neuro-degenerative disorders, wherein the method comprises administration of any one the compounds, compositions, and/or formulations described above to a subject in need thereof.

In certain aspects, the neuro-degenerative disorders include: Alzheimer's disease, amyotrophic lateral sclerosis (ALS), Batten disease, Friedreich ataxia, Huntington's disease, Lewy body disease, motor neuron disease, multiple sclerosis, Parkinson's disease, prion disease, spinal muscular atrophy, neuro-degenerative conditions due to viral (e.g., HIV) or bacterial infection, neuro-degenerative conditions due or substance/medication, and other aging-related and non-aging related neurodegenerative conditions.

In certain aspects, the present invention includes a method for treating a disease and/or disorder selected from the group consisting of sexual dysfunctions delayed ejaculation, erectile disorder, female orgasmic disorder, female sexual interest/arousal disorder, genito-pelvic pain/penetration disorder, male hypoactive sexual desire disorder, premature (early) ejaculation, substance/medication induced sexual dysfunction, other specified and unspecified sexual dysfunction, wherein the method comprises administration of any one the compounds, compositions, and/or formulations described above to a subject in need thereof.

In certain aspects, the present invention includes a method for treating gender dysphoria, wherein the method comprises administration of any one the compounds, compositions, and/or formulations described above to a subject in need thereof.

In certain aspects, the present invention includes a method for treating a neuro-degenerative disorder, wherein the method comprises administration of any one the compounds, compositions, and/or formulations described above to a subject in need thereof.

In certain aspects, the neurocognitive disorder (NCDs) includes delirium, NCD due to Alzheimer's disease, vascular NCD, NCD with Lewy bodies, NCD due to Parkinson's disease, frontotemporal NCD, NCD due to traumatic brain injury, NCD due to HIV infection, substance/medication-induced NCD; NCD due to Huntington's disease, NCD due to prion disease; NCD due to another medical condition, NCD due to multiple etiologies, and unspecified NCD.

In certain aspects, the neurocognitive disorder is a neurocognitive/learning dysfunction including memory problems, a lack of mental clarity, poor concentration, and/or an inability to focus arising from infections (viral/bacterial/prion/other) or other specified or unspecified disorders, diseases, or other unknown causes.

In certain aspects, the neurocognitive disorder is reduction in memory, cognition and/or learning, with or without obvious signs of neurodegenerative disorders or neurodevelopmental disorders, and/or prevention of reduction in memory, cognition and/or learning, with or without obvious signs of neurodegenerative disorders or neurodevelopmental disorders and regardless of age.

In certain aspects, the neurocognitive disorder is a neurological and/or neuropsychiatric disorders and/or conditions associated with normal aging and/or progeroid syndromes.

In certain aspects, the present invention includes a method for treating a neurological disease caused by viral infection, wherein the method comprises administration of any one the compounds, compositions, and/or formulations described above to a subject in need thereof, wherein the neurological diseases caused by viral infections that utilize neuronal cells surface receptors for entry including serotonergic (5-HT) receptors (in particular 5-HT2A receptor), such as progressive multifocal leukoencephalopathy (PML) caused by JC virus.

In certain aspects, the present invention includes a method for reduction and/or prevention of a psychedelic's side effects, wherein the method comprises administration of any one the compounds, compositions, and/or formulations described above to a subject in need thereof.

In certain aspects, the present invention includes a method for maintain or improving well being, wherein the method comprises administration of any one the compounds, compositions, and/or formulations described above to a subject in need thereof.

In certain aspects, the present invention includes a method for treatment of diseases and/or disorders comprising a therapeutic mechanism linked to 5-HT1 receptor activation, agonism at one or more 5-HT1 receptor subtypes such as 5-HT1A, 1B, 1D, 1E, and 1F wherein the method comprises administration of the compound of any one the compounds, compositions, and/or formulations described above to a subject in need thereof.

In certain aspects, the present invention includes a method for treatment of treatment of diseases and/or disorders associated with cognitive/learning/memory deficit or decline, wherein the therapeutic mechanism is linked to 5-HT6 receptor activation (agonism), wherein the method comprises administration of any one the compounds, compositions, and/or formulations described above to a subject in need thereof.

In certain aspects, the present invention includes a method for treatment of diseases and/or disorders wherein the therapeutic mechanism is linked to 5-HT2A receptor activation (agonism), wherein the method comprises administration of any one the compounds, compositions, and/or formulations described above to a subject in need thereof.

In certain aspects, the present invention includes a method for treatment of a disease or disorder wherein the therapeutic mechanism is linked to D2-like receptor, such as D2 and D4 receptor subtypes, activation (agonism), wherein the method comprises administration of any one the compounds, compositions, and/or formulations described above to a subject in need thereof.

In certain aspects, the treatment excludes a hallucinogenic effect and does not induce tolerance to said compound of any one the compounds, compositions, and/or formulations described above.

These and other features, embodiments, and advantages of the present disclosure are mentioned not to limit or define the disclosure, but to provide examples to aid in the understanding thereof when read with the following Description and with reference to the accompanying drawings.

BRIEF DESCRIPTION OF THE DRAWINGS

Embodiments will now be described, by way of example only, with reference to the Figures.

FIG. 13B, pre-treatment of mice with the "E559 polymorph" almost completely blocked the DOI induced HTR during the first 10 minutes, and this blockage was gradually reduced until after 40-60 minutes, the blockage was no longer detected;

FIGS. 14A, 14B, 14C, and 14D are graphs showing LSD polymorph E559 binding and functional effects on the 5HT2B receptor. In (A), (B) and (C) LSD shows potent agonism of the 5-HT2B receptor as seen by all three functional assessments while the E559 polymorph does not show the agonism seen with LSD. In (D), the E559 polymorph produced only weak blockade of hERG channel activity at very high concentrations (EC50=31.6 µM), indicating that it exhibits low risk of causing cardiac arrhythmias in humans;

FIGS. 19A, 19B, 19C, 19D, 19E, and 19F: shows the E559 polymorph promotes neuroplasticity: (A) representative Sholl tracings of neurons treated with the vehicle (control) or increasing concentration of the E559 polymorph; (B) displays the total number of Sholl radii crossings by MAP2-positive neurites following treatment with vehicle (control), E559 polymorph or ketamine; (C) shows the total number of dendritic arbor length from neurons in FIG. 19A and FIG. 19B; (D) exhibits representative fluorescent images of dendritic spines in cortical neurons treatment with vehicle (control), the E559 polymorph or ketamine; (E) shows total number of spines per 10 µm section (see FIG.

Figure 21A:
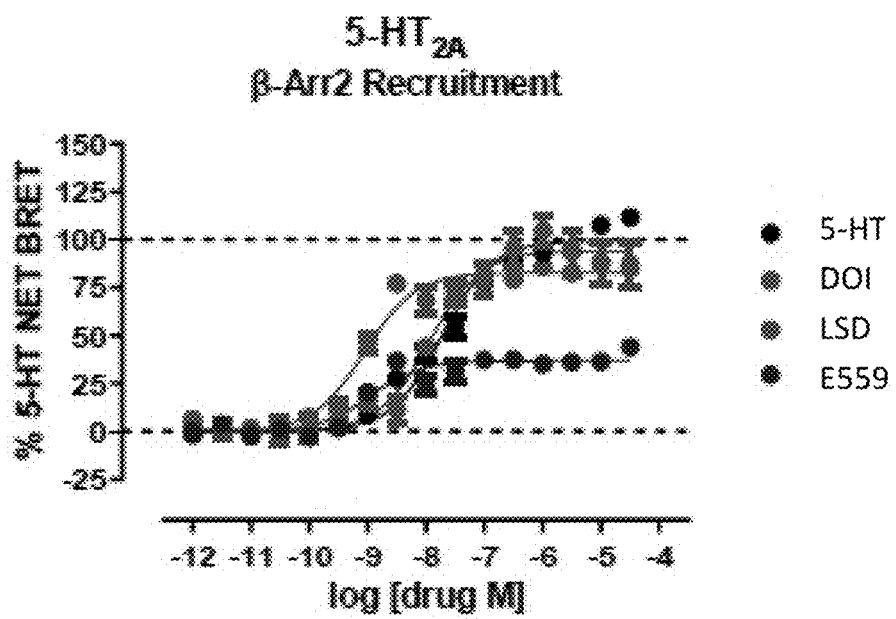
Figure 22:
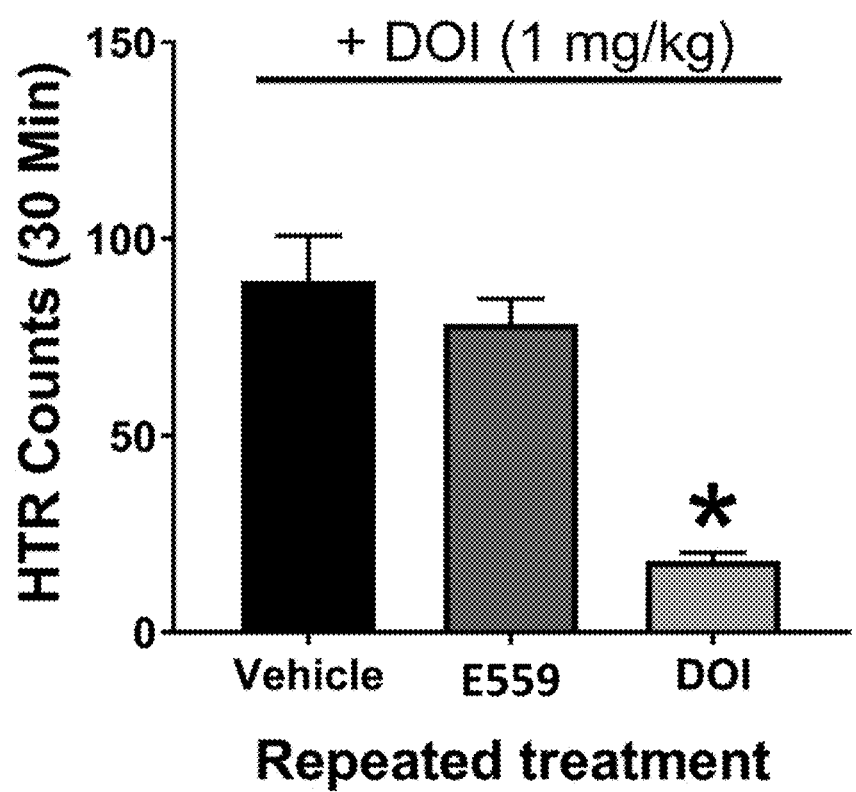

18B) on the longest apical dendrite that was scored from the first branch point; and (F) shows the ratio of living to dead neuronal cells in randomly selected 40× objective fields of view in cell viability assay. Horizontal lines in all figure panels represent the means±standard error of the mean (S.E.M.);

FIGS. 20A, 20B, and 20C demonstrate the E559 polymorph-mediated neuroplasticity is acting via 5-HT2A receptor: (A) shows tracings of the cortical neurons (DIV 3) treated with volinanserin (Vol) at 0.1, 0.5 or 1 mM followed by either vehicle or E559 polymorph (1 µM): (B) shows the total number of Sholl crossings for neurons treated in FIG. 20A; (C) represents the total dendritic arbour length for neurons treated in FIG. 20A;

FIG. 21A/B shows that the E559 polymorph repeated dosing does not induce tolerance in vitro. (A) is a graph showing that the "E559 polymorph" is a weak recruiter of β-Arrestin2 compared to DOI and LSD activity at the 5-HT2A receptor using the BRET-based β-arrestin2 recruitment assay (described in Example 8); (B) is a graph showing that the E559 polymorph exhibits only weak internalization of the 5-HT2A receptor in contrast to potent internalization by LSD, DOI, and 5-HT;

FIG. 22 is a graph showing that repeated treatment with the E559 polymorph does not induce tolerance in vivo (using HTR model in mice) compared to significant tolerance induced by repeated dosing of DOI.

Figures 24A, 24B:
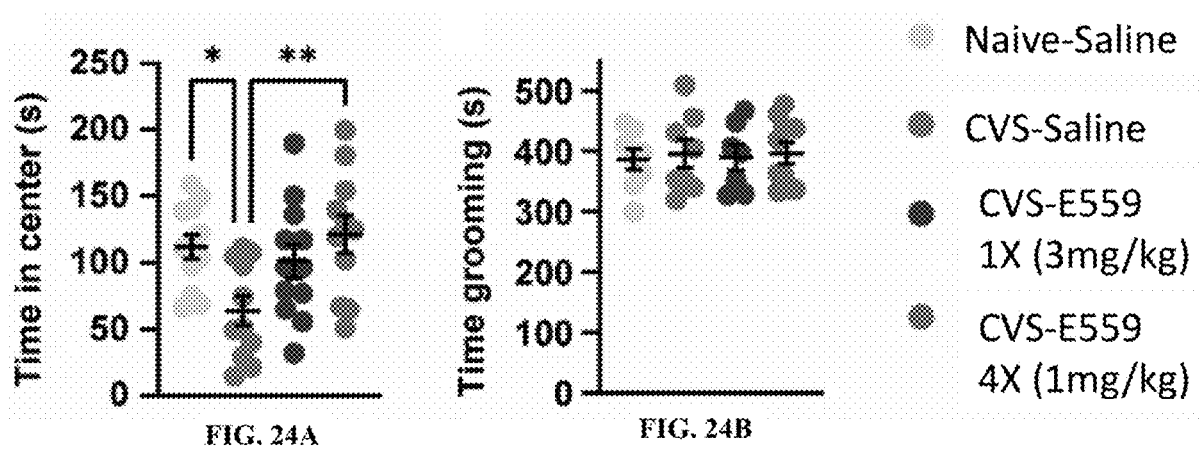
Figure 27:
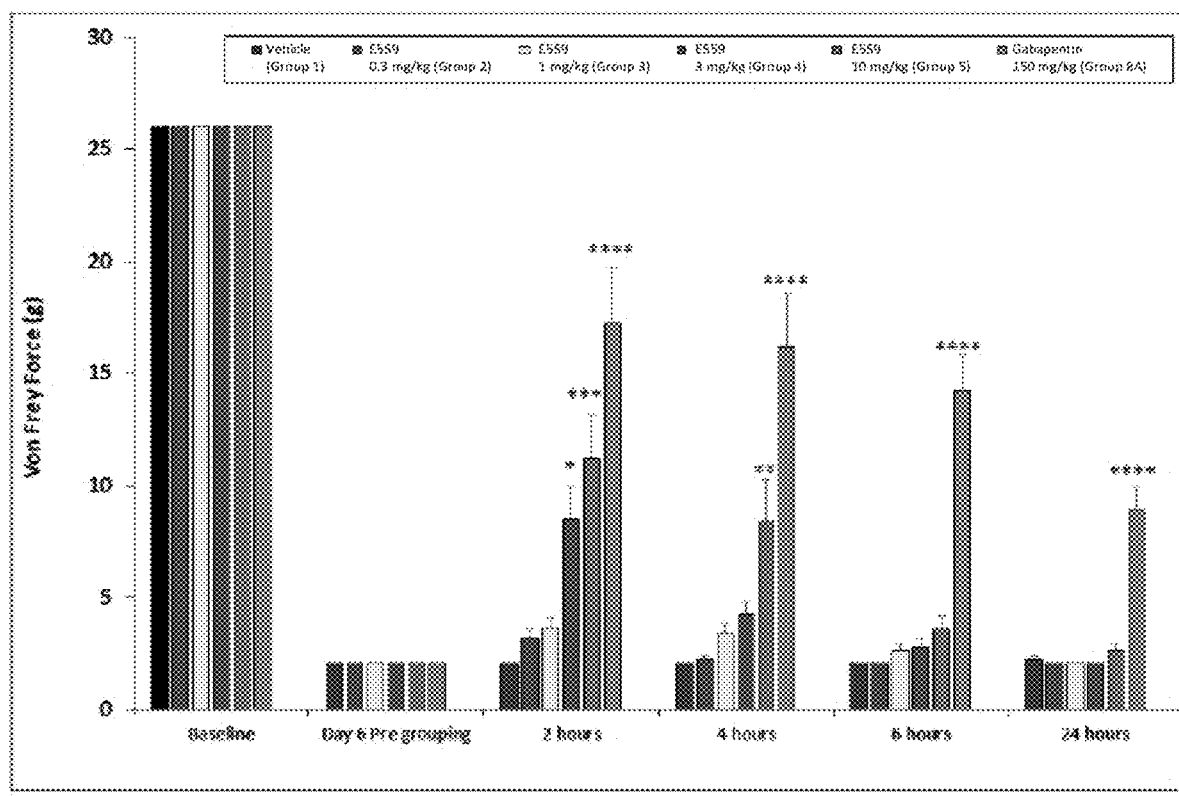
Figure 28:
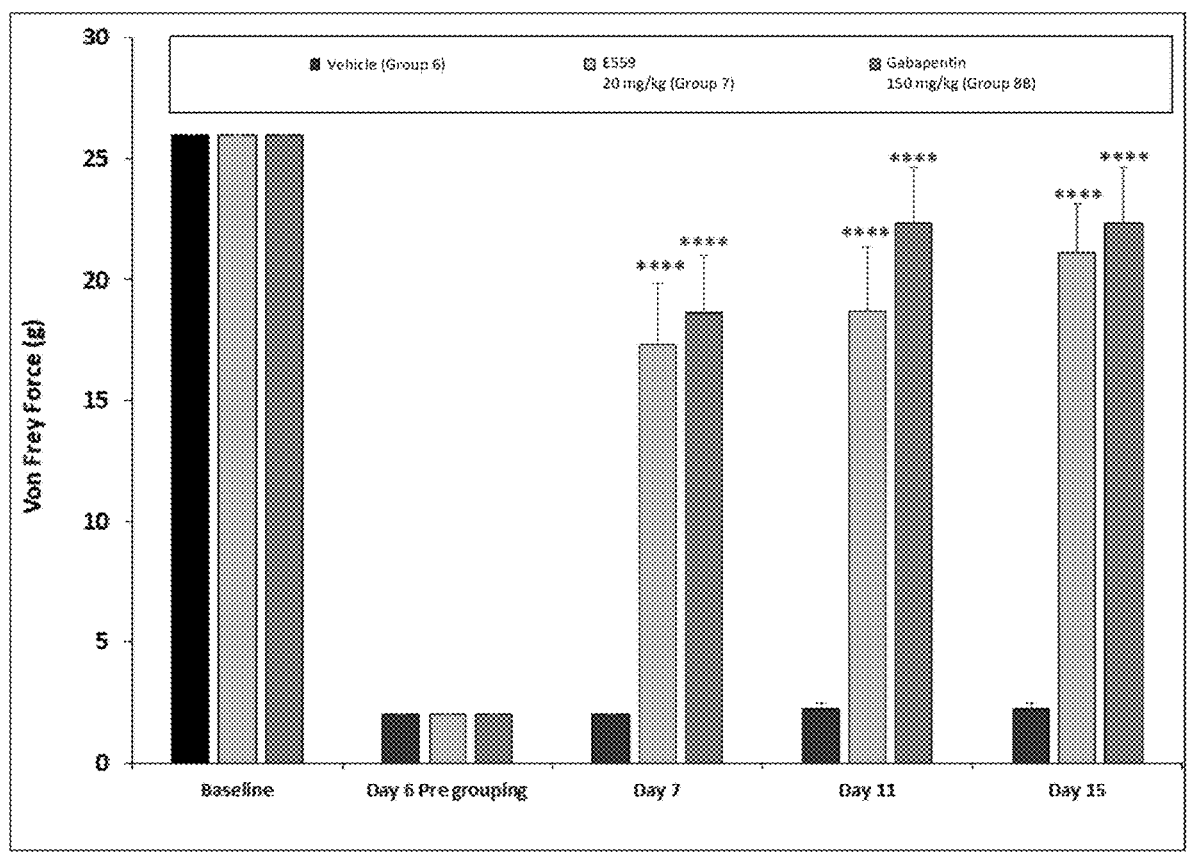

FIGS. 23A, 23B, 23C, and 23D demonstrate the E559 polymorph exhibits anti-depressant/anxiolytic activity in a chronic stressed animal model: (A) shows the study design of the self-grooming splash test; (B) represents distance travelled in the open field by female mice treated with E559 polymorph: (C) represents time spend in the center of the open field of mice in FIG. 23B; (D) shows time spent self-grooming in the splash test by female mice treated as described in FIG. 23A. Horizontal lines represent the mean±standard error of the mean (S.E.M.) and asterisks indicate statistical significances;

FIGS. 24A and 24B: demonstrate the long-term anti-depressant and anxiolytic effects of the E559 polymorph 28 days after experiment described in FIG. 23: (A) The effect of CVS in reducing the time in center in OFT remained reversed (at levels similar to the acute effect of the E559 polymorph 28 days after the last E559 polymorph treatment, CVS-saline vs CVS-E559 polymorph 4×1 mg/kg **p=0.0052; (B) represents time spent self-grooming in the splash test by female mice 28 days after the last E559 polymorph" treatment as indicated in FIG. 23A;

FIGS. 25A, 25B, 25C, 25D, 25E, 25F, 25G, 25H, and 25I demonstrate the E559 polymorph exhibits anti-depressant/anxiolytic activity in an acute stressed animal model: (A) depicts the study design where female/male mice (n=10/group/sex) were treated by IP injection with the E559 polymorph or vehicle (saline) followed by open field and force swim test 24 hours post treatment; (B) and (E) represent the total distance travelled in the open field test 24 hours after vehicle or the E559 polymorph in female and male mice, respectively; (C) and (F) represent the time in the center of the open field by female and male mice, respectively; (D) and (G) represent the immobility time during the last 4 minutes of the forced swim test in female and male mice, respectively. Horizontal lines represent the mean±standard error of the mean (S.E.M.) and asterisks indicate statistical significances;

FIGS. 26A, 26B, 26C, and 26D demonstrate the E559 polymorph exhibits anti-depressant/anxiolytic effects involves the 5-HT2A receptor in vivo using the tests of Example 14: (A) volinanserin pre-treatment blocked the decrease in immobility induced by the E559 polymorph in the FST in female mice; (B) volinanserin pre-treatment blocked the decrease in immobility induced by the E559 polymorph in the FST in female mice; (C) and (D) volinanserin or a combination of volinanserin and the E559 polymorph did not affect locomotion in the OFT in female or male mice;

FIG. 27 is a graph showing pain response assessment results after single dose treatment of the E559 polymorph, vehicle or gabapentin on day 7 post-surgery using a von Frey filament in rat spared nerve injury (SNI) model. The E559 polymorph exhibits potent analgesic activity in a neuropathic pain model in single administration; and FIG. 28 is a graph showing pain response assessment results after multiple dose treatments of the E559 polymorph, vehicle or gabapentin starting on day 7 post-surgery. The E559 polymorph exhibits potent analgesic activity in a neuropathic pain model in repeated administration.

Figure 29:
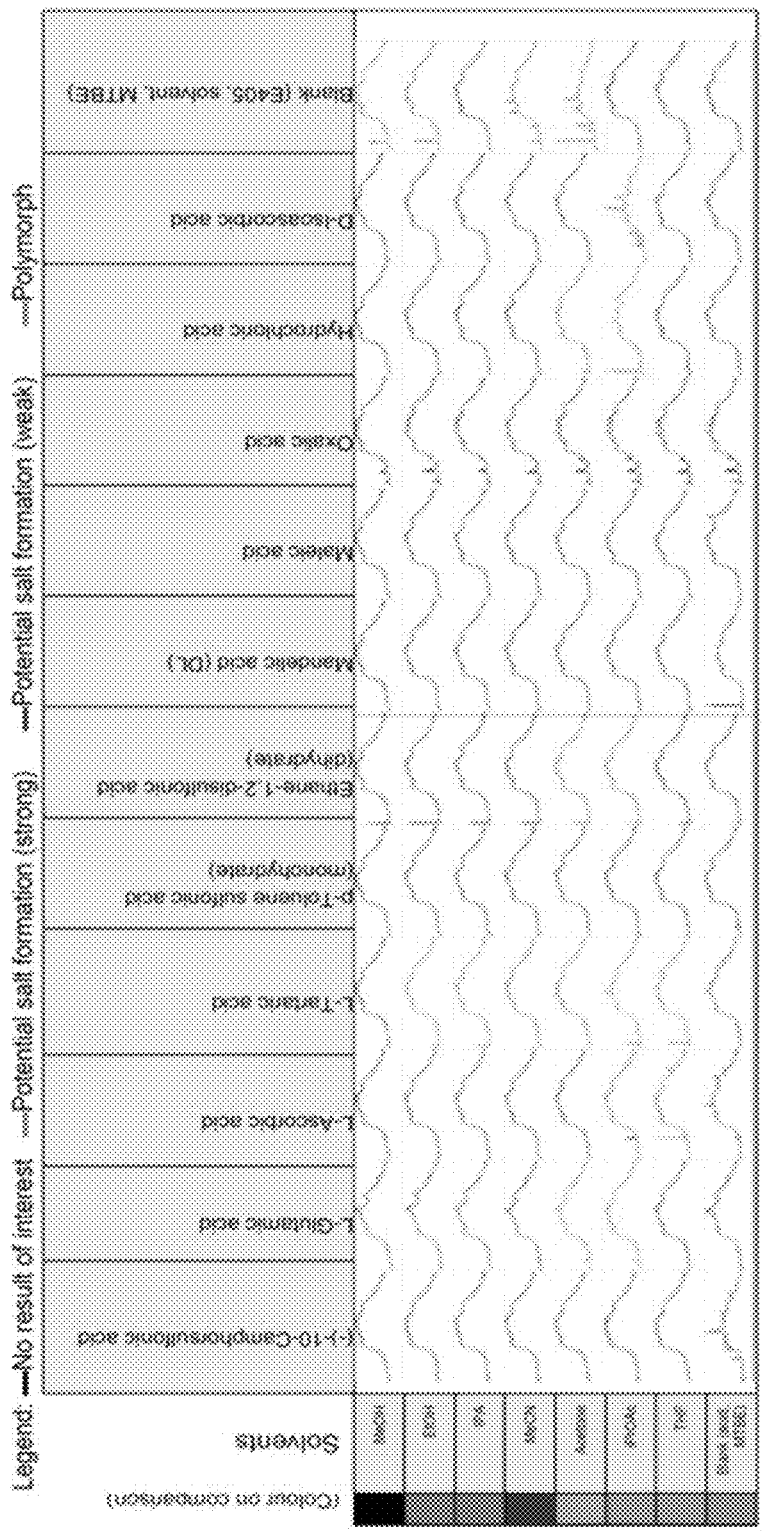

FIG. 29 is a graph showing the x-ray diffraction in-situ after recrystallization of 2-bromo-LSD in various solvent and acid conditions.

DETAILED DESCRIPTION OF ASPECTS/EMBODIMENTS

As used herein, the terms "invention" or "present invention" are non-limiting terms and not intended to refer to any single aspect of the particular invention but encompass all possible aspects as described in the specification and the claims.

All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

In the case of conflict, the present specification, including definitions, will control. Unless defined otherwise, all technical and scientific terms used herein have the same meaning as is commonly understood by one of skill in the art to which the subject matter herein belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Reference to "one embodiment," "an embodiment," "a preferred embodiment" or any other phrase mentioning the word "embodiment" means that a particular feature, structure, or characteristic described in connection with the embodiment is included in at least one embodiment of the-disclosure and also means that any particular feature, structure, or characteristic described in connection with one embodiment can be included in any embodiment or can be omitted or excluded from any embodiment. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others and may be omitted from any embodiment. Furthermore, any particular feature, structure, or characteristic described herein may be optional. Similarly, various requirements are described which may be requirements for some embodiments but not other embodiments. Where appropriate any of the features discussed herein in relation to one aspect or embodiment of the invention may be applied to another aspect or embodiment of the invention. Similarly, where appropriate any of the features discussed herein in relation to one aspect or embodiment of the invention may be optional with respect to and/or omitted from that aspect or embodiment of the invention or any other aspect or embodiment of the invention discussed or disclosed herein.

Definitions

Unless otherwise indicated, the definitions and embodiments described in this and other sections are intended to be applicable to all embodiments and aspects of the present application herein described for which they are suitable as would be understood by a person skilled in the art.

It is to be understood that all amounts are approximate and are provided for description. Although methods and materials similar or equivalent to those described herein can be used in the practice or testing of this application, suitable methods and materials are described below.

In understanding the scope of the present application, the articles "a", "an", and "the" are intended to mean that there are one or more of the elements. Additionally, the term "comprising" and its derivatives, as used herein, are intended to be open ended terms that specify the presence of, for example, the stated features, elements, compounds/molecules, components, groups, integers, and/or steps, but do not exclude the presence, for example, of other unstated features, elements, compounds/molecules, components, groups, integers and/or steps. The foregoing also applies to words having similar meanings such as the terms, "including", "having" and their derivatives.

It will be understood that any aspects described as "comprising" certain, for example, features, elements, compounds/molecules, components, groups, integers, and/or steps may also "consist of" or "consist essentially of," wherein "consisting of" has a closed-ended or restrictive meaning and "consisting essentially of" means including, for example, the stated features, elements, compounds/molecules, components, groups, integers, and/or steps specified but excluding other components except for materials present as impurities, unavoidable materials present as a result of processes used to provide, for example, the stated features, elements, compounds/molecules, components, groups, integers, and/or steps, and components added for a purpose other than achieving the technical effect of the invention. For example, a composition defined using the phrase "consisting essentially of" encompasses any known acceptable additive, excipient, diluent, carrier, and the like. Typically, a composition consisting essentially of a set of components will comprise less than 5% by weight, typically less than 3% by weight, more typically less than 1%, and even more typically less than 0.1% by weight of non-specified component(s).

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The abbreviation, "e.g." is derived from the Latin exempli gratia and is used herein to indicate a non-limiting example. Thus, the abbreviation "e.g." is synonymous with the term "for example."

The phrase "such as" should be interpreted as "for example, including."

The term "and/or" as used herein means that the listed items are present, or used, individually or in combination. In effect, this term means that "at least one of" or "one or more" of the listed items is used or present.

The phrase "at least one of" is understood to be one or more. The phrase "at least one of . . . and . . . " is understood to mean at least one of the elements listed or a combination thereof, if not explicitly listed. For example, "at least one of A, B, and C" is understood to mean A alone or B alone or C alone or a combination of A and B or a combination of A and C or a combination of B and C or a combination of A, B, and C. "At least one of at least one of A, at least one of B, and at least one of C" is understood to mean at least one of A alone or at least one of B alone or at least one of C alone or a combination of at least one of A and at least one of B or a combination of at least one of A and at least one of C or a combination of at least one of B and at least one of C or a combination of at least one of A, at least one of B, and at least one of C.

All language such as "up to," "at least," "greater than," "less than," and the like, include the number recited and refer to ranges which can subsequently be broken down into ranges and subranges. A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use and aspect of a described embodiment or feature contained in the same, or a definitive decision to use a specific skill regarding a described embodiment or feature contained in the same. In this latter context, the modal verb "may" has the same meaning and connotation as the auxiliary verb "can."

As used herein, the terms "reduce," "decrease," "lessen" and similar terms mean a decrease of at least about 10%, about 15%, about 20%, about 25%, about 35%, about 50%, about 75%, about 80%, about 85%, about 90%, about 95%, about 97%, or more.

As used herein, the terms "improve," "increase," "enhance," and similar terms indicate an increase of at least about 10%, about 15%, about 20%, about 25%, about 50%, about 75%, about 100%, about 150%, about 200%, about 300%, about 400%, about 500%, or more.

Disease and disorders are defined as described in the Diagnostic and Statistical Manual of Mental Disorders (DSM-5), published by the American Psychiatric Association, or in International Classification of Diseases (ICD), published by the World Health Organization.

As used herein, the phrase "substantially non-hallucinogenic" or "without substantial hallucinations" or similar statements, mean a derivative that, compared to LSD, exhibits a reduction in hallucinogenicity to either no detectable levels of hallucinogenicity, or significantly reduced intensity in hallucinogenicity, or significantly reduced duration of hallucinogenicity, and where significant shall mean ≥50% reduction of the derivative's hallucinogenic activity compared to the hallucinogenic activity or surrogate measure thereof in an animal model seen with LSD. Hallucinations are psychedelic/psychomimetic effects experienced by a human subject upon administration of a psychelic drug. In mouse models, the head-twitch response in mice, is considered to be the most reliable animal surrogate of hallucinogenic activity of a compound in man (Halbertstad A L et al. *Neuropharmacology*, Volume 167, 1 May 2020, 107933; Adam L. Halberstadt and Mark A. Geyer. *Psychopharmacology* (Berl). 2013 June; 227(4)).

As used herein, the phrases "effective amount" or "therapeutically effective amount" (used interchangeably herein) refer to the amount of a composition or formulation described herein that will elicit the diagnostic, biological or medical response of a tissue, system, animal, or human that is being sought by the researcher, veterinarian, medical doctor or other clinician.

As used herein, the term "modulate" means decreasing or inhibiting and/or increasing or augmenting.

As used herein, a "subject" may be interchangeable with "patient" or "individual" and means an animal, which may be a human or non-human animal, in need of treatment.

As used herein, the term "a subject in need thereof" refers to a human or non-human subject that can be treated with any of the compounds or pharmaceutical compositions disclosed herein when the compounds or pharmaceutical compositions are utilized as therapeutic agents.

As used herein, "pharmaceutically acceptable" refers to materials and compositions that are physiologically tolerable and do not typically produce an allergic or similar untoward reaction, such as gastric upset, dizziness and the like, when administered to a human. Typically, as used herein, the term "pharmaceutically acceptable" means approved by a regulatory agency of the Federal or a state government or listed in the U.S. Pharmacopeia or other generally recognized pharmacopeia for use in animals, and more particularly in humans.

The phrase "pharmaceutically acceptable salt(s)," as used herein includes, but is not limited to, salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions including, but not limited to, sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. Compounds included in the present compositions that include an amino moiety may form pharmaceutically acceptable salts with various amino acids, in addition to the acids mentioned above.

As used herein, the term "pharmaceutically acceptable carriers" can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material. In powders, the carrier is a finely divided solid which is in a mixture with the finely divided active component. In tablets, the active component or components is mixed with the carrier having the necessary binding properties in suitable proportions and compacted in the shape and size desired. Liquid form preparations include solutions, suspensions, and emulsions, for example, water or water propylene glycol solutions. For parenteral injection liquid preparations can be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

As used herein, a "therapeutic agent" may refer to any agent that is administering to a subject in thereof in order to treat the subject. A therapeutic agent may refer to an agent that modulates the biological activity of ornithine aminotransferase (OAT), for example where the agent inhibits the biological activity of OAT to catalyze the synthesis of glutamate or glutamine. A therapeutic agent may refer to an agent that modulates the biological activity of γ-aminobutyric acid aminotransferase (GABA-AT), for example where the agent inhibits the biological activity of GABA-AT to degrade GABA to succinic semialdehyde (SSA). Therapeutic agents may include, but are not limited to, small molecules or compounds as disclosed herein. Therapeutic agents may include, but are not limited to, pharmaceutical compositions comprising small molecules or compounds as disclosed herein.

As used herein, the term "binders" or "excipients" refers to agents used to impart cohesive qualities to the powdered material. Binders, or "granulators" as they are sometimes known, impart cohesiveness to the tablet formulation, which insures the tablet remaining intact after compression, as well as improving the free-flowing qualities by the formulation of granules of desired hardness and size. Materials commonly used as binders include starch; gelatin; sugars, such as sucrose, glucose, dextrose, molasses, and lactose; natural and synthetic gums, such as acacia, sodium alginate, extract of Irish moss, panwar gum, ghatti gum, mucilage of isapol husks, carboxymethylcellulose, methylcellulose, polyvinylpyrrolidone, Veegum, microcrystalline cellulose, microcrystalline dextrose, amylose, and larch arabogalactan, and the like. "Excipient" means an essentially inert substance used as a diluent or to give form or consistency to a formulation In general, excipients may be defined as the constituents of the pharmaceutical form that is taken by or administered to the patient, other than the active substance; see, e.g., Annex of Directive 2001/83/EC. Certain excipients can also serve as disintegrants, i.e., they assist the dispersion of solid pharmaceutical compositions upon exposure to body fluids.

As used herein, "diluents" are inert substances added to increase the bulk of the formulation to make the tablet a practical size for compression. Commonly used diluents include calcium phosphate, calcium sulfate, lactose, kaolin, mannitol, sodium chloride, dry starch, powdered sugar, silica, and the like.

The term "unit dosage form" refers to physically discrete units suitable as unitary dosages, such as a pill, tablet, caplet, hard capsule or soft capsule, each unit containing a predetermined quantity of LSA derivative(s), including a pharmaceutically acceptable salt thereof. By "hard capsule" is meant a capsule that includes a membrane that forms a two-part, capsule-shaped, container capable of carrying a solid or liquid payload of drug and excipients. By "soft capsule" is meant a capsule molded into a single container carrying a liquid or semisolid payload of drug and excipients.

The term "extended release", "controlled release" or "sustained release", as used herein interchangeably, refers to a mode of releasing, for example, derivative(s) of lysergic acid diethylamide (LSD), including polymorphs thereof, from the formulation thereof such that it is absorbed by the body over a period of time, increasing the $t_{1/2}$ and reducing the Cmax relative to that observed for administration of immediate release formulations administered at the same dosing level. An extended release formulation of an active agent may be accomplished, e.g., by embedding the active agent in a web of substance that the body is slow to dissolve, such that the active ingredient slowly and regularly leeches from the coating, or by swelling up the active agent to form a gel with a nearly impenetrable surface, wherein the drug slowly exits the semipermeable layer.

As used herein, the term "dry weight" refers to a measurement of the mass of a sample after removing all, or substantially all, the liquid from the sample. In one embodiment, removing liquid comprises dehydrating, heating, stirring, filtering, and/or any other method suitable for liquid water. In one embodiment, dry weight is measured by pounds. In one embodiment, dry weight is measured by ounces. In one embodiment, dry weight is measured by grams, e.g., milligrams, kilograms, etc.

As used herein, the term "dried powder" refers to a substance composed of fine particles and comprising little or no liquid material.

As used herein, the term "mass percent", "percent by mass", "mass %", etc., refers to the amount of a compound relative to the entire mass of a sample as a fraction of 100. In one embodiment, mass percent is calculated with the following formula for a compound of interest: (mass of compound of interest in grams)/(total mass of composition in grams)×100%.

The term "purified" refers to a compound that is between 80% to 100% pure, meaning that the compound makes up 80% to 100% of the total mass of the composition. In one embodiment, the term "purified" refers to a compound that is between 90% to 100% pure, meaning that the compound makes up 90% to 100% of the total mass of the composition. In one embodiment, the term "purified" refers to a compound that is between 95% to 100% pure, meaning that the compound makes up 95% to 100% of the total mass of the composition. In one embodiment, the term "purified" refers to a compound that is between 99% to 100% pure, meaning that the compound makes up 99% to 100% of the total mass of the composition.

In one embodiment, the term "purified" refers to a compound that is about 99.1%, 99.2%. 99.3%, 99.4%, 99.5%, 99.6%, 99.7%, 99.8%, or 99.9% to 100% pure, meaning that the compound makes up 99.9% to 100% of the total mass of the composition.

As used herein, and unless otherwise specified, the term "substantially pure" when used to describe a polymorph, a crystal form, or a solid form of a compound or complex described herein means a solid form of the compound or complex that comprises a particular polymorph and is substantially free of other polymorphic and/or amorphous forms of the compound.

As used herein and unless otherwise specified, a composition that is "substantially free" of a compound means that the composition contains less than about 20 percent by weight, less than about 10 percent by weight, less than about 5 percent by weight, less than about 3 percent by weight, or less than about 1 percent by weight of the compound.

As used herein, and unless otherwise specified, the term "stable" refers to a compound or composition that does not readily decompose or change in chemical makeup or physical state. A stable composition or formulation provided herein does not significantly decompose under normal manufacturing or storage conditions. In some embodiments, the term "stable," when used in connection with a formulation or a dosage form, means that the active ingredient of the formulation or dosage form remains unchanged in chemical makeup or physical state for a specified amount of time and does not significantly degrade or aggregate or become otherwise modified (e.g., as determined, for example, by HPLC, FTIR, or XRPD). In some embodiments, about 70 percent or greater, about 80 percent or greater, about 90 percent or greater, about 95 percent or greater, about 98 percent or greater, or about 99 percent or greater of the compound remains unchanged after the specified period. In one embodiment, a polymorph provided herein is stable upon long-term storage (e.g., no significant change in polymorph form after about 1, 2, 3, 4, 5, 6, 7, 8, 9, 10, 11, 12, 18, 24, 30, 36, 42, 48, 54, 60, or greater than about 60 months).

It will be understood that any component defined herein as being included may be explicitly excluded from the claimed invention by way of proviso or negative limitation.

In addition, all ranges given herein include the end of the ranges and also any intermediate range points, whether explicitly stated or not.

Definitions of specific functional groups and chemical terms are described in more detail below. The chemical elements are identified in accordance with the Periodic Table of the Elements, CAS version, Handbook of Chemistry and Physics, 75th ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5th ed., John Wiley & Sons, Inc., New York, 2001; Larock, Comprehensive Organic Transformations, VCH Publishers, Inc., New York, 1989; and Carruthers, Some Modern Methods of Organic Synthesis, 3rd ed., Cambridge University Press, Cambridge, 1987.

With respect to compound terminology, generally, reference to a certain element such as hydrogen or H is meant to, if appropriate, include all isotopes of that element.

Where the term "alkyl group" is used, either alone or within other terms such as "haloalkyl group" and "alkylamino group", it encompasses linear or branched carbon radicals having, for example, one to about twenty carbon atoms or, in specific embodiments, one to about twelve carbon atoms. In other embodiments, alkyl groups are "lower alkyl" groups having one to about six carbon atoms. Examples of such groups include, but are not limited thereto, methyl, ethyl, n-propyl, isopropyl, n-butyl, isobutyl, sec-butyl, tert-butyl, pentyl, iso-amyl, hexyl and the like. In more specific embodiments, lower alkyl groups have one to four carbon atoms.

The term "alkenyl group" encompasses linear or branched carbon radicals having at least one carbon-carbon double bond. The term "alkenyl group" can encompass conjugated and non-conjugated carbon-carbon double bonds or combinations thereof. An alkenyl group, for example and without being limited thereto, can encompass two to about twenty carbon atoms or, in a particular embodiment, two to about twelve carbon atoms. In embodiments, alkenyl groups are "lower alkenyl" groups having two to about four carbon atoms. Examples of alkenyl groups include, but are not limited thereto, ethenyl, propenyl, allyl, propenyl, butenyl and 4-methylbutenyl. The terms "alkenyl group" and "lower alkenyl group", encompass groups having "cis" and "trans" orientations, or alternatively, "E" and "Z" orientations.

The term "alkynyl group" denotes linear or branched carbon radicals having at least one carbon-carbon triple bond. The term "alkynyl group" can encompass conjugated and non-conjugated carbon-carbon triple bonds or combinations thereof. Alkynyl group, for example and without being limited thereto, can encompass two to about twenty carbon atoms or, in a particular embodiment, two to about twelve carbon atoms. In embodiments, alkynyl groups are "lower alkynyl" groups having two to about ten carbon atoms. Some examples are lower alkynyl groups having two to about four carbon atoms. Examples of such groups include propargyl, butynyl, and the like.

The term "halo" means halogens such as fluorine, chlorine, bromine or iodine atoms.

The term "haloalkyl group" encompasses groups wherein any one or more of the alkyl carbon atoms is substituted with halo as defined above. Specifically encompassed are monohaloalkyl, dihaloalkyl and polyhaloalkyl groups including perhaloalkyl. A monohaloalkyl group, for one example, may have either an iodo, bromo, chloro or fluoro atom within the group. Dihalo and polyhaloalkyl groups may have two or more of the same halo atoms or a combination of different halo groups. "Lower haloalkyl group" encompasses groups having 1-6 carbon atoms. In some embodiments, lower haloalkyl groups have one to three carbon atoms. Examples of haloalkyl groups include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl.

The term "hydroxyalkyl group" encompasses linear or branched alkyl groups having, for example and without being limited thereto, one to about ten carbon atoms, any one of which may be substituted with one or more hydroxyl groups. In embodiments, hydroxyalkyl groups are "lower hydroxyalkyl" groups having one to six carbon atoms and one or more hydroxyl groups. Examples of such groups include hydroxymethyl, hydroxyethyl, hydroxypropyl, hydroxybutyl and hydroxyhexyl.

The term "alkoxy group" encompasses linear or branched oxy-containing groups each having alkyl portions of, for example and without being limited thereto, one to about ten carbon atoms. In embodiments, alkoxy groups are "lower alkoxy" groups having one to six carbon atoms. Examples of such groups include methoxy, ethoxy, propoxy, butoxy and tert-butoxy. In certain embodiments, lower alkoxy groups have one to three carbon atoms. The "alkoxy" groups may be further substituted with one or more halo atoms, such as fluoro, chloro or bromo, to provide "haloalkoxy" groups. In other embodiments, lower haloalkoxy groups have one to three carbon atoms. Examples of such groups include fluoromethoxy, chloromethoxy, trifluoromethoxy, trifluoroethoxy, fluoroethoxy, and fluoropropoxy.

The term "aromatic group" or "aryl group" means an aromatic group having one or more rings wherein such rings may be attached together in a pendent manner or may be fused. In particular embodiments, an aromatic group is one, two or three rings. Monocyclic aromatic groups may contain 4 to 10 carbon atoms, typically 4 to 7 carbon atoms, and more typically 4 to 6 carbon atoms in the ring. Typical polycyclic aromatic groups have two or three rings. Polycyclic aromatic groups having two to three rings typically have 8 to 16 carbon atoms, preferably 8 to 14 carbon atoms in the rings. Examples of aromatic groups include, but are not limited to, phenyl, naphthyl, tetrahydronaphthyl, indanyl, biphenyl, phenanthryl, anthryl or acenaphthyl.

The term "heteroatom" means an atom other than carbon. Typically, heteroatoms are selected from the group consisting of sulfur, phosphorous, nitrogen and oxygen atoms. Groups containing more than one heteroatom may contain different heteroatoms.

The term "heteroaromatic group" or "heteroaryl group" means an aromatic group having one or more rings wherein such rings may be attached together in a pendent manner or may be fused, wherein the aromatic group has at least one heteroatom. Monocyclic heteroaromatic groups may contain 4 to 10 member atoms, typically 4 to 7 member atoms, and more typically 4 to 6 member atoms in the ring. Typical polycyclic heteroaromatic groups have two or three rings. Polycyclic aromatic groups having two to three rings typically have 8 to 16 member atoms, more typically 8 to 14 member atoms in the rings. Examples of heteroaromatic groups include, but are not limited thereto, pyrrole, imidazole, thiazole, oxazole, furan, thiophene, triazole, pyrazole, isoxazole, isothiazole, pyridine, pyrazine, pyridazine, pyrimidine, triazine, indole, benzofuran, benzothiophene, benzimidazole, benzthiazole, quinoline, isoquinoline, quinazoline, quinoxaline and the like.

The term "carbocyclic group" means a saturated or unsaturated carbocyclic hydrocarbon ring. Carbocyclic groups are not aromatic. Carbocyclic groups are monocyclic or polycyclic. Polycyclic carbocyclic groups can be fused, spiro, or bridged ring systems. Monocyclic carbocyclic groups may contain 4 to 10 carbon atoms, typically 4 to 7 carbon atoms, and more typically 5 to 6 carbon atoms in the ring. Bicyclic carbocyclic groups may contain 8 to 12 carbon atoms, typically 9 to 10 carbon atoms in the rings.

The term "heterocyclic group" means a saturated or unsaturated ring structure containing carbon atoms and 1 or more heteroatoms in the ring. Heterocyclic groups are not aromatic. Heterocyclic groups are monocyclic or polycyclic. Polycyclic heterocyclic groups can be fused, spiro, or bridged ring systems. Monocyclic heterocyclic groups may contain 4 to 10 member atoms (i.e., including both carbon atoms and at least 1 heteroatom), typically 4 to 7, and more typically 5 to 6 in the ring. Bicyclic heterocyclic groups may contain 8 to 18 member atoms, typically 9 or 10 member atoms in the rings. Representative heterocyclic groups include, by way of example, pyrrolidine, imidazolidine, pyrazolidine, piperidine, 1,4-dioxane, morpholine, thiomorpholine, piperazine, 3-pyrroline and the like.

The term "heterogeneous group" means a saturated or unsaturated chain comprising carbon atoms and at least one heteroatom. Heterogeneous groups typically have 1 to 25 member atoms. More typically, the chain contains 1 to 12 member atoms, 1 to 10, and most typically 1 to 6. The chain may be linear or branched. Typical branched heterogeneous groups have one or two branches, more typically one branch. Typically, heterogeneous groups are saturated. Unsaturated heterogeneous groups may have one or more double bonds, one or more triple bonds, or both. Typical unsaturated heterogeneous groups have one or two double bonds or one triple bond. More typically, the unsaturated heterogeneous group has one double bond.

The term "hydrocarbon group" or "hydrocarbyl group" means a chain of carbon atoms. In certain aspects, the term includes 1 to 25 carbon atoms, typically 1 to 12 carbon atoms, more typically 1 to 10 carbon atoms, and most typically 1 to 8 carbon atoms. Hydrocarbon groups may have a linear or branched chain structure. Typical hydrocarbon groups have one or two branches, typically one branch. The hydrocarbon groups encompass saturated, unsaturated, conjugated, unconjugated, and combinations thereof. Unsaturated hydrocarbon groups may have one or more double bonds, one or more triple bonds, or combinations thereof.

When the term "unsaturated" is used in conjunction with any group, the group may be fully unsaturated or partially unsaturated. However, when the term "unsaturated" is used in conjunction with a specific group defined herein, the term maintains the limitations of that specific group. For example, an unsaturated "carbocyclic group", based on the limitations of the "carbocyclic group" as defined herein, does not encompass an aromatic group.

The terms "carboxy group" or "carboxyl group", whether used alone or with other terms, such as "carboxyalkyl group", denotes —(C=O)—O—.

The term "carbonyl group", whether used alone or with other terms, such as "aminocarbonyl group", denotes —(C=O)—.

The terms "alkylcarbonyl group" denotes carbonyl groups which have been substituted with an alkyl group. In certain embodiments, "lower alkylcarbonyl group" has lower alkyl group as described above attached to a carbonyl group.

The term "aminoalkyl group" encompasses linear or branched alkyl groups having one to about ten carbon atoms any one of which may be substituted with one or more amino groups. In some embodiments, the aminoalkyl groups are "lower aminoalkyl" groups having one to six carbon atoms and one or more amino groups. Examples of such groups include aminomethyl, aminoethyl, aminopropyl, aminobutyl and aminohexyl.

The term "alkylaminoalkyl group" encompasses aminoalkyl groups having the nitrogen atom independently substituted with an alkyl group. In certain embodiments, the alkylaminoalkyl groups are "loweralkylaminoalkyl" groups having alkyl groups of one to six carbon atoms. In other embodiments, the lower alkylaminoalkyl groups have alkyl groups of one to three carbon atoms. Suitable alkylaminoalkyl groups may be mono or dialkyl substituted, such as N-methylaminomethyl, N, N-dimethyl-aminoethyl, N, N-diethylaminomethyl and the like.

The term "aralkyl group" encompasses aryl-substituted alkyl groups. In embodiments, the aralkyl groups are "lower aralkyl" groups having aryl groups attached to alkyl groups having one to six carbon atoms. In other embodiments, the lower aralkyl groups phenyl is attached to alkyl portions having one to three carbon atoms. Examples of such groups include benzyl, diphenylmethyl and phenylethyl. The aryl in said aralkyl may be additionally substituted with halo, alkyl, alkoxy, haloalkyl and haloalkoxy.

The term "arylalkenyl group" encompasses aryl-substituted alkenyl groups. In embodiments, the arylalkenyl groups are "lower arylalkenyl" groups having aryl groups attached to alkenyl groups having two to six carbon atoms. Examples of such groups include phenylethenyl. The aryl in said arylalkenyl may be additionally substituted with halo, alkyl, alkoxy, haloalkyl and haloalkoxy.

The term "arylalkynyl group" encompasses aryl-substituted alkynyl groups. In embodiments, arylalkynyl groups are "lower arylalkynyl" groups having aryl groups attached to alkynyl groups having two to six carbon atoms. Examples of such groups include phenylethynyl. The aryl in said aralkyl may be additionally substituted with halo, alkyl, alkoxy, haloalkyl and haloalkoxy. The terms benzyl and phenylmethyl are interchangeable.

The term "alkylthio group" encompasses groups containing a linear or branched alkyl group, of one to ten carbon atoms, attached to a divalent sulfur atom. In certain embodiments, the lower alkylthio groups have one to three carbon atoms. An example of "alkylthio" is methylthio, ($CH_3S$—).

The term "alkylamino group" denotes amino groups which have been substituted with one alkyl group and with two alkyl groups, including terms "N-alkylamino" and "N,N-dialkylamino". In embodiments, alkylamino groups are "lower alkylamino" groups having one or two alkyl groups of one to six carbon atoms, attached to a nitrogen atom. In other embodiments, lower alkylamino groups have one to three carbon atoms. Suitable "alkylamino" groups may be mono or dialkylamino such as N-methylamino, N-ethylamino, N,N-dimethylamino, N,N-diethylamino and the like.

The term "arylamino group" denotes amino groups which have been substituted with one or two aryl groups, such as N-phenylamino. The "arylamino" groups may be further substituted on the aryl ring portion of the group.

The term "heteroarylamino" denotes amino groups which have been substituted with one or two heteroaryl groups, such as N-thienylamino. The "heteroarylamino" groups may be further substituted on the heteroaryl ring portion of the group.

The term "aralkylamino group" denotes amino groups which have been substituted with one or two aralkyl groups. In other embodiments, there are phenyl-$C_1$-$C_3$-alkylamino groups, such as N-benzylamino. The "aralkylamino" groups may be further substituted on the aryl ring portion of the group.

The term "alkylaminoalkylamino group" denotes alkylamino groups which have been substituted with one or two alkylamino groups. In embodiments, there are $C_1$-$C_3$-alkylamino-$C_1$-$C_3$-alkylamino groups.

The term "arylthio group" encompasses aryl groups of six to ten carbon atoms, attached to a divalent sulfur atom. An example of "arylthio" is phenylthio. The term "aralkylthio group" encompasses aralkyl groups as described above, attached to a divalent sulfur atom. In certain embodiments there are phenyl-$C_1$-$C_3$-alkylthio groups. An example of "aralkylthio" is benzylthio.

The term "aryloxy group" encompasses optionally substituted aryl groups, as defined above, attached to an oxygen atom. Examples of such groups include phenoxy.

The term "aralkoxy group" encompasses oxy-containing aralkyl groups attached through an oxygen atom to other groups. In certain embodiments, aralkoxy groups are "lower aralkoxy" groups having optionally substituted phenyl groups attached to lower alkoxy group as described above.

The term "cycloalkyl group" includes saturated carbocyclic groups. In certain embodiments, cycloalkyl groups include $C_3$-$C_6$ rings. In embodiments, there are compounds that include, cyclopentyl, cyclopropyl, and cyclohexyl.

The term "cycloalkenyl group" includes carbocyclic groups that have one or more carbon-carbon double bonds; conjugated or non-conjugated, or a combination thereof "Cycloalkenyl" and "cycloalkyldienyl" compounds are included in the term "cycloalkenyl". In certain embodiments, cycloalkenyl groups include $C_3$-$C_6$ rings. Examples include cyclopentenyl, cyclopentadienyl, cyclohexenyl and cycloheptadienyl. The "cycloalkenyl" group may have 1 to 3 substituents such as lower alkyl, hydroxyl, halo, haloalkyl, nitro, cyano, alkoxy, lower alkylamino, and the like.

The term "suitable substituent", "substituent" or "substituted" used in conjunction with the groups described herein refers to a chemically acceptable group, i.e., a moiety that maintains the utility of the inventive compounds. It is understood that substituents and substitution patterns on the compounds of the invention may be selected by one of ordinary skill in the art to provide compounds that are chemically stable and that can be readily synthesized by techniques known in the art, as well as those methods set forth below. If a substituent is itself substituted with more than one group, it is understood that these multiple groups may be on the same carbon/member atom or on different carbons/member atoms, as long as a stable structure results. Illustrative examples of some suitable substituents include, cycloalkyl, heterocyclyl, hydroxyalkyl, benzyl, carbonyl, halo, haloalkyl, perfluoroalkyl, perfluoroalkoxy, alkyl, alkenyl, alkynyl, hydroxy, oxo, mercapto, alkylthio, alkoxy, aryl or heteroaryl, aryloxy or heteroaryloxy, aralkyl or heteroaralkyl, aralkoxy or heteroaralkoxy, HO—(C=O)—, amido, amino, alkyl- and dialkylamino, cyano, nitro, carbamoyl, alkylcarbonyl, alkoxycarbonyl, alkylaminocarbonyl, dialkylaminocarbonyl, arylcarbonyl, aryloxycarbonyl, alkylsulfonyl, and arylsulfonyl. Typical substituents include aromatic groups, substituted aromatic groups, hydrocarbon groups including alkyl groups such as methyl groups, substituted hydrocarbon groups such as benzyl, and heterogeneous groups including alkoxy groups such as methoxy groups.

The term "fused" means in which two or more carbons/member atoms are common to two adjoining rings, e.g., the rings are "fused rings".

The term "leaving group" is well understood in the art and is a molecular fragment that departs with a pair of electrons in a heterolytic bond cleavage. Leaving groups can be anions or neutral molecules, and is able to stabilize the additional electron density that results from bond heterolysis.

The term "isotopic forms" refer to variants of a particular chemical element. All isotopes of a given element share the same number of protons, and each isotope differs from the others in its number of neutrons.

The term "solvate" refers to solvate forms of the compound(s) described herein that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "salt(s)" includes salts of the compound(s) which are prepared from suitable acids or bases, depending on the particular substituents found on the compound(s) described herein. When compound(s) described herein contain relatively basic functionalities, acid salts can be obtained by contacting the neutral form of such compound(s) with a sufficient amount of the desired acid. Examples of inorganic acid salts include those derived from inorganic acids such as hydrochloric acid, hydrobromic acid, nitric acid, carbonic acid, monohydrogencarbonic acid, phosphoric acid, monohydrogenphosphoric acid, dihydrogenphosphoric acid, sulfuric acid, monohydrogensulfuric acid, hydriodic acid, ethanedisulfonic acid, phosphorous acids, a combination thereof or the like. Examples of organic acid salts include those derived from organic acids such as acetic acid, propionic acid, isobutyric acid, butyric acid, maleic acid, mandelic acid (D or L), ethane-1,2-disulfonic acid (dihydrate), toluene sulfonic acid (e.g. monohydrate), p-toluene sulfonic acid (e.g. monohydrate), 10-camphorsulfonic acid (e.g. (–)-10-camphorsulfonic acid), malic acid, malonic acid, benzoic acid, succinic acid, suberic acid, fumaric acid, lactic acid, mandelic acid, phthalic acid, benzenesulfonic acid, p-tolylsulfonic acid, citric acid, tartaric acid (L-tartaric acid or D-tartaric acid), mesotartaric acid (or erythraric acid), methanesulfonic acid, glutamic acid (L-glutamic acid or D-glutamic acid), ascorbic acid (L-ascorbic acid or D-ascorbic acid), isoascorbic acid (L-isoascorbic acid or D-isoascorbic acid), a combination thereof or the like.

The term "hemi" means the ratio of compound:acid (whether organic or inorganic) is 1:0.5 (or 2:1), respectively, in the crystal structure of the salt of the compound (e.g. Formula I).

With respect to the formation of suitable salts, any suitable counterions may form. A "counterion" or "anionic counterion" is a negatively charged group associated, for example, with a cationic quaternary amino group in order to maintain electrostatic neutrality. Exemplary counterions include halide ions (e.g., $F^-$, $Cl^-$, $Br^-$, $I^-$) $NO_3^-$, $ClO_4^-$, $OH^-$, $H_2PO_4^-$, $HSO_4^-$, $^-BF_4$, $^-PF_6$, sulfonate ions, and carboxylate ions.

The salts of the compound(s) described herein can be synthesized from the compound(s) described herein. Generally, the salts of the basic compound(s) are prepared by reacting the free base with stoichiometric amounts or with an excess of the desired salt-forming inorganic or organic acid in a suitable solvent or various combinations of solvents.

In addition, International Union of Pure and Applied Chemistry (IUPAC) nomenclature that is generated for 2-halo-LSD related compounds, show the chiral centers at carbons 6 and 9 positions. A more common numbering system has been adopted herein, however, that is consistent with the halo group being bonded to the second carbon, putting the two chiral carbons at the 5 and 8 positions, as confirmed in the structures herein. In addition, as used herein, stereocenter nomenclature for "5aR,8R", "5aR,8S", "5aS,8R", and "5aS,8S" is interchangeable with "5R,8R", "5R,8S", "5S,8R", and "5S,8S", respectively.

The term "derivative" generally refers to a molecule that has been modified and/or changed in any way relative to a reference molecule or starting molecule.

The term "polymorph" refers to a crystal structure in which a compound (e.g. salt or solvate thereof) can crystallize in a specific crystal packing arrangement. Different polymorphs usually have different X-ray diffraction patterns, infrared spectra, melting points, density hardness, crystal shape, optical and electrical properties, stability and/or solubility. Recrystallization solvent, rate of crystallization, storage temperature, and other factors may cause one polymorph to dominate. A polymorph of the compound can be prepared by crystallization under different conditions.

It is to be understood that the present description encompasses any racemic form, optically-active form, stereoisomeric form, and/or polymorphic form.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Lysergic Acid Diethylamide (LSD)—Derivatives and Polymorph(s) Thereof

Novel derivative(s) and polymorphs of LSD are provided. These are represented by Formula I. These compounds are demonstrated to have desirable biological effects, are substantially non-hallucinogenic and do not induce tolerance. The novel derivative(s) and polymorphs of LSD of Formula I comprise desirable properties (such as but not limited to mechanical, thermal, physical and chemical properties) resulting in desired influences on the bioavailability, hygroscopicity, stability and other performance characteristics. As such the compounds of the invention are suitable for development in therapeutic(s) products.

i) Certain embodiments include a compound having the structure of Formula I:

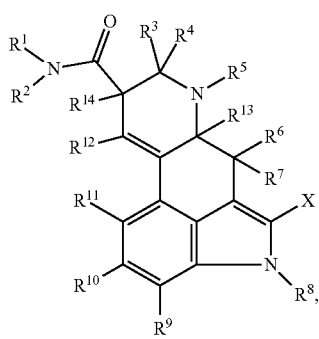

Formula I a pharmaceutically acceptable salt, hydrate, solvate, tautomer, enantiomer, diastereomer, racemate, polymorph, or combination thereof; wherein: $R^1$ to $R^{14}$ are each independently selected from H, or a substituted or unsubstituted hydrocarbon group and X is selected from a halo group. In an embodiment, the compound is crystalline. In a more specific embodiment, the compound is an isolated crystalline form.

In another embodiment, the compound comprises polymorphs of Formula I. In a further embodiment, the compound comprises a single polymorph thereof. In another embodiment, the compound is an isolated polymorph thereof. In other embodiments, wherein i) the compound is a diastereomer and/or enantiomer; and/or ii) is crystalline, optionally, polymorphs thereof or a single polymorph thereof.

In further embodiments, i) the compound is one or more polymorphs thereof; and/or ii) the compound comprises one or more compounds, each having two stereocenters, independently selected from 5S,8R; 5R,8R; 5R,8S; or 5S,8S; iii) the compound comprises one or more compounds, each having two stereocenters, independently selected from 5R,8S; 5R,8R; or 5S,8R; iv) the compound comprises one or more compounds, each having two stereocenters, independently selected from 5R,8S or 5R,8R; v) the compound has two stereocenters, which are 5R,8R; or vi) the compound has two stereocenters, which are 5R,8S. In one or more of these embodiments, the compound is a pharmaceutically acceptable salt, hydrate and/or solvate thereof. In an embodiment, the compound is an acid salt. The salt may be formed from any suitable organic or inorganic acid(s) such as hydrochloric acid, hydrobromic acid, nitric acid, carbonic acid, monohydrogencarbonic acid, phosphoric acid, monohydrogenphosphoric acid, dihydrogenphosphoric acid, sulfuric acid, monohydrogensulfuric acid, hydriodic acid, ethanedisulfonic acid or phosphorous acids, acetic acid, propionic acid, isobutyric acid, butyric acid, maleic acid, mandelic acid (D or L), ethane-1,2-disulfonic acid (dihydrate), toluene sulfonic acid (e.g. monohydrate), p-toluene sulfonic acid (e.g. monohydrate), 10-camphorsulfonic acid (e.g. (−)-10-camphorsulfonic acid), malic acid, malonic acid, benzoic acid, succinic acid, suberic acid, fumaric acid, lactic acid, mandelic acid, phthalic acid, benzenesulfonic acid, p-tolylsulfonic acid, citric acid, tartaric acid (L-tartaric acid or D-tartaric acid), mesotartaric acid (or erythraric acid), methanesulfonic acid, glutamic acid (L-glutamic acid or D-glutamic acid), ascorbic acid (L-ascorbic acid or D-ascorbic acid), isoascorbic acid (L-isoascorbic acid or D-isoascorbic acid), or a combination thereof or the like. In any salt embodiments, the salt may be a hemisalt.

With respect to the options for Formula I, Formula I may be any suitable embodiment listed above and as follows, in any combination:

In embodiments of Formula I, $R^1$ to $R^{14}$ are each independently selected from H, substituted or unsubstituted alkyl group, substituted or unsubstituted alkenyl group, or substituted or unsubstituted alkynyl group. In other embodiments, $R^1$ to $R^{14}$ are each independently selected from H, substituted or unsubstituted $C_1$-$C_6$ alkyl group, substituted or unsubstituted $C_2$-$C_6$ alkenyl group, or substituted or unsubstituted $C_2$-$C_6$ alkynyl group. In further embodiments, $R^1$ to $R^{14}$ are each independently selected from H, or substituted or unsubstituted $C_1$-$C_6$ alkyl group. In further embodiments, $R^1$ to $R^{14}$ are each independently selected from H, a methyl group or an ethyl group. In another embodiment, $R^1$ and $R^2$ are each independently selected from H, a methyl group or an ethyl group; $R^3$, $R^4$, and $R^6$ to $R^{14}$ are each H, and $R^5$ is a methyl group. In another embodiment, $R^1$ and $R^2$ are each independently selected from a methyl group or an ethyl group; $R^3$, $R^4$, and $R^6$ to $R^{14}$ are each H; and $R^5$ is a methyl group. In another embodiment, $R^1$ and $R^2$ are each ethyl groups; $R^3$, $R^4$, and $R^6$ to $R^{14}$ are each H; and $R^5$ is a methyl group.

In further embodiments of Formula I, X is selected from bromo, chloro, fluoro or iodo. In other embodiments, X is selected from bromo, chloro, or fluoro. In another embodiment, X is selected from bromo or chloro. In yet another embodiment, X is bromo.

ii) Other embodiments include a compound having the structure of Formula I':

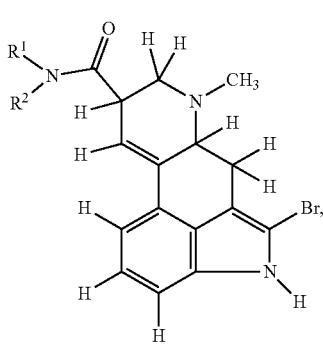

Formula I' a pharmaceutically acceptable salt, hydrate, solvate, tautomer, enantiomer, diastereomer, racemate, polymorph, or combination thereof; wherein: $R^1$ and $R^2$ are each independently selected from H, or a substituted or unsubstituted hydrocarbon group. In an embodiment, the compound is crystalline. In a more specific embodiment, the compound is an isolated crystalline form.

In another embodiment, the compound comprises polymorphs thereof. In a further embodiment, the compound comprises a single polymorph thereof. In another embodiment, the compound is an isolated polymorph thereof. In other embodiments, wherein i) the compound is a diastereomer and/or enantiomer; and/or ii) is crystalline, optionally, polymorphs thereof or a single polymorph thereof.

In further embodiments, i) the compound is one or more polymorphs thereof; and/or ii) the compound comprises one or more compounds, each having two stereocenters, independently selected from 5S,8R; 5R,8R; 5R,8S; or 5S,8S; iii) the compound comprises one or more compounds, each having two stereocenters, independently selected from 5R,8S; 5R,8R; or 5S,8R; iv) the compound comprises one or more compounds, each having two stereocenters, independently selected from 5R,8S or 5R,8R; v) the compound has two stereocenters, which are 5R,8R; or vi) the compound has two stereocenters, which are 5R,8S. In one or more of these embodiments, the compound is a pharmaceutically acceptable salt, hydrate and/or solvate thereof. In a typical embodiment, the compound is an acid salt. The salt may be formed from any suitable organic or inorganic acid(s) such as hydrochloric acid, hydrobromic acid, nitric acid, carbonic acid, monohydrogencarbonic acid, phosphoric acid, monohydrogenphosphoric acid, dihydrogenphosphoric acid, sulfuric acid, monohydrogensulfuric acid, hydriodic acid, ethanedisulfonic acid or phosphorous acids, acetic acid, propionic acid, isobutyric acid, butyric acid, maleic acid, mandelic acid (D or L), ethane-1,2-disulfonic acid (dihydrate), toluene sulfonic acid (e.g. monohydrate), p-toluene sulfonic acid (e.g. monohydrate), 10-camphorsulfonic acid (e.g. (−)-10-camphorsulfonic acid), malic acid, malonic acid, benzoic acid, succinic acid, suberic acid, fumaric acid, lactic acid, mandelic acid, phthalic acid, benzenesulfonic acid, p-tolylsulfonic acid, citric acid, tartaric acid (L-tartaric acid or D-tartaric acid), mesotartaric acid (or erythraric acid), methanesulfonic acid, glutamic acid (L-glutamic acid or D-glutamic acid), ascorbic acid (L-ascorbic acid or D-ascorbic acid), isoascorbic acid (L-isoascorbic acid or D-isoascorbic acid), or a combination thereof or the like. In any salt embodiments, the salt may be a hemisalt.

With respect to the options for Formula I', Formula I' may be any suitable embodiment listed above and as follows, in any combination:

In embodiments of Formula I', $R^1$ and $R^2$ are each independently selected from H, substituted or unsubstituted alkyl group, substituted or unsubstituted alkenyl group, or substituted or unsubstituted alkynyl group. In other embodiments, $R^1$ and $R^2$ are each independently selected from H, substituted or unsubstituted $C_1$-$C_6$ alkyl group, substituted or unsubstituted $C_2$-$C_6$ alkenyl group, or substituted or unsubstituted $C_2$-$C_6$ alkynyl group. In further embodiments, $R^1$ and $R^2$ are each independently selected from H, or substituted or unsubstituted $C_1$-$C_6$ alkyl group. In further embodiments, $R^1$ and $R^2$ are each independently selected from H, a methyl group or an ethyl group. In another embodiment, $R^1$ and $R^2$ are each independently selected from a methyl group or an ethyl group. In another embodiment, $R^1$ and $R^2$ are each ethyl groups.

iii) In other embodiments, wherein the compound is selected from:

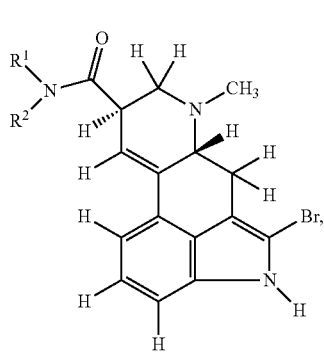

Formula Ia

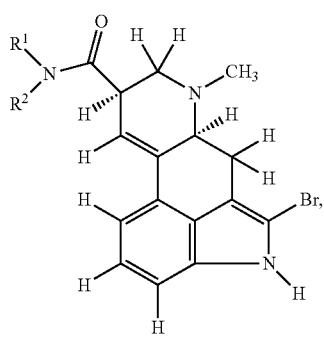

Formula Ib

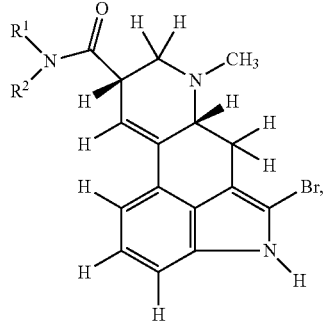

Formula Ic

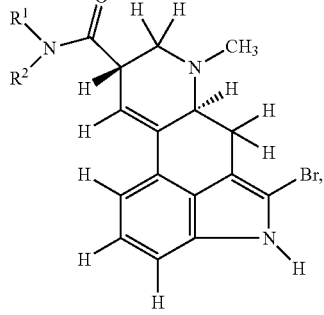

Formula Id a pharmaceutically acceptable salt, hydrate, solvate, tautomer, polymorph or combination thereof; wherein: $R^1$ and $R^2$ are each independently selected from H, or a substituted or unsubstituted hydrocarbon group. In an embodiment, the compound is crystalline. In a more specific embodiment, the compound is an isolated crystalline form.

In another embodiment, the compound comprises polymorphs thereof. In a further embodiment, the compound comprises a single polymorph thereof. In another embodiment, the compound is an isolated polymorph thereof. In other embodiments, wherein i) the compound is a diastereomer and/or enantiomer; and/or ii) is crystalline, optionally, polymorphs thereof or a single polymorph thereof.

In further embodiments, i) the compound is one or more polymorphs thereof; and/or ii) the compound comprises one or more compounds, each having two stereocenters, independently selected from 5S,8R; 5R,8R; 5R,8S; or 5S,8S; iii) the compound comprises one or more compounds, each having two stereocenters, independently selected from 5R,8S; 5R,8R; or 5S,8R; iv) the compound comprises one or more compounds, each having two stereocenters, independently selected from 5R,8S or 5R,8R; v) the compound has two stereocenters, which are 5R,8R; or vi) the compound has two stereocenters, which are 5R,8S. In one or more of these embodiments, the compound is a pharmaceutically acceptable salt, hydrate and/or solvate thereof. In a typical embodiment, the compound is an acid salt. The salt may be formed from any suitable organic or inorganic acid(s) such as hydrochloric acid, hydrobromic acid, nitric acid, carbonic acid, monohydrogencarbonic acid, phosphoric acid, monohydrogenphosphoric acid, dihydrogenphosphoric acid, sulfuric acid, monohydrogensulfuric acid, hydriodic acid, ethanedisulfonic acid or phosphorous acids, acetic acid, propionic acid, isobutyric acid, butyric acid, maleic acid, mandelic acid (D or L), ethane-1,2-disulfonic acid (dihydrate), toluene sulfonic acid (e.g. monohydrate), p-toluene sulfonic acid (e.g. monohydrate), 10-camphorsulfonic acid (e.g. (−)-10-camphorsulfonic acid), malic acid, malonic acid, benzoic acid, succinic acid, suberic acid, fumaric acid, lactic acid, mandelic acid, phthalic acid, benzenesulfonic acid, p-tolylsulfonic acid, citric acid, tartaric acid (L-tartaric acid or D-tartaric acid), mesotartaric acid (or erythraric acid), methanesulfonic acid, glutamic acid (L-glutamic acid or D-glutamic acid), ascorbic acid (L-ascorbic acid or D-ascorbic acid), isoascorbic acid (L-isoascorbic acid or D-isoascorbic acid), or a combination thereof or the like. In any salt embodiments, the salt may be a hemisalt.

With respect to the options above, the compound may be any suitable embodiment listed above and as follows, in any combination:

In embodiments, $R^1$ and $R^2$ are each independently selected from H, substituted or unsubstituted alkyl group, substituted or unsubstituted alkenyl group, or substituted or unsubstituted alkynyl group. In other embodiments, $R^1$ and $R^2$ are each independently selected from H, substituted or unsubstituted $C_1$-$C_6$ alkyl group, substituted or unsubstituted $C_2$-$C_6$ alkenyl group, or substituted or unsubstituted $C_2$-$C_6$ alkynyl group. In further embodiments, $R^1$ and $R^2$ are each independently selected from H, or substituted or unsubstituted $C_1$-$C_6$ alkyl group. In further embodiments, $R^1$ and $R^2$ are each independently selected from H, a methyl group or an ethyl group. In another embodiment, $R^1$ and $R^2$ are each independently selected from a methyl group or an ethyl group. In another embodiment, $R^1$ and $R^2$ are each ethyl groups.

iv) In other embodiments, wherein the compound is selected from:

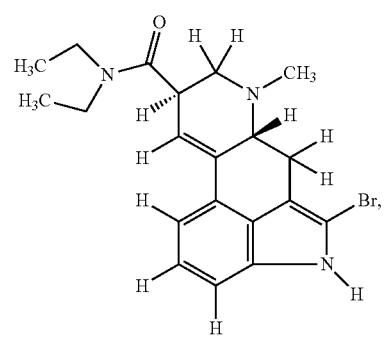

Formula Ia'

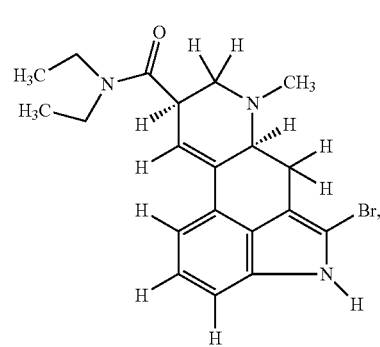

Formula Ib'

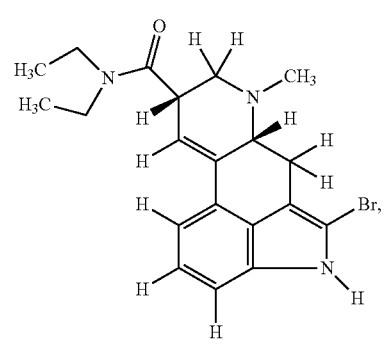

Formula Ic'

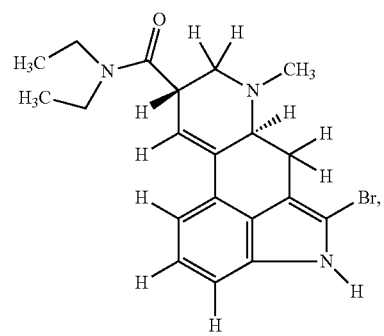

Formula Id' a pharmaceutically acceptable salt, hydrate, solvate, tautomer, polymorph or combination thereof. In an embodiment, the compound is crystalline. In a more specific embodiment, the compound is an isolated crystalline form.

In another embodiment, the compound comprises polymorphs thereof. In a further embodiment, the compound comprises a single polymorph thereof. In another embodiment, the compound is an isolated polymorph thereof. In other embodiments, wherein i) the compound is a diastereomer and/or enantiomer; and/or ii) is crystalline, optionally, polymorphs thereof or a single polymorph thereof.

In further embodiments, i) the compound is one or more polymorphs thereof; and/or ii) the compound comprises one or more compounds, each having two stereocenters, independently selected from 5S,8R; 5R,8R; 5R,8S; or 5S,8S; iii) the compound comprises one or more compounds, each having two stereocenters, independently selected from 5R,8S; 5R,8R; or 5S,8R; iv) the compound comprises one or more compounds, each having two stereocenters, independently selected from 5R,8S or 5R,8R; v) the compound has two stereocenters, which are 5R,8R; or vi) the compound has two stereocenters, which are 5R,8S. In one or more of these embodiments, the compound is a pharmaceutically acceptable salt, hydrate and/or solvate thereof. In a typical embodiment, the compound is an acid salt. The salt may be formed from any suitable organic or inorganic acid(s) such as hydrochloric acid, hydrobromic acid, nitric acid, carbonic acid, monohydrogencarbonic acid, phosphoric acid, monohydrogenphosphoric acid, dihydrogenphosphoric acid, sulfuric acid, monohydrogensulfuric acid, hydriodic acid, ethanedisulfonic acid or phosphorous acids, acetic acid, propionic acid, isobutyric acid, butyric acid, maleic acid, mandelic acid (D or L), ethane-1,2-disulfonic acid (dihydrate), toluene sulfonic acid (e.g. monohydrate), p-toluene sulfonic acid (e.g. monohydrate), 10-camphorsulfonic acid (e.g. (−)-10-camphorsulfonic acid), malic acid, malonic acid, benzoic acid, succinic acid, suberic acid, fumaric acid, lactic acid, mandelic acid, phthalic acid, benzenesulfonic acid, p-tolylsulfonic acid, citric acid, tartaric acid (L-tartaric acid or D-tartaric acid), mesotartaric acid (or erythraric acid), methanesulfonic acid, glutamic acid (L-glutamic acid or D-glutamic acid), ascorbic acid (L-ascorbic acid or D-ascorbic acid), isoascorbic acid (L-isoascorbic acid or D-isoascorbic acid), or a combination thereof or the like. In any salt embodiments, the salt may be a hemisalt.

v) In other embodiments, wherein the compound is a 2-bromo-LSD acid salt selected from:

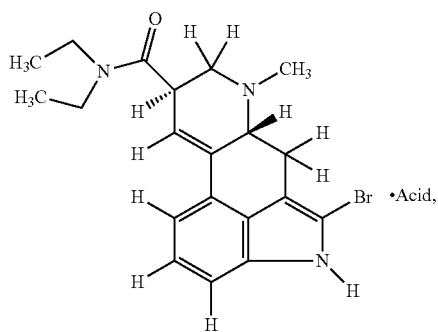

Formula Ia″

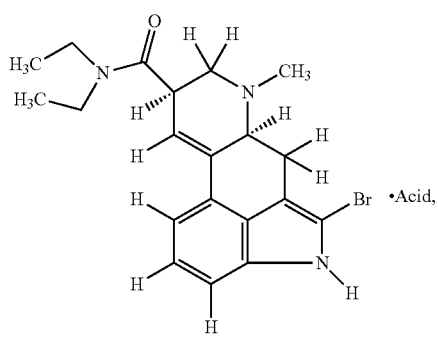

Formula Ib″

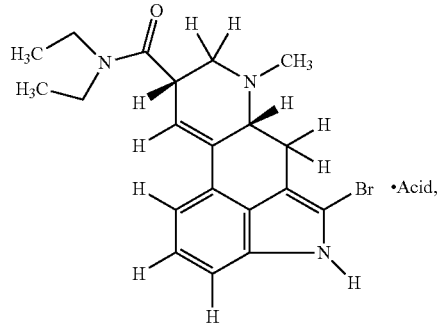

Formula Ic″

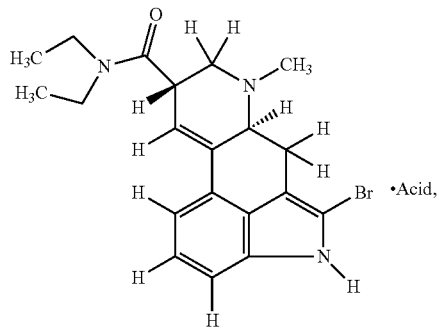

Formula Id″ or combination thereof. In an embodiment, the compound is crystalline. In a more specific embodiment, the compound is an isolated crystalline form.

In another embodiment, the compound comprises polymorphs thereof. In a further embodiment, the compound comprises a single polymorph thereof. In another embodiment, the compound is an isolated polymorph thereof. In other embodiments, wherein i) the compound is a diastereomer and/or enantiomer; and/or ii) is crystalline, optionally, polymorphs thereof or a single polymorph thereof.

In further embodiments, i) the compound is one or more polymorphs thereof; and/or ii) the compound comprises one or more compounds, each having two stereocenters, independently selected from 5S,8R; 5R,8R; 5R,8S; or 5S,8S; iii) the compound comprises one or more compounds, each having two stereocenters, independently selected from 5R,8S; 5R,8R; or 5S,8R; iv) the compound comprises one or more compounds, each having two stereocenters, independently selected from 5R,8S or 5R,8R; v) the compound has two stereocenters, which are 5R,8R; or vi) the compound has two stereocenters, which are 5R,8S. The acid may be any suitable organic or inorganic acid(s) such as hydrochloric acid, hydrobromic acid, nitric acid, carbonic acid, monohydrogencarbonic acid, phosphoric acid, monohydrogenphosphoric acid, dihydrogenphosphoric acid, sulfuric acid, monohydrogensulfuric acid, hydriodic acid, ethanedisulfonic acid, phosphorous acids, acetic acid, propionic acid, isobutyric acid, butyric acid, maleic acid, mandelic acid (D or L), ethane-1,2-disulfonic acid (dihydrate), toluene sulfonic acid (e.g. monohydrate), p-toluene sulfonic acid (e.g. monohydrate), 10-camphorsulfonic acid (e.g. (−)-10-camphorsulfonic acid), malic acid, malonic acid, benzoic acid, succinic acid, suberic acid, fumaric acid, lactic acid, mandelic acid, phthalic acid, benzenesulfonic acid, p-tolylsulfonic acid, citric acid, tartaric acid (L-tartaric acid or D-tartaric acid), mesotartaric acid (or erythraric acid), methanesulfonic acid, glutamic acid (L-glutamic acid or D-glutamic acid), ascorbic acid (L-ascorbic acid or D-ascorbic acid), isoascorbic acid (L-isoascorbic acid or D-isoascorbic acid), or a combination thereof or the like. In any salt embodiments, the salt may be a hemisalt.
vi) In specific embodiments, the compound may be selected from 2-bromo-LSD acid salts:
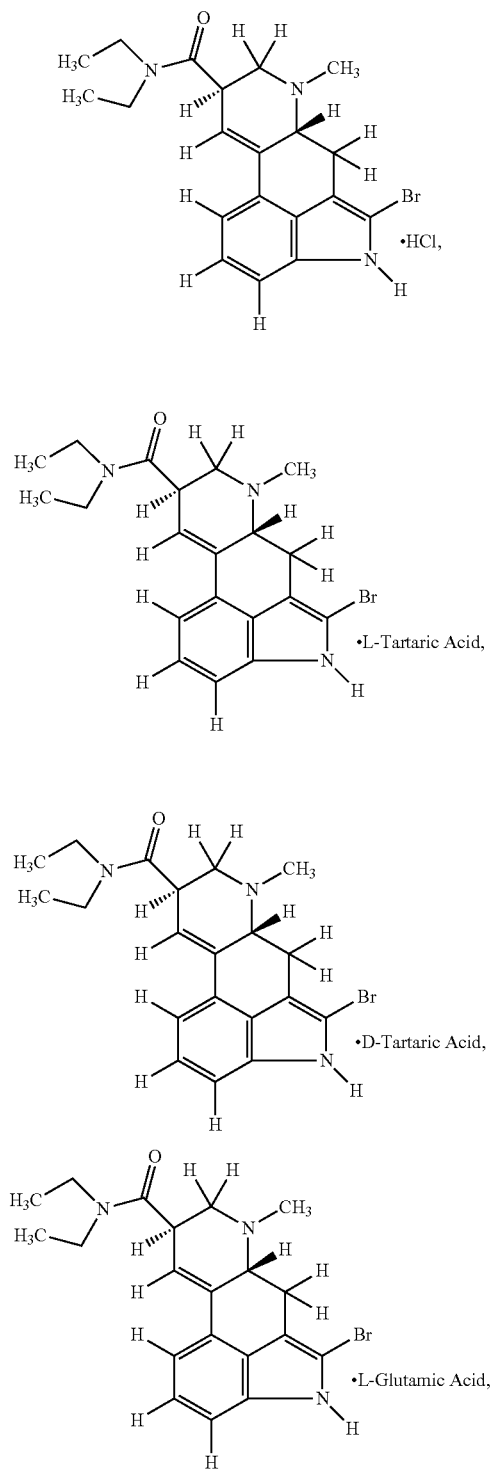
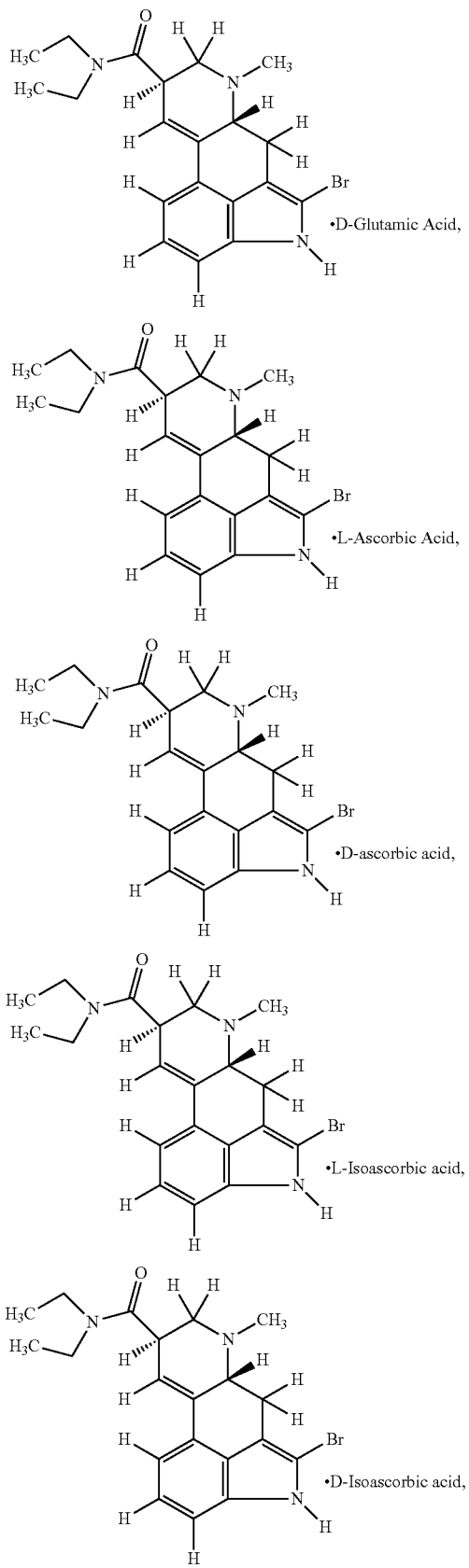

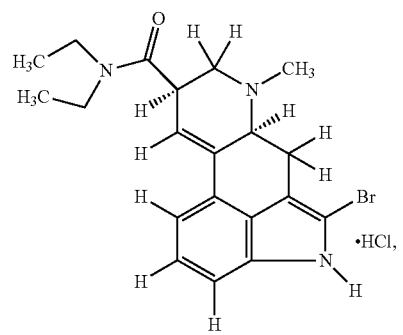
•HCl,
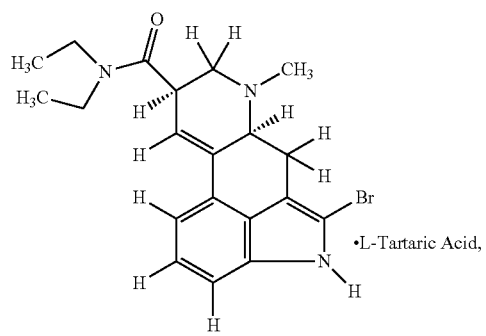
•L-Tartaric Acid,
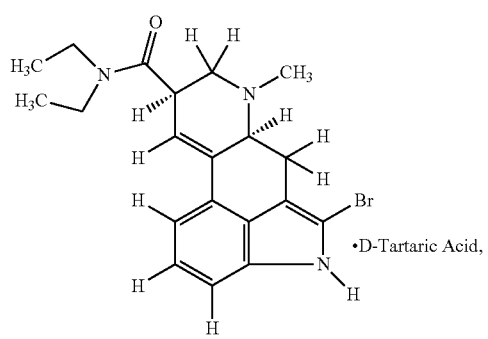
•D-Tartaric Acid,
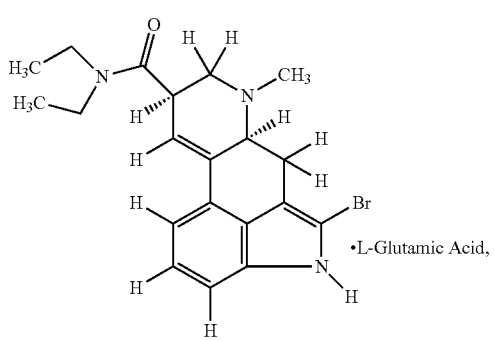
•L-Glutamic Acid,
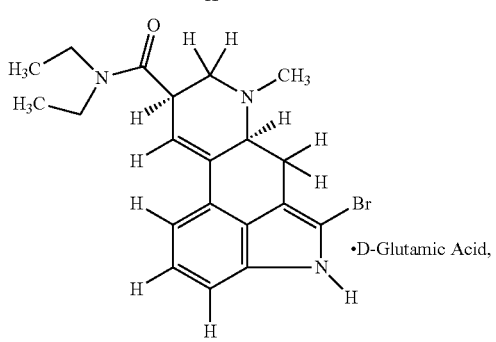
•D-Glutamic Acid,
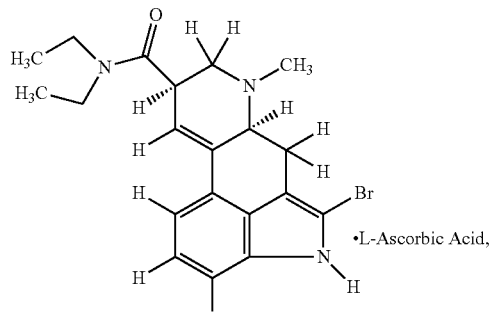
•L-Ascorbic Acid,
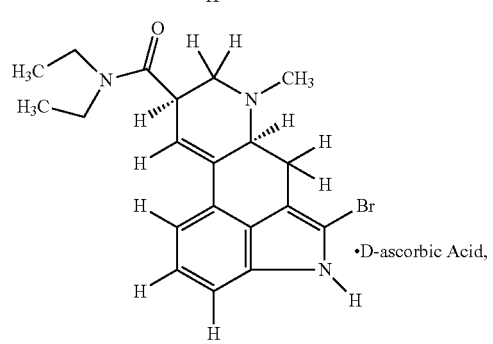
•D-ascorbic Acid,
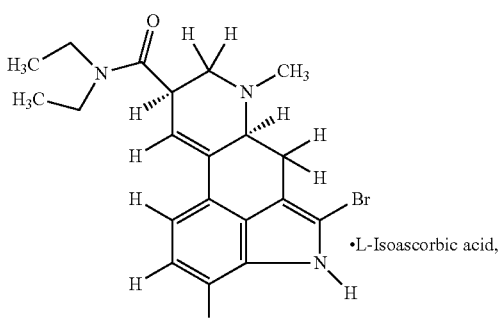
•L-Isoascorbic acid,
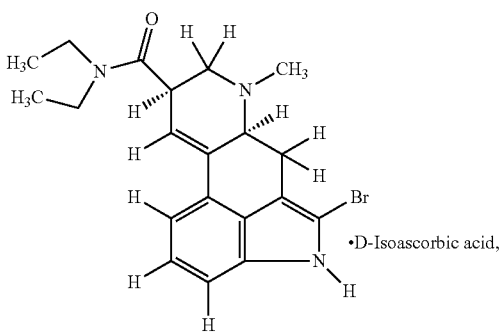
•D-Isoascorbic acid,
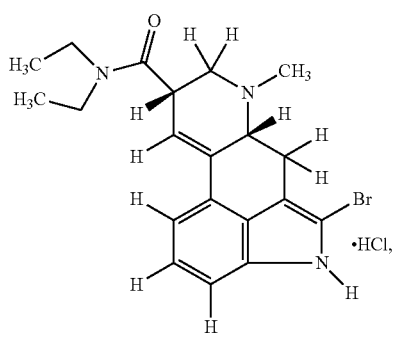
•HCl,

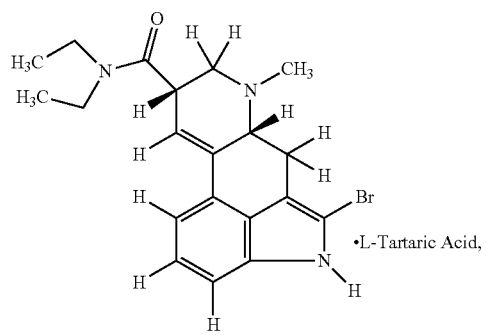
•L-Tartaric Acid,
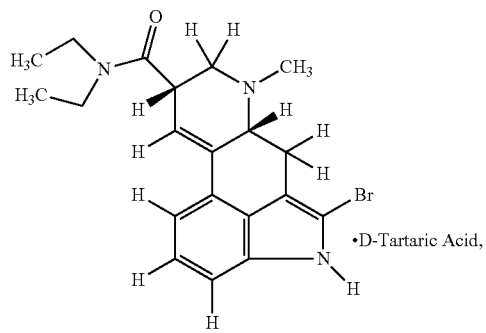
•D-Tartaric Acid,
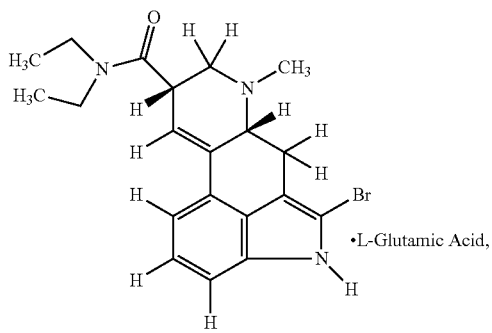
•L-Glutamic Acid,
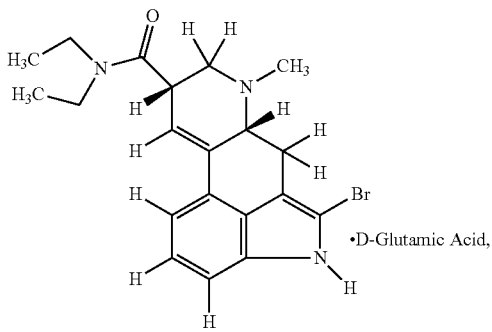
•D-Glutamic Acid,
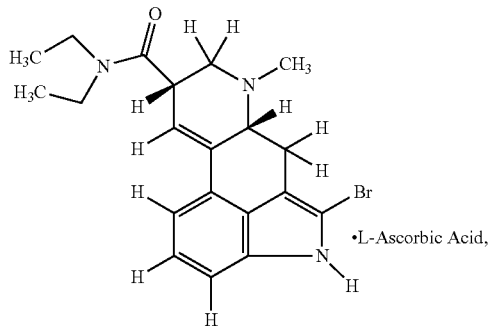
•L-Ascorbic Acid,
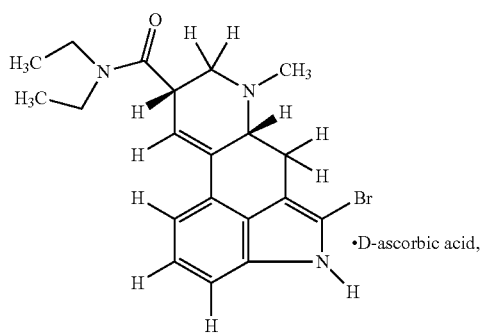
•D-ascorbic acid,
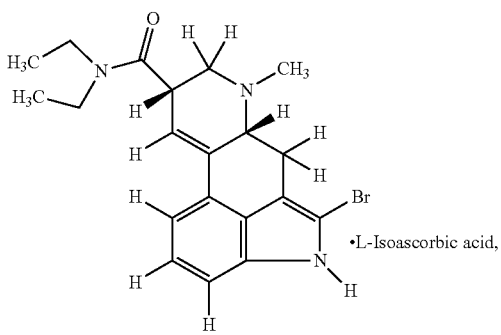
•L-Isoascorbic acid,
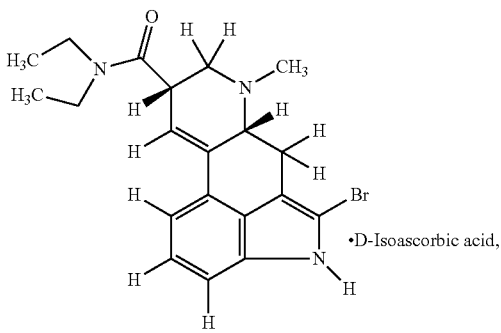
•D-Isoascorbic acid,
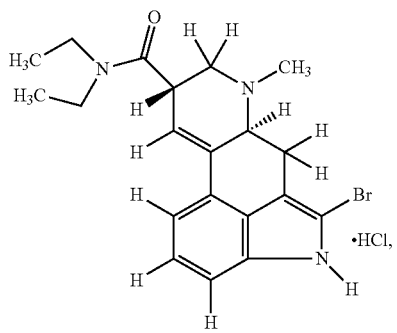
•HCl,
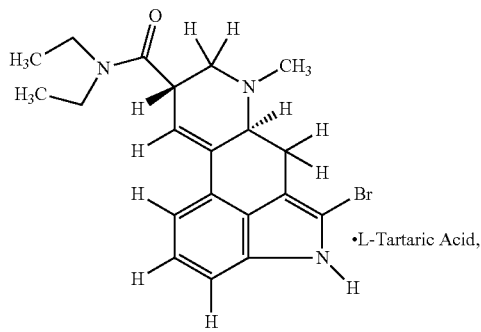
•L-Tartaric Acid,

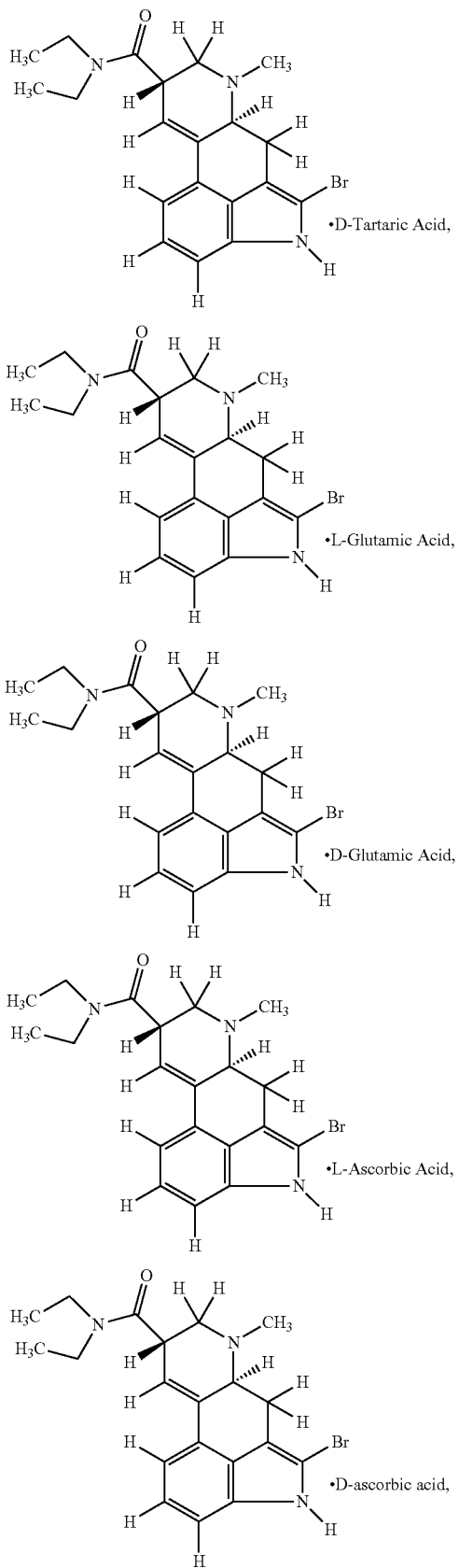

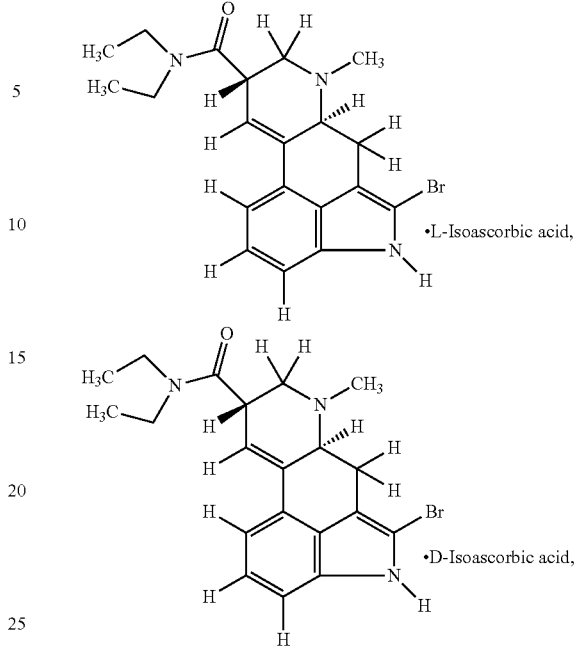

or combination thereof. In other embodiments, wherein the compound is a polymorph thereof. In an embodiment, the compound is crystalline. In a more specific embodiment, the compound is an isolated crystalline form.

In another embodiment, the compound comprises polymorphs thereof. In a further embodiment, the compound comprises a single polymorph thereof. In another embodiment, the compound is an isolated polymorph thereof. In other embodiments, wherein i) the compound is a diastereomer and/or enantiomer; and/or ii) is crystalline, optionally, polymorphs thereof or a single polymorph thereof.

In further embodiments, i) the compound is one or more polymorphs thereof; and/or ii) the compound comprises one or more compounds, each having two stereocenters, independently selected from 5S,8R; 5R,8R; 5R,8S; or 5S,8S; iii) the compound comprises one or more compounds, each having two stereocenters, independently selected from 5R,8S; 5R,8R; or 5S,8R; iv) the compound comprises one or more compounds, each having two stereocenters, independently selected from 5R,8S or 5R,8R; v) the compound has two stereocenters, which are 5R,8R; or vi) the compound has two stereocenters, which are 5R,8S. In further embodiments, wherein the compound comprises 2-bromoLSD tartrate salt (about 1:about 0.5) and/or (about 1:about 1), i) the compound is one or more polymorphs thereof; and/or ii) the compound comprises one or more compounds, each having two stereocenters, independently selected from 5S,8R; 5R,8R; 5R,8S; or 5S,8S; iii) the compound comprises one or more compounds, each having two stereocenters, independently selected from 5R,8S; 5R,8R; or 5S,8R; iv) the compound comprises one or more compounds, each having two stereocenters, independently selected from 5R,8S or 5R,8R; v) the compound has two stereocenters, which are 5R,8R; or vi) the compound has two stereocenters, which are 5R,8S.

In any of the acid derivative(s) of LSD described above, the ratio of the 4-ringed compound of Formula I, I', Ia, Ib, Ic, Id, Ia', Ib', Ic', or Id' to the acid of Formula I, I', Ia, Ib, Ic, Id, Ia', Ib', Ic', or Id' may be in any suitable ratio, such as, and typically, a hemisalt (0.5:1 or 2:1). In embodiments, the ratio need not be the perfect balance of positive and negative charge. For example, the charge balanced ratio of 2-bromoLSD to tartrate can be 2 to 1, as 2-bromoLSD is about +1 and tartrate is about −2. With L-tartrate, salt formed can be about 1 to about 1, meaning there is an excess of negative charge. This can be balanced by hydrogen. A phosphate salt may occur in a ratio of 1:3, 1:2, 1:1, or 2:1 and ratios above and below these, where other spectator ions/counterions may be used such as, for example, hydrogen, hydroxide, sodium, chloride, calcium and potassium may be used to balance the charge. In embodiments, the ratio depends on the total charge of the acid. In certain embodiments, the ratio is from about 0.5:1 to about 2:1 (hemisalt)(based on mol/mol) and any increment therebetween such as about 0.6:1 to about 2:1; about 0.7:1 to about 2:1; about 0.8:1 to about 2:1; about 0.9:1 to about 2:1; about 1:1 to about 2:1; about 1.1:1 to about 2:1; about 1.2:1 to about 2:1; about 1.3:1 to about 2:1; about 1.4:1 to about 2:1; about 1.5:1 to about 2:1; about 1.6:1 to about 2:1; about 1.7:1 to about 2:1; about 1.8:1 to about 2:1; about 1.9:1 to about 2:1; about 0.5:1 to about 1.9:1; about 0.5:1 to about 1.8:1; about 0.5:1 to about 1.7:1; about 0.5:1 to about 1.6:1; about 0.5:1 to about 1.5:1; about 0.5:1 to about 1.4:1; about 0.5:1 to about 1.3:1; about 0.5:1 to about 1.2:1; about 0.5:1 to about 1.1:1; about 0.5:1 to about 1:1; about 0.5:1 to about 0.9:1; about 0.5:1 to about 0.8:1; about 0.5:1 to about 0.7:1; or about 0.5:1 to about 0.6:1.

In embodiments, the compound of Formula I, I', Ia, Ib, Ic, Id, Ia', Ib', Ic', or Id' has a powder X-ray Diffraction (PXRD) pattern comprising a peak at about 10.3° (2θ). In other embodiments, the compound has an X-ray powder diffraction (PXRD) pattern comprising a peak at about 4.7° (2θ), about 9.4° (2θ), and about 10.3° (2θ). In other embodiments, the compound has an X-ray powder diffraction (PXRD) pattern comprising a peak at about 4.7° (2θ), about 9.4° (2θ), about 10.3° (2θ), and about 20.1° (2θ).

In embodiments, the compound of Formula I, I', Ia, Ib, Ic, Id, Ia', Ib', Ic', or Id' 74 has a powder X-ray Diffraction (PXRD) pattern comprising a peak at about 10.3° (2θ) and d value of about 8.6 Å. In other embodiments, the compound has an X-ray powder diffraction (PXRD) pattern comprising a peak at about 4.7° (2θ) and d value of about 18.8 Å, about 9.4° (2θ) and d value of about 9.4 Å, and about 10.3° (2θ) and d value of about 8.6 Å. In other embodiments, the compound has an X-ray powder diffraction (PXRD) pattern comprising a peak at about 4.7° (2θ) and d value of about 18.8 Å, about 9.4° (2θ) and d value of about 9.4 Å, about 10.3° (2θ) and d value of about 8.6 Å, and about 20.1° (2θ) and d value of about 4.4 Å. In still further embodiments, the compound has a Powder X-ray Diffraction (PXRD) pattern comprising a peak at 10.3°±0.2° (2θ). In other embodiments, the compound has an X-ray powder diffraction (PXRD) pattern comprising a peak at 4.7°±0.2° (2θ), 9.4°±0.2° (2θ), and 10.3°±0.2° (2θ). In another embodiment, the compound has an X-ray powder diffraction (PXRD) pattern comprising a peak at 4.7°±0.2° (2θ), 9.4°±0.2° (2θ), 10.3°±0.2° (2θ), and 20.1°±0.2° (2θ).

In embodiments, the compound of Formula I, I', Ia, Ib, Ic, Id, Ia', Ib', Ic', or Id' has optical rotation of about 0.30° to about 0.40°; optionally, about 0.30° to about 0.35°.

Method of Making Derivative(s) of LSD, Including Polymorph(s) Thereof

Described herein is a method for making derivatives and polymorphs of LSD. In general, the method described herein for making derivative(s) of LSD, including polymorph(s) thereof, does not use lysergic acid diethylamide (LSD) as a substrate or an intermediate. Not using a scheduled substance as a starting material or in any step of the synthesis method is beneficial as it eliminates the need for specialized controlled substance handling permits. The method produces derivatives and polymorphs of LSD intended for use in humans and thus Good Manufacturing Practices (GMP) are applicable. The method controls the levels of impurities to ensure the compounds of the invention are produced to consistently meet a predetermined specification. The method can be used on a commercial scale, that is, inter alia, safe, scalable, efficient, economically viable, and/or having other desirable properties.

In embodiments of the method for making the compounds described herein, the groups ($R^1$-$R^{14}$, and X) are defined as in the previous section and R is —$NR_1R_2$ or —$OR_1$, wherein $R_1$ and $R_2$ are each independently selected from any suitable group that such that the CO(R) group can undergo hydrolysis. $R_1$ and $R_2$ are each independently selected from H, halo group, hydroxyl group, amino group, a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic. In embodiments, $R_1$ and $R_2$ are each independently selected from H, a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic. In other embodiments, $R_1$ and $R_2$ are each independently selected from H, or a substituted or unsubstituted heteroaromatic.

In an embodiment of the method, the compounds can be made as follows:

a) a compound of Formula IA is hydrolyzed to form an intermediate of Formula IB:

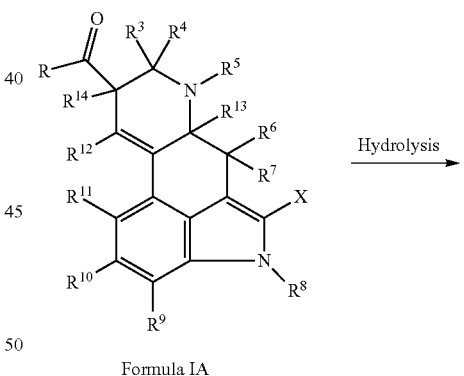

Formula IA

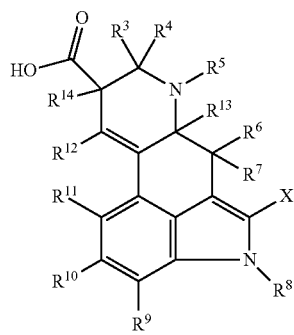

Formula IB wherein hydrolysis is acid or base hydrolysis. The substrates employed in the first step of the synthesis of these compounds may be obtained commercially or are prepared using methods well known to those skilled in the art. Hydrochloric acid, sulfuric acid, trifluoroacetic acid, formic acid, hydrofluoric acid, and/or nitric acid may be used in acid hydrolysis; however, any suitable acid may be used. Potassium hydroxide, sodium hydroxide, potassium t-butoxide, barium hydroxide, lithium hydroxide, and tetrabutylammoniun hydroxide may be used in base hydrolysis; however, any suitable base may be used. The reaction may be carried out in water-miscible solvents (e.g. alcohols (methanol, ethanol, isopropyl alcohol (IPA), etc.), acetonitrile, acetone, isopropyl acetate, THF, 2-methyl-THF, etc.) and/or heated to suitable reaction temperatures. In embodiments, the temperature ranges from about 50° C. to about 95° C. In certain embodiments, the temperature ranges from about 50° C. to about 95° C., about 60° C. to about 95° C., about 70° C. to about 95° C., about 80° C. to about 95° C., about 90° C. to about 95° C., about 50° C. to about 90° C., about 50° C. to about 80° C., about 50° C. to about 75° C., about 50° C. to about 70° C., about 50° C. to about 65° C., or about 50° C. to about 60° C.

b) the intermediate of Formula IB is reacted with $R^1$—NH—$R^2$ to form Formula IC (e.g. free base).

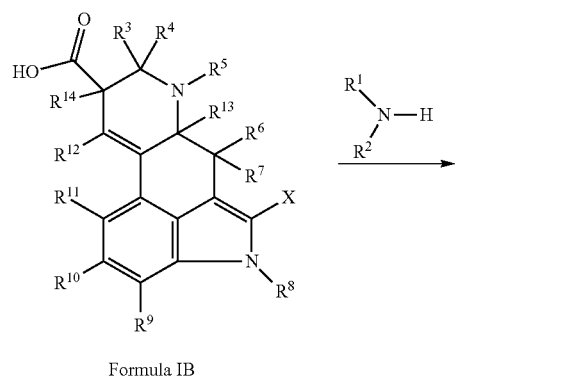

Formula IB

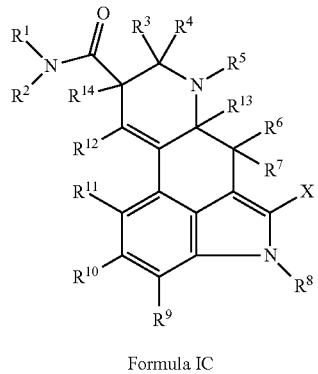

Formula IC

The hydroxyl group of the carboxylic acid may be converted to a better leaving group (LG). Any suitable leaving group can be used and, for example, can be selected from a weak base such as halides (e.g., Cl, Br, I), tosylates, mesylates, and perfluoroalkylsulfonates. In order to convert the hydroxyl group to a better leaving group to assist in the reaction with the amine ($R^1$—NH—$R^2$), any suitable reactant may be used. For example, conversion to acid chlorides may be done using phosphoryl chloride or thionyl chloride. Alternatively, the reaction may proceed with the amine ($R^1$—NH—$R^2$) under base catalyzed amide bond formation. Any suitable bases may be used. For example, using N-methylmorpholine (NMM) and 1,1'-carbonyldiimidazole (CDI) (e.g. coupling agent). The reaction may be carried out in any suitable solvent for forming a solution of reactants (e.g. THF, 2-methyl-THF, etc.). The reaction is carried out at any suitable reaction temperature. In embodiments, the temperature ranges from about 50° C. to about 95° C. In certain embodiments, the temperature ranges from about 50° C. to about 95° C., about 60° C. to about 95° C., about 70° C. to about 95° C., about 80° C. to about 95° C., about 90° C. to about 95° C., about 50° C. to about 90° C., about 50° C. to about 80° C., about 50° C. to about 75° C., about 50° C. to about 70° C., about 50° C. to about 65° C., or about 50° C. to about 60° C.

In embodiments, the reaction proceeds via base-catalyzed amide bond formation of Formula IB upon its reaction with the amine ($R^1$—NH—$R^2$), in the presence of a coupling agent. Any suitable coupling agents may be used. Coupling agents such as, and without being limited thereto, are selected from carbonyldiimidazole (CDI), 2-chloro-4,6-dimethoxy-1,3,5 triazine (CDMT), 1-hydroxybenzotriazole (HOBt), hexafluorophosphate azabenzotriazole tetramethyl uronium (HATU), propylphosphonic anhydride (T3P), phosphorous oxychloride ($POCl_3$), ethyl 2-cyano-2-(hydroxyamino) acetate (OxymaPure), benzotriazome-1-yloxy-tris-(dimethylamino)-phosphonium hexafluorophosphate (BOP), 1-[(1-(cyano-2-ethoxy-2-oxoethylindeneaminooxy) dimethylaminomorpholino)] uranium hexafluorphosphate (COMU), 2-(1H-benzotriazole-1-yl)-1,1,3,3-tetramethyluronium hexafluorophosphate (HBTU), O-(1H-6-chlorobenzotriazole-1-yl)-1,1,3,3-tetramethyluronium hexafluorophosphate (HCTU), (3-Hydroxy-3H-1,2,3-triazolo[4,5-b]pyridinato-O)tri-1-pyrrolidinyl-phosphorus hexafluorophosphate (PyAOP), (1H-benzotriazol-1-yloxy)(tri-1-pyrrolidinyl)phosphonium hexafluorophosphate (PyBOP), 6-chloro-benzotriazole-1-yloxy-tris-pyrrolidinophosphonium hexafluorophosphate (PyClock), (E)-(ethyl cyano({[tris(pyrrolidin-1-yl)phosphaniumyl]oxy}imino)formate) (PyOxim), and (5E)-6-cyano-N,N,2-trimethyl-7-oxo-4,8-dioxa-2,5-diazadec-5-en-3-iminium tetrafluoroborate (TOTU), or a combination thereof. In specific embodiments, the coupling agent is selected from carbonyldiimidazole (CDI), 2-chloro-4,6-dimethoxy-1,3,5 triazine (CDMT), 1-hydroxybenzotriazole (HOBt), hexafluorophosphate azabenzotriazole tetrameth86raniumium (HATU), propylphosphonic anhydride (T3P), phosphorous oxychloride ($POCl_3$), or a combination thereof.

In steps (a) and (b), the pH of the intermediates of Formulae IB and IC were adjusted to form a precipitate. The pH may be adjusted, for example, from about 4 to about 8 or from about 6 to about 8 (e.g. hydrochloric acid).

Formula IC may also be converted to any suitable salt or hydrate (Formula ID) where appropriate, in-situ with (b) or in a separate reaction, using any suitable organic or inorganic acid(s) such as hydrochloric acid, hydrobromic acid, nitric acid, carbonic acid, monohydrogencarbonic acid, phosphoric acid, monohydrogenphosphoric acid, dihydrogenphosphoric acid, sulfuric acid, monohydrogensulfuric acid, hydriodic acid, ethanedisulfonic acid or phosphorous acids, acetic acid, propionic acid, isobutyric acid, butyric acid, maleic acid, mandelic acid (D or L), ethane-1,2-disulfonic acid (dihydrate), toluene sulfonic acid (e.g. monohydrate), p-toluene sulfonic acid (e.g. monohydrate), 10-camphorsulfonic acid (e.g. (−)-10-camphorsulfonic acid), malic acid, malonic acid, benzoic acid, succinic acid, suberic acid, fumaric acid, lactic acid, mandelic acid, phthalic acid, benzenesulfonic acid, p-tolylsulfonic acid, citric acid, tartaric acid (L-tartaric acid or D-tartaric acid), mesotartaric acid (or erythraric acid), methanesulfonic acid, glutamic acid (L-glutamic acid or D-glutamic acid), ascorbic acid (L-ascorbic acid or D-ascorbic acid), isoascorbic acid (L-isoascorbic acid or D-isoascorbic acid), or a combination thereof or the like. With respect to the formation of suitable salts, as outlined in the definitions, the counterion can be any negatively charged group associated, for example, with the amide (e.g. Formula IC). Exemplary counterions include halide ions (e.g., $F^-$, $Cl^-$, $Br^-$, $I^-$) $NO_3^-$, $ClO_4^-$, $OH^-$, $H_2PO_4^-$, $HSO_4^-$, $^-BF_4$, $^-PF_6$, sulfonate ions, and carboxylate ions (e.g., acetate, ascorbate, ethanoate, isoascorbate, propanoate, benzoate, glycerate, lactate, tartrate, glutamate, glycolate, and the like). The reaction may occur in any suitable solvent, such as but not limited to, water-miscible solvents (e.g. alcohols (methanol, ethanol, isopropyl alcohol (IPA), etc.), acetonitrile, acetone, isopropyl acetate, THF, 2-methyl-THF, etc.).

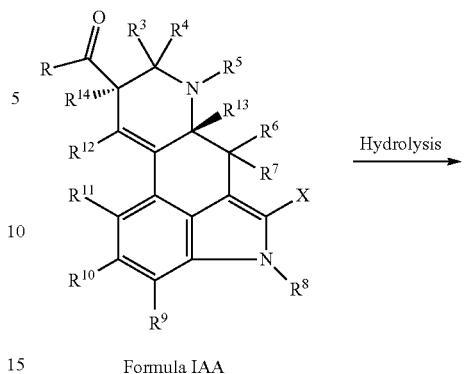

In embodiments, the temperature ranges from about 50° C. to about 95° C. In certain embodiments, the temperature ranges from about 50° C. to about 95° C., about 60° C. to about 95° C., about 70° C. to about 95° C., about 80° C. to about 95° C., about 90° C. to about 95° C., about 50° C. to about 90° C., about 50° C. to about 80° C., about 50° C. to about 75° C., about 50° C. to about 70° C., about 50° C. to about 65° C., or about 60° C. to about 65° C. In embodiments, heating the compound of Formula IC with the organic or inorganic acid is heated for any suitable time (e.g. about 30 minutes to about 1 hour). It may then be cooled, for example, to about room temperature. In other embodiments, cooled to about 0 to about 10° C., optionally, about 3 to about 7° C., optionally about 5° C., and optionally for about 30 minutes to about 2 h.

In another embodiment of the method for making the compounds described herein, the compounds can be made as follows and the groups (R, $R^1$-$R^{14}$, and X) are defined as in the previous section:

a) a compound of Formula IAA (5R,8R) is hydrolyzed to form an intermediate of Formula IBB:

wherein hydrolysis is acid or base hydrolysis. The substrates employed in the first step of the synthesis of these compounds may be obtained commercially or are prepared using methods well known to those skilled in the art. Hydrochloric acid, sulfuric acid, trifluoroacetic acid, formic acid, hydrofluoric acid, and/or nitric acid may be used in acid hydrolysis; however, any suitable acid may be used. Potassium hydroxide, sodium hydroxide, potassium t-butoxide, barium hydroxide, lithium hydroxide, and tetrabutylammoniun hydroxide may be used in base hydrolysis; however, any suitable base may be used. The reaction may be carried out in water-miscible solvents (e.g. alcohols (methanol, ethanol, isopropyl alcohol (IPA), etc.), acetonitrile, acetone, isopropyl acetate, THF, 2-methyl-THF, etc.) and/or heated to suitable reaction temperatures. In embodiments, the temperature ranges from about 50° C. to about 95° C. In certain embodiments, the temperature ranges from about 50° C. to about 95° C., about 60° C. to about 95° C., about 70° C. to about 95° C., about 80° C. to about 95° C., about 90° C. to about 95° C., about 50° C. to about 90° C., about 50° C. to about 80° C., about 50° C. to about 75° C., about 50° C. to about 70° C., about 50° C. to about 65° C., or about 50° C. to about 60° C.

b) the intermediate of Formula IBB is reacted with $R^1$—NH—$R^2$ to form Formula ICC (e.g. free base).

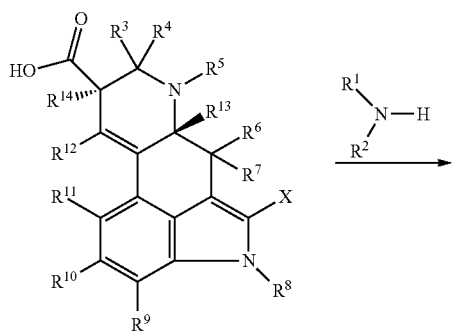

Formula IBB

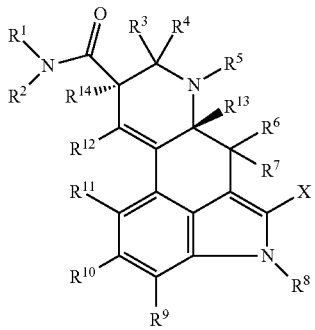

Formula ICC

The hydroxyl group of the carboxylic acid may be converted to a better leaving group (LG). Any suitable leaving group can be used and, for example, can be selected from a weak base such as halides (e.g., Cl, Br, I), tosylates, mesylates, and perfluoroalkylsulfonates. In order to convert the hydroxyl group to a better leaving group to assist in the reaction with the amine ($R^1$—NH—$R^2$), any suitable reactant may be used. For example, conversion to acid chlorides may be done using phosphoryl chloride or thionyl chloride. Alternatively, the reaction may proceed with the amine ($R^1$—NH—$R^2$) under base catalyzed amide bond formation. Any suitable bases may be used. For example, using N-methylmorpholine (NMM) and 1,1'-carbonyldiimidazole (CDI) (e.g. coupling agent). The reaction may be carried out in any suitable solvent for forming a solution of reactants (e.g. THF, 2-methyl-THF, etc.). The reaction is carried out at any suitable reaction temperature. In embodiments, the temperature ranges from about 50° C. to about 95° C. In certain embodiments, the temperature ranges from about 50° C. to about 95° C., about 60° C. to about 95° C., about 70° C. to about 95° C., about 80° C. to about 95° C., about 90° C. to about 95° C., about 50° C. to about 90° C., about 50° C. to about 80° C., about 50° C. to about 75° C., about 50° C. to about 70° C., about 50° C. to about 65° C., or about 50° C. to about 60° C.

In embodiments, the reaction proceeds via base-catalyzed amide bond formation of Formula IBB upon its reaction with the amine ($R^1$—NH—$R^2$), in the presence of a coupling agent. Any suitable coupling agents may be used. Coupling agents such as, and without being limited thereto, are selected from carbonyldiimidazole (CDI), 2-chloro-4,6-dimethoxy-1,3,5 triazine (CDMT), 1-hydroxybenzotriazole (HOBt), hexafluorophosphate azabenzotriazole tetramethyl uroniumium (HATU), propylphosphonic anhydride (T3P), phosphorous oxychloride (POCl$_3$), ethyl 2-cyano-2-(hydroxyamino) acetate (OxymaPure), benzotriazome-1-yl-oxy-tris-(dimethylamino)-phosphonium hexafluorophosphate (BOP), 1-[(1-(cyano-2-ethoxy-2-oxo-ethylindeneaminooxy) dimethylaminomorpholino)] uranium hexafluorphosphate (COMU), 2-(1H-benzotriazole-1-yl)-1,1,3,3-tetramethyluronium hexafluorophosphate (HBTU), O-(1H-6-chlorobenzotriazole-1-yl)-1,1,3,3-tetramethyluronium hexafluorophosphate (HCTU), (3-Hydroxy-3H-1,2,3-triazolo[4,5-b]pyridinato-O)tri-1-pyrrolidinyl-phosphorus hexafluorophosphate (PyAOP), (1H-benzotriazol-1-yloxy)(tri-1-pyrrolidinyl)phosphonium hexafluorophosphate (PyBOP), 6-chloro-benzotriazole-1-yloxy-tris-pyrrolidinophosphonium hexafluorophosphate (PyClock), (E)-(ethyl cyano({[tris(pyrrolidin-1-yl)phosphaniumyl]oxy}imino)formate) (PyOxim), and (5E)-6-cyano-N,N,2-trimethyl-7-oxo-4,8-dioxa-2,5-diazadec-5-en-3-iminium tetrafluoroborate (TOTU), or a combination thereof. In specific embodiments, the coupling agent is selected from carbonyldiimidazole (CDI), 2-chloro-4,6-dimethoxy-1,3,5 triazine (CDMT), 1-hydroxybenzotriazole (HOBt), hexafluorophosphate azabenzotriazole tetrameth90raniumium (HATU), propylphosphonic anhydride (T3P), phosphorous oxychloride (POCl$_3$), or a combination thereof.

In steps (a) and (b), the acidity of the intermediates of Formulae IBB and ICC were adjusted to form a precipitate. The pH may be adjusted, for example, from about 6 to about 8 with an acid (e.g. hydrochloric acid).

Formula ICC may also be converted to any suitable salt or hydrate (Formula IDD) where appropriate, in-situ with (b) or in a separate reaction, using any suitable organic or inorganic acid(s) such as hydrochloric acid, hydrobromic acid, nitric acid, carbonic acid, monohydrogencarbonic acid, phosphoric acid, monohydrogenphosphoric acid, dihydrogenphosphoric acid, sulfuric acid, monohydrogensulfuric acid, hydriodic acid, ethanedisulfonic acid or phosphorous acids, acetic acid, propionic acid, isobutyric acid, butyric acid, maleic acid, mandelic acid (D or L), ethane-1,2-disulfonic acid (dihydrate), toluene sulfonic acid (e.g. monohydrate), p-toluene sulfonic acid (e.g. monohydrate), 10-camphorsulfonic acid (e.g. (−)-10-camphorsulfonic acid), malic acid, malonic acid, benzoic acid, succinic acid, suberic acid, fumaric acid, lactic acid, mandelic acid, phthalic acid, benzenesulfonic acid, p-tolylsulfonic acid, citric acid, tartaric acid (L-tartaric acid or D-tartaric acid), mesotartaric acid (or erythraric acid), methanesulfonic acid, glutamic acid (L-glutamic acid or D-glutamic acid), ascorbic acid (L-ascorbic acid or D-ascorbic acid), isoascorbic acid (L-isoascorbic acid or D-isoascorbic acid), or a combination thereof or the like. With respect to the formation of suitable salts, as outlined in the definitions, the counterion can be any negatively charged group associated, for example, with the amide (e.g. Formula IC). Exemplary counterions include halide ions (e.g., $F^-$, $Cl^-$, $Br^-$, $I^-$) $NO_3^-$, $ClO_4^-$, $OH^-$, $H_2PO_4^-$, $HSO_4^-$, $^-BF_4$, $^-PF_6$, sulfonate ions, and carboxylate ions (e.g., acetate, ascorbate, ethanoate, isoascorbate, propanoate, benzoate, glycerate, lactate, tartrate, glutamate, glycolate, and the like). The reaction may occur in any suitable solvent, such as but not limited to, water-miscible solvents (e.g. alcohols (methanol, ethanol, isopropyl alcohol (IPA), etc.), acetonitrile, acetone, isopropyl acetate, THF, 2-methyl-THF, etc.).

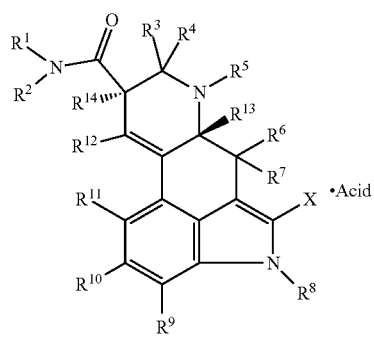

Formula IDD

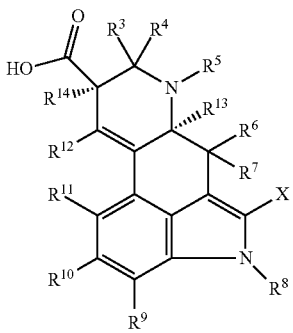

Formula IBB'

In embodiments, the temperature ranges from about 50° C. to about 95° C. In certain embodiments, the temperature ranges from about 50° C. to about 95° C., about 60° C. to about 95° C., about 70° C. to about 95° C., about 80° C. to about 95° C., about 90° C. to about 95° C., about 50° C. to about 90° C., about 50° C. to about 80° C., about 50° C. to about 75° C., about 50° C. to about 70° C., about 50° C. to about 65° C., or about 60° C. to about 65° C. In embodiments, heating the compound of Formula ICC with the organic or inorganic acid is heated for any suitable time (e.g. about 30 minutes to about 1 hour). It may then be cooled, for example, to about room temperature. In other embodiments, cooled to about 0 to about 10° C., optionally, about 3 to about 7° C., optionally about 5° C., and optionally for about 30 minutes to about 2 h.

In another embodiment of the method for making the compounds described herein, the compounds can be made as follows and the groups (R, $R^1$-$R^{14}$, and X) are defined as in the previous section:

a) a compound of Formula IAA' (5S,8R) is hydrolyzed to form an intermediate of Formula IBB':

wherein hydrolysis is acid or base hydrolysis. The substrates employed in the first step of the synthesis of these compounds may be obtained commercially or are prepared using methods well known to those skilled in the art. Hydrochloric acid, sulfuric acid, trifluoroacetic acid, formic acid, hydrofluoric acid, and/or nitric acid may be used in acid hydrolysis; however, any suitable acid may be used. Potassium hydroxide, sodium hydroxide, potassium t-butoxide, barium hydroxide, lithium hydroxide, and tetrabutylammoniun hydroxide may be used in base hydrolysis; however, any suitable base may be used. The reaction may be carried out in water-miscible solvents (e.g. alcohols (methanol, ethanol, isopropyl alcohol (IPA), etc.), acetonitrile, acetone, isopropyl acetate, THF, 2-methyl-THF, etc.) and/or heated to suitable reaction temperatures. In embodiments, the temperature ranges from about 50° C. to about 95° C. In certain embodiments, the temperature ranges from about 50° C. to about 95° C., about 60° C. to about 95° C., about 70° C. to about 95° C., about 80° C. to about 95° C., about 90° C. to about 95° C., about 50° C. to about 90° C., about 50° C. to about 80° C., about 50° C. to about 75° C., about 50° C. to about 70° C., about 50° C. to about 65° C., or about 50° C. to about 60° C.

b) the intermediate of Formula IBB' is reacted with $R^1$—NH—$R^2$ to form Formula ICC' (e.g. free base).

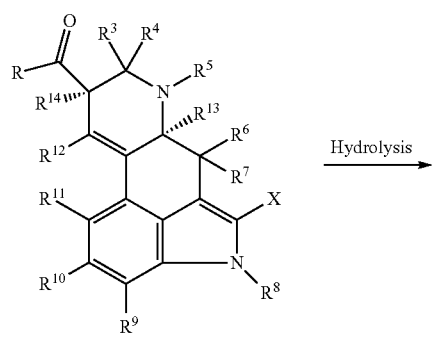

Formula IAA'

Hydrolysis

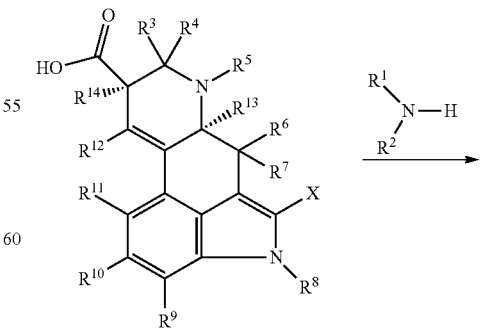

Formula IBB'

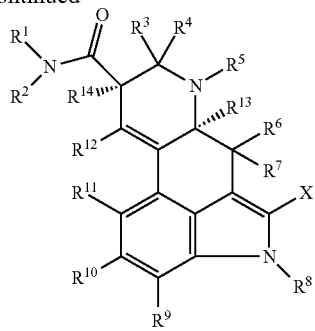

Formula ICC'

The hydroxyl group of the carboxylic acid may be converted to a better leaving group (LG). Any suitable leaving group can be used and, for example, can be selected from a weak base such as halides (e.g., Cl, Br, I), tosylates, mesylates, and perfluoroalkylsulfonates. In order to convert the hydroxyl group to a better leaving group to assist in the reaction with the amine ($R^1$—NH—$R^2$), any suitable reactant may be used. For example, conversion to acid chlorides may be done using phosphoryl chloride or thionyl chloride. Alternatively, the reaction may proceed with the amine ($R^1$—NH—$R^2$) under base catalyzed amide bond formation. Any suitable bases may be used. For example, using N-methylmorpholine (NMM) and 1,1'-carbonyldiimidazole (CDI) (e.g. coupling agent). The reaction may be carried out in any suitable solvent for forming a solution of reactants (e.g. THF, 2-methyl-THF, etc.). The reaction is carried out at any suitable reaction temperature. In embodiments, the temperature ranges from about 50° C. to about 95° C. In certain embodiments, the temperature ranges from about 50° C. to about 95° C., about 60° C. to about 95° C., about 70° C. to about 95° C., about 80° C. to about 95° C., about 90° C. to about 95° C., about 50° C. to about 90° C., about 50° C. to about 80° C., about 50° C. to about 75° C., about 50° C. to about 70° C., about 50° C. to about 65° C., or about 50° C. to about 60° C.

In embodiments, the reaction proceeds via base-catalyzed amide bond formation of Formula IBB' upon its reaction with the amine ($R^1$—NH—$R^2$), in the presence of a coupling agent. Any suitable coupling agents may be used. Coupling agents such as, and without being limited thereto, are selected from carbonyldiimidazole (CDI), 2-chloro-4,6-dimethoxy-1,3,5 triazine (CDMT), 1-hydroxybenzotriazole (HOBt), hexafluorophosphate azabenzotriazole tetramethyl uronium (HATU), propylphosphonic anhydride (T3P), phosphorous oxychloride (POCl$_3$), ethyl 2-cyano-2-(hydroxyamino) acetate (OxymaPure), benzotriazome-1-yloxy-tris-(dimethylamino)-phosphonium hexafluorophosphate (BOP), 1-[(1-(cyano-2-ethoxy-2-oxoethylindeneaminooxy) dimethylaminomorpholino)] uranium hexafluorphosphate (COMU), 2-(1H-benzotriazole-1-yl)-1,1,3,3-tetramethyluronium hexafluorophosphate (HBTU), O-(1H-6-chlorobenzotriazole-1-yl)-1,1,3,3-tetramethyluronium hexafluorophosphate (HCTU), (3-Hydroxy-3H-1,2,3-triazolo[4,5-b]pyridinato-O)tri-1-pyrrolidinyl-phosphorus hexafluorophosphate (PyAOP), (1H-benzotriazol-1-yloxy)(tri-1-pyrrolidinyl)phosphonium hexafluorophosphate (PyBOP), 6-chloro-benzotriazole-1-yloxy-tris-pyrrolidinophosphonium hexafluorophosphate (PyClock), (E)-(ethyl cyano({[tris(pyrrolidin-1-yl)phosphaniumyl]oxy}imino)formate) (PyOxim), and (5E)-6-cyano-N,N,2-trimethyl-7-oxo-4,8-dioxa-2,5-diazadec-5-en-3-iminium tetrafluoroborate (TOTU), or a combination thereof. In specific embodiments, the coupling agent is selected from carbonyldiimidazole (CDI), 2-chloro-4,6-dimethoxy-1,3,5 triazine (CDMT), 1-hydroxybenzotriazole (HOBt), hexafluorophosphate azabenzotriazole tetrameth94raniumium (HATU), propylphosphonic anhydride (T3P), phosphorous oxychloride (POCl$_3$), or a combination thereof.

In steps (a) and (b), the acidity of the intermediates of Formulae IBB' and ICC' were adjusted to form a precipitate. The pH may be adjusted, for example, from about 6 to about 8 with an acid (e.g. hydrochloric acid).

Formula ICC' may also be converted to any suitable salt or hydrate (Formula IDD') where appropriate, in-situ with (b) or in a separate reaction, using any suitable organic or inorganic acid(s) such as hydrochloric acid, hydrobromic acid, nitric acid, carbonic acid, monohydrogencarbonic acid, phosphoric acid, monohydrogenphosphoric acid, dihydrogenphosphoric acid, sulfuric acid, monohydrogensulfuric acid, hydriodic acid, ethanedisulfonic acid or phosphorous acids, acetic acid, propionic acid, isobutyric acid, butyric acid, maleic acid, mandelic acid (D or L), ethane-1,2-disulfonic acid (dihydrate), toluene sulfonic acid (e.g. monohydrate), p-toluene sulfonic acid (e.g. monohydrate), 10-camphorsulfonic acid (e.g. (–)-10-camphorsulfonic acid), malic acid, malonic acid, benzoic acid, succinic acid, suberic acid, fumaric acid, lactic acid, mandelic acid, phthalic acid, benzenesulfonic acid, p-tolylsulfonic acid, citric acid, tartaric acid (L-tartaric acid or D-tartaric acid), mesotartaric acid (or erythraric acid), methanesulfonic acid, glutamic acid (L-glutamic acid or D-glutamic acid), ascorbic acid (L-ascorbic acid or D-ascorbic acid), isoascorbic acid (L-isoascorbic acid or D-isoascorbic acid), or a combination thereof or the like. With respect to the formation of suitable salts, as outlined in the definitions, the counterion can be any negatively charged group associated, for example, with the amide (e.g. Formula IC). Exemplary counterions include halide ions (e.g., F$^-$, Cl$^-$, Br$^-$, I$^-$) NO$_3^-$, ClO$_4^-$, OH$^-$, H$_2$PO$_4^-$, HSO$_4^-$, $^-$BF$_4$, $^-$PF$_6$, sulfonate ions, and carboxylate ions (e.g., acetate, ascorbate, ethanoate, isoascorbate, propanoate, benzoate, glycerate, lactate, tartrate, glutamate, glycolate, and the like). The reaction may occur in any suitable solvent, such as but not limited to, water-miscible solvents (e.g. alcohols (methanol, ethanol, isopropyl alcohol (IPA), etc.), acetonitrile, acetone, isopropyl acetate, THF, 2-methyl-THF, etc.).

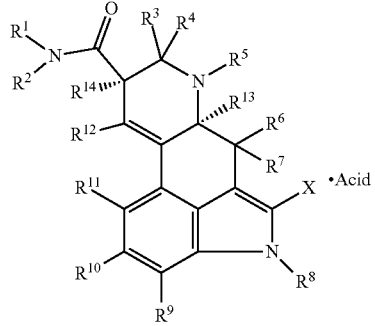

Formula IDD'

In embodiments, the temperature ranges from about 50° C. to about 95° C. In certain embodiments, the temperature ranges from about 50° C. to about 95° C., about 60° C. to about 95° C., about 70° C. to about 95° C., about 80° to about 95° C., about 90° C. to about 95° C., about 50° C. to about 90° C., about 50° C. to about 80° C., about 50° C. to about 75° C., about 50° C. to about 70° C., about 50° C. to about 65° C., or about 60° C. to about 65° C. In embodiments, heating the compound of Formula ICC' with the organic or inorganic acid is heated for any suitable time (e.g. about 30 minutes to about 1 hour). It may then be cooled, for example, to about room temperature. In other embodiments, cooled to about 0 to about 10° C., optionally, about 3 to about 7° C., optionally about 5° C., and optionally for about 30 minutes to about 2 h.

In another embodiment of the method for making the compounds described herein, the compounds can be made as follows and the groups (R, $R^1$-$R^{15}$, and X) are defined as in the previous section:

a) a compound of Formula IAA" (5S,8S) is hydrolyzed to form an intermediate of Formula IBB":

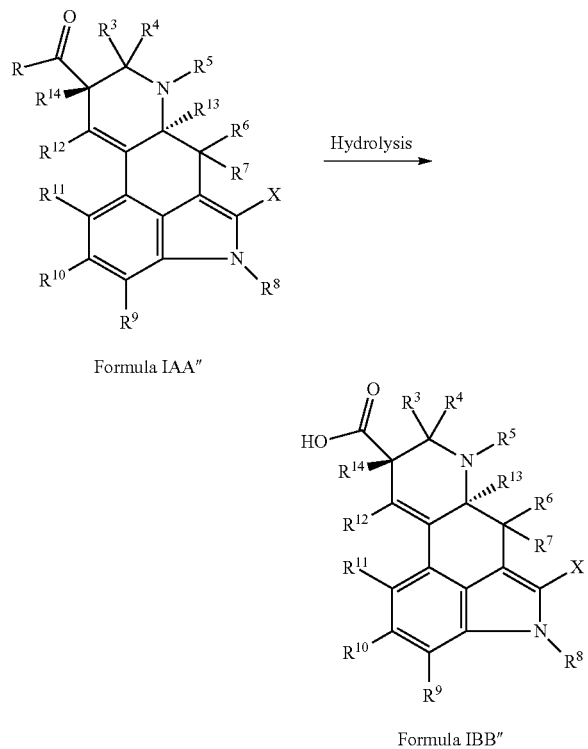

Formula IAA"

Formula IBB"

wherein hydrolysis is acid or base hydrolysis. The substrates employed in the first step of the synthesis of these compounds may be obtained commercially or are prepared using methods well known to those skilled in the art. Hydrochloric acid, sulfuric acid, trifluoroacetic acid, formic acid, hydrofluoric acid, and/or nitric acid may be used in acid hydrolysis; however, any suitable acid may be used. Potassium hydroxide, sodium hydroxide, potassium t-butoxide, barium hydroxide, lithium hydroxide, and tetrabutylammoniun hydroxide may be used in base hydrolysis; however, any suitable base may be used. The reaction may be carried out in water-miscible solvents (e.g. alcohols (methanol, ethanol, isopropyl alcohol (IPA), etc.), acetonitrile, acetone, isopropyl acetate, THF, 2-methyl-THF, etc.) and/or heated to suitable reaction temperatures. In embodiments, the temperature ranges from about 50° C. to about 95° C. In certain embodiments, the temperature ranges from about 50° C. to about 95° C., about 60° C. to about 95° C., about 70° C. to about 95° C., about 80° C. to about 95° C., about 90° C. to about 95° C., about 50° C. to about 90° C., about 50° C. to about 80° C., about 50° C. to about 75° C., about 50° C. to about 70° C., about 50° C. to about 65° C., or about 50° C. to about 60° C.

b) the intermediate of Formula IBB" is reacted with $R^1$—NH—$R^2$ to form Formula ICC" (e.g. free base).

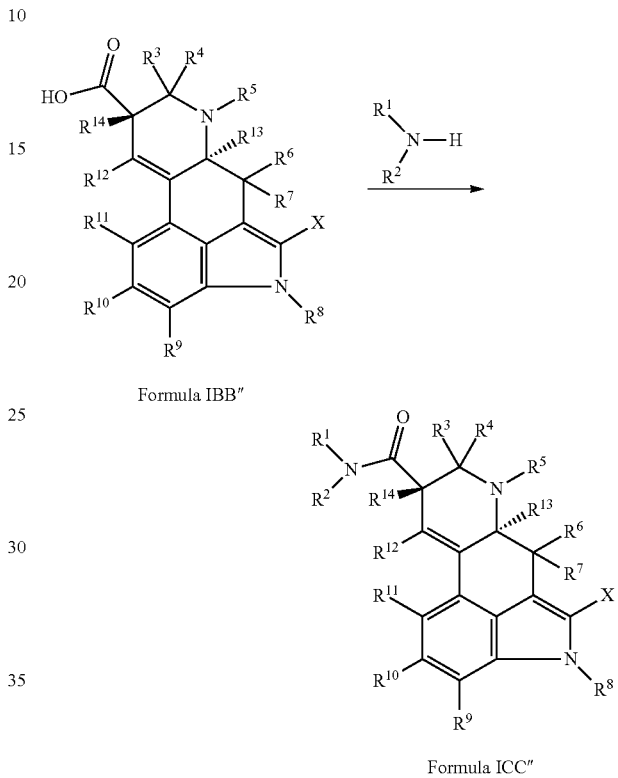

Formula IBB"

Formula ICC"

The hydroxyl group of the carboxylic acid may be converted to a better leaving group (LG). Any suitable leaving group can be used and, for example, can be selected from a weak base such as halides (e.g., Cl, Br, I), tosylates, mesylates, and perfluoroalkylsulfonates. In order to convert the hydroxyl group to a better leaving group to assist in the reaction with the amine ($R^1$—NH—$R^2$), any suitable reactant may be used. For example, conversion to acid chlorides may be done using phosphoryl chloride or thionyl chloride. Alternatively, the reaction may proceed with the amine ($R^1$—NH—$R^2$) under base catalyzed amide bond formation. Any suitable bases may be used. For example, using N-methylmorpholine (NMM) and 1,1'-carbonyldiimidazole (CDI) (e.g. coupling agent). The reaction may be carried out in any suitable solvent for forming a solution of reactants (e.g. THF, 2-methyl-THF, etc.). The reaction is carried out at any suitable reaction temperature. In embodiments, the temperature ranges from about 50° C. to about 95° C. In certain embodiments, the temperature ranges from about 50° C. to about 95° C., about 60° C. to about 95° C., about 70° C. to about 95° C., about 80° C. to about 95° C., about 90° C. to about 95° C., about 50° C. to about 90° C., about 50° C. to about 80° C., about 50° C. to about 75° C., about 50° C. to about 70° C., about 50° C. to about 65° C., or about 50° C. to about 60° C.

In embodiments, the reaction proceeds via base-catalyzed amide bond formation of Formula IBB" upon its reaction with the amine (R¹—NH—R²), in the presence of a coupling agent. Any suitable coupling agents may be used. Coupling agents such as, and without being limited thereto, are selected from carbonyldiimidazole (CDI), 2-chloro-4,6-dimethoxy-1,3,5 triazine (CDMT), 1-hydroxybenzotriazole (HOBt), hexafluorophosphate azabenzotriazole tetramethyl uronium (HATU), propylphosphonic anhydride (T3P), phosphorous oxychloride ($POCl_3$), ethyl 2-cyano-2-(hydroxyamino) acetate (OxymaPure), benzotriazome-1-yloxy-tris-(dimethylamino)-phosphonium hexafluorophosphate (BOP), 1-[(1-(cyano-2-ethoxy-2-oxo-ethylindeneaminooxy) dimethylaminomorpholino)] uranium hexafluorphosphate (COMU), 2-(1H-benzotriazole-1-yl)-1,1,3,3-tetramethyluronium hexafluorophosphate (HBTU), O-(1H-6-chlorobenzotriazole-1-yl)-1,1,3,3-tetramethyluronium hexafluorophosphate (HCTU), (3-Hydroxy-3H-1,2,3-triazolo[4,5-b]pyridinato-O)tri-1-pyrrolidinyl-phosphorus hexafluorophosphate (PyAOP), (1H-benzotriazol-1-yloxy)(tri-1-pyrrolidinyl)phosphonium hexafluorophosphate (PyBOP), 6-chloro-benzotriazole-1-yloxy-tris-pyrrolidinophosphonium hexafluorophosphate (PyClock), (E)-(ethyl cyano({[tris(pyrrolidin-1-yl)phosphaniumyl]oxy}imino)formate) (PyOxim), and (5E)-6-cyano-N,N,2-trimethyl-7-oxo-4,8-dioxa-2,5-diazadec-5-en-3-iminium tetrafluoroborate (TOTU), or a combination thereof. In specific embodiments, the coupling agent is selected from carbonyldiimidazole (CDI), 2-chloro-4,6-dimethoxy-1,3,5 triazine (CDMT), 1-hydroxybenzotriazole (HOBt), hexafluorophosphate azabenzotriazole tetrameth98raniumium (HATU), propylphosphonic anhydride (T3P), phosphorous oxychloride ($POCl_3$), or a combination thereof.

In steps (a) and (b), the acidity of the intermediates of Formulae IBB" and ICC" were adjusted to form a precipitate. The pH may be adjusted, for example, from about 6 to about 8 with an acid (e.g. hydrochloric acid).

Formula ICC" may also be converted to any suitable salt or hydrate (Formula IDD") where appropriate, in-situ with (b) or in a separate reaction, using any suitable organic or inorganic acid(s) such as hydrochloric acid, hydrobromic acid, nitric acid, carbonic acid, monohydrogencarbonic acid, phosphoric acid, monohydrogenphosphoric acid, dihydrogenphosphoric acid, sulfuric acid, monohydrogensulfuric acid, hydriodic acid, ethanedisulfonic acid or phosphorous acids, acetic acid, propionic acid, isobutyric acid, butyric acid, maleic acid, mandelic acid (D or L), ethane-1,2-disulfonic acid (dihydrate), toluene sulfonic acid (e.g. monohydrate), p-toluene sulfonic acid (e.g. monohydrate), 10-camphorsulfonic acid (e.g. (−)-10-camphorsulfonic acid), malic acid, malonic acid, benzoic acid, succinic acid, suberic acid, fumaric acid, lactic acid, mandelic acid, phthalic acid, benzenesulfonic acid, p-tolylsulfonic acid, citric acid, tartaric acid (L-tartaric acid or D-tartaric acid), mesotartaric acid (or erythraric acid), methanesulfonic acid, glutamic acid (L-glutamic acid or D-glutamic acid), ascorbic acid (L-ascorbic acid or D-ascorbic acid), isoascorbic acid (L-isoascorbic acid or D-isoascorbic acid), or a combination thereof or the like. With respect to the formation of suitable salts, as outlined in the definitions, the counterion can be any negatively charged group associated, for example, with the amide (e.g. Formula IC). Exemplary counterions include halide ions (e.g., $F^-$, $Cl^-$, $Br^-$, $I^-$) $NO_3^-$, $ClO_4^-$, $OH^-$, $H_2PO_4^-$, $HSO_4^-$, $^-BF_4$, $^-PF_6$, sulfonate ions, and carboxylate ions (e.g., acetate, ascorbate, ethanoate, isoascorbate, propanoate, benzoate, glycerate, lactate, tartrate, glutamate, glycolate, and the like). The reaction may occur in any suitable solvent, such as but not limited to, water-miscible solvents (e.g. alcohols (methanol, ethanol, isopropyl alcohol (IPA), etc.), acetonitrile, acetone, isopropyl acetate, THF, 2-methyl-THF, etc.).

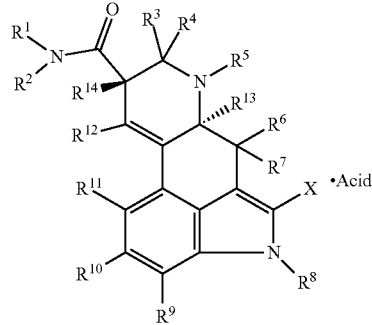

Formula IDD"

In embodiments, the temperature ranges from about 50° C. to about 95° C. In certain embodiments, the temperature ranges from about 50° C. to about 95° C., about 60° C. to about 95° C., about 70° C. to about 95° C., about 80° C. to about 95° C., about 90° C. to about 95° C., about 50° C. to about 90° C., about 50° C. to about 80° C., about 50° C. to about 75° C., about 50° C. to about 70° C., about 50° C. to about 65° C., or about 60° C. to about 65° C. In embodiments, heating the compound of Formula ICC" with the organic or inorganic acid is heated for any suitable time (e.g. about 30 minutes to about 1 hour). It may then be cooled, for example, to about room temperature. In other embodiments, cooled to about 0 to about 10° C., optionally, about 3 to about 7° C., optionally about 5° C., and optionally for about 30 minutes to about 2 h.

In another embodiment of the method for making the compounds described herein, the compounds can be made as follows and the groups (R, $R^1$-$R^{14}$, and X) are defined as in the previous section:

a) a compound of Formula IAA'''(5S,8R) is hydrolyzed to form an intermediate of Formula IBB''':

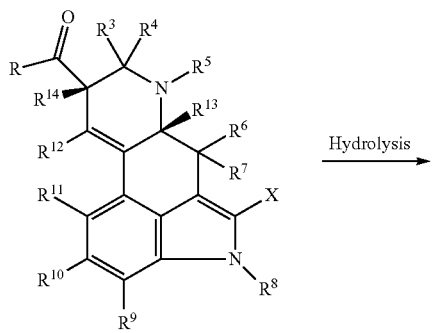

Formula IAA'''

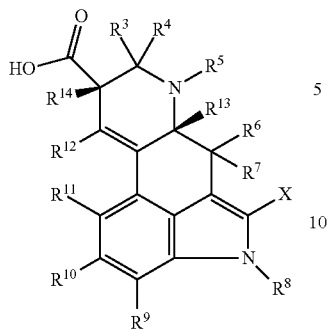

Formula IBB'''

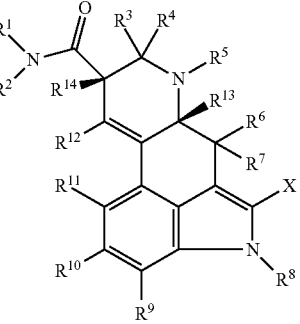

Formula ICC'''' wherein hydrolysis is acid or base hydrolysis. The substrates employed in the first step of the synthesis of these compounds may be obtained commercially or are prepared using methods well known to those skilled in the art. Hydrochloric acid, sulfuric acid, trifluoroacetic acid, formic acid, hydrofluoric acid, and/or nitric acid may be used in acid hydrolysis; however, any suitable acid may be used. Potassium hydroxide, sodium hydroxide, potassium t-butoxide, barium hydroxide, lithium hydroxide, and tetrabutylammoniun hydroxide may be used in base hydrolysis; however, any suitable base may be used. The reaction may be carried out in water-miscible solvents (e.g. alcohols (methanol, ethanol, isopropyl alcohol (IPA), etc.), acetonitrile, acetone, isopropyl acetate, THF, 2-methyl-THF, etc.) and/or heated to suitable reaction temperatures. In embodiments, the temperature ranges from about 50° C. to about 95° C. In certain embodiments, the temperature ranges from about 50° C. to about 95° C., about 60° C. to about 95° C., about 70° C. to about 95° C., about 80° C. to about 95° C., about 90° C. to about 95° C., about 50° C. to about 90° C., about 50° C. to about 80° C., about 50° C. to about 75° C., about 50° C. to about 70° C., about 50° C. to about 65° C., or about 50° C. to about 60° C.

b) the intermediate of Formula IBB''' is reacted with $R^1$—NH—$R^2$ to form Formula ICC''''(e.g. free base).

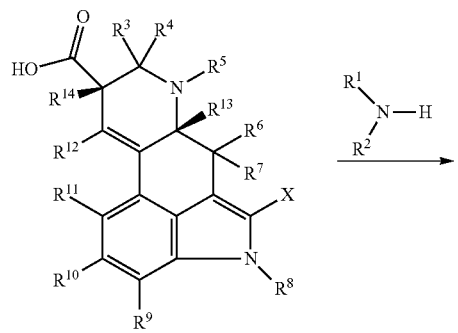

Formula IBB'''

The hydroxyl group of the carboxylic acid may be converted to a better leaving group (LG). Any suitable leaving group can be used and, for example, can be selected from a weak base such as halides (e.g., Cl, Br, I), tosylates, mesylates, and perfluoroalkylsulfonates. In order to convert the hydroxyl group to a better leaving group to assist in the reaction with the amine ($R^1$—NH—$R^2$), any suitable reactant may be used. For example, conversion to acid chlorides may be done using phosphoryl chloride or thionyl chloride. Alternatively, the reaction may proceed with the amine ($R^1$—NH—$R^2$) under base catalyzed amide bond formation. Any suitable bases may be used. For example, using N-methylmorpholine (NMM) and 1,1'-carbonyldiimidazole (CDI) (e.g. coupling agent). The reaction may be carried out in any suitable solvent for forming a solution of reactants (e.g. THF, 2-methyl-THF, etc.). The reaction is carried out at any suitable reaction temperature. In embodiments, the temperature ranges from about 50° C. to about 95° C. In certain embodiments, the temperature ranges from about 50° C. to about 95° C., about 60° C. to about 95° C., about 70° C. to about 95° C., about 80° C. to about 95° C., about 90° C. to about 95° C., about 50° C. to about 90° C., about 50° C. to about 80° C., about 50° C. to about 75° C., about 50° C. to about 70° C., about 50° C. to about 65° C., or about 50° C. to about 60° C.

In embodiments, the reaction proceeds via base-catalyzed amide bond formation of Formula IBB''' upon its reaction with the amine ($R^1$—NH—$R^2$), in the presence of a coupling agent. Any suitable coupling agents may be used. Coupling agents such as, and without being limited thereto, are selected from carbonyldiimidazole (CDI), 2-chloro-4,6-dimethoxy-1,3,5 triazine (CDMT), 1-hydroxybenzotriazole (HOBt), hexafluorophosphate azabenzotriazole tetramethyl uronium (HATU), propylphosphonic anhydride (T3P), phosphorous oxychloride ($POCl_3$), ethyl 2-cyano-2-(hydroxyamino) acetate (OxymaPure), benzotriazome-1-yloxy-tris-(dimethylamino)-phosphonium hexafluorophosphate (BOP), 1-[(1-(cyano-2-ethoxy-2-oxoethylindeneaminooxy) dimethylaminomorpholino)] uranium hexafluorphosphate (COMU), 2-(1H-benzotriazole-1-yl)-1,1,3,3-tetramethyluronium hexafluorophosphate (HBTU), O-(1H-6-chlorobenzotriazole-1-yl)-1,1,3,3-tetramethyluronium hexafluorophosphate (HCTU), (3-Hydroxy-3H-1,2,3-triazolo[4,5-b]pyridinato-O)tri-1-pyrrolidinyl-phosphorus hexafluorophosphate (PyAOP), (1H-benzotriazol-1-yloxy)(tri-1-pyrrolidinyl)phosphonium hexafluorophosphate (PyBOP), 6-chloro-benzotriazole-1-yloxy-tris-pyrrolidinophosphonium hexafluorophosphate (PyClock), (E)-(ethyl cyano({[tris(pyrrolidin-1-yl)phosphaniumyl]oxy}imino)formate) (PyOxim), and (5E)-6-cyano- N,N,2-trimethyl-7-oxo-4,8-dioxa-2,5-diazadec-5-en-3-iminium tetrafluoroborate (TOTU), or a combination thereof. In specific embodiments, the coupling agent is selected from carbonyldiimidazole (CDI), 2-chloro-4,6-dimethoxy-1,3,5 triazine (CDMT), 1-hydroxybenzotriazole (HOBt), hexafluorophosphate azabenzotriazole tetrameth102raniumium (HATU), propylphosphonic anhydride (T3P), phosphorous oxychloride ($POCl_3$), or a combination thereof.

In steps (a) and (b), the acidity of the intermediates of Formulae IBB" and ICC" were adjusted to form a precipitate. The pH may be adjusted, for example, from about 6 to about 8 with an acid (e.g. hydrochloric acid).

Formula ICC''' may also be converted to any suitable salt or hydrate (Formula IDD''') where appropriate, in-situ with (b) or in a separate reaction, using any suitable organic or inorganic acid(s) such as hydrochloric acid, hydrobromic acid, nitric acid, carbonic acid, monohydrogencarbonic acid, phosphoric acid, monohydrogenphosphoric acid, dihydrogenphosphoric acid, sulfuric acid, monohydrogensulfuric acid, hydriodic acid, ethanedisulfonic acid or phosphorous acids, acetic acid, propionic acid, isobutyric acid, butyric acid, maleic acid, mandelic acid (D or L), ethane-1,2-disulfonic acid (dihydrate), toluene sulfonic acid (e.g. monohydrate), p-toluene sulfonic acid (e.g. monohydrate), 10-camphorsulfonic acid (e.g. (−)-10-camphorsulfonic acid), malic acid, malonic acid, benzoic acid, succinic acid, suberic acid, fumaric acid, lactic acid, mandelic acid, phthalic acid, benzenesulfonic acid, p-tolylsulfonic acid, citric acid, tartaric acid (L-tartaric acid or D-tartaric acid), mesotartaric acid (or erythraric acid), methanesulfonic acid, glutamic acid (L-glutamic acid or D-glutamic acid), ascorbic acid (L-ascorbic acid or D-ascorbic acid), isoascorbic acid (L-isoascorbic acid or D-isoascorbic acid), or a combination thereof or the like. With respect to the formation of suitable salts, as outlined in the definitions, the counterion can be any negatively charged group associated, for example, with the amide (e.g. Formula IC). Exemplary counterions include halide ions (e.g., $F^-$, $Cl^-$, $Br^-$, $I^-$) $NO_3^-$, $ClO_4^-$, $OH^-$, $H_2PO_4^-$, $HSO_4^-$, $^-BF_4$, $^-PF_6$, sulfonate ions, and carboxylate ions (e.g., acetate, ascorbate, ethanoate, isoascorbate, propanoate, benzoate, glycerate, lactate, tartrate, glutamate, glycolate, and the like). The reaction may occur in any suitable solvent, such as but not limited to, water-miscible solvents (e.g. alcohols (methanol, ethanol, isopropyl alcohol (IPA), etc.), acetonitrile, acetone, isopropyl acetate, THF, 2-methyl-THF, etc.).

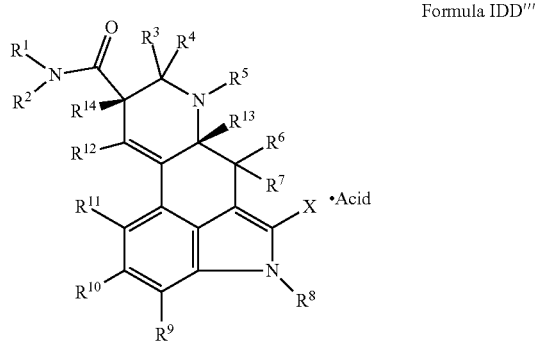

Formula IDD'''

In embodiments, the temperature ranges from about 50° C. to about 95° C. In certain embodiments, the temperature ranges from about 50° C. to about 95° C., about 60° C. to about 95° C., about 70° C. to about 95° C., about 80° C. to about 95° C., about 90° C. to about 95° C., about 50° C. to about 90° C., about 50° C. to about 80° C., about 50° C. to about 75° C., about 50° C. to about 70° C., about 50° C. to about 65° C., or about 60° C. to about 65° C. In embodiments, heating the compound of Formula ICC''' with the organic or inorganic acid is heated for any suitable time (e.g. about 30 minutes to about 1 hour). It may then be cooled, for example, to about room temperature. In other embodiments, cooled to about 0 to about 10° C., optionally, about 3 to about 7° C., optionally about 5° C., and optionally for about 30 minutes to about 2 h.

In the methods described herein, the products and intermediates may be purified with washing and recrystallization, without any need for chromatography; however, chromatography may be used as well. Recrystallization of compound of Formula ID, IDD, IDD', IDD", or IDD''' form a crystalline compound such as an isolated crystalline form, polymorphs thereof, a single polymorph thereof, or an isolated polymorph thereof. The compound of Formula IC, is recrystallized using water-miscible solvents, optionally, alcohols (e.g. methanol, ethanol, isopropyl alcohol (IPA), etc.), acetonitrile, acetone, isopropyl acetate, THF, 2-methyl-THF, etc.) or a combination thereof. The water-miscible solvent may be selected from methanol, ethanol, isopropyl alcohol (IPA) or a combination thereof; optionally, wherein the water-miscible solvent is selected from ethanol, isopropyl alcohol (IPA) or a combination thereof; optionally, ethanol or isopropyl alcohol (IPA). Recrystallization can comprise heating the salt or hydrate of the compound Formula ID, IDD, IDD', IDD", or IDD''' in the solvent to a suitable temperature for a suitable time period and cooling to form the compound. In embodiments, recrystallization comprises heating the compound Formula ID, IDD, IDD', IDD", or IDD'''(e.g. the salt or hydrate of the compound of Formula IC, ICC, ICC', ICC", or ICC''') in the solvent of from about 60° C. to about 80° C., optionally, from about 60° C. to about 70° C. In another embodiment, recrystallization comprises heating the compound Formula ID, IDD, IDD', IDD", or IDD''' in the solvent of from about 60° C. to about 80° C., optionally, from about 60° C. to about 70° C., for about 1 h to about 2 h. In a further embodiment, recrystallization comprises heating the salt or hydrate of the compound Formula ID, IDD, IDD', IDD", or IDD''' in the solvent of from about 60° C. to about 80° C., optionally, from about 60° C. to about 70° C., for about 1 h to about 2 h, and cooling the compound in solution to about 0 to about 10° C., optionally, about 3 to about 7° C., optionally about 5° C., and optionally for about 1 h to about 2 h. In embodiments, the recrystallized compound is about 99% to about 99.9% purity, optionally, about 99.5% to about 99.9% purity.

In other examples, Formula IA, IAA, IAA', IAA", or IAA''' is a bromine-containing ergoline derivative such as bromocriptine mesylate. These substrates can be prepared by known methods and/or are commercially available.

With respect to the methods outlined above and in embodiments, the methods provide polymorphs of Formula ID, IDD, IDD', IDD", or IDD'''. In an embodiment of the methods, R is —$NR_1R_2$ or —$OR_1$, wherein $R_1$ and $R_2$ are each independently selected from any suitable group that such that the CO(R) group can undergo hydrolysis; $R^3$-$R^{14}$ are each independently selected from H or methyl; X is bromo; and $R^1$ and $R^2$ are each independently selected from H, methyl, or ethyl.

It is understood that in any of the methods of making the acid derivative(s) of LSD described above, the ratio of the compound (e.g. Formula I, I', Ia, Ib, Ic, Id, Ia', Ib', Ic', or Id') to the acid may be in any suitable ratio, such as, and typically, a hemisalt (0.5:1 or 2:1). In embodiments, the ratio need not be the perfect balance of positive and negative charge. For example, the charge balanced ratio of 2-bromoLSD to tartrate can be 2 to 1, as 2-bromoLSD is about +1 and tartrate is about −2. With L-tartrate, salt formed can be about 1 to about 1, meaning there is an excess of negative charge. This can be balanced by hydrogen. A phosphate salt may occur in a ratio of 1:3, 1:2, 1:1, or 2:1 and ratios above and below these, where other spectator ions/counterions may be used such as, for example, hydrogen, hydroxide, sodium, chloride, calcium and potassium may be used to balance the charge. In embodiments, the ratio depends on the total charge of the acid. In certain embodiments, the ratio is from about 0.5:1 to about 2:1 (hemisalt) (based on mol/mol) and any increment therebetween such as about 0.6:1 to about 2:1; about 0.7:1 to about 2:1; about 0.8:1 to about 2:1; about 0.9:1 to about 2:1; about 1:1 to about 2:1; about 1.1:1 to about 2:1; about 1.2:1 to about 2:1; about 1.3:1 to about 2:1; about 1.4:1 to about 2:1; about 1.5:1 to about 2:1; about 1.6:1 to about 2:1; about 1.7:1 to about 2:1; about 1.8:1 to about 2:1; about 1.9:1 to about 2:1; about 0.5:1 to about 1.9:1; about 0.5:1 to about 1.8:1; about 0.5:1 to about 1.7:1; about 0.5:1 to about 1.6:1; about 0.5:1 to about 1.5:1; about 0.5:1 to about 1.4:1; about 0.5:1 to about 1.3:1; about 0.5:1 to about 1.2:1; about 0.5:1 to about 1.1:1; about 0.5:1 to about 1:1; about 0.5:1 to about 0.9:1; about 0.5:1 to about 0.8:1; about 0.5:1 to about 0.7:1; or about 0.5:1 to about 0.6:1.

Formulations—LSD Derivative(s) and Polymorph(s) Thereof

LSD derivative(s) and polymorph(s) thereof as disclosed herein may be provided as formulations suitable for administration to a mammal. In aspects for human and/or veterinary use.

In some embodiments, the disclosed compounds may be formulated as pharmaceutical compositions that include: (a) an amount of one or more compounds as disclosed herein or (b) a therapeutically effective amount of one or more compounds as disclosed herein, and (c) one or more pharmaceutically acceptable carriers, excipients, or diluents. The pharmaceutical composition may include the compound in any desired range as is understood by one of skill in the art. For example, non limiting ranges can be a range of about 0.001 to 2000 mg (preferably about 0.05 to 500 mg, and more preferably about 0.25 to 100 mg). The pharmaceutical composition may be administered to provide the compound at a daily dose of about 0.005 to about 1000 mg/kg body weight (preferably about 0.01 to about 500 mg/kg body weight, more preferably about 0.01 to about 100 mg/kg body weight). In some embodiments, after the pharmaceutical composition is administered to a subject (e.g., after about 1, 2, 3, 4, 5, or 6 hours post-administration), the concentration of the compound at the site of action may be within a concentration range bounded by end-points selected from 0.001 µM, 0.005 µM, 0.01 µM, 0.5 µM, 0.1 µM, 1.0 µM, 10 µM, and 100 µM (e.g., 0.1 µM-10.0 µm).

The disclosed compounds and pharmaceutical compositions comprising the disclosed compounds may be administered in methods/uses for treating a subject in need thereof. In some embodiments of the disclosed treatment methods/uses, the subject may be administered a dose of a compound as low as for example but not limited to 0.25 mg, 0.75 mg, 1.25 mg, 2.5 mg, 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 42.5 mg, 45 mg, 47.5 mg, 50 mg, 52.5 mg, 55 mg, 57.5 mg, 60 mg, 62.5 mg, 65 mg, 67.5 mg, 70 mg, 72.5 mg, 75 mg, 77.5 mg, 80 mg, 82.5 mg, 85 mg, 87.5 mg, 90 mg, 100 mg, 200 mg, 500 mg, 1000 mg, or 2000 mg once daily, twice daily, three times daily, four times daily, once weekly, twice weekly, or three times per week in order to treat the disease or disorder in the subject. In some embodiments, the subject may be administered a dose of a compound as high as 0.25 mg, 0.75 mg, 1.25 mg, 2.5 mg, 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 42.5 mg, 45 mg, 47.5 mg, 50 mg, 52.5 mg, 55 mg, 57.5 mg, 60 mg, 62.5 mg, 65 mg, 67.5 mg, 70 mg, 72.5 mg, 75 mg, 77.5 mg, 80 mg, 82.5 mg, 85 mg, 87.5 mg, 90 mg, 100 mg, 200 mg, 500 mg, 1000 mg, or 2000 mg, once daily, twice daily, three times daily, four times daily, once weekly, twice weekly, or three times per week in order to treat the disease or disorder in the subject. Minimal and/or maximal doses of the compounds may include doses falling within dose ranges having as end-points any of these disclosed doses (e.g., 2.5 mg-200 mg).

In some embodiments, a minimal dose level of a compound for achieving therapy in the disclosed methods/uses for treatment may be at least about 10, 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, 1900, 2000, 3000, 4000, 5000, 6000, 7000, 8000, 9000, 10000, 15000, or 20000 ng/kg body weight of the subject. In some embodiments, a maximal dose level of a compound for achieving therapy in the disclosed methods/uses for treatment may not exceed about 10, 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, 1900, 2000, 3000, 4000, 5000, 6000, 7000, 8000, 9000, 10000, 15000, or 20000 µg/kg body weight of the subject. Minimal and/or maximal dose levels of the compounds for achieving therapy in the disclosed methods/uses for treatment may include dose levels falling within ranges having as end-points any of these disclosed dose levels (e.g., 5-2000 µg/kg body weight of the subject).

The compounds utilized in the methods/uses disclosed herein may be formulated as a pharmaceutical composition in solid dosage form, although any pharmaceutically acceptable dosage form can be utilized. Exemplary solid dosage forms include, but are not limited to, tablets, capsules, sachets, lozenges, powders, pills, or granules, and the solid dosage form can be, for example, a fast melt dosage form, controlled release dosage form, lyophilized dosage form, delayed release dosage form, extended release dosage form, pulsatile release dosage form, mixed immediate release and controlled release dosage form, or a combination thereof.

The compounds utilized in the methods/uses disclosed herein may be formulated as a pharmaceutical composition that includes a carrier. For example, the carrier may be selected from the group consisting of proteins, carbohydrates, sugar, talc, magnesium stearate, cellulose, calcium carbonate, and starch-gelatin paste.

The compounds utilized in the methods/uses disclosed herein may be formulated as a pharmaceutical composition that includes one or more binding agents, filling agents, lubricating agents, suspending agents, sweeteners, flavoring agents, preservatives, buffers, wetting agents, disintegrants, and effervescent agents. Filling agents may include lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (Pro- Solv SMCC™). Suitable lubricants, including agents that act on the flowability of the powder to be compressed, may include colloidal silicon dioxide, such as Aerosil®200, talc, stearic acid, magnesium stearate, calcium stearate, and silica gel. Examples of sweeteners may include any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like. Examples of preservatives may include potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride.

Suitable diluents may include pharmaceutically acceptable inert fillers, such as microcrystalline cellulose, lactose, dibasic calcium phosphate, saccharides, and mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

Crystalline LSD polymorphs herein described can be formulated as a pharmaceutical composition with one or more pharmaceutically acceptable carriers or excipients.

In some embodiments, the disclosure provides a pharmaceutical formulation comprising high purity LSD derivatives and polymorphs and one or more pharmaceutically acceptable carriers or excipients. In some embodiments, the disclosure provides a pharmaceutical formulation comprising crystalline LSD and one or more pharmaceutically acceptable carriers or excipients. In some embodiments, the disclosure provides a pharmaceutical formulation comprising crystalline LSD polymorph and one or more pharmaceutically carriers or excipients. In some embodiments, the disclosure provides a pharmaceutical formulation comprising high purity crystalline LSD polymorphs and one or more pharmaceutically acceptable carriers or excipients. In some embodiments, the disclosure provides a pharmaceutical formulation comprising high purity crystalline LSD polymorphs and one or more pharmaceutically acceptable carriers or excipients. In some embodiments, the disclosure provides a pharmaceutical formulation comprising high purity crystalline LSD polymorphs and one or more pharmaceutically acceptable carriers or excipients.

Preferred pharmaceutical excipients for an oral formulation include: diluents, such as microcrystalline cellulose, starch, mannitol, calcium hydrogen phosphate anhydrous or co mixtures of silicon dioxide, calcium carbonate, microcrystalline cellulose and talc; disintegrants, such as sodium starch glycolate or croscarmellose sodium; binders, such as povidone, co povidone or hydroxyl propyl cellulose; lubricants, such as magnesium stearate or sodium stearyl fumurate; glidants, such as colloidal silicon dioxide; and film coats, such as Opadry II white or PVA based brown Opadry II. Oral dosage forms also comprise a disintegrant, such as, but not limited to: starch glycolate, croscarmellose sodium, and/or mixtures thereof. An oral dosage form in aspects comprises 3% or less by wt disintegrant, less than 3% by wt disintegrant and greater than 0.001% by wt disintegrant, about 2.5% by wt or less disintegrant; 2% by wt or less disintegrant; 1.5% by wt or less disintegrant; 1% by wt or less disintegrant; 0.7% by wt or less disintegrant; 0.5% by wt or less disintegrant, or 0.3% by wt or less disintegrant. The disintegrant is sodium starch glycolate present at less than 3% wt, present at about 2% by wt or less, about 2% by wt; about 1% by wt or less, about 1% by wt; about 0.7% by wt or less, about 0.7% by wt; about 0.5% by wt or less, or about 0.5% by wt. In still other embodiments, the sodium starch glycolate is present at about 0.5% to 1% by wt.

The compounds utilized in the methods/uses disclosed herein may be formulated as a pharmaceutical composition for delivery via any suitable route. For example, the pharmaceutical composition may be administered via oral, intravenous, intramuscular, subcutaneous, topical, and pulmonary route. Examples of pharmaceutical compositions for oral administration include capsules, syrups, concentrates, powders and granules. In some embodiments, the compounds are formulated as a composition for administration orally (e.g., in a solvent such as 5% DMSO in oil such as vegetable oil).

The compounds utilized in the methods/uses disclosed herein may be administered in conventional dosage forms prepared by combining the active ingredient with standard pharmaceutical carriers or diluents according to conventional procedures well known in the art. These procedures may involve mixing, granulating and compressing or dissolving the ingredients as appropriate to the desired preparation.

Pharmaceutical compositions comprising the compounds may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions. Suitable excipients for tablets or hard gelatine capsules include lactose, maize starch or derivatives thereof, stearic acid or salts thereof. Suitable excipients for use with soft gelatine capsules include for example vegetable oils, waxes, fats, semi-solid, or liquid polyols etc.

In one embodiment of the invention, oral tablets can be manufactured by direct compression of a compound disclosed herein. It is known generally that the advantages of direct compression include few manufacturing steps involved, physical stability and elimination of heat and moisture. Direct-compression tablets according to the invention can additionally contain binders, disintegrants, and colorants such as are familiar to those knowledgeable in the art. In another embodiment, pre-manufactured oral capsules contain compound disclosed herein along with excipients. Following compression of the tablets, or closure of the capsules, pharmaceutically acceptable coatings can be applied to these presentations of the invention in order to further modify release characteristics of the active agent in the gastrointestinal tract. The selection of the optimal release site depends on the type of disease, the intended plasma peak concentrations, the intended plasma time/concentration-profile and the intended time/concentration profile at the target site.

In a further embodiment, the present invention relates to a process for preparing a medicament based on a formulation of a compound disclosed herein which is suitable for oral administration, wherein the formulation is directly compressed into tablets, optionally, wherein it is mixed with one or more excipient(s) (pregelatinized starch, microcrystalline cellulose, colloidal silicon dioxide, and stearic acid) and the mixture is filled in size 4, white opaque, hard gelatin, two-piece capsules to provide 5 mg or 10 mg a compound disclosed herein per capsule, which can be used as an oral formulation for immediate release in the gastrointestinal tract.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis.

Pharmaceutical compositions adapted for topical administration may be formulated as ointments, creams, suspensions, lotions, powders, solutions, pastes, gels, impregnated dressings, sprays, aerosols or oils and may contain appropriate conventional additives such as preservatives, solvents to assist drug penetration and emollients in ointments and creams.

For applications to the eye or other external tissues, for example the mouth and skin, the pharmaceutical compositions are preferably applied as a topical ointment or cream. When formulated in an ointment, the compound may be employed with either a paraffinic or a water-miscible ointment base. Alternatively, the compound may be formulated in a cream with an oil-in-water cream base or a water-in-oil base.

Pharmaceutical compositions adapted for topical administration to the eye include eye drops where the active ingredient is dissolved or suspended in a suitable carrier, especially an aqueous solvent.

Pharmaceutical compositions adapted for nasal administration where the carrier is a solid include a coarse powder having a particle size (e.g., in the range 20 to 500 microns) which is administered in the manner in which snuff is taken (i.e., by rapid inhalation through the nasal passage from a container of the powder held close up to the nose). Suitable formulations where the carrier is a liquid, for administration as a nasal spray or as nasal drops, include aqueous or oil solutions of the active ingredient.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavoring or coloring agents.

In some embodiments, the pharmaceutical compositions disclosed herein are modified release dosage forms which provide modified release profiles. Modified release profiles may exhibit immediate release, delayed release, or extended release profiles. Conventional (or unmodified) release oral dosage forms such as tablets, capsules, suppositories, syrups, solutions and suspensions typically release medications into the mouth, stomach or intestines as the tablet, capsule shell or suppository dissolves, or, in the case of syrups, solutions and suspensions, when they are swallowed. The pattern of drug release from modified release (MR) dosage forms is deliberately changed from that of a conventional dosage form to achieve a desired therapeutic objective and/or better patient compliance. Types of MR drug products include orally disintegrating dosage forms (ODDFs) which provide immediate release, extended release dosage forms, delayed release dosage forms (e.g., enteric coated), and pulsatile release dosage forms.

An ODDF is a solid dosage form containing a medicinal substance or active ingredient which disintegrates rapidly, usually within a matter of seconds when placed upon the tongue. The disintegration time for ODDFs generally range from one or two seconds to about a minute. ODDFs are designed to disintegrate or dissolve rapidly on contact with saliva. This mode of administration can be beneficial to people who may have problems swallowing tablets whether it be from physical infirmity or psychiatric in nature. Some subjects with an eye disorder may exhibit such behavior. ODDF's can provide rapid delivery of medication to the blood stream through mucosa resulting in a rapid onset of action. Examples of ODDFs include orally disintegrating tablets, capsules and rapidly dissolving films and wafers.

Extended release dosage forms (ERDFs) have extended release profiles and are those that allow a reduction in dosing frequency as compared to that presented by a conventional dosage form, e.g., a solution or unmodified release dosage form. ERDFs provide a sustained duration of action of a drug. Suitable formulations which provide extended release profiles are well-known in the art. For example, coated slow release beads or granules ("beads" and "granules" are used interchangeably herein) in which any of the compounds described herein are applied to beads, e.g., confectioners nonpareil beads, and then coated with conventional release retarding materials such as waxes, enteric coatings and the like. In embodiments, beads can be formed in which any of the compounds described herein are mixed with a material to provide a mass from which the compound leaches out. In embodiments, the beads may be engineered to provide different rates of release by varying characteristics of the coating or mass, e.g., thickness, porosity, using different materials, etc. Beads having different rates of release may be combined into a single dosage form to provide variable or continuous release. The beads can be contained in capsules or compressed into tablets.

Therapy modalities may include: monotherapy; adjunctive therapy (i.e. add-on to standard of care drug treatment); use in combination with other agents approved for use in the treatment of neurological and neurodegenerative disorders; use in combination with other agents approved for use in the treatment of psychiatric and related disorders; use in combination with other agents approved for use in the treatment of different pain disorders; combination with anti-depressants and related agents (such as serotonin and noradrenaline reuptake inhibitors (SNRIs), selective serotonin reuptake inhibitors (SNRI), tricyclic anti-depressants, monoamine oxidase inhibitors, noradrenaline and specific serotoninergic antidepressants (NASSAs), ketamines, N, N-dimethyltryptamine and other tryptamine derivatives, 3,4-methylenedioxymethamphetamine (MDMA) and related derivatives, psilocybin and related derivatives, ibogaine and related derivatives) for treatment of neuro-psychiatric disorders; combination with other agents for treatment of neuro-psychiatric disorders; combination with standard of care agents for treatment of neurodegenerative diseases; combination with standard of care agents for treatment of different pain disorders; combination with neuroprotectant agents (such as dihydrohonokiol-B) for treatment of neuro-degenerative diseases (including Alzheimers disease, Parkinson's disease, normal aging and progeroid syndromes); combination with anti-anxiety and similar agents (including benzodiazepines, cannabinoids, and dihydrohoniol-B) for treatment of neuropsychiatric disorders; combination with psychedelic's to reduce the psychedelic's side effects in treatment of neuropsychiatric disorders.

A schedule for treatment may comprise induction treatment and/or maintenance treatment, which includes short-term maintenance, mid-term maintenance, long-term maintenance and variations thereof.

The LSD derivatives and polymorphs herein described can be provided as: a discreet dosage form comprising capsules or tablets for sublingual or buccal administration; for inhalation as a nasal spray, a metered dose inhaler or similar; as a patch for controlled release over one or many days; and as a depot formulation for controlled release Within the context of this disclosure, it is understood that a sample may comprise small amounts of liquid that are negligible in the final measurement of a sample. In one example, it is acceptable for a composition of this disclosure to comprise for example up to about 7% water as measured by mass percent.

An effective amount of the pharmaceutical composition or compound(s) disclosed herein, as described herein, will provide therapeutic benefit without causing substantial toxicity. The skilled artisan will appreciate that the toxicity of the pharmaceutical composition or compound(s) disclosed herein can be determined by standard pharmaceutical procedures in cell cultures or experimental animals, for example, by determining the LD50 (the dose lethal to 50% of the population) or the LD100 (the dose lethal to 100% of the population). In some embodiments, the dose ratio between toxic and therapeutic effect is the therapeutic index. In some embodiments, the data obtained from these cell culture assays and animal studies can be used in formulating a dosage range that is not toxic for use in human. In some embodiments, the dosage of the compounds described herein lies within a range of circulating concentrations that include the effective dose with little or no toxicity. In some embodiments, the dosage may vary within this range depending upon the dosage form employed and the route of administration utilized. In some embodiments, the exact formulation, route of administration and dosage can be chosen by the individual physician in view of the patient's condition. (See, e.g., Fingl et al., 1996, In: The Pharmacological Basis of Therapeutics, 9th ed., Chapter 2, p. 29, Elliot M. Ross)

Examples of therapeutically effective doses of the pharmaceutical composition or compound(s) disclosed herein for various mental and/or mood disorders are set forth below. In some embodiments, the term "about" when used in reference to the amount of the pharmaceutical composition or compound(s) disclosed herein means about +/−1%. In some embodiments, the term "about" when used in reference to the amount of the pharmaceutical composition or compound (s) disclosed herein means about +/−2%. In some embodiments, the term "about" when used in reference to the amount of the pharmaceutical composition or compound(s) disclosed herein means about +/−2.5%. In some embodiments, the term "about" when used in reference to the amount of the pharmaceutical composition or compound(s) disclosed herein means about +/−5%. In some embodiments, the term "about" when used in reference to the amount of the pharmaceutical composition or compound(s) disclosed herein means about +/−10%. In some embodiments, the term "about" when used in reference to the amount of the pharmaceutical composition or compound(s) disclosed herein means about +/−15%. In some embodiments, the term "about" when used in reference to the amount of the pharmaceutical composition or compound(s) disclosed herein means about +/−20%.

With respect to the pharmaceutical compositions disclosed herein, pharmaceutically acceptable carriers include diluents and excipients generally used in pharmaceutical preparations, such as fillers, extenders, binders, moisturizers, disintegrators, surfactant, lubricants, etc. Non-limiting examples of suitable carriers are described herein.

Diluents

A diluent may be selected from, for example, calcium carbonate, calcium phosphate dibasic, calcium phosphate tribasic, calcium sulfate, microcrystalline cellulose, microcrystalline silicified cellulose, powdered cellulose, dextrate, dextrose, fructose, lactitol, lactose anhydrous, lactose monohydrate, lactose dihydrate, lactose trihydrate, mannitol, sorbitol, starch, pregelatinized starch, sucrose, talc, xylitol, maltose, maltodextrin, maltitol. In some embodiments, the diluent is selected from starches, lactose, cellulose derivatives, confectioner's sugar and the like. Different grades of lactose include, but are not limited to, lactose monohydrate, lactose DT (direct tableting), lactose anhydrous, and others. Different starches include, but are not limited to, maize starch, potato starch, rice starch, wheat starch, pregelatinized starch, and others. Different celluloses that can be used include crystalline celluloses, such as a microcrystalline cellulose, and powdered celluloses. Other useful diluents include, but are not limited to, carmellose, sugar alcohols such as mannitol, sorbitol, and xylitol, calcium carbonate, magnesium carbonate, dibasic calcium phosphate, and tribasic calcium phosphate.

Binders

A binder may be selected from, for example, acacia, alginic acid, carbomer, carboxymethylcellulose calcium, carbomethylcellulose sodium, microcrystalline cellulose, powdered cellulose, ethyl cellulose, gelatin liquid glucose, guar gum, hydroxyethyl cellulose, hydroxypropyl cellulose, hydroxypropylmethyl cellulose, maltodextrin, methylcellulose, polydextrose, polyethtylene oxide, povidone, sodium alginate, starch paste, pregelatinized starch, sucrose, tragacanth, low-substituted hydroxypropyl cellulose, glucose, sorbitol.

Fillers

A suitable filler may be selected from, for example, starch derivatives, such as corn starch, potato starch or rice starch, polysaccharides such as dextrins, maltodextrins, dextrates, microcrystalline cellulose, powdered cellulose, mixture of microcrystalline cellulose and guar gum, coprocessed blends of microcrystalline cellulose; and polyhydric alcohols, such as xylitol and sorbitol.

Disintegrants

A disintegrant may be selected from, for example, alginic acid, carbon dioxide, carboxymethylcellulose calcium, carboxymethylcellulose sodium, microcrystalline cellulose, powdered cellulose, croscarmelose sodium, crospovidone, sodium docusate, gaur gum, hydroxypropyl cellulose, methylcellulose, polacrilin potassium, poloxamer, povidone, sodium alginate, sodium glycine carbonate, sodium lauryl sulfate, sodium starch glycolate, starch, pregelatinized starch, low-substituted hydroxypropyl cellulose.

Glidants

A glidant may be selected from, for example, calcium silicate, powdered cellulose, starch, talc, colloidal silicon dioxide.

Lubricants

A lubricant may be selected from, for example, magnesium stearate, stearic acid, sodium stearyl fumarate, magnesium lauryl sulphate, talc, polyethylene glycol, and glyceryl behenate, glyceryl monostearates, palmitic acid, talc, carnauba wax, calcium stearate sodium, sodium or magnesium lauryl sulfate, calcium soaps, zinc stearate, polyoxyethylene monostearates, calcium silicate, silicon dioxide, hydrogenated vegetable oils and fats, stearic acid, and any combinations thereof.

The pharmaceutical composition of the present disclosure may be formulated as an ordinary pharmaceutical preparation, for example in the form of tablets, flash melt tablets, pills, powder, liquid, suspension, emulsion, granules, capsules, suppositories or injection (liquid, suspension, etc.), troches, intranasal spray percutaneous patch and the like.

Absorption Enhancers

Absorption enhancers for use in accordance with certain embodiments of the present disclosure include, for example, Gelucire 44/14; Gelucire 50/13; Tagat TO; Tween 80; isopropyl myristate, polysorbates, sorbitan esters, poloxamer block copolymers, PEG-35 castor oil, PEG-40 hydrogenated castor oil, caprylocaproyl macrogol-8 glycerides, PEG-8 caprylic/capric glycerides, sodium lauryl sulfate, dioctyl sulfosuccinate, polyethylene lauryl ether, ethoxydiglycol, propylene glycol mono-di-caprylate, glycerol monocaprylate, glyceryl fatty acids (C8-C18) ethoxylated, oleic acid, linoleic acid, glyceryl caprylate/caprate, glyceryl monooleate, glyceryl monolaurate, caprylic/capric triglycerides, ethoxylated nonylphenols, PEG-(8-50) stearates, olive oil PEG-6 esters, triolein PEG-6 esters, lecithin, d-alpha tocopheryl polyethylene glycol 1000 succinate, polycarbonate, sodium glycocholate, sodium taurocholate, cyclodextrins, citric acid, sodium citrate, triacetin, combinations thereof, and the like. In certain preferred embodiments, the absorption enhancer is triacetin.

Sweeteners/Flavoring Agents

A suitable sweetener may be selected from sugars such as sucrose, lactose and glucose; cyclamate and salts thereof; saccharin and salts thereof; and aspartame. Flavoring agents may be incorporated in the composition may be chosen from synthetic flavors oils and flavoring aromatics, natural oils, plant extracts. Examples include cinnamon oil, oil of wintergreen, peppermint oil, clove oil, bay oil, anise oil, eucalyptus, thyme oil, cedar leaf oil, nutmeg oil, sage oil or almond oil. Examples of flavoring agents include, but are not limited to, almond, apple, banana, berry, bubblegum, caramel, citrus, cherry, chocolate, coconut, grape, green tea, honey, lemon, licorice, lime, mango, maple, mint, orange, peach, pineapple, raisin, strawberry, vanilla, watermelon and combinations thereof. Flavors may be present in an amount ranging from about 0.0010% to about 5% by total weight of the formulation. In some embodiments, the flavoring agent may be selected from natural or synthetic flavors such as, for example, strawberry flavor, wild cherry flavor, green apple flavor, spearmint flavor and peppermint flavor. In some embodiments, the flavoring agents are selected from menthol, peppermint, wintergreen, orange, cherry, and other fruits, vanilla, almond and other nuts, etc.

In some embodiments the pharmaceutical compositions of the present disclosure are in the form of tablets, which may include one or more pharmaceutically acceptable carriers or excipients selected from lactose, saccharose, sodium chloride, glucose, urea, starch, xylitol, mannitol, erythritol, sorbitol, calcium carbonate, kaolin, crystalline cellulose, silic acid and other excipients; water, ethanol, propanol, simple syrup, glucose solution, starch solution, gelatin solution, carboxymethyl cellulose, shellac, methyl cellulose, potassium phosphate, polyvinyl pyrrolidone and other binders; dried starch, sodium alginate, agar powder, laminaran powder, sodium hydrogencarbonate, calcium carbonate, polyoxyethylene sorbitan fatty acid esters, sodium lauryl sulfate, stearic acid monoglyceride, starch, lactose and other disintegrators; white sugar, stearin, cacao butter, hydrogenated oil and other disintegration inhibitors; quaternary ammonium salt, sodium lauryl sulfate and other absorption accelerator; glycerine, starch and other moisture retainers; starch, lactose, kaolin, bentonite, colloidal silic acid and other adsorbents; and refined talc, stearate, boric acid powder, polyethylene glycol and other lubricants and the like. Tablets can also be formulated with ordinary coatings, such as sugar-coated tablets, gelatin-coated tablets, enteric coated tablets and film coated tablets, as well as double tablets and multilayered tablets.

In some embodiments the pharmaceutical compositions of the present disclosure are in the form of pills, which may include one or more pharmaceutically acceptable carriers or excipients selected from glucose, lactose, starch, cacao butter, hardened vegetable oil, kaolin, talc and other excipients; gum arabic powder, traganth powder, gelatin, ethanol and other binders; and laminaran, agar and other disintegrators and the like.

In some embodiments the pharmaceutical compositions of the present disclosure are in the form of capsules. Capsules are prepared according to ordinary methods by mixing carbostyril derivatives such as anhydrous aripiprazole crystals as the first ingredient and serotonin reuptake inhibitor as the second ingredient, and the various carriers described above and packing them in hard gelatin capsules, soft capsules hydroxypropylmethyl cellulose capsules (HPMC capsules) and the like.

In some embodiments the pharmaceutical compositions of the present disclosure are in the form of suppositories, which may include one or more pharmaceutically acceptable carriers or excipients selected from polyethylene glycol, cacao butter, higher alcohol, esters of higher alcohol, gelatin semi-synthetic glyceride and the like.

Routes of Administration and Dosage Forms

Administration to a subject of the formulations according to the present disclosure may be via any common route so long as the target tissue is available via that route. The formulations may conveniently be presented in dosage unit form and may be prepared by any of the methods well known in the art of pharmacy. In some embodiments, the formulations are prepared by uniformly and intimately bringing the active components into association with a liquid carrier or a finely divided solid carrier or both, and then, if necessary, shaping the product into the desired dosage form. Of course, the skilled artisan will recognize that the active components (e.g. compound(s) disclosed herein) are included in an amount sufficient to produce the desired pharmacologic effect.

In some embodiments, the composition is administered depending on the type of preparation form, and the age, gender and other condition of the patient (degree and conditions of the disease, etc.). For example, tablets, pills, liquids, suspensions, emulsions, granules and capsules are administered orally. In case of an injectable preparation, it is administered intravenously by either singly or mixed with a common auxiliary liquid such as solutions of glucose or amino acid. Further, if necessary, the injectable preparation is singly administered intracutaneously, subcutaneously, intramuscularly or intraperitoneally. In case of a suppository, it is administered intrarectally.

In some embodiments, the pharmaceutical composition or compound(s) disclosed herein is administered at a dosage, such as described herein, at least once a day. In some embodiments, the pharmaceutical composition or compound(s) disclosed herein is administered at a dosage, such as described herein, at least twice a day. In some embodiments, the pharmaceutical composition or compound(s) disclosed herein is administered at a dosage, such as described herein, at least three times a day.

In other embodiments, the pharmaceutical composition or compound(s) disclosed herein is administered at a dosage, such as described herein, at least once every other day. In yet other embodiments, the pharmaceutical composition or compound(s) disclosed herein is administered at a dosage, such as described herein, at least once every third day. In further embodiments, the pharmaceutical composition or compound(s) disclosed herein is administered at a dosage, such as described herein, at least once every fourth day. In further embodiments, the pharmaceutical composition or compound(s) disclosed herein is administered at a dosage, such as described herein, or at least once every fifth day.

In some embodiments, the methods and formulations can be practiced as a single, one time dose or chronically. By chronic it is meant that the methods and compositions of the disclosure are practiced more than once to a given subject or individual. For example, chronic administration can be multiple doses of a pharmaceutical composition administered to a subject, on a daily basis, a weekly basis, a biweekly basis, monthly basis, or more or less frequently, as will be apparent to those of skill in the art. Chronic administration can continue for weeks, months, or years if appropriate according to the judgment of the practitioner of skill in the art. Furthermore, if certain doses, in the judgment of the practitioner of skill in the art, show tolerability profiles which may not be acceptable, the practitioner can reduce the dose to reduce such profiles.

Use of LSD Derivative(s) and Polymorph(s) Thereof for Treatment

The novel LSD derivative(s) and polymorph(s) thereof as disclosed herein are suitable formulated as therapeutic agents for treating a subject in need thereof. They are demonstrated to promote synaptic growth (promote neuroplasticity) and may result in "rewiring" the central and/or peripheral nervous system producing long-lasting results without hallucinations. They are also demonstrated to be non-hallucinogenic and surprisingly do not induce tolerance such that they can be used in a plurality of daily, weekly, monthly and so forth doses. This advantageously avoids the need to have spaced apart dosing schedules where a subject may wait days (for e.g. 3 days or more) before administration of the next dose.

The Applicant has synthesized novel LSD derivative polymorphs characterized as a moderate to potent agonist across all the 5-HT1 receptor subtypes with slight decrease in Emax (maximal drug effect) relative to LSD. The Examples disclosed herein disclose E559 polymorph [(a (5R,8R)-2-Br-LSD hemi-D-Tartrate] characterized with potency/activity at 5-HT1F and 5-HT1D receptors known as anti-migraine and pain perception drug targets (Ramirez Rosas et al. Activation of 5-hydroxytryptamine$_{1B/1D/1F}$ receptors as a mechanism of action of antimigraine drugs, *Expert Opinion on Pharmacotherapy*, 2013, 14:12, 1599-1610) and (Clemow, D. B. et al. Lasmiditan mechanism of action—review of a selective 5-HT$_{1F}$ agonist. *J Headache Pain*, 2020, 21, 71). The demonstration of the E559 polymorph as a potent agonist at 5-HT1F and 1D receptor subtypes demonstrates its therapeutic potential to relieve the symptoms of for example headaches, migraines, and pain disorders.

The E559 polymorph has been characterized herein to be a 5-HT6 partial agonist, similar to LSD. 5-HT6 is an emerging target receptor for treating cognitive deficits and disorders (Drop et al., 2-Phenyl-1H-pyrrole-3-carboxamide as a New Scaffold for Developing 5-HT6 Receptor Inverse Agonists with Cognition-Enhancing Activity. ACS *Chemical Neuroscience* 2021 12 (7), 1228-1240) and (Khoury et al., The role of 5 HT6-receptor antagonists in Alzheimer's disease: an update, *Expert Opinion on Investigational Drugs*, 2018, 27:6, 523-533). Therefore, the E559 polymorph, demonstrated as a potent partial agonist at 5-HT6 receptor, has therapeutic use in the treatment of cognition, learning and memory and thus for treatment for example of cognitive disorders including cognitive decline associated with neurological and psychiatric disorders such as, but not limited to, Alzheimer's disease, Parkinson's disease, schizophrenia, Down syndrome, and autism spectrum disorders.

The E559 polymorph is characterized herein as a partial agonist at 5-HT2A and 5-HT1A receptor subtypes, that are known drug targets in treatment of mood disorders such as depression and anxiety (Celada et al., The therapeutic role of 5-HT$_{1A}$ and 5-HT$_{2A}$ receptors in depression. *J Psychiatry Neurosci.* 2004 July; 29(4): 252-265), and thus has use for treatment of anti-depressant or anxiolytic therapeutic.

The E559 polymorph is demonstrated herein to have high potency (agonism) at D2-like receptors including D2 and D4. As a potent agonist at D2/D4 dopamine receptors, it has therapeutic potential in D2/D4-linked neuropsychiatric disorders including, but not limited to, Parkinson's disease, schizophrenia, restless legs syndrome, psychosis, attention deficit hyperactivity disorder (ADHD), substance use disorders, hyperprolactinemia, and Neuroleptic Malignant Syndrome (Bonifazi et al., Novel and Potent Dopamine $D_2$ Receptor Go-Protein Biased Agonists. *ACS Pharmacology & Translational Science* 2019 2 (1), 52-65) and (Paul E Keck Jr & Susan L McElroy. Aripiprazole: a partial dopamine D2 receptor agonist antipsychotic, Expert Opinion on Investigational Drugs, 2003, 12:4, 655-662) and (Woolley et al., Selective dopamine D4 receptor agonist (A-412997) improves cognitive performance and stimulates motor activity without influencing reward-related behaviour in rat. *Behavioural Pharmacology*: December 2008—Volume 19—Issue 8—p765-776.).

Depressive Disorders

In some embodiments, the pharmaceutical composition or compound(s) disclosed herein can be used to treat a disease and/or disorder selected from the group consisting of: depression, major depressive disorder (including major depressive episode), disruptive mood dysregulation disorder, atypical depression, psychotic major depression, catatonic depression, post-partum depression, premenstrual dysphoric disorder, seasonal affective disorder, substance/medication-induced depressive disorder, double depression, depressive personality disorder, persistent depressive disorder (dysthemia), recurrent brief depression, minor depressive disorder, depressive disorder due to a medical condition, and depressive disorder not otherwise specified. In some embodiments, the subject has a depressive disorder that is resistant to treatment.

In some embodiments suitable doses for use for this group of depression disorders is as follows:

| Mental and/or Mood Disorder | µg/kg/bodyweight/day |
|---|---|
| Major Depressive Disorder | about 25-500 |
| Atypical Depression | about 25-500 |
| Melancholid Depression | about 25-500 |
| Psychotic major depression | about 50-2000 |
| Catatonic Depression | about 50-2000 |
| Postpartum Depression | about 25-500 |
| Dysthymia | about 25-500 |
| Double Depression | about 25-500 |
| Depressive Disorder Not Otherwise Specified | about 25-500 |
| Depressive personality disorder | about 25-500 |
| Recurrent brief depression | about 25-500 |
| Minor Depressive disorder | about 10-500 |

The term "major depressive disorder" refers to a condition characterized by a time period of low mood that is present across most situations. Major depressive disorder is often accompanied by low self-esteem, loss of interest in normally enjoyable activities, low energy, and pain without a clear cause. In some instances, major depressive order is characterized by two weeks, years or nearly always present signs and symptoms. Major depressive disorder can negatively affect a person's personal, work, or school life, as well as sleeping, eating habits, and general health. Dysthymia is a subtype of major depressive disorder consisting of the same cognitive and physical problems as major depressive disorder with less severe but longer-lasting symptoms. Exemplary symptoms of a major depressive disorder include, but are not limited to, feelings of sadness, tearfulness, emptiness or hopelessness, angry outbursts, irritability or frustration, even over small matters, loss of interest or pleasure in most or all normal activities, sleep disturbances, including insomnia or sleeping too much, tiredness and lack of energy, reduced appetite, weight loss or gain, anxiety, agitation or restlessness, slowed thinking, speaking, or body movements, feelings of worthlessness or guilt, fixating on past failures or self-blame, trouble thinking, concentrating, making decisions, and remembering things, frequent thoughts of death, suicidal thoughts, suicide attempts, or suicide, and unexplained physical problems, such as back pain or headaches.

"Atypical depression" refers to a condition wherein an individual shows signs of mood reactivity (i.e., mood brightens in response to actual or potential positive events), significant weight gain, increase in appetite, hypersomnia, heavy, leaden feelings in arms or legs, and/or long-standing pattern of interpersonal rejection sensitivity that results in significant social or occupational impairment. Exemplary symptoms of atypical depression include, but are not limited to, daily sadness or depressed mood, loss of enjoyment in things that were once pleasurable, major changes in weight (gain or loss) or appetite, insomnia or excessive sleep almost every day, a state of physical restlessness or being rundown that is noticeable by others, daily fatigue or loss of energy, feelings of hopelessness, worthlessness, or excessive guilt almost every day, problems with concentration or making decisions almost every day, recurring thoughts of death or suicide, suicide plan, or suicide attempt.

"Catatonic depression" refers to a condition causing an individual to remain speechless and motionless for an extended period. Exemplary symptoms of catatonic depression include, but are not limited to, feelings of sadness, which can occur daily, a loss of interest in most activities, sudden weight gain or loss, a change in appetite, trouble falling asleep, trouble getting out of bed, feelings of restlessness, irritability, feelings of worthlessness, feelings of guilt, fatigue, difficulty concentrating, difficulty thinking, difficulty making decisions, thoughts of suicide or death, and/or a suicide attempt.

"Depressive disorder due to a medical condition" refers to a condition wherein an individual experiences depressive symptoms caused by another illness. Examples of medical conditions known to cause a depressive disorder include, but are not limited to, HIV/AIDS, diabetes, arthritis, strokes, brain disorders such as Parkinson's disease, Huntington's disease, multiple sclerosis, and Alzheimer's disease, metabolic conditions (e.g. vitamin B12 deficiency), autoimmune conditions (e.g., lupus and rheumatoid arthritis), viral or other infections (hepatitis, mononucleosis, herpes.

"Postpartum depression" refers to a condition as the result of childbirth and hormonal changes, psychological adjustment to parenthood, and/or fatigue. Postpartum depression is often associated with women, but men can also suffer from postpartum depression as well. Exemplary symptoms of postpartum depression include, but are not limited to, feelings of sadness, hopeless, emptiness, or overwhelmed; crying more often than usual or for no apparent reason; worrying or feeling overly anxious; feeling moody, irritable, or restless; oversleeping, or being unable to sleep even when the baby is asleep; having trouble concentrating, remembering details, and making decisions; experiencing anger or rage; losing interest in activities that are usually enjoyable; suffering from physical aches and pains, including frequent headaches, stomach problems, and muscle pain; eating too little or too much; withdrawing from or avoiding friends and family; having trouble bonding or forming an emotional attachment with the baby; persistently doubting his or ability to care for the baby; and thinking about harming themselves or the baby.

"Premenstrual dysphoric disorder" refers to a condition wherein an individual expresses mood lability, irritability, dysphoria, and anxiety symptoms that occur repeatedly during the premenstrual phase of the cycle and remit around the onset of menses or shortly thereafter. Exemplary symptoms of premenstrual dysphoric disorder includes, but are not limited to, lability (e.g., mood swings), irritability or anger, depressed mood, anxiety and tension, decreased interest in usual activities, difficulty in concentration, lethargy and lack of energy, change in appetite (e.g., overeating or specific food cravings), hypersomnia or insomnia, feeling overwhelmed or out of control, physical symptoms (e.g., breast tenderness or swelling, joint or muscle pain, a sensation of 'bloating' and weight gain), self-deprecating thoughts, feelings of being keyed up or on edge, decreased interest in usual activities (e.g., work, school, friends, hobbies), subjective difficulty in concentration, and easy fatigability.

"Seasonal affective disorder" refers to a condition wherein an individual experiences mood changes based on the time of the year. In some instances, an individual experiences low mood, low energy, or other depressive symptoms during the fall and/or winter season. In some instances, an individual experiences low mood, low energy, or other depressive symptoms during the spring and/or summer season.

In some embodiments, the methods of the disclosure reduce at least one sign or symptom of depression. In some embodiments, the sign or symptom of depression is depressed mood, diminished interest in activities, weight loss or gain, decrease or increase in appetite, insomnia or hypersomnia, psychomotor agitation or retardation, fatigue or loss of energy, feelings of worthlessness or excessive or inappropriate guilt, diminished ability to concentrate or indecisiveness, or suicidal ideation or behavior.

In some embodiments, the methods described herein are provided to a subject with depression that is newly diagnosed. In some embodiments, the subject has been treated with one or more other anti-depressant treatments but is not obtaining adequate depression symptoms control or is obtaining adequate depression symptoms control but is adversely affected by side effects of the treatment. In some embodiments, the methods described herein are provided to a subject with depression that is resistant to treatment. In some embodiments, the subject has been diagnosed with "treatment-resistant depression" referring to a kind of depression that does not respond or is resistant to at least one or more treatment attempts of adequate dose and duration.

In some embodiments, the methods provided herein reduce at least one sign or symptom of a depressive disorder. In some embodiments, the methods provided herein reduce at least one sign or symptom of a depressive disorder by between about 5% to about 100% compared to prior to treatment.

In some embodiments, the methods provided herein reduce at least one sign or symptom of major depressive disorder. In some embodiments, the methods provided herein reduce at least one sign or symptom of major depressive disorder by about 5% to about 100% compared to prior to treatment.

In some embodiments, the methods provided herein reduce at least one sign or symptom of atypical depression. In some embodiments, the methods provided herein reduce at least one sign or symptom of atypical depression by about 5% to about 100%, compared to prior to treatment.

In some embodiments, the methods provided herein reduce at least one sign or symptom of catatonic depression by about 5% to about 100 compared to prior to treatment.

In some embodiments, the methods provided herein reduce at least one sign or symptom of a depressive disorder due to a medical condition by about 5% to about 100%, compared to prior to treatment.

In some embodiments, the methods provided herein reduce at least one sign or symptom of postpartum depression, or premenstrual dysphoric disorder by about 5% to about 100%, compared to prior to treatment.

In some embodiments, no other treatment is administered to the subject to reduce the sign or symptom of depression after administration of the LSD derivative or polymorph disclosed herein.

In some embodiments, the method of the present disclosure further comprises administering to the subject at least one additional therapeutic to reduce the sign or symptom of depression. In some embodiments, at least one additional therapeutic is a selective serotonin reuptake inhibitor, a serotonin and norepinephrine reuptake inhibitor, a tricyclic antidepressant, a tetracyclic antidepressant, a dopamine reuptake inhibitor, a 5-HT1A receptor antagonist, a 5-HT2 receptor antagonist, a 5-HT3 receptor antagonist, a monoamine oxidase inhibitor, or a noradrenergic antagonist. In some embodiments, at least one additional therapeutic is administered prior to administration of the LSD derivative or polymorph herein disclosed, on the same day as the administration of the LSD derivative or and polymorph herein disclosed, or after administration of the LSD derivative or polymorph herein disclosed. In some embodiments, at least one additional therapeutic is administered on the same schedule as the LSD derivative or polymorph herein disclosed (e.g. once every other day or twice weekly or once weekly). In some embodiments, at least one additional therapeutic is administered on a different schedule to that of the LSD derivative or polymorph herein disclosed. In some embodiments, the duration of treatment with the LSD derivative or polymorph may be the same, or shorter, or longer than the duration of the additional therapeutic treatment.

Bipolar and Related Disorders

According to another embodiment, the pharmaceutical composition or compound(s) disclosed herein are for use in the treatment of bipolar and related disorders including bipolar I disorder, bipolar II disorder, cyclothymic disorder, substance/medication-induced bipolar and related disorders, and bipolar disorder not otherwise specified.

In some embodiments the doses to be used for this group of disorders is as in table below:

| Mental and/or Mood Disorder | µg/kg/bodyweight/day |
|---|---|
| Bipolar Disorders: | |
| Bipolar I | about 25-1000 |
| Bipolar II | about 25-1000 |
| Cyclothymia | about 25-1000 |
| Bipolar disorder not otherwise specified | about 25-1000 |

"Bipolar disorder" refers to a condition that causes an individual to experience unusual shifts in mood, energy, activity levels, and the ability to carry out day-to-day tasks. Individuals with bipolar disorder experience periods of unusually intense emotion, changes in sleep patterns and activity levels, and unusual behaviors. These distinct periods are called"mood episodes." Mood episodes are drastically different from the moods and behaviors that are typical for the person. Exemplary symptoms of mania, excessive behavior, include, but are not limited to, abnormally upbeat, jumpy, or wired behavior; increased activity, energy, or agitation, exaggerated sense of well-being and self-confidence, decreased need for sleep, unusual talkativeness, racing thoughts, distractibility, and poor decision-making.

Bipolar disorder includes bipolar I disorder, bipolar II disorder, and cyclothymic disorder. Bipolar I disorder is defined by manic episodes that last at least 7 days or by severe manic symptoms that require hospitalization. A subject with bipolar I disorder may also experience depressive episodes typically lasting at least 2 weeks. Episodes of depression with mixed features, i.e. depressive and manic symptoms at the same time, are also possible. Bipolar II disorder is characterized by a pattern of depressive and hypomanic episodes, but not severe manic episodes typical of bipolar I disorder. Cyclothymic disorder (also referred to as cyclothymia) is characterized by periods of hypomanic symptoms (elevated mood and euphoria) and depressive symptoms lasting over a period of at least 2 years.

In some embodiments, the methods provided herein reduce at least one sign or symptom of bipolar disorder. In some embodiments, the methods provided herein reduce at least one sign or symptom of bipolar disorder by about 5% to about 10000, compared to prior to treatment.

In some embodiments, the methods provided herein reduce at least one sign or symptom of bipolar I disorder by about 5% to about 100%, compared to prior to treatment.

In some embodiments, the methods provided herein reduce at least one sign or symptom of bipolar II disorder by about 5% to about 100%, compared to prior to treatment.

Schizophrenia Spectrum and Other Psychotic Disorders

According to another embodiment, the pharmaceutical composition or compound(s) disclosed herein are for use in the treatment of schizophrenia spectrum and other psychotic disorders including delusional disorder, brief psychotic disorder, schizophrenia, schizophreniform disorder, schizoaffective disorder, substance/medication-induced psychotic disorder, schizotypal (personality) disorders, psychotic disorders due to another medical condition, catatonia associated with another mental disorder, and other specified or unspecified schizophrenia spectrum and other psychotric disorders.

In some embodiments the doses to be used for this group of disorders is as in table below:

| Mental and/or Mood Disorder | µg/kg/bodyweight/day |
|---|---|
| Schizophrenia | about 50-2000 |
| Schizophreniform | about 50-2000 |

Personality Disorders

In further embodiments, the pharmaceutical composition or compound(s) disclosed herein can be used to treat a personality disorder as classified in the Diagnostic and Statistical Manual of Mental Disorders, 5$^{th}$ Edition (DSM-5); American Psychiatric Association, 2013, the disclosure of which is incorporated herein in its entirety by reference. Briefly, personality disorders are classified by the DSM-5 into 10 specific disorders: paranoid personality disorder (a pattern of distrust and suspiciousness such that others' motives are interpreted as malevolent); schizoid personality disorder (a pattern of detachment from social relationships and a restricted range of emotional expression); schizotypal personality disorder (a pattern of acute discomfort in close relationships, cognitive or perceptual distortions, and eccentricities of behavior); antisocial personality disorder (a pattern of disregard for, and violation of, the rights of others); borderline personality disorder (a pattern of instability in interpersonal relationships, self-image, and affects, and marked impulsivity); histrionic personality disorder (a pattern of excessive emotionality and attention seeking); narcissistic personality disorder (a pattern of grandiosity, need for admiration, and lack of empathy); avoidant personality disorder (a pattern of social inhibition, feelings of inadequacy, and hypersensitivity to negative evaluation); dependent personality disorder (a pattern of submissive and clinging behavior related to an excessive need to be taken care of); obsessive-compulsive personality disorder (a pattern of preoccupation with orderliness, perfectionism, and control); personality change due to another medical condition (a persistent personality disturbance that is judged to be due to the direct physiological effects of a medical condition); and other specified personality disorder and unspecified personality disorder.

Anxiety Disorders

According to another embodiment, the pharmaceutical composition or compound(s) disclosed herein are for use in the treatment of anxiety disorders as classified in the Diagnostic and Statistical Manual of Mental Disorders, 5$^{th}$ Edition (DSM-5); American Psychiatric Association, 2013, the disclosure of which is incorporated herein in its entirety by reference. Briefly, anxiety disorders are classified by the DSM-5 into: generalized anxiety disorder, separation anxiety disorder, panic disorder, selective mutism, specific phobia (animal, natural environment, fear of blood/injection/injury, situational, other), social anxiety disorder, panic disorder, panic attack specifier, agoraphobia, substance/medication-induced anxiety disorder, anxiety disorder due to other medical conditions, and other specified or unspecified anxiety disorders.

In some embodiments the doses to be used for the above group of disorders is as in table below:

| Mental and/or Mood Disorder | µg/kg/bodyweight/day |
|---|---|
| Generalized Anxiety Disorder | about 10-1000 |
| Separation Anxiety Disorder | about 10-1000 |
| Panic Disorder | about 10-1000 |
| Selective Mutism | about 10-1000 |
| Specific Phobias | about 10-1000 |
| Social Anxiety Disorder | about 10-1000 |

Trauma- and Stressor-Related Disorders

According to another embodiment, the pharmaceutical composition or compound(s) disclosed herein are for use in the treatment of trauma- and stressor-related disorders including attachment disorder, disinhibited social engagement disorder, posttraumatic stress disorder (PTSD), acute stress disorder, adjustment disorders, other specified or unspecified trauma- and stressor-related disorders.

In some embodiments the doses to be used for the above group of disorders is as in table below:

| Mental and/or Mood Disorder | µg/kg/bodyweight/day |
|---|---|
| Attachement Disorder | about 10-1000 |
| PTSD | about 10-1000 |
| Acute Stress Disorder | about 10-1000 |
| Adjustment Disorders | about 10-1000 |
| Disinhibited Social Engagement Disorder | about 10-1000 |

Obsessive-Compulsive and Related Disorders

According to another embodiment, the pharmaceutical composition or compound(s) disclosed herein are for use in the treatment of obsessive-compulsive and related disorders including obsessive-compulsive disorder (OCD), body dysmorphic disorder, hoarding disorder, trichotillomania (hair-pulling disorder), excoriation (skin-picking) disorder, substance/medication-induced obsessive-compulsive and related disorder, obsessive-compulsive and related disorder due to another medical condition, and other specified and unspecified obsessive-compulsive and related disorders (e.g., body-focused repetitive behavior disorder, obsessional jealousy).

In some embodiments the doses to be used for the above group of disorders is as in table below:

| Mental and/or Mood Disorder | μg/kg/bodyweight/day |
|---|---|
| OCD | about 10-1000 |
| Body Dysmorphic Disorder | about 10-1000 |

Disruptive, Impulse-Control, and Conduct Disorders

According to another embodiment, the pharmaceutical composition or compound(s) disclosed herein are for use in the treatment of disruptive, impulse-control, and conduct disorders including oppositional defiant disorder, intermittent explosive disorder, conduct disorder, antisocial personality disorder, pyromania, kleptomania, trichotillomania, and other specific and unspecified disruptive, impulse-control, and conduct disorders.

Feeding and Eating Disorders

According to another embodiment, the pharmaceutical composition or compound(s) disclosed herein are for use in the treatment of feeding and eating disorders including pica, rumination disorder, avoidant/restrictive food intake disorder, anorexia nervosa, binge-eating disorder, bulimia nervosa, polyphagia or over-eating disorders, diabetic hyperphagia, Prader-Willi Syndrome, and hypothalamic obesity, body dismorphic disorders, and other specified and unspecified feeding or eating disorders.

Dissociative Disorders

According to another embodiment, the pharmaceutical composition or compound(s) disclosed herein are for use in the treatment of dissociative disorders including dissociative identity disorder, dissociative amnesia, depersonalization/derealization disorders, and other specified and unspecified dissociative disorders.

Somatic Symptom and Related Disorders

According to another embodiment, the pharmaceutical composition or compound(s) disclosed herein are for use in the treatment of somatic symptom and related disorders including somatic symptom disorder, illness anxiety disorder, conversion disorder (functional neurological symptom disorder), factitious disorder (imposed on self and on another), and other specified and unspecified somatic symptom and related disorders.

Neurodevelopmental Disorders

According to another embodiment, the pharmaceutical composition or compound(s) disclosed herein are for use in the treatment of disease and/or disorder selected from the group consisting of: neurodevelopmental disorders including intellectual disability (intellectual developmental disorder), global developmental delay, communication (language, speech/sound, childhood-onset fluency or stuttering, social, unspecified) disorders, autism spectrum disorders, attention-deficit disorder (ADD), attention-deficit hyperactivity disorder (ADHD), specific learning disorders, motor disorders (developmental coordination, stereotypic movement, tourette's disorder, persistent/chronic motor or vocal tic disorder, provisional tic disorder), and other specified or unspecified neurodevelopmental disorders.

According to another embodiment, the pharmaceutical composition or compound(s) disclosed herein are for use in the treatment of disease and/or disorder selected from the group consisting of seizures (including generalized seizures, focal seizures, unknown onset seizures, and focal to bilateral seizures) and epilepsy (including generalized epilepsy, focal epilepsy, generalized and focal epilepsy, Dravet syndrome, and unknown onset epilepsy).

Sleep-Wake Disorders

According to another embodiment, the pharmaceutical composition or compound(s) disclosed herein are for use in the treatment of a disease and/or disorder selected from the group consisting of sleep-wake disorders including: insomnia disorder, hypersomnolence disorder, narcolepsy, breathing-related sleep disorders (e.g., obstructive sleep apnea hypopnea, central sleep apnea, idiopathic central sleep apnea, sleep-related hypoventilation), circadian rhythm sleep-wake disorders, non-rapid eye movement (NREM) sleep arousal disorders, nightmare disorder, rapid eye movement (REM) sleep behavior disorder, restless legs syndrome, substance/medication-induced sleep disorder, and other specified and unspecified sleep-wake disorders.

Substance-Related and Addictive Disorders

According to another embodiment, the pharmaceutical composition or compound(s) disclosed herein are for use in the treatment of a disease and/or disorder selected from the group consisting of substance-related disorders (SRD) and addictive disorders including, but not limited to, the following class of drugs: alcohol, nicotine, cannabis, hallucinogens, inhalants, opioids, sedatives, hypnotics, anxiolytics, stimulants (amphetamine-type substances, cocaine, and other stimulants), and solvent abuse, pharmaceutical drugs, and other specified or unspefied substance-induced disorders.

According to another embodiment, the pharmaceutical composition or compound(s) disclosed herein are for use in the treatment of non-substance-related disorders including, but not limited to, gambling disorders.

SRD, also known as substance dependence disorder, or drug use disorder or substance abuse disorder, is a condition in which the use of one or more substances leads to significant impairment, dysfunction or distress. Addiction and dependence are components of a SRD, where addiction represents the more severe form of the disorder.

Headache Disorders

In further embodiments, the pharmaceutical composition or compound(s) disclosed herein can be used to treat a headache as classified in Headache Classification Committee of the International Headache Society (IHS) (The International Classification of Headache Disorders, 3rd Edition. *Cephalalgia*, 2018, 38 (1), 1-211), the disclosure of which is incorporated herein in its entirety by reference. Briefly, headaches are classified by the IHS in three broad categories as primary headaches, secondary headaches or other headache disorders.

In some embodiments, the pharmaceutical composition or compound(s) disclosed herein can be used to treat and/or prevent and/or reduce onset/duration of a headache as classified by the HIS as "primary headaches" which include migraines (including migraines without aura, migraines with aura, and chronic migraines), tension-type headaches (including infrequent episodic-, frequent episodic-, and chronic tension-type headache), trigeminal autonomic cephalgias (including cluster headaches, paroxysmal hemicrania, short-lasting unilateral neuraligiform headache attacks, and hemicrania continua), and other primary headache disorders.

Trigeminal autonomic cephalgias (TAC) include cluster headaches (sometimes referred to as familial cluster headaches, histamine cephalgia or vasogenic facial pain) including all its subgroups such as episodic cluster headaches and recurrent or chronic cluster headaches; and short-lasting unilateral neuralgiform headache attacks (SUNHA) and its subgroups short-lasting unilateral neuralgiform headache attacks with conjunctival injection and tearing (SUNCT) and short-lasting unilateral neuralgiform headache attacks with cranial autonomic symptoms (SUNA). The main sub-categories of TAC are defined by the IHS as follows:

Trigeminal Autonomic Cephalalgias (TACs)
1. Cluster headache
    1.1. Episodic cluster headache
    1.2. Chronic cluster headache
2. Paroxysmal hemicrania
    2.1. Episodic paroxysmal hemicrania
    2.2. Chronic paroxysmal hemicrania
3. Short-lasting unilateral neuralgiform headache attacks
    3.1. Short-lasting unilateral neuralgiform headache attacks with conjunctival injection and tearing (SUNCT)
        3.1.1. Episodic SUNCT
        3.1.2. Chronic SUNCT
    3.2. Short-lasting unilateral neuralgiform headache attacks with cranial autonomic symptoms (SUNA)
        3.2.1. Episodic SUNA
        3.2.2. Chronic SUNA
4. Hemicrania continua
    4.1. Hemicrania continua, remitting subtype
    4.2. Hemicrania continua, unremitting subtype
5. Probable trigeminal autonomic cephalalgia
    5.1. Probable cluster headache
    5.2. Probable paroxysmal hemicrania
    5.3. Probable short-lasting unilateral neuralgiform headache attacks
    5.4. Probable hemicrania continua In some embodiments, the pharmaceutical composition or compound(s) disclosed herein can be used to treat and/or prevent and/or reduce onset/duration of a headache as classified by the IHS as "secondary headaches" which include headaches attributed to trauma or injury to the head and/or neck, headaches attributed to cranial and/or cervical vascular disorder, headaches attributed to non-vascular intracranial disorder, headaches attributed to a substance or its withdrawal, headaches attributed to infection, headaches attributed to disorder of homeostasis, headaches or facial pain attributed to disorder of the cranium, neck, eyes, ears, nose, sinuses, teeth, mouth or other facial or cervical structure, headaches attributed to psychiatric disorder, and the headached category of painful lesions of the cranial nerve and other facial pain which includes pain attributed to lesion or disease of the trigeminal nerve.

Trigeminal neuralgia (TN) has been defined by IHS, as "a disorder characterized by recurrent unilateral brief electric shock-like pain, abrupt in onset and termination, limited to the distribution of one or more divisions of the trigeminal nerve and triggered by innocuous stimuli" [**], and includes both Classical TN (previously called Idiopathic Trigeminal Neuralgia) that relates to TN that is caused exclusively by neurovascular compression, and it is classified into two subforms: 1) Classical TN, purely paroxysmal and 2) Classical TN with concomitant persistent facial pain; and Secondary TN that relates to Trigeminal neuralgia-like pain that is related to an underlying disease, including tumors, trauma, viral infection, and multiple sclerosis, where such Secondary TN has a similar clinical presentation as classical TN, but may also present some additional and/or different features (for instance, TN attributed to multiple sclerosis which may have a bilateral presentation and TN related to tumors which frequently display abnormalities in electrophysiological tests, such as trigeminal brainstem reflexes).

In some embodiments, the pharmaceutical composition or compound(s) disclosed herein can be used to treat and/or prevent and/or reduce onset/duration of a headache as classified by the IHS as "other headache disorders" which include those not classified elsewhere and those that are not specified.

Pain

According to another embodiment, the pharmaceutical composition or compound(s) disclosed herein are for use in the treatment of pain caused by conditions including inflammation (e.g. rheumatoid arthritis, lupus, Behcet's disease), genetic factors (e.g. erythromelalgia), neuropathic factors which include conditions causing nerve damage leading to pain such as in diabetes, cancer and cancer treatments such as chemotherapy, neurological conditions such as multiple sclerosis (MS), neurodegenerative conditions such as Parkinson's disease, stroke, shingles, HIV, leprosy, Guillain-Barre syndrome, blood vessel disease, vascular malformations and autoimmune conditions, all neuropathies including peripherial neuropathy, autonomic neuropathy, focal neuropathy, proximal neuropathy, diabetic neuropathy and compression mononeuropathy, phantom limb pain, residual limb pain, and complex regional pain syndrome (CRPS), trigeminal neuralgia, postherpetic neuralgia, radicular pain, radiculitis and all radiculopathies including thoracic or lumbar radiculopathy, nociceptive pain (e.g. injury-induced pain, cancer pain), high prevalence of somatization or nociplastic pain (e.g. chronic widespread pain, fibromyalgia, chronic temporomandibular joint disorders, chronic low back pain of unknown causes, irritable bowel syndrome, chronic primary bladder pain syndrome, chronic primary pelvic pain syndromes), and various other forms of chronic pain regardless of etiology (e.g. chronic lower back pain).

In further embodiments, the pharmaceutical composition or compound(s) disclosed herein can be used to treat chronic pain as classified by the International Association for the Study of Pain (IASP) taskforce (PAIN: June 2015—Volume 156—Issue 6—p 1003-1007) the disclosure of which is incorporated herein in its entirety by reference. Briefly, chronic pain is defined as persistent or recurrent pain lasting longer than 3 months and classified in the following seven categories: chronic primary pain (which includes fibromyalgia, chronic pelvic pain, non-specific back pain, and chronic primary pain not otherwise specified); chronic cancer pain (which includes pain due to cancer and metastases, chemotherapy-induced pain, pain due to radiotherapy, pain due to cancer surgery, and other chronic pain related to cancer); chronic post-surgical and post-traumatic pain (which includes all post-surgical and post-traumatic pain, and the post-surgical/traumatic pain not otherwise specified); chronic neuropathic pain (which includes peripheral neuropathic pain, central neuropathic pain, and other neuropathic pain and neuropathic pain not otherwise specified); chronic headache and orofacial pain (which includes chronic primary headaches, chronic secondary headaches, chronic orofacial pain, and headache and orofacial pain not otherwise specified); chronic visceral pain (which includes chronic visceral pain from persistent inflammation, and/or vascular mechanisms, and/or obstruction/distension, and/or traction/compression, and/or combined mechanisms, or chronic visceral pain referred from other locations, from cancer, or functional or unexplained chronic pain); and chronic musculoskeletal pain (which includes chronic muscloskeletal pain from persistent inflammation, and/or structural osteoarticular changes, and/or chronic musculoskeletal pain originating from diseases of the nervous system such as spastic pain, and chronic non-specific musculoskeletal pain and related pain syndromes).

In further embodiments, the pharmaceutical composition or compound(s) disclosed herein can be used to treat acute pain and/or prevent or reduce onset/duration of acute pain, which is defined as pain that lasts for short period, from some hours or days or up to 3 months, regardless of type of pain and including inflammatory, nociceptive, neuropathic, nociplastic and other kinds of pain, and which includes acute pain from tissue injury including those arising from any kind of surgery, dental work, labor and childbirth, cuts, burns, broken bones and other accidents or trauma, acute pain arising from any disease state, acute pain arising from any kind of trauma, and acute pain arising from undetermined causes.

Spasticity

According to another embodiment, the pharmaceutical composition or compound(s) disclosed herein are for use in the treatment of conditions associated with spasticity, with or without neuropathic pain, including, but not limited to, cerebral palsy, stroke, multiple sclerosis (MS), traumatic brain injury (TBI), amyotrophic lateral sclerosis (ALS), hereditary spastic paraplegias, adrenoleukodystrophy (ALD), phenylketonuria, krabbe disease, and spinal cord injury.

Nerve Injury

According to another embodiment, the pharmaceutical composition or compound(s) disclosed herein are for use in the treatment of a disorders and diseases associated with nerve injury or trauma from: peripheral nerve injury or trauma regardless of cause and/or central nervous system (brain and spinal cord) nerve injury or trauma regardless of cause. These include disorders and diseases arising from external physical factors such as accidents, sports injury, fall, gunshots or an explosive blaststroke; or internal factors such as stroke, ruptured brain aneurysm, lack of oxygen, infection (viral, bacterial, prion, or other), and autoimmune diseases; and they include all other nerve injury or trauma caused directly or indirectly by external factors, and/or nerve injury or trauma that arise directly or indirectly from disease states.

Fatigue

According to another embodiment, the pharmaceutical composition or compound(s) disclosed herein are for use in the treatment of chronic fatigue (e.g. physical fatigue, psychological fatigue or mental fatigue) from traumatic brain injury (TBI), chronic fatigue syndrome (CFS), and related conditions, and other diseases and/or disorders causing chronic fatigue.

Neuro-Degenerative

According to another embodiment, the pharmaceutical composition or compound(s) disclosed herein are for use in the treatment of a disease and/or disorder selected from the group consisting of: neuro-degenerative disorders such as Alzheimer's disease, amyotrophic lateral sclerosis (ALS), Batten disease, Friedreich ataxia, Huntington's disease, Lewy body disease, motor neuron disease, multiple sclerosis, Parkinson's disease, prion disease, spinal muscular atrophy, neuro-degenerative conditions due to viral (e.g., HIV) or bacterial infection, neuro-degenerative conditions due or substance/medication, and other aging-related and non-aging related neurodegenerative conditions.

Sexual Dysfunctions and Gender Dysphoria Disorders

According to another embodiment, the pharmaceutical composition or compound(s) disclosed herein are for use in the treatment of a disease and/or disorder selected from the group consisting of sexual dysfunctions including delayed ejaculation, erectile disorder, female orgasmic disorder, female sexual interest/arousal disorder, genito-pelvic pain/penetration disorder, male hypoactive sexual desire disorder, premature (early) ejaculation, substance/medication induced sexual dysfunction, other specified and unspecified sexual dysfunction.

According to another embodiment, the pharmaceutical composition or compound(s) disclosed herein are for use in the treatment of a disease and/or disorder selected from the group consisting of gender dysphoria in children, adolescent, adults, and other specified and unspecified gender dysphoria.

Neurocognitive Disorders

According to another embodiment, the pharmaceutical composition or compound(s) disclosed herein are for use in the treatment of a disease and/or disorder selected from the group consisting of neurocognitive disorders (NCDs) including delirium, NCD due to Alzheimer's disease, vascular NCD, NCD with Lewy bodies, NCD due to Parkinson's disease, frontotemporal NCD, NCD due to traumatic brain injury, NCD due to HIV infection, substance/medication-induced NCD; NCD due to Huntington's disease, NCD due to prion disease; NCD due to another medical condition, NCD due to multiple etiologies, and unspecified NCD.

According to another embodiment, the pharmaceutical composition or compound(s) disclosed herein are for use in the treatment of neurocognitive/learning dysfunction including memory problems, a lack of mental clarity, poor concentration, and/or an inability to focus arising from infections (viral/bacterial/prion/other) or other specified or unspecified disorders, diseases, or other unknown causes.

According to another embodiment, the pharmaceutical composition or compound(s) disclosed herein are for use in the treatment of reduction in memory, cognition and/or learning, with or without obvious signs of neurodegenerative disorders or neurodevelopmental disorders, and/or prevention of reduction in memory, cognition and/or learning, with or without obvious signs of neurodegenerative disorders or neurodevelopmental disorders and regardless of age.

According to another embodiment, the pharmaceutical composition or compound(s) disclosed herein are for use in the treatment of reduction in memory, cognition and/or learning, with or without obvious signs of neurodegenerative disorders associated with normal aging.

According to another embodiment, the pharmaceutical composition or compound(s) disclosed herein are for use in the treatment of a disease and/or disorder selected from the group consisting of: neurological and/or neuropsychiatric disorders and/or conditions associated with normal aging and/or progeroid syndromes.

According to another embodiment, the pharmaceutical composition or compound(s) disclosed herein are for use in the treatment of a disease and/or disorder selected from the group consisting of: neurological and/or neuropsychiatric disorders and/or conditions associated with normal aging and/or progeroid syndromes.

Neurological—Viral Infection

According to another embodiment, the pharmaceutical composition or compound(s) disclosed herein are for use in the treatment of a disease and/or disorder selected from the group consisting of: neurological diseases caused by viral infections that utilize neuronal cells surface receptors for entry including serotonergic (5-HT) receptors (in particular 5-HT2A receptor), such as progressive multifocal leukoencephalopathy (PML) caused by JC virus.

Counteracting Other Drug's Side Effects

According to another embodiment, the pharmaceutical composition or compound(s) disclosed herein are for use in the treatment of a disease and/or disorder selected from the group consisting of: reduction and/or prevention of a psychedelic's (e.g. psilocybin and LSD) side effects (such as hallucination, bad trips).

Well-being

In other embodiments, the pharmaceutical composition or compound(s) disclosed herein can be used for self administration for providing a general feeling of wellness.

5-HT1 Receptor-Mediated Therapeutic Effects in Headache and Pain Disorders

According to another embodiment, the pharmaceutical composition or compound(s) disclosed herein are for use in the treatment of diseases and/or disorders, for example headache and pain disorders, wherein the therapeutic mechanism is linked to 5-HT1 receptor activation (agonism at one or more 5-HT1 receptor subtypes such as 5-HT1A, 1B, 1D, 1E, and 1F).

5-HT6 Receptor-Mediated Therapeutic Effects in Cognition, Learning, and Memory

According to another embodiment, the pharmaceutical composition or compound(s) disclosed herein are for use in the treatment of diseases and/or disorders associated with cognitive/learning/memory deficit or decline, for example Alzheimer's disease, Parkinson's disease, schizophrenia, Down syndrome, and autism spectrum disorders, wherein the therapeutic mechanism is linked to 5-HT6 receptor activation (agonism).

5-HT2A Receptor-Mediated Therapeutic Effects in Depressive and Anxiety-Related Disorders According to another embodiment, the pharmaceutical composition or compound(s) disclosed herein are for use in the treatment of diseases and/or disorders, for example depressive and anxiety-related disorders, wherein the therapeutic mechanism is linked to 5-HT2A receptor activation (agonism).

D2-Like Receptor-Mediated Therapeutic Effects in Various Neuropsychiatric Disorders According to another embodiment, the pharmaceutical composition or compound(s) disclosed herein are for use in the treatment of diseases and/or disorders, for example depressive disorders, Parkinson's disease, schizophrenia, restless legs syndrome, psychosis, attention deficit hyperactivity disorder (ADHD), substance use disorders, hyperprolactinemia, and Neuroleptic Malignant Syndrome, wherein the therapeutic mechanism is linked to D2-like receptor (such as D2 and D4 receptor subtypes) activation (agonism).

Non-Hallucinogenic and Neuroplastogen and Receptors

Hallucinations caused by LSD or other serotonergic psychedelic compounds are believed to be driven by agonism at the 5HT2A receptor (Halberstadt A. L. *Behavioural Brain Research*. 2015, 15; 277:99-120). LSD derivatives that are 5HT2A agonists are therefore expected to be psychedelic, that is cause hallucinations. It is therefore unexpected and novel for an LSD derivative that has 5HT2A agonism to also be substantially non-hallucinogenic.

There are several subtypes of 5-HT receptors identified to date in mammals including: 5HT-1A, 1B, 1D, 1E, 1F, 2A, 2B, 2C, 3, 4, 5A, 5B, 6 and 7. LSD is known to also exhibit 5HT-2B receptor agonism. This agonism at the 5HT-2B receptor is undesirable as it is believed to lead to fibrosis and consequent cardiovascular side effects such as cardiac valvulopathies caused by LSD (Cavero and Guillon, *Journal of Pharmacological and Toxicological Methods,* 2014, 69:150-161). An LSD derivative that has 5HT2A agonism and is not a 5HT-2B agonist would be novel and unexpected.

Neuroplastogen is any compound that induces/promotes neuroplasticity. Neural plasticity may be defined as structural and functional changes in the nervous system including neurogenesis, modulation of neuron or astrocyte soma or neurite size, shape and length, or synaptic plasticity (including synaptogenesis, synaptic strengthening, spinogenesis, loss of synaptic spines, "pruning", changes in synaptic spine volume, changes in synaptic densities) or changes in specific synaptic proteins and pathways. Promotion of neuroplasticity is considered to be an important therapeutic mechanism for treatment of most neuropsychiatric and neurological diseases and/or disorders.

Therefore, in some embodiments, the LSD derivative(s) or polymorph(s) thereof disclosed herein, are substantially non-hallucinogenic and exhibit a degree of agonism at the 5HT2A receptor.

In further embodiments, the LSD derivative(s) or polymorph(s) thereof disclosed herein, are substantially non-hallucinogenic and exhibit neuroplastogen properties with or without a degree of agonism at the 5HT2A receptor.

In further embodiments, the LSD derivative(s) or polymorph(s) thereof disclosed herein, are substantially non-hallucinogenic, exhibit poor to no agonism or antagonism or reverse agonism at the 5HT2B receptor, and exhibit neuroplastogen properties with or without a degree of agonism at the 5HT2A receptor.

In further embodiments, the LSD derivatives and polymorphs thereof disclosed herein do not impart a substantial hallucinogenic effect and thus are suitable as a "neuroplastogen drug" or "neuroplastogen" with a potential for modulating neural plasticity and provided formulated as a "neuroplastogen dose".

In further embodiments, administration of the LSD derivatives and polymorphs thereof disclosed herein are at safe and well tolerated doses able to exert neuroplastogen effects for inducing/improving neuroplasticity which aids in treatment of: psychiatric diseases/disorders; for treating and/or prevention/reduction in decline of cognition, learning and memory in all age groups and particularly with normal aging; for treating and/or prevention/reduction in decline of cognition, learning and memory in neurological diseases/disorders regardless of age; and/or for treating and/or prevention/reduction in decline of cognition, learning and memory in psychiatric diseases/disorders regardless of age.

In further treatment embodiments, the LSD derivatives and polymorphs thereof disclosed herein are useful for the modulation of a neurological receptor, the modulation being agonism, antagonism or partial variations of either, where modulation of the neurological receptor aids in treatment of a disease or disorder. As a non-limiting example, the LSD derivatives and polymorphs disclosed herein may modulate 5-HT receptors such as 5-HT2A subtype thus affecting 5-HT type impacted neurological and psychiatric disorders, these would include depression, anxiety, PTSD, and various forms of pain.

In further embodiments, transporters called solute carriers (SLCs) may be modulated by the novel LSD derivatives and polymorphs of the disclosure, the modulation being agonism, antagonism or partial variations of either, and where modulation of the transporter aids in treatment of a disease or disorder.

Therefore, in some embodiments, the LSD derivative(s) or polymorph(s) thereof disclosed herein, are substantially non-hallucinogenic and exhibit a degree of agonism at the 5HT2A receptor.

In further embodiments, the LSD derivative(s) or polymorph(s) thereof disclosed herein, are substantially non-hallucinogenic and exhibit neuroplastogen properties with or without a degree of agonism at the 5HT2A receptor.

In further embodiments, the LSD derivative(s) or polymorph(s) thereof disclosed herein, are substantially non-hallucinogenic, exhibit poor to no agonism or antagonism or reverse agonism at the 5HT2B receptor, and exhibit neuroplastogen properties with or without a degree of agonism at the 5HT2A receptor.

In further embodiments, the LSD derivatives and polymorphs thereof disclosed herein do not impart a substantial hallucinogenic effect and thus are suitable as a "neuroplastogen drug" or "neuroplastogen" with a potential for modulating neural plasticity and provided formulated as a "neuroplastogen dose".

In further embodiments, administration of the LSD derivatives and polymorphs thereof disclosed herein are at safe and well tolerated doses to exert neuroplastogen effects for inducing/improving neuroplasticity which aids in treatment of: psychiatric diseases/disorders; for helping cognition, learning and memory in all age groups and particularly with normal aging; for helping cognition, learning and memory in neurological diseases/disorders regardless of age; and/or for helping cognition, learning and memory in psychiatric diseases/disorders regardless of age.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Nomenclature

The names, structures and synthesis codes are shown in Table I:

TABLE I

The names, structures and synthesis codes are shown in Table I:

| STRUCTURE | FORMULA AND MOLECULAR WEIGHT (g/mol) | COMPOUND CODE | NAME(S) |
|---|---|---|---|
| 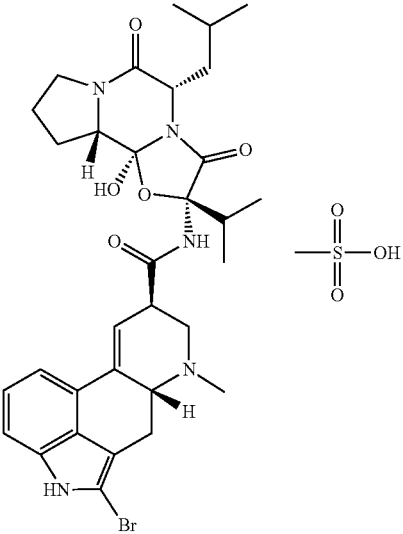 | $C_{33}H_{44}BrN_5O_8S$ 750.70 | E402 | Bromocriptine mesylate |
| 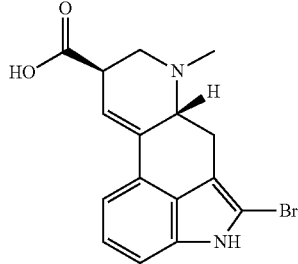 [SMILES: CN1C[C@H](C(=O)O)C=C2c3cccc4[nH]c(Br)c(c34)C[C@H]21] | $C_{16}H_{15}BrN_2O_2$ 347.21 | E404 | 2-Br-LSA; 2-bromo-lysergic acid |

TABLE I-continued

The names, structures and synthesis codes are shown in Table I:

| STRUCTURE | FORMULA AND MOLECULAR WEIGHT (g/mol) | COMPOUND CODE | NAME(S) |
|---|---|---|---|
| 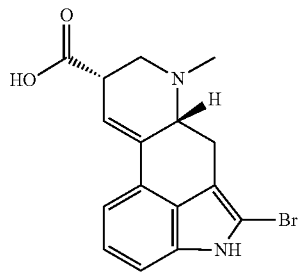 [SMILES: CN1C[C@@H](C(=O)O)C=C2c3cccc4[nH]c(Br)c(c34)C[C@H]21] | $C_{16}H_{15}BrN_2O_2$ 347.21 | E404-Iso | (5aR,8S) iso-2-Br-lysergic acid; (5R-8S) iso-2-Br-lysergic acid |
| 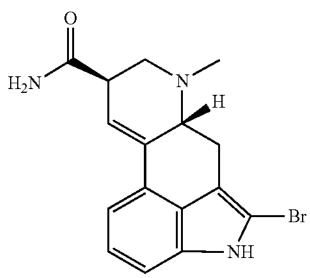 [SMILES: CN1C[C@H](C(N)=O)C=C2c3cccc4[nH]c(Br)c(c34)C[C@H]21] | $C_{16}H_{16}BrN_3O$ 346.2 | — | 2-bromo-lysergic amide |
| | $C_{20}H_{24}BrN_3O$ 402.33 | E405 | 2-Br-LSD; (5aR, 8R)-2-Bromo-9,10-didehydro-N,N-diethyl-6-methylergoline-8-carboxamide; (5R, 8R)-2-Bromo-9,10-didehydro-N,N-diethyl-6-methylergoline-8-carboxamide |
| | $C_{20}H_{24}BrN_3O$ 402.33 | E558 | Iso-2-Br-LSD; (5aR, 8S)-2-Bromo-9,10-didehydro-N,N-diethyl-6-methylergoline-8-carboxamide; (5R, 8S)-2-Bromo-9,10-didehydro-N,N-diethyl-6-methylergoline-8-carboxamide |
| 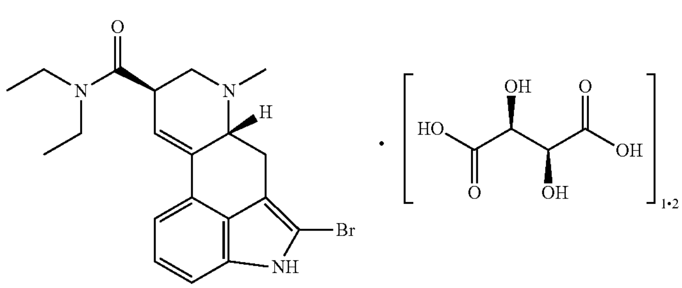 | $C_{22}H_{27}BrN_3O_4$ 477.37 | E559 | 2-Br-LSD hemi D-tartrate; (5aR, 8R)-2-Bromo-9,10-didehydro-N,N-diethyl-6-methylergoline-8-carboxamide hemi-L-tartrate; (5R, 8R)-2-Bromo-9,10-didehydro-N,N-diethyl-6-methylergoline-8-carboxamide hemi-D-tartrate |

TABLE I-continued

The names, structures and synthesis codes are shown in Table I:

| STRUCTURE | FORMULA AND MOLECULAR WEIGHT (g/mol) | COMPOUND CODE | NAME(S) |
|---|---|---|---|
| (structure shown) | $C_{22}H_{27}BrN_3O_4$ 477.37 | E560 | 2-Br-LSD hemi L-tartrate; (5aR, 8R)-2-Bromo-9,10-didehydro-N,N-diethyl-6-methylergoline-8-carboxamide hemi-L-tartrate; (5R, 8R)-2-Bromo-9,10-didehydro-N,N-diethyl-6-methylergoline-8-carboxamide hemi-L-tartrate |

It is noted that International Union of Pure and Applied Chemistry (IUPAC) names generated for many 2-bromo-LSD related compounds show the chiral centers at carbons 6 and 9. A numbering has been adopted, however, that is consistent with the bromine being bonded to the second carbon, putting the two chiral carbons at the 5 and 8 positions, as confirmed in the structures above.

Example 1: Synthesis 2-Bromolysergic Acid (i) 2-Bromolysergic Acid (B) was Prepared Via Basic Hydrolysis of Bromocriptine Mesylate (A)

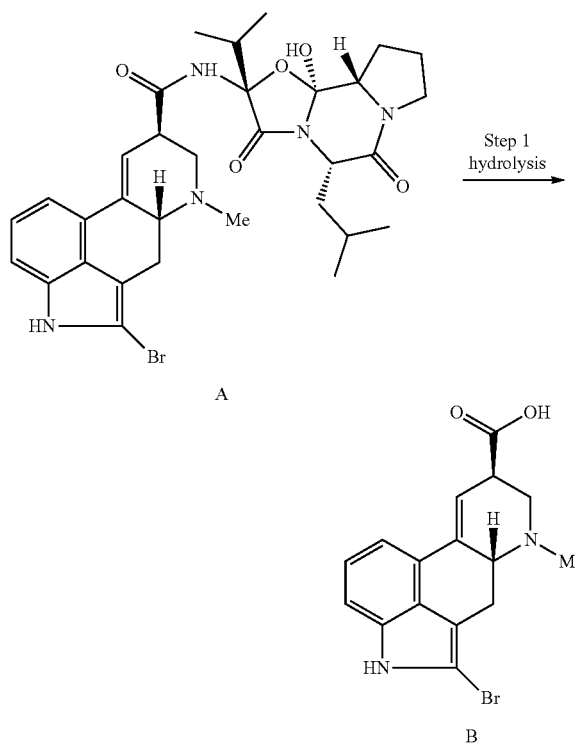

The reaction proceeded via basic hydrolysis of bromocriptine mesylate (A) to 2-bromolysergic acid (B).
General Reaction:

A solution of aqueous potassium hydroxide (KOH) was charged to bromocriptine mesylate at about room temperature and the resulting mixture was heated at different temperatures. Different water-miscible solvents were prepared, such as ethanol, THF, 2-methyl-THF and isopropyl alcohol (IPA) to reduce clumping of the solids. The resulting mixtures were heated at different temperatures. Shorter reaction times were achieved and a relatively smooth filtration of the product. The reaction mixture was cooled to about 5° C., neutralized with about 2.5 equivalents HCl to pH of about 6.0. The formed solid was filtered, dried and washed with an ether such as MTBE. In order to completely remove residual water, THF was added to the MTBE/water mixture to conduct azeotropic distillation. Further purging of water can be achieved by dissolving the product in THF and evaporating or filtering one or more times.

Chemicals:

All chemicals and solvents were purchased from commercial sources and used without further purification (e.g. bromocriptine mesylate (CAS 22260-51-1) from Teva Pharmaceutical Industries Ltd; IPA, water, methyl tert-butyl ether (MTBE), and tetrahydrofuran (THF) from Caledon Laboratories Ltd; and the concentrated HCl from Fisher Scientific Company).

Reaction Equipment and Conditions:

High vacuum (0.02 mbar) was created by using an oil pump (Vacuubrand Model RZ 6).

The reactions were stirred with a magnetic stirrer unless noted otherwise.

Potassium permanganate ($KMnO_4$) solution used as a staining agent for TLC detection was prepared as follows: Potassium permanganate, $KMnO_4$, (about 1.5 g) and potassium carbonate, $K_2CO_3$, (about 10 g) were dissolved in distilled water (about 150 mL) at room temperature.

Reaction:

A 5 L, 3-neck flask equipped with a condenser, thermometer, overhead agitation and nitrogen inlet was charged with bromocriptine mesylate (about 250 g, 0.333 mol, 1.0 eq), IPA (about 500 mL, 2 vol) and water (about 1500 mL, 6 vol). At a temperature of about 25° C., aq. KOH 45% w/w solution (about 394 mL, 1.6 vol) was added in one portion, and the reaction mixture was adjusted to gentle reflux (about 85° C.) for about 2-3 h. The mixture slowly dissolves upon heating at gentle reflux to a dark brown solution. The reaction solution was cooled to about 22° C. Ultra-performance liquid chromatograph (UPLC) analysis shows a complete conversion of the starting material.

Upon scale up, about 23.4 kg of bromocriptine were charged to a 400 L glass lined reactor, followed by about 36.8 kg of isopropyl alcohol (2 volumes) under a nitrogen purge. After mixing, about 140.4 kg of deionized water (6 volumes) were added to the reactor. The temperature of the mixture was adjusted to about 22±3° C. and the mixture was stirred for a further about 30 minutes. After stirring, about 13.8 equivalents of potassium hydroxide were added to the reactor in the form of about 53.6 kg of a 45% w/w aqueous solution. To ensure all the potassium hydroxide was added to the reactor, the addition lines were flushed with about 9.4 kg of deionized water. The temperature of the mixture was increased to about 81° C. to reflux the mixture for about 2 hours. The reactor was kept under nitrogen throughout the process. After reflux, the mixture was cooled to about 25° C. UPLC analysis showed that less than about 0.05% of the bromocriptine was remaining after the reaction.

Work-up: The solution was distilled to about 8.0-9.0 vol (about 2.0-2.3 L) under reduced pressure at an internal temperature of about 45° C. The residual solution was then cooled to a temperature of about 25° C. and charged with water (about 500 mL, 2.0 vol). The reaction flask was then adjusted to an internal temperature of about 3° C. (about 0-6° C.). About 2.5M HCl solution (about 1125 mL, 4.5 vol) was added to the reaction flask maintaining an internal temperature at about 10° C. and stirred for about 15 min to adjust the pH value to about 5.8-6.2. The mixture was then allowed to warm to room temperature and stirred for about 1-2 h. The precipitate was filtered under vacuum with nitrogen flow through a Buchner funnel prepared with filter paper and polyester filter cloth, washed with water (2× about 500 mL), MTBE (2× about 250 mL), and dried under vacuum with nitrogen flow for about 18 h.

Upon scale up, the mixture was cooled to about 10° C. and distilled under about −12.8 psig vacuum. After the vacuum was achieved, the mixture was heated to about 24° C. and the reaction mixture volume was reduced to about 200 L. A further about 46.8 kg of deionized water (2 volumes) was charged to the reactor and the temperature reduced to about 4.0° C. About 4.5 volumes of about 2.5M HCl were added to the reactor over the course of about one hour while cooling to maintain the reaction mixture temperature between about 5.0 and about 5.8° C. The pH was adjusted from about 13.3 to about 5.75 by adding about 43.3 L additional 2.5 M HCl. The temperature of the mixture was increased to about 22° C. and stirred for about 1.5 hours. The precipitate was collected from the resulting slurry by filtration over double layer cotton/polyester filter cloths under nitrogen and protected from light. The reactor was rinsed twice with about 2 volumes each time of deionized water, which was warmed to about room temperature and then used to wash the filter cake. The reactor and filter cake were then washed twice with about one volume each time of MTBE. The product was dried for about 116 hours at about 45° C. with a stream of nitrogen pulled through the solids. UPLC analysis showed that the purity of the (5R,8R) 2-bromo-lysergic acid was about 93.5%. The major impurity was the stereo-isomer, (5R,8S) 2-bromo-lysergic acid which was about 4.6%.

Purification and Azeotropic Drying: THF (about 1250 mL, 5 vol) was added to the isolated wet product into a 5 L, 3-neck reaction flask equipped with a distillation apparatus and thermometer. The suspension was stirred for about 30 min at about room temperature, and concentrated under reduced pressure and the internal temperature raised to about 40° C. to target about 1.5-2.0 vol (about 375-500 mL) final volume. This process was repeated about three times. The precipitate was filtered under vacuum with nitrogen flow through a Buchner funnel prepared with filter paper and polyester filter cloth, washed with THF (2× about 125 mL), and dried under vacuum with nitrogen flow for about 18 h. The product was stored at about 2-8° C. in the dark.

Upon scale up, about 9 kg dried (5R,8R) 2-bromo-lysergic acid were charged to a reactor along with about 104 kg tetrahydrofuran (about 5 volumes) and mixed for about 15 minutes. The reactor temperature was adjusted to about 7° C. and vacuum applied to about −13.3 psig vacuum. The temperature was increased to about 10° C. and the volume reduced to about 45 L under nitrogen. About 104 kg tetrahydrofuran (about 5 volumes) were added and the distillation repeated, this time at about −13.8 psig and about 15° C. A third portion of about 104 kg tetrahydrofuran was added and distillation repeated a final time. The temperature was adjusted to about 21° C. and the product stirred for about one hour. The precipitate was recovered by filtration over double layer cotton/polyester filter cloths. The reactor is rinsed and filter cake washed with 3× about 0.5 volume washes. The cake was dried under vacuum and nitrogen at about 40° C. for about 106 hours. UPLC analysis showed that the purity of the (5R,8R) 2-bromo-lysergic acid was 95.3%. The major impurity was the stereo-isomer, (5R,8S) 2-bromo-lysergic acid which was 2.4%.

Final analysis for small scale batch: KF: about 0.93%, HPLC: about 98.55%, and Yield: about 86 g, 74%.

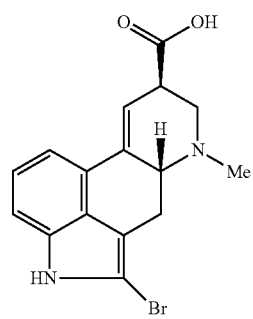

Chemical Formula: $C_{16}H_{15}BrN_2O_2$
Exact Mass: 346.03
Molecular Weight: 347.21

$^{13}$C and $^1$H Nuclear Magnetic Resonance Spectra

Figure 1A:
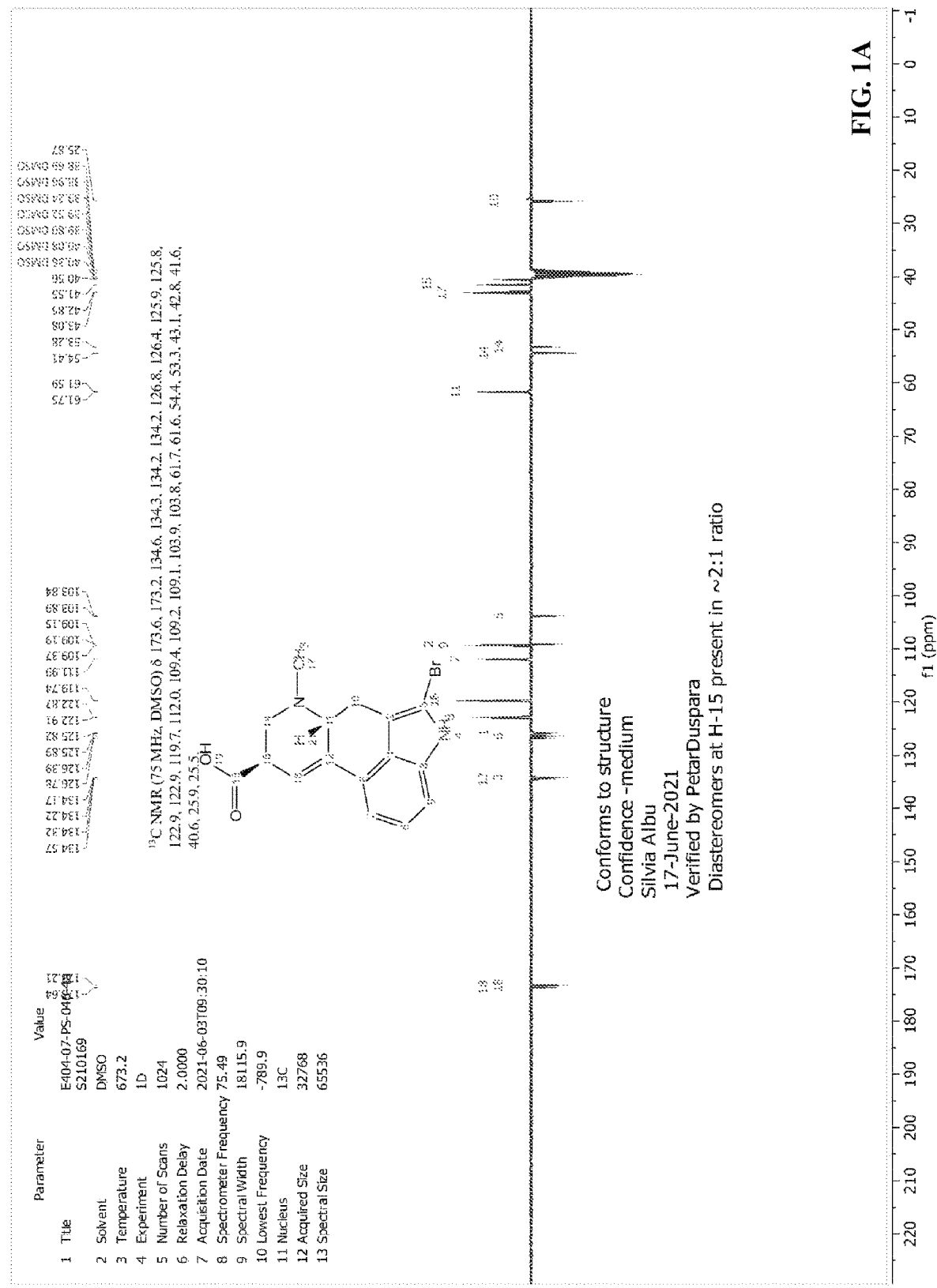
FIGS. 1A and 1B show examples of $^1$H-NMR and $^{13}$C-NMR spectra of 2-bromolysergic acid (B) in DMSO-$d_6$, respectively.
Figure 1B:
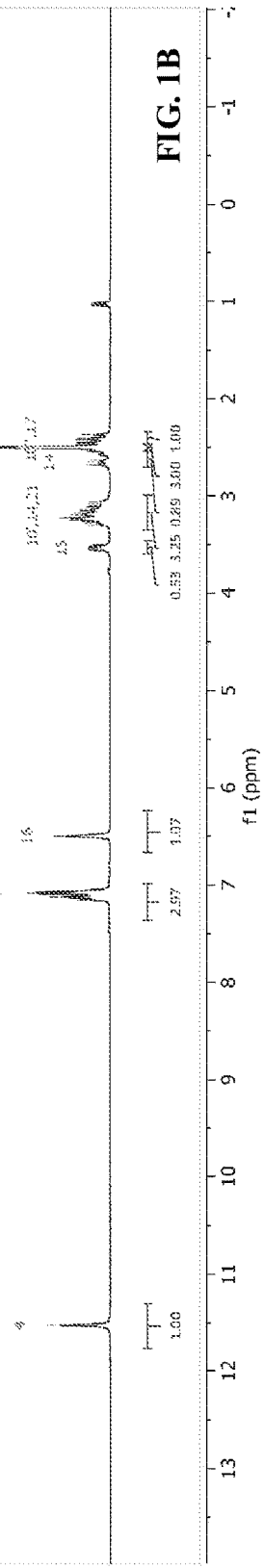

The 500 MHz $^1$H-NMR and the 125 MHz $^{13}$C-NMR spectra of (B) in DMSO-$d_6$ are as follows (see also FIGS. 1A and 1B):

$^{13}$C NMR (75 MHz, DMSO) δ 273.6, 173.2, 134.6, 134.3, 134.2, 134.2, 126.8, 126.4, 125.9, 125.8, 122.9, 122.9, 119.7, 112.0, 109.4, 109.2, 109.1, 103.9, 103.8, 61.7, 61.6, 54.5, 53.3, 43.1, 42.8, 41.6, 40.6, 25.9, 25.5.

$^1$H NMR (300 MHz, DMSO-$d_6$) δ 11.52 (s, 1H), 7.36-6.99 (m, 3H), 6.50 (t, J=2.6 Hz, 1H), 3.54 (ddt, J=11.0, 5.6, 3.0 Hz, 1H), 3.35-2.99 (m, 3H), 2.70-2.53 (m, 1H), 2.50 (s, 3H), 2.46-2.34 (m, 1H).

High Resolution Mass Spectra

Figure 2A:
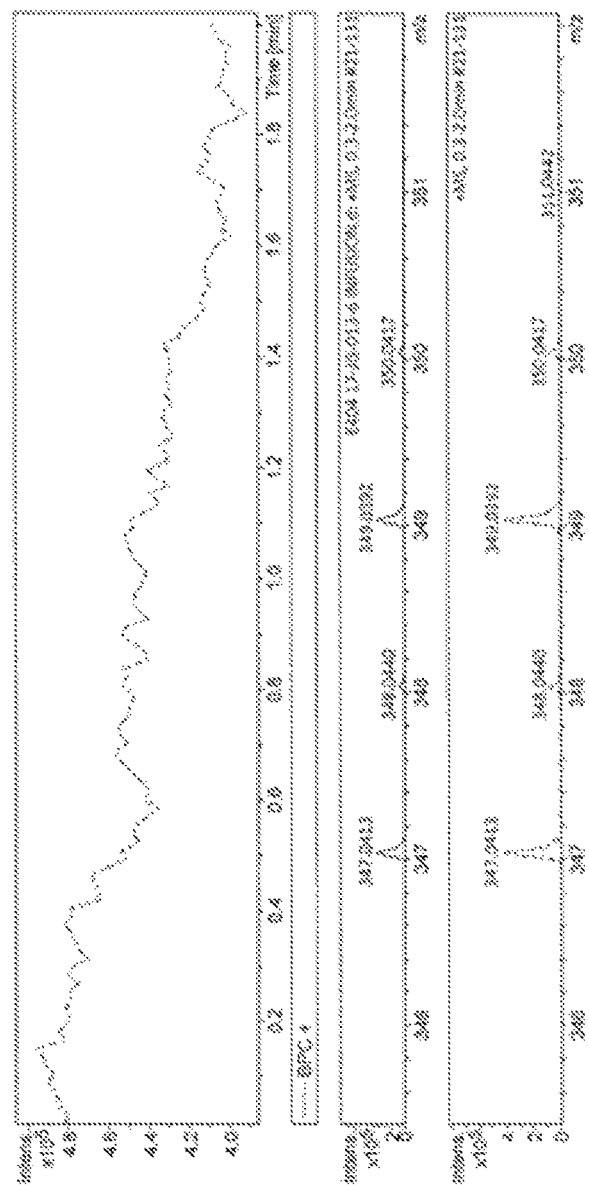
FIGS. 2A and 2B show an examples of an electrospray ionization mass spectra of 2-bromo-LSD €.
Figure 2B:
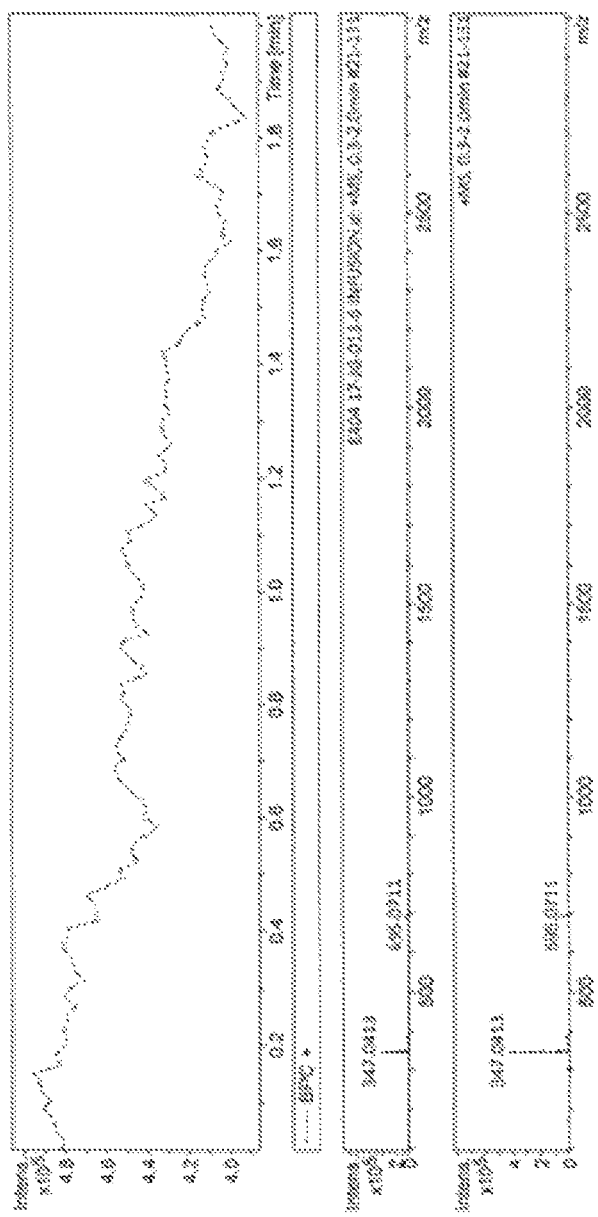

The electrospray ionization mass spectra of (B) are shown in FIGS. 2A and 2B.

(ii) 2-Bromo-LSD (C) is Prepared Via the
2-Bromolysergic Acid (B) with Diethylamine

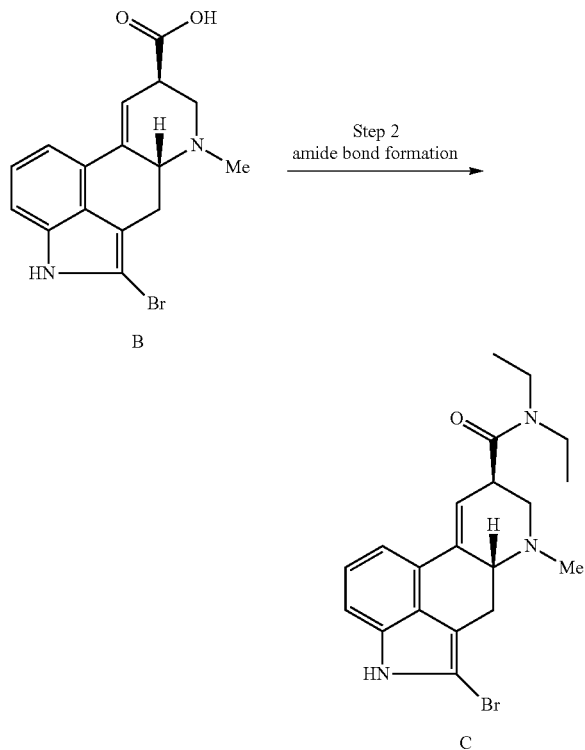

The reaction proceeded via base-catalyzed amide bond formation of the 2-bromolysergic acid (B) upon its reaction with diethylamine, in the presence of a coupling agent. 2-bromo-LSD free base (C) was recovered through precipitation.

General Reaction:

Different coupling agents, solvents, temperatures, rates and order of mixing the reactants, and reaction times have been completed. The reaction was generally complete and specific for the 5R,8R isomer, although 5R,8S isomer was also formed. After coupling, the reaction mixture was cooled to about 5° C., water was added, and then the pH was lowered with different acids such as aqueous HCl solution to different pH values in the range of about 6 to about 8. The precipitate was collected by filtration. Further purification was afforded by dissolving the product in THF with subsequent concentration and filtration.

Chemicals:

All chemicals and solvents were purchased from commercial sources as noted above and used without further purification.

Reaction Equipment and Conditions:

High vacuum (0.02 mbar) was created by using an oil pump (Vacuubrand Model RZ 6).

The reactions were stirred with a magnetic stirrer unless noted otherwise.

Potassium permanganate ($KMnO_4$) solution used as a staining agent for TLC detection was prepared as follows: Potassium permanganate, $KMnO_4$, (about 1.5 g) and potassium carbonate, $K_2CO_3$, (about 10 g) were dissolved in distilled water (about 150 mL) at room temperature.

Reaction:

A mixture of 2-bromo-lysergic acid (B) (about 5.20 g) and N-methylmorpholine (NMM) (about 3 equiv. or 4.56 g) in THF (about 3 vol or 15.6 mL) was stirred for about 1 h at about room temperature, and treated with a solution of carbonyldiimidazole (CDI) (about 2 equiv. or 14.6 g) in THF (about 5 vol or 26 mL). The solution was stirred at about room temperature for about 2 h, and cooled to about 0° C. Diethylamine (DEA) (2.2 equiv. or 7.25 g) was added at about 0° C., the reaction solution was allowed to warm to about room temperature, and stirred at this temperature. The mixture was monitored by HPLC, which confirmed full consumption of the starting material after about 18 h.

Work-up: The solution was cooled to about 5° C., diluted with about 5 volumes of water and slowly treated with HCl (about 1M, 7 equivalents, 1.7 vol/vol) over about 3 hours to adjust the pH value to about 5.9. A further 18.3 volumes of water are added. The precipitated product was filtered and washed with water, 3×2volumes.

Final analysis: KF: 0.93%, HPLC: 98.55%

High Resolution Mass Spectra

Figure 4:
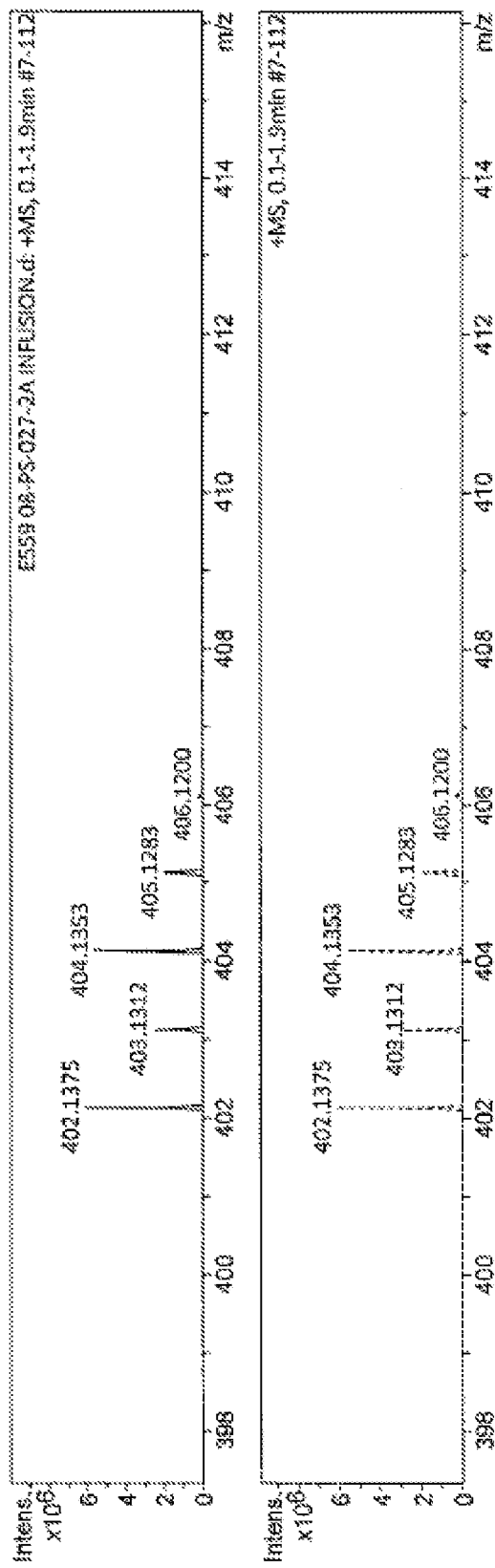
FIG. 4 shows an example of an electrospray ionization mass spectra of 2-bromo-LSD €.

The electrospray ionization mass spectra of (C) is shown in FIG. 4.

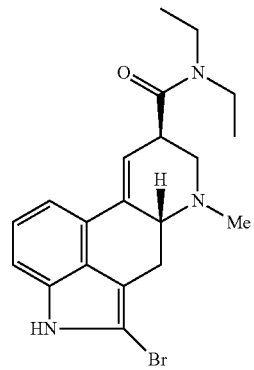

Chemical Formula: $C_{20}H_{24}BrN_3O$
Exact Mass: 401.11
Molecular Weight: 402.34

$^{13}C$ and $^1H$ Nuclear Magnetic Resonance Spectra

The 125 MHz $^{13}C$-NMR spectra of (C) in DMSO-$d_6$ is as follows:

$^{13}C$ NMR (75 MHz, $CDCl_3$) δ 171.57, 135.37, 134.30, 126.92, 126.43, 123.37, 120.21, 113.26, 110.71, 109.11, 103.51, 77.48, 67.98, 62.68, 55.99, 43.89, 42.13, 40.40, 39.76, 26.77, 25.62, 14.91, 13.18.

Selection of a Coupling Agent

A component of the Step 2 reaction is the coupling agent. Any suitable coupling agents may be used. Coupling agents such as carbonyldiimidazole (CDI), 2-chloro-4,6-dimethoxy-1,3,5 triazine (CDMT), 1-hydroxybenzotriazole (HOBt), hexafluorophosphate azabenzotriazole tetramethyl uronium (HATU), propylphosphonic anhydride (T3P) and phosphorous oxychloride ($POCl_3$) have been evaluated. Results from the coupling agent screening are shown below in Table II:

TABLE II

| Trial | Scale & E404 Lots | Description | Conditions | UPLC @ 239 nm | | | | Comments |
|---|---|---|---|---|---|---|---|---|
| | | | | E404- RRT 0.62 348.95 m/z | E404-Iso RRT 0.84 3.68.96 m/z | E405 RRT 1.00 404.10 m/z | E558 RRT 1.01 404.10 m/z | |
| E404 Starting Material - PS-063-3A | | — | | 56.00 | 31.28 | — | — | Ratio = 1.79:1 E404:iso-E4-4 |
| 07-PS-068 | 0.5 g 07-PS- 063-3A | Activation- 0.5 h Quench- 18 h | Charged SM, 2 eq. CD4, 10 vol NMP (anhyd), stir for 0.5 h at 0° C., charged 5 eq DEA, let stir at 0° C. for 2 h, then at RT for 18 h | 11.70 11.39 | 3.66 3.57 | 47.37 47.28 | 15.52 15.37 | Ratio = 3.05:1 E405:E558 |
| 07-PS-069 | 0.5 g 07-PS- 063-3A | Activation- 0.5 h Quench- 18 h | Charged SM, 1.05 eq CDMT, 10 vol NMP (anhyd), stir for 0.5 h at 0° C., charged 3 eq NMM, stir for 0.5 h at 0° C., charged 5 eq DEA, let stir at 0° C. for 2 h, then at RT for 18 h | 17.17 17.57 | 5.27 5.46 | 44.31 42.08 | 13.60 14.27 | Ratio 3.26:1 E405:E558 |
| 07-PS-070 | 0.5 g 07-PS- 063-3A | Activation- 0.5 h Quench- 18 h | Charged SM, 1.05 eq HOBt, 1.1 eq EDC, 10 vol NMP (anhyd), stir for 0.5 h at 0° C., charged 2 eq NMM, stir for 0.5 h at 0° C., charged 5 eq DEA warm to RT and stir 18 h | 45.81 44.22 | 14.56 14.37 | 17.46 17.57 | 4.85 4.83 | Ratio 3.64:1 E405:558 |
| 07-PS-071 | 0.5 g 07-PS- 063-3A | Activation- 0.5 h Quench- 18 h | Charged SM, 2 eq HATU, 10 vol NMP (anhyd), stir for 0.5 h at RT, charged 5 eq DEA, let stir at RT for 2 h, then at RT for 18 h | 6.21 5.63 | 3.27 3.17 | 24.11 24.53 | 10.90 10.27 | Ratio 2.22:1 E405:E558 |
| 07-PS-072 | 0.5 g 07-PS- 063-3A | Activation- 0.5 h Quench- 18 h | Charged SM, 5 eq DEA, 10 vol NMP (anhyd), stir for 0.5 h at RT, charged 3 eq T3P, let stir at RT for 2 h, then at RT for 18 h | 14.17 9.28 | 5.20 3.67 | 47.42 52.19 | 23.06 24.32 | Ratio 2.06:1 E405:E558 |
| 07-PS-073 | 0.5 g 07-PS- 063-3A | Stir with DEA-0.5 h POCl3- 1 h | Charged SM, 5 eg DEA, 10 vol DCM (anhyd), stir for 0.5 h at reflux, cool to RT, charged 1.3 eq POCl3, let stir at RT for 1 h | 63.68 — | 28.72 — | 0.24 48.37 | 0.08 38.69 | Ratio 1.25:1 E405:E558 |

Isomerization Improvement

When performing the amidation of 2-bromo lysergic acid (B), it was found that a similar racemic mixture of (5R,8R)-2-bromo-LSD and (5R,8S)-2-bromo-iso-LSD was formed, regardless of the quality of the starting material (input ratio) as illustrated in TABLE III:

TABLE III

| Trial | Scale & E404 Lots | Description | Conditions | UPLC @ 239 nm | | | | Comments |
|---|---|---|---|---|---|---|---|---|
| | | | | E404- RRT 0.62 348.95 m/z | E404-Iso RRT 0.84 3.68.96 m/z | E405 RRT 1.00 404.10 m/z | E558 RRT 1.01 404.10 m/z | |
| E404 Starting Material - PS-053-3A | | | Charged SM, CDI (2 eq), NMP:THF (1:1, 10 vol), stir for 2 h at RT, Charged DEA (5 eq) at 0° C., warm to RT and stir for 18 h | 87.58 | 5.60 | — | — | Similar E405:E558 ratio obtained regardless of E404: iso-E404 input ratio pH ca. 8.5 after DEA addition |
| 07 PS-060 | 2.47 g | Quench- 18 h | | 2.02 | 1.71 | 51.41 | 18.23 | |
| E404 Starting Material - 07-PS-53-5B | | | | 72.66 | 14.17 | — | — | |
| 07-PS-061 | 3.11 g | Quench- 18 h | | — | — | 53.01 | 32.73 | |

It was found that (5R,8S)-2-bromo-iso-LSD was formed by basic conditions, while the (5R,8R)-2-bromo-LSD isomer was formed by acidic conditions. In addition, addition of N-methylmorpholine (NMM) to the THF slurry also preferred the formation of (5R,8R)-2-bromo-LSD. Subsequently, it was found that the isomers can interconvert over time, favoring (5R,8R)-2-bromo-LSD over (5R,8S)-2-bromo-iso-LSD. As shown below, both the yield and the purity can increase when the stir time after addition of acid was increased from about 30 minutes to about 6 hours:

At 5° C., over about six hours the yield improves from about 44% to about 48% at close to 99% isomer purity overall (TABLE IV).

TABLE IV

| Experiment | Scale and E404 Lot# | Entry (type) | Conditions | UPLC @ 239 nm | | | | | | | | |
|---|---|---|---|---|---|---|---|---|---|---|---|---|
| | | | | Dis-Br E404 RRT 0.56-0.66 268.30 m/z | E404 RRT 0.62 348.95 m/z | E404-iso RRT 0.84 348.96 m/z | Amide-imp RRT 0.90 346.95 m/z | Dimer RRT 0.92 695.07 m/z | Iso-Z RRT 0.93 362.05 m/z | RRT 0.99 | E404 RRT 1.00 | E405-iso RRT 1.01 |
| 05-JP-057 | 10 g Alphora 04-JP-060-1 | 04-LP-060-(SM | 1) E404, THF (20 vol), NMM (3 eq), 2 h at RT, CDM (2.0 eq)), 3 h at RT no dissolution | — | 96.55 | 0.13 | — | — | — | — | — | — |
| | | 1 (Crude, SM, 18 h) | 2) Diethylamine (2 eq), 0 C. stir for 18 h at RT, sample for UPLC 3) Charge water (5 vol) sample for UPLC Run, Splits for work up (2 g in-put each) | — | — | — | 0.05 | 0.05 | 0.07 | 0.22 | 62.69 | 30.99 |
| | | Part A (solid) | Part A: Cooled to 5 C.-IT charged 1M HCl (20 vol)to pH - 6.0, after 10 min, filter/wash/dry, 1.06 g X 4.4% w/w, 44% yield | — | — | — | — | — | — | 0.18 | 99.82 | 0.05 |
| | | Part B (solid) | Part B: Cooled to 5 C. -IT, charged 1M HCL (20 vol) to pH 6.0, stir 3 h, filter/wash/dry X 1.34 g, 4.75% w/w, 47% yield | — | — | — | — | — | — | 0.34 | 98.79 | 1.05 |
| | | Part C (solid) | Part C:Cooled to 5 C. -IT, charged 1M HCL (20 vol) to pH 6.0, stir 6 h, filter/wash/dry, X 1.17 g 4.55% w/w, 48% yield | — | — | — | — | — | — | 0.32 | 98.96 | 0.93 |
| | | Part D (solid) | Part D: Cooled to 5 C. -IT, charged 1M HCL (20 vol) slow add (1.25 h) Cooled to 5 C.+ IT, charged 1 m HCL (20 vol) to pH 6.0, stir 30 min, filter/wash/dry, 1.55 g, X 4.11% w/w, 44% yield | — | — | — | — | — | — | 0.18 | 88.96 | 10.88 |
| | | Part E (solid) | Part E: Cooled to 5 C. -IT, charged 1 m HCL (20 vol) fast add (12 min) to pH 6.0, stir 30 min, filter/wash/dry, 1.47 g, X 4.7% w/w, 41% yield | — | — | — | — | — | — | 0.15 | 85.79 | 13.77 |

Unexpectedly, the yield and isomeric purity can be affected by the concentration of hydrochloric acid used, the final pH target, and the volumes of water and hydrochloric acid used. TABLE V illustrates different combinations of these parameters and the effect on yield and isomeric purity:

TABLE V

| | | E405 Isolation | | | | | | | E559 Salt Formation | | | | | E559 Recrystallization | | | | |
|---|---|---|---|---|---|---|---|---|---|---|---|---|---|---|---|---|---|---|
| Entry | Lot # | HCl conc | HCl Vol | Water vol | pH | E405 | E558 | Yield | Trial | ES59 | Iso-E559 | Yield | Total Yield | Trial | E559 | Iso-E559 | Yield | Total Yield |
| 1 | 05-JP-002-A | 1M | 8.5 | 5 | 7.4 | 67.53 | 30.89 | 76 | | | | | | | | | | |
| 2 | 05-JP-002-B | 1M | 13 | 5 | 7.0 | 71.59 | 26.96 | 88 | | | | | | | | | | |
| 3 | 05-JP-003-A | 1M | 8.5 | 10 | 7.4 | 68.24 | 30.29 | 95 | | | | | | | | | | |
| 4 | 05-JP-003-B | 1M | 13 | 10 | 7.0 | 72.13 | 26.49 | 83 | | | | | | | | | | |
| 5 | 05-JP-006-1 | 1M | 17.25 | 5 | 6.5 | 74.84 | 24.97 | 80 | 05-JP-023-1 | 75.99 | 21.30 | 66 | 52.8 | 05-JP-025-1 | 93.44 | 3.89 | 40 | 21.1 |
| 6 | | 1M | 17.5 | 5 | 6.45 | 79.39 | 19.68 | 68 | — | — | — | — | — | 05-JP-030-1 | 98.68 | 1.32 | 43 | 29.2 |
| 7 | | 1M | 20 | 5 | 6.0 | 98.76 | 1.03 | 52 | | | | | | | | | | |
| 8 | | 1M | 20 | 10 | 6.0 | 98.17 | 1.60 | 53 | — | — | — | — | — | 05-JP-039-1 | 99.92 | 0.08 | 63 | 33.4 |
| 9 | | 2M | 8.75 | 5 | 6.5 | 97.54 | 1.29 | 34 | | | | | | | | | | |
| 10 | | 2M | 10 | 5 | 6.09 | 97.12 | 1.81 | 16 | | | | | | | | | | |
| 11 | | 2M | 8.25 | 10 | 6.49 | 76.98 | 22.24 | 67 | | | | | | | | | | |
| 12 | | 2M | 9.75 | 10 | 5.85 | 97.40 | 1.31 | 37 | 05-JP-024-1 | 98.39 | 0.12 | 89 | 32.9 | 05-JP-025-1 | 97.35 | 0.07 | 70 | 23.1 |
| 13 | | 2M | 6.5 | 5 | 7.0 | 96.41 | 1.43 | 36 | | | | | | | | | | |
| 14 | | 0.5M | 20 | 5 | 7.5 | 65.67 | 33.72 | 90 | | | | | | | | | | |
| 15 | | 0.5M | 28 | 5 | 7.0 | 82.28 | 17.64 | 86 | | | | | | | | | | |
| 16 | | 0.5M | 35 | 5 | 6.5 | 81.59 | 18.11 | 87 | — | — | — | — | — | 05-JP-038-1 | 93.28 | 3.72 | 42 | 36.5 |

Figure 3A:
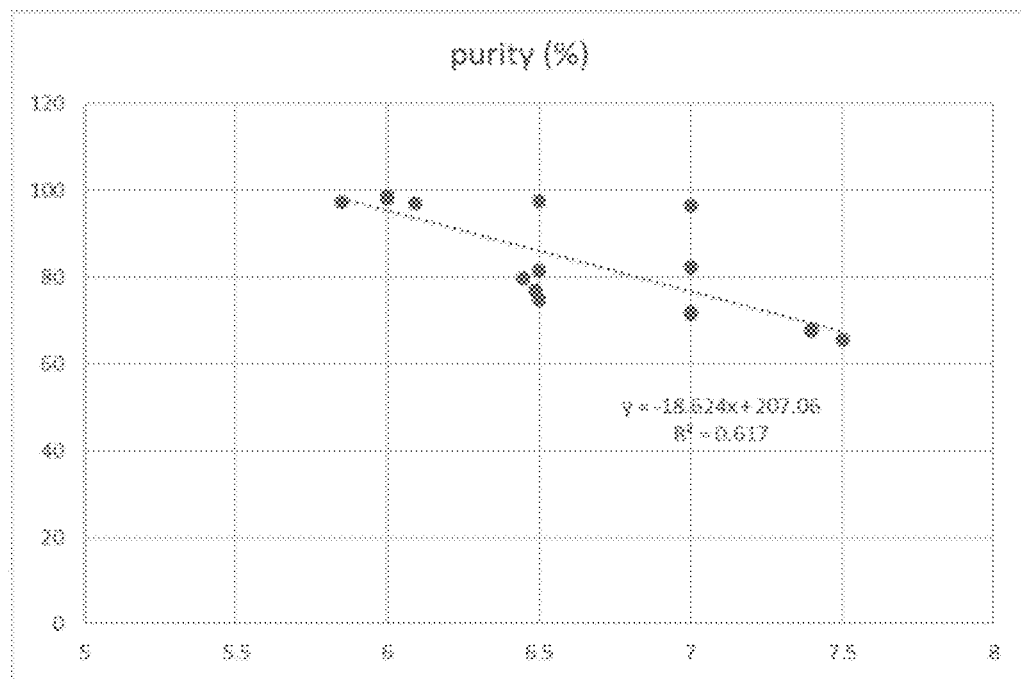
FIGS. 3A and 3B show an example of the effect of pH on purity and yield of E405.
Figure 3B:
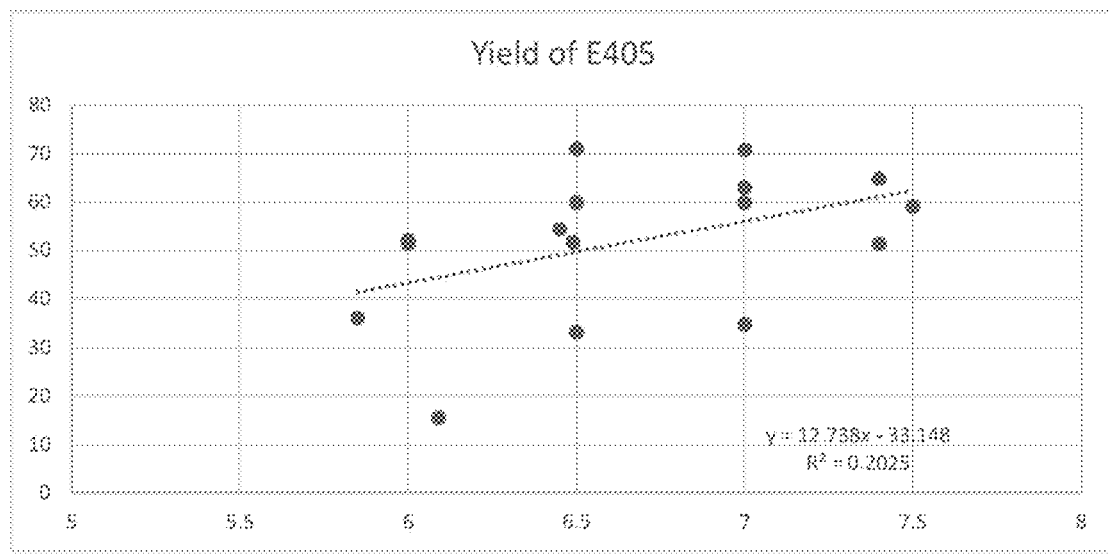

The effect of pH on yield and purity appeared to be affected opposite to each other. The pH did not appear to affect the yield of E405 (see FIGS. 3A and 3B).

Secondary factors such as the concentration of HCl and the amount of water added were examined and found to yield experimental advantages, as mentioned above.

(iii) 2-Bromo-LSD Acid Salt (D) is Prepared Via Combining 2-Bromo-LSD (C) with an Organic Acid

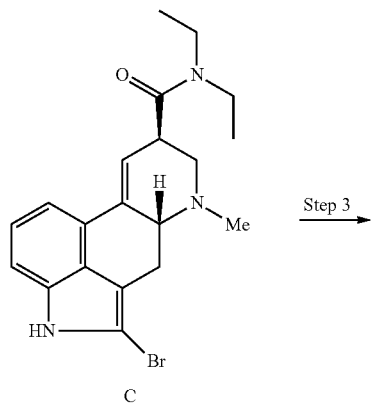

C

Step 3

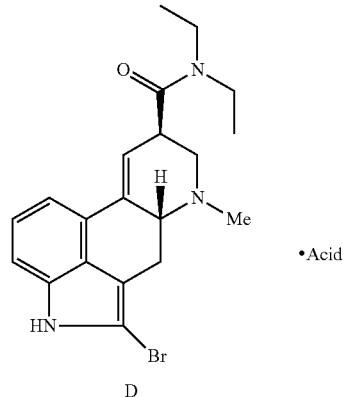

D 2-bromo-LSD acid salt (D) was prepared from heating 2-bromo-LSD (C) with the corresponding acid in a suitable solvent, such as isopropyl alcohol (IPA).

The product was purified by recrystallization from solvents. There was no need to purify by chromatography.

Hemi-Tartrate Salts (a) 2-Bromo-LSD D-Tartrate Salt: (5R,8R) 2-Bromo-LSD Hemi-D-Tartrate Salt Salt formation: 2-bromo-lysergicdiamide (C) (about 3.0 g) in IPA (about 7 vol or about 21 mL) was heated to about 65° C. for about 30 min. To this solution, D-tartaric acid (about 1 equiv.) in IPA (about 8 vol) was added, and the combined solution became clear, and was further heated at about 65° C. After about 30 min, the mixture was brought to about room temperature, and cooled to about 5° C. over about 30 min. The solid (about 2.77 g)

was collected by filtration and dried over about 18 h. HPLC showed the ratio of product (5R,8R):isomer (5R,8S) to be about 87:13.

Recrystallization: (D) (6 g) was suspended in EtOH (8 vol) and heated to about 65° C. for about 1 h, cooled to about room temperature, then cooled to about 5° C. over about 1 h. The solid was filtered and dried to obtain about 3.54 g of the target product (D).

Final analysis: HPLC[5R,8R]: 99.67%, yield: about 64%

Any impurities were mainly the (5R,8S)-2-bromo-LSD hemi-D-tartrate salt, 2-bromo-lysergic acid and LSD.

In another method, D-tartaric acid (about 1 equiv) was dissolved in about 3.3 volumes of ethanol and adjusted to about 40° C. and E405 (about 1 equiv) was dissolved in about 6.7 volumes of ethanol. The E405 solution was added to the D-tartaric acid solution and the temperature raised to about 50° C. and stirred for at least about 30 minutes. The temperature is then adjusted over about 2-3 hours to about 22° C. and stirred for about 30-60 minutes. The temperature is then raised to about 50° C. over about 1-2 hours, stirred for about 1-2 hours and then lowered again to about 22° C. over about 2-3 hours and stirred for about 1-2 hours. The crystalline slurry is then filtered and dried under vacuum at less than about 55° C. for at least about 14 hours. The resulting purity of E559 was about 99.85% with yield about 61%. The result was a hemi-D-tartrate salt of 5R,8R-2-bromo-LSD.

After further optimization, E559 crystallization was carried out at about 15 and about 200 gram scales. Crystallization to E559 resulted in a chiral purity of about 99.71% (15 g scale) and about 99.85% (200 g scale). The result was a hemi-D-tartrate salt of 5R,8R-2-bromo-LSD that was less hygroscopic (about 3.4% weight gain vs. about 6.3% at 75% relative humidity) and had a higher melting point (about 193° C. vs. about 169° C.) indicated better long term stability than the L-tartrate salt (method described below).

In another example, 2-bromo-LSD was crystallized and re-crystallized from ethanol. 2-bromo-LSD free base is dissolved in about 6.7 volume equivalents of ethanol and heated to about 50° C. About 1 equivalent of D-tartaric acid is added in about 3.3 additional volumes of ethanol and stirred. The two solutions are combined and then the combined solution is cooled to about 28° C. over about 2 hours. The solution is reheated to about 50° C. and stirred and finally cooled again to room temperature over about 1.5 hours. Finally, the resulting crystal slurry is filtered, washed, and dried under vacuum with a nitrogen purge and packaged. Four batches prepared by this method yielded comparable results over four different scales as shown in Table VI:

TABLE VI

E404 to E559

| Trial | Scale | E559 | iso-E559 | Total Yield |
|---|---|---|---|---|
| Optimization | 2 g | 99.92 | 0.08 | 33.4 |
| Small Scale | 10 g | 99.46 | 0.32 | 33.2 |
| Typical Trial | 26 g | 99.93 | 0.01 | 32.3 |
| Demo Batch | 350 g | 99.52 | 0.43 | 38.3 |

In the approximately 26 g and approximately 350 g scales, the amount of residual LSD found was about 27 ppm and about 18 ppm, respectively. These are very low levels of residual LSD and near the limit of quantitation for a mass spectroscopy based assay. All other specifications for active pharmaceutical ingredients were met, as shown in Table VII.

TABLE VII

| Product Description | | TD-0148A D-tartaric Acid Salt Drug Substance | |
|---|---|---|---|
| Test | Specification | Typical (0.56-1) | Demo (0.64-1) |
| Description | Report Results | Off-white solid | Off-white solid |
| Identification by LCMS | Conforms to mass | [M + H]+ 404.1 | [M + H]+ 404.1 |
| Identification by NMR | Conforms to structure | Conforms | Conforms |
| ID by RT by HPLC Assay | Conforms to reference RT | Conforms | Conforms |
| and Impurities by HPLC | Report Assay Results | TBD | TBD by SQ |
| | Report Purity Results | 99.7% a/a | 99.6% a/a |
| | | RRT 0.97: 0.1% | RRT 0.97: <0.1% |
| | | Isomer 0.1% a/a | Isomer 0.2% a/a |
| | | RRT 1.09: 0.1 | RRT 1.09: 0.1 |
| Residual Solvents by GC | ICH limits | EtOH: 1898 pp, IPA: ND MTBE: ND THF: 240 ppm NMM: ND DEA: 860 ppm | EtOH: 2378 pp, IPA: ND MTBE: ND THF: 240 ppm NMM: ND DEA: 717 ppm |
| Tartaric acid content | Report only % w/w | 15.16 % w/w | 15.76% w/w |
| Water content by KF | Report only, % w/w | 3.57% w/w | 0.97% w/w |
| Chiral Purity by Optical Rotation | Report only | 0.30* | 0.34* |
| ROI | Report only, % w/w | 0.18% w/w | 0.05% w/w |
| LSD Assay at ExperChem | Report only | 27 ppm | 18 ppm |
| LSD Assay at Alphora | Report only | <50 ppm | <20 ppm |

Recrystallization: (D) (about 5.99 g) was suspended in IPA (about 20 vol) and heated to about 65° C. for about 1 h, cooled to about room temperature, then to about 5° C. over about 1 h. The solid was filtered and dried to obtain about 2.52 g of the target product (D).

Final analysis: HPLC (5R,8R): 99.52%, yield: about 56%

$^1$H Nuclear Magnetic Resonance Spectra for the D-Tartrate Salt (E559)

Figure 5:
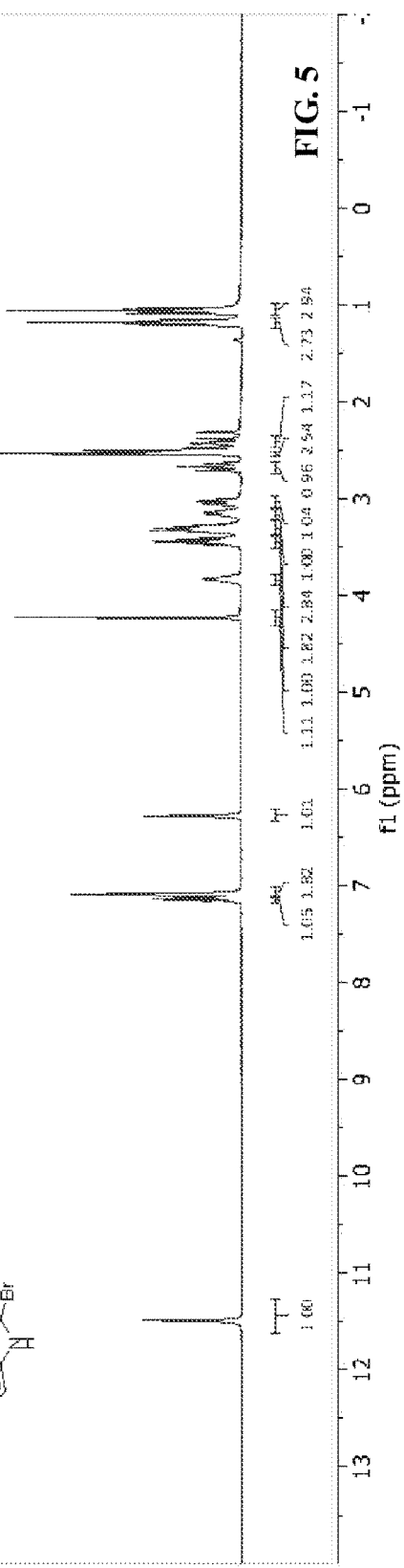
FIG. 5 shows an example of $^1$H-NMR spectrum of (5R,8R)-2-Bromo-LSD hemi-D-tartrate in DMSO-$d_6$.

The 500 MHz $^1$H-NMR in DMSO-$d_6$ is in FIG. 5.

High Resolution PXRD for D-Tartrate Salt (E559)

Figure 6A:
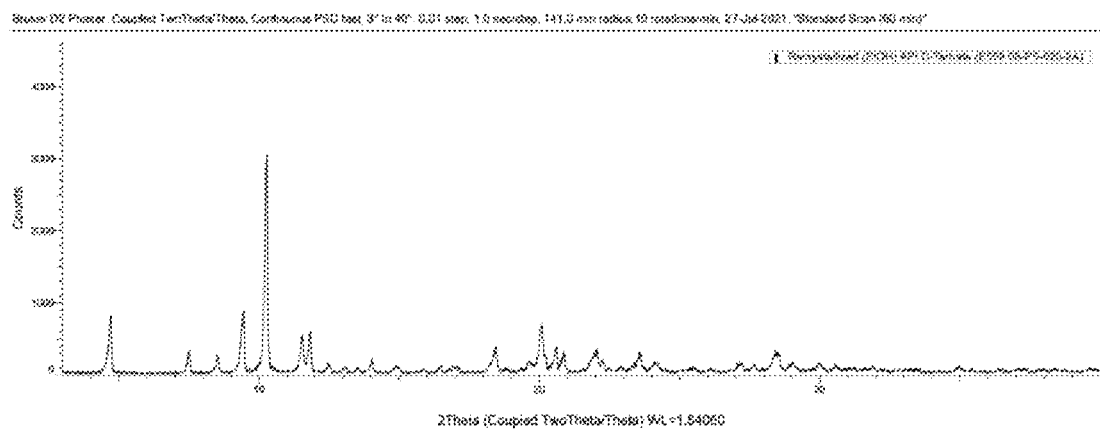
FIGS. 6A to 6D show examples of high resolution PXRD of (5R,8R)-2-Bromo-LSD hemi-D-tartrate: (6A) shows a small scale crystallization from ethanol; (6B) shows a crystallization from IPA; (6C) shows an overlay of the crystallization from ethanol (black) and IPA (red); and (6D) shows a crystallization from ethanol performed at an approximately 350 g scale.
Figure 6B:
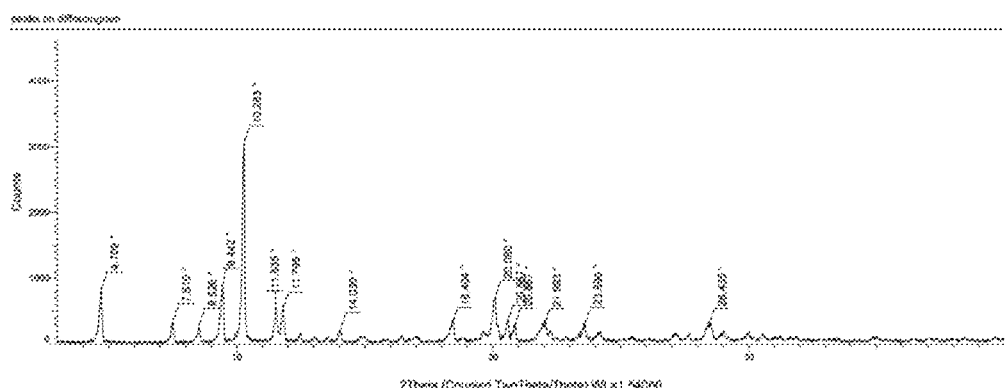
Figure 6C:
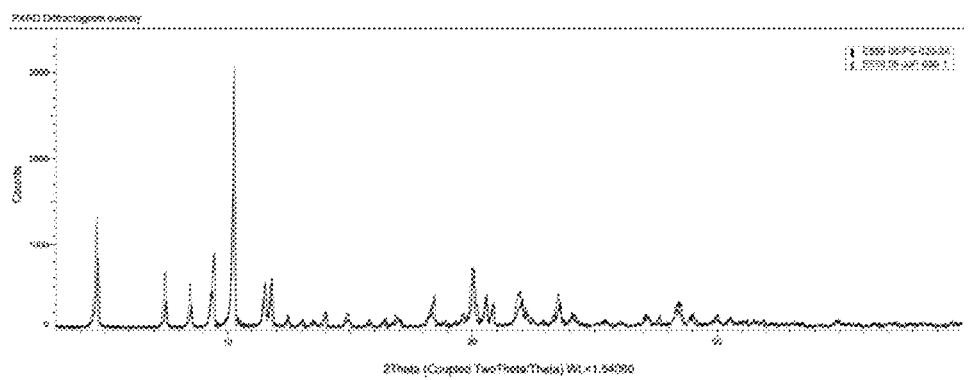
Figure 6D:
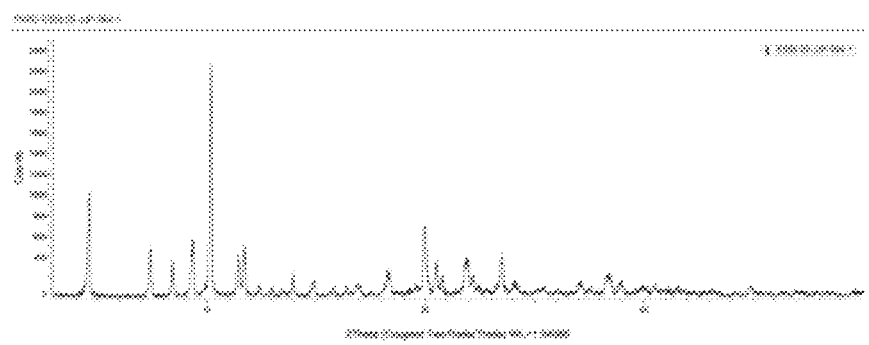

PXRD data for D-Tartrate salt (E559) is shown in FIGS. 6A-6D and in Table VIII. Recrystallization from IPA and ethanol at different scales gave the same (5R,8R) hemi-D-tartrate salt of 2-bromo-LSD, and with the same crystal structure. FIG. 6A shows a small scale crystallization from ethanol, FIG. 6B shows a crystallization from IPA. FIG. 6C shows an overlay of the crystallization from ethanol (black) and IPA (red), and FIG. 6D shows a crystallization from ethanol performed at the approximately 350 g scale.

TABLE VIII

Peak List

| Name | d Value | Angle | Rel. Intensity |
|---|---|---|---|
| Peak #1 | 18.74875 Å | 4.709° | 26.6% |
| Peak #2 | 11.76161 Å | 7.510° | 10.6% |
| Peak #3 | 10.36260 Å | 8.526° | 8.3% |
| Peak #4 | 9.35929 Å | 9.442° | 28.1% |
| Peak #5 | 8.59579 Å | 10.283° | 100.0% |
| Peak #6 | 7.66510 Å | 11.535° | 16.7% |
| Peak #7 | 7.49586 Å | 11.797° | 16.1% |
| Peak #8 | 4.81651 Å | 18.406° | 8.4% |
| Peak #9 | 4.41841 Å | 20.080° | 21.7% |
| Peak #10 | 4.31497 Å | 20.567° | 9.2% |
| Peak #11 | 4.25362 Å | 20.867° | 7.9% |
| Peak #12 | 4.03827 Å | 21.993° | 7.3% |
| Peak #13 | 3.76840 Å | 23.590° | 8.0% |
| Peak #14 | 3.13632 Å | 28.435° | 7.3% |

High Resolution Mass Spectra

Figure 7A:
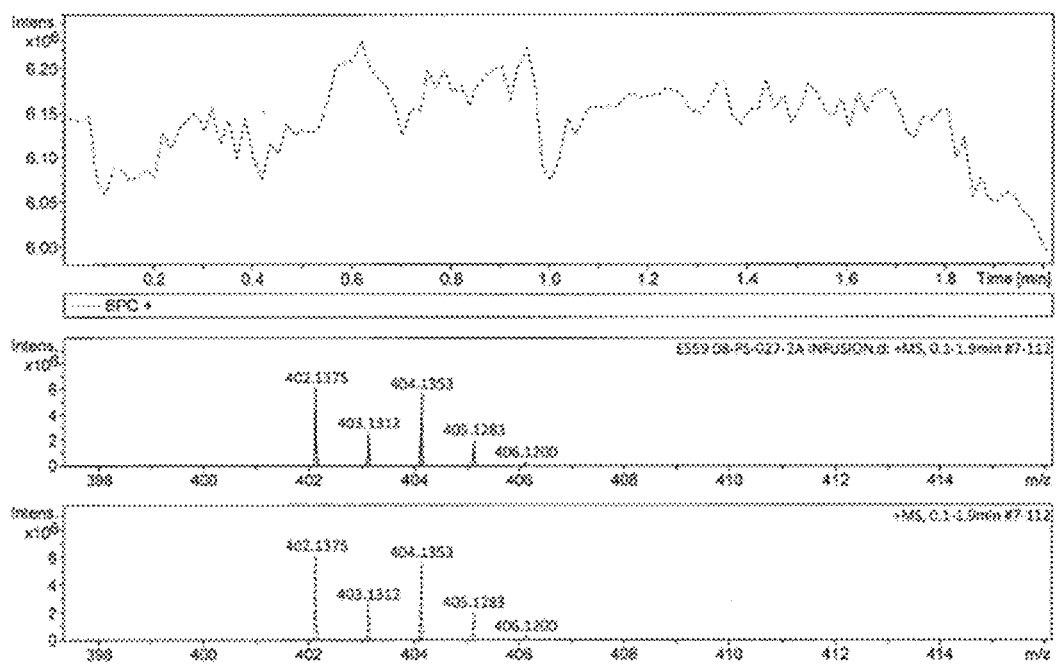
FIGS. 7A, 7B, and 7C show examples of mass spectra of (5R,8R)-2-Bromo-LSD hemi-D-tartrate and a SEM images for (5R,8R)-2-Bromo-LSD hemi-D-tartrate.

MS Spectra for (D)-(D-Tartrate salt) E559 conforms to the expected form (see FIG. 7A).

SEM Images

Figure 7B:
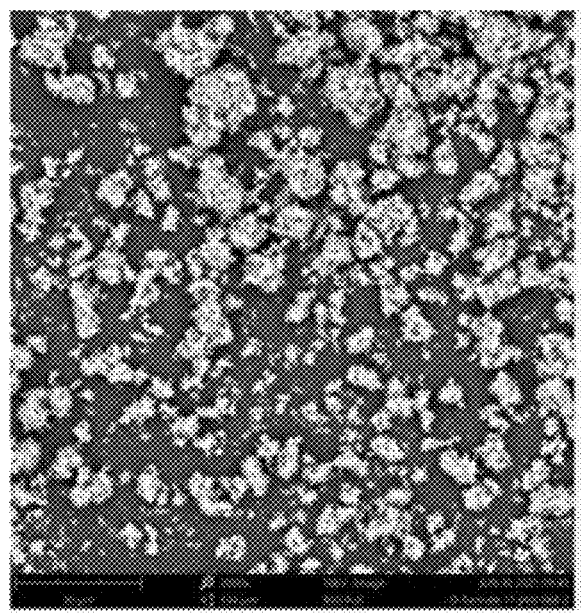
Figure 7C:
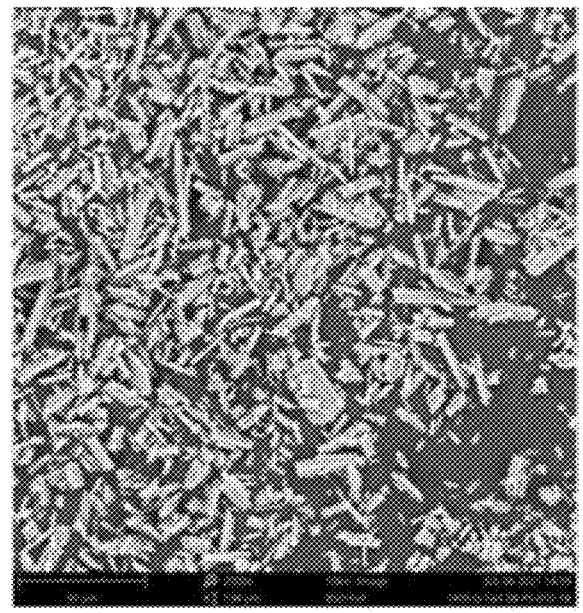

SEM image for (D)-(D-Tartrate salt) E559 from ethanol (see FIGS. 7B (crude salt) and 7C (recrystallized salt)). SEM images showed similar morphology for the D-Tartrate salt E559 from IPA (data not shown). SEM images showed comparable morphology for L-Tartrate salt E560 (data not shown).

(b) 2-Bromo-LSD·L-Tartrate Salt: (5R,8R) 2-Bromo-LSD Hemi-L-Tartrate Salt

Salt formation: 2-bromolysergicdiamide (C) (about 6.0 g) in IPA (about 7 vol) was heated to about 65° C. for about 30 min. To this solution, L-tartaric acid (about 1 equiv.) in IPA (about 8 vol) was added, and the combined solution became clear, and further heated at about 65° C. After about 30 min, the mixture was brought to about room temperature, and cooled to about 5° C. over about 30 min. The solid (about 4.77 g) was collected by filtration and dried over about 18 h. HPLC show the ratio of product (5R,8R):isomer (5R,8S) to be about 87:13.

Recrystallization: (D) (5.99 g) was suspended in IPA (20 vol) and heated to about 65° C. for about 1 h, cooled to about room temperature, then to about 5° C. over about 1 h. The solid was filtered and dried to obtain about 2.52 g of the target product (D).

Final analysis: HPLC: 99.52%, yield: about 56%

High resolution PXRD for L-Tartrate (E560)

Figure 8:
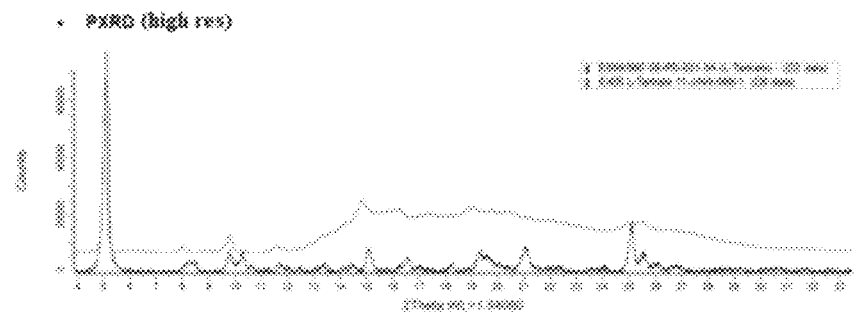
FIG. 8 shows an example of a high resolution PXRD of (5R,8R)-2-Bromo-LSD hemi-L-tartrate, recrystallized from ethanol.

PXRD data for L-Tartrate (E560) is shown in FIG. 8.

Characterization of (D)-Hemi-Tartrate Salts (E559 and E560)

Figure 9:
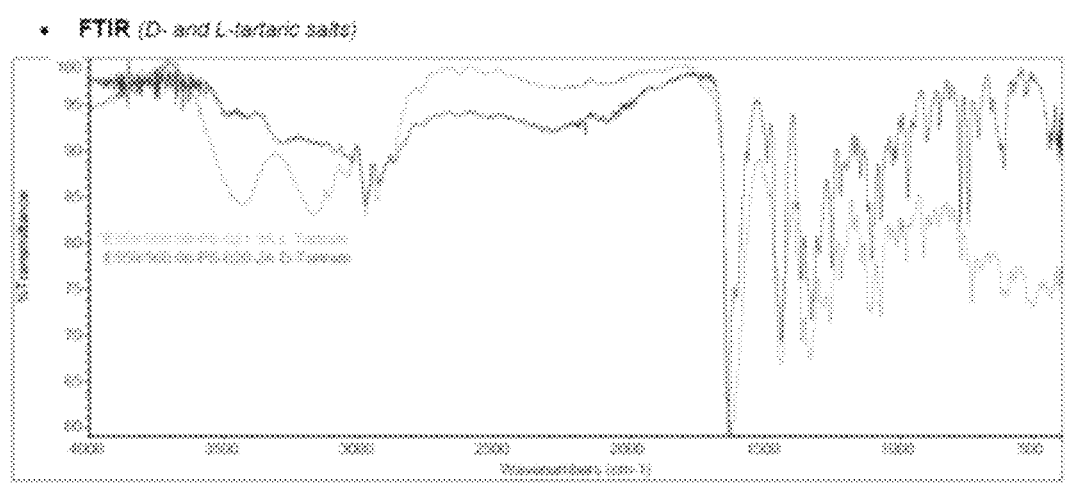
FIG. 9 shows an example of FTIR spectra for (5R,8R)-2-Bromo-LSD hemi-D-tartrate and (5R,8R)-2-Bromo-LSD hemi-L-tartrate.

FTIR spectra is shown in FIG. 9.

Comparative Data for (D)-Hemi-(D,L)-Tartrate Salts (E559 and E560)

Table IX shows additional comparative data.

TABLE IX

| | L-Tartrate | D-Tartrate |
|---|---|---|
| PXRD | Cystalline Material Appravently more than 1 form Only 1 PXRD pattern was observed in the current process (crude from IPA, recyst from IPA) | Cystalline Material Appravently more than 1 form Reproducible PXRD patterns in crude (from IPA) and multiple recyst from EtOH |
| SEM | Medium-sized particles with smooth surfaces in crude salt Medium (larger) sized particles with smooth surfaces observed with recrystallization | Small particles with agglomeration in crude salt Very large particles with smooth surfaces after recrystallization |
| DVS (hold at 75% RH) DVS (0-90-0 2 cycles) | Crude material shows 6.3% mass increase (~5 hr run time) Hygroscopic- absorbed mad 12% water at 90% RH exposure (~24 hr run time) | Crude material shows 3.4% mass increase (~5 hr run time) Hygroscopic- absorbed max 7% water at 90% RH exposure ((~24 hr run time) |
| DSC | Melting onset- 160° C | Melting onset- 188° C. |

A screen was performed on a variety of acids and solvents to determine if other crystal forms were possible for 2-bromo-LSD. The solvents and acids used are shown in Table X.

TABLE X

| Solvents | Acids |
|---|---|
| A. Methanol | 1. (−)-10-Camphorsulfonic aicd |
| B. Ethanol | 2. L-Glutamic acid |
| C. Isopropyl alcohol | 3. L-Ascorbic acid |
| D. Acetonitrile | 4. L-Tartaric acid |
| E. Acetone | 5. p-Toluene sulfonic acid (monohydrate) |
| F. Isopropyl acetate | 6. Ethane-1,2-disulfonic acid (dehydrate) |
| G. Tetrahydro furan | 7. Mandelic acid (DL) |
| | 8. Maleic acid |
| | 9. Oxalic acid |
| | 10. Hydrochloric acid |
| | 11. D-Isoascorbic acid |

Screens were performed at small scale in a 96 well plate and after crystallization, the resulting crystals were analyzed by x-ray diffraction in-situ. The results of the x-ray diffraction are shown in FIG. 29:

These results show other pathways to crystalline salts of 2-bromo-LSD. Table XI lists examples of the combinations of solvents and acids that showed crystallization of 2-bromo-LSD:

TABLE XI

| Acid | Solvent | Crystalline results |
|---|---|---|
| L-glutamic Acid | Acetone | Strong pattern |
| L-glutamic Acid | Isopropyl acetate | Strong pattern |
| L-ascorbic Acid | Isopropyl acetate | Weaker pattern |
| L-ascorbic Acid | Tetrahydrofuran | Weaker pattern |
| L-tartaric Acid | Ethanol | Strong pattern |
| L-tartaric Acid | Iso-propyl alcohol | Strong pattern |
| L-tartaric Acid | Acetonitrile | Weaker pattern |
| L-tartaric Acid | Acetone | Weaker pattern |
| L-tartaric Acid | Isopropyl acetate | Strong pattern |
| L-tartaric Acid | Tetrahydrofuran | Strong pattern |
| Ethane-1,2-disulfonic Acid | Acetone | Weaker pattern |
| Ethane-1,2-disulfonic Acid | Isopropyl acetate | Weaker pattern |
| Ethane-1,2-disulfonic Acid | Ethanol | Weaker pattern |

TABLE XI-continued

| Acid | Solvent | Crystalline results |
|---|---|---|
| Hydrochloric Acid | Acetone | Strong pattern |
| Hydrochloric Acid | Isopropyl acetate | Strong pattern |
| Hydrochloric Acid | Tetrahydrofuran | Pattern matches control |
| D-Isoascorbic acid | Isopropyl acetate | Strong pattern |

Example 2: LSD Derivative Polymorph Lacks Hallucinogenic Activity

Hallucinogens such as LSD induce a head-twitch response (HTR) in rodents (for example in rats and mice) described as a rapid side-to-side rotational head movement. The HTR mouse model is widely used as a proxy behavioral assay for hallucinogenic activity in humans [Halbertstad et al., *Neuropharmacology*, 2020, V167: 107933; Halberstadt et. al., *Psychopharmacology* (Berl). 2013, 227(4):727-39].

Figure 10A:
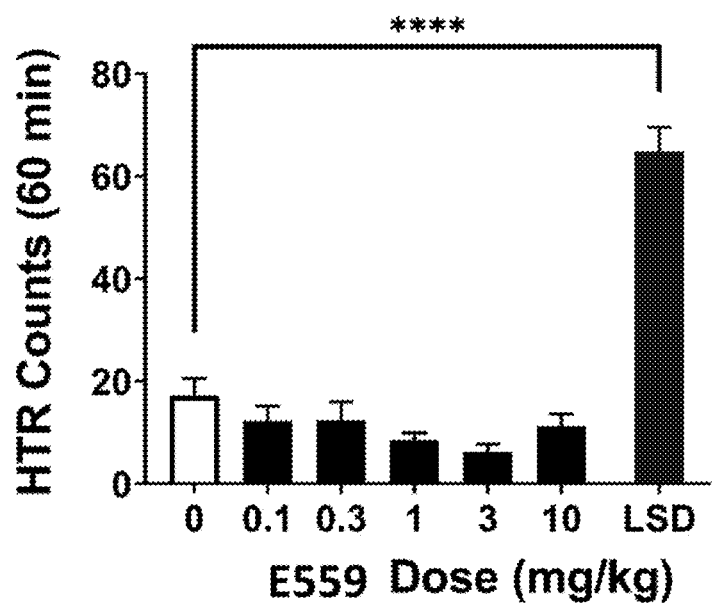
FIGS. 10A/10B are graphs demonstrating that the LSD polymorph E559 lacks hallucinogenic activity using a head-twitch response (HTR) in rodents. E559 polymorph was administered at 0.1, 0.3, 1, 3, and 10 mg/kg, or LSD (0.1 mg/kg). Data are represented as group means±standard deviation for the entire 60 minutes test session (A) and individual data points per 2 minutes blocks (B)
Figure 10B:
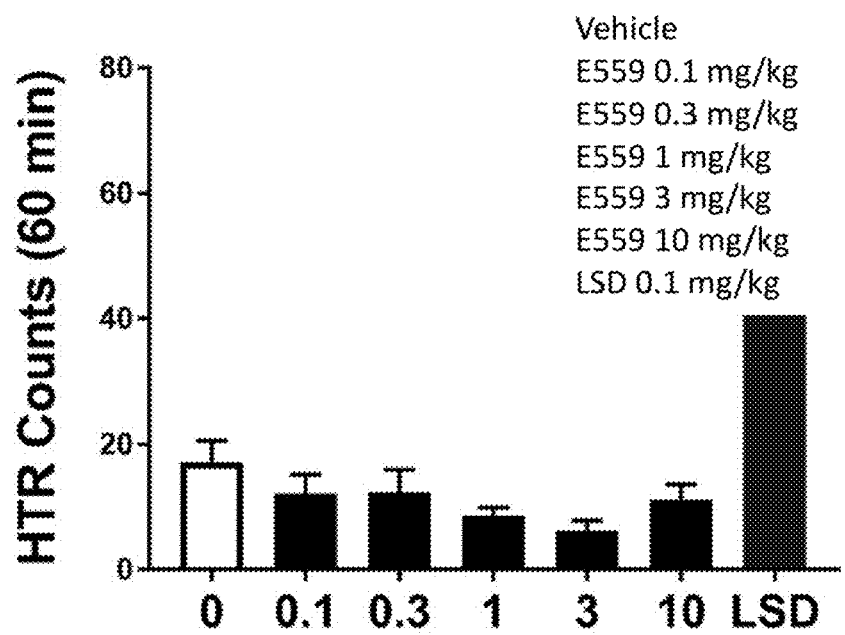

The (5R,8R) 2-bromo-LSD hemi-D-tartrate salt polymorph compound from Example 1 (is herein referred to as the "E559 polymorph") was shown to be negative in HTR at all doses tested in the HTR mouse model (FIG. 10A and FIG. 10B). In brief, seven groups of male C57BL/6J mice with magnet implants (n=5 per group) were injected intraperitoneally with vehicle (negative control), "E559 polymorph" at 0.1, 0.3, 1, 3, and 10 mg/kg, or LSD (0.1 mg/kg) and then behaviour recorded in a magnetometer chamber for 60 minutes. The magnet implants mounting and magnetometer assessments were conducted as described previously (Halberstadt et al., *Psychopharmacology* (Berl). 2013 227 (4): 727-739). Data are represented as group means±standard deviation for the entire 60 minutes test session (FIG. 10A) and individual data points per 2 minutes blocks (FIG. 10B). Asterisks indicate statistical significances compared to the control (0 mg/kg).

In marked contrast to LSD, which elicited a strong HTR at 0.1 mg/kg, the "E559 polymorph" did not induce HTR above baseline at any tested dose including the highest dose of 10 mg/kg (FIG. 10A). Based on this HTR surrogate mouse model the "E559 polymorph" is predicted to lack hallucinogenic activity in humans.

Example 3: LSD Derivative Polymorph is Bioavailable and Crosses the Blood-Brain Barrier A pharmacokinetic (PK) study of the "E559 polymorph" was conducted following a single intraperitoneal (IP) injection in CD-1 mice. PK analysis of the "E559 polymorph" was performed in plasma samples and in brain tissue taken at different time points post injection. Three groups of male mice and three groups of female mice (n=24 per group) were administered "E559" at different doses (0.75, 2.25, or 6.75 mg/kg) by IP injection at time zero. In each dose group, three mice/sex were sacrificed to collect plasma and brain samples at pre-dose, and 0.17, 0.5, 1, 2, 4, 8, and 24 hours post-dose. Levels of the "E559 polymorph" in plasma and brain tissue were assessed by LC-MS/MS method. Briefly, to extract the plasma samples, 200 µL of acetonitrile containing 10 ng/mL LSD-d3 was added to 50 µL of plasma. The mixture was vortexed vigorously, centrifuged (13,000 rpm) for 2 min at 4° C., and then 50 µL of supernatant was combined with 200 µL methanol/water (1:1, v/v) for LC-MS/MS analysis. Brain tissues were weighed and homogenized for ~1 min in cold acetonitrile at a ratio of 1:1.5 (w/v) brain tissue to extraction solvent. The brain samples were then centrifuged at 13,000 rpm for 2 min at 4° C. and the supernatant was collected for LC-MS/MS analysis. In LC-MS/MS method, isocratic elution was performed on an ACE Excel 5 SuperC18™ column at 25° C., with a run time of 6.5 min. The mobile phase consisted of methanol-water (8:2, v/v) plus 0.1% $NH_4OH$ at a flow rate of 0.8 mL/min. The injection volume was 10 µL/sample. For the MS/MS analysis, electrospray ionization was used in positive ion mode (gas temperature 350° C., gas flow 13 L/min; nebulizer 60 psi, capillary voltage 4 kV).

The "E559 polymorph" was quantified by selected reaction monitoring of the following mass transitions (2-Br-LSD m/z 403.3→302, LSD-$d_3$ internal standard m/z 327.2→226.1). The quantification of the "E559 polymorph" concentration in samples was achieved by using appropriate calibration standards. The calibration curve was fitted linearly using a weighting factor ($1/x^2$). The pharmacokinetic parameters were determined by the non-compartmental analysis using the validated Phoenix®WinNonlin® version 8.2 software (Certara Inc).

Figure 11A:
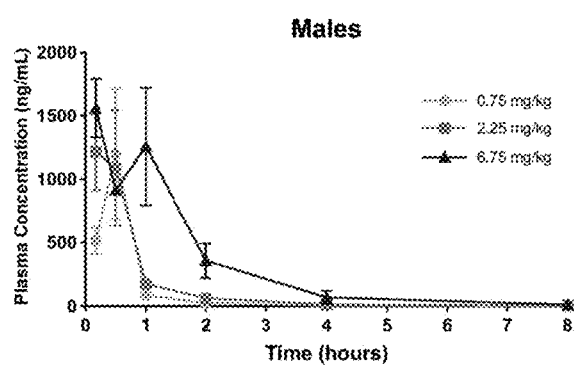
FIGS. 11A, 11B, 11C, and 11D are graphs demonstrating that the LSD polymorph E559 crosses the blood-brain barrier. Plasma levels of the "E559 polymorph" increases in time-dependent and dose-dependent manners and appears in plasma quickly (10 minutes) post dose in all dosing groups of male and female mice (A) and (B). Brain tissue exposure to the compound increases proportionally in time-dependent and dose-dependent manners (C) and (D)
Figure 11B:
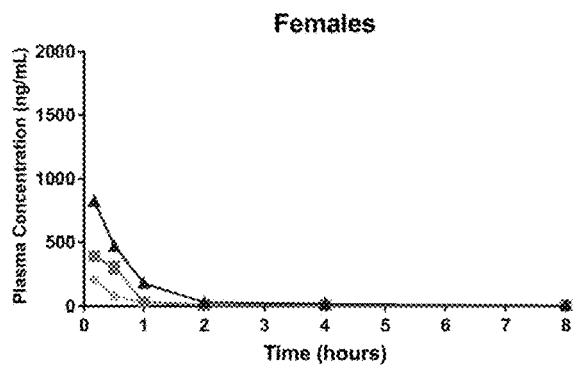

PK analysis of the "E559 polymorph" in plasma samples demonstrates that the plasma levels of the "E559 polymorph" increases in time-dependent and dose-dependent manners and appears in plasma quickly (10 minutes) post dose in all dosing groups of male and female mice (FIG. 11A and FIG. 11B; the "E559 polymorph" concentration in plasma samples is shown as ng/mL of plasma).

Figure 11C:
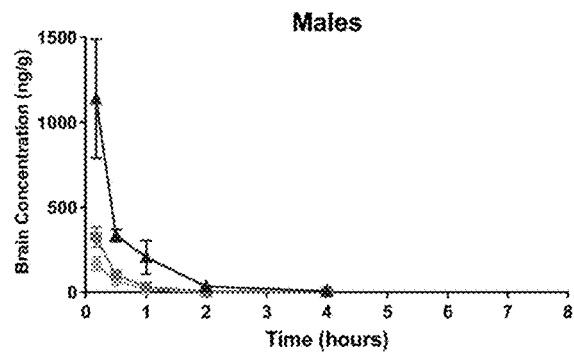
Figure 11D:
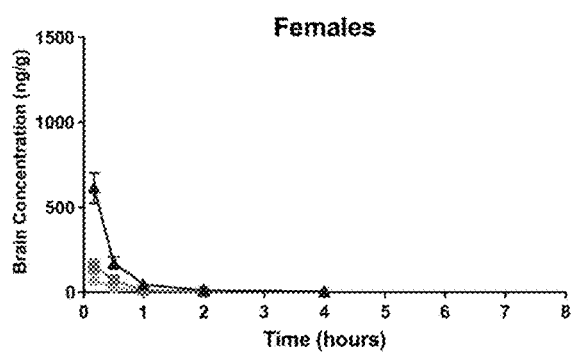

PK analysis of "E559 polymorph" levels in brain samples shows the brain tissue exposure to the compound increases proportionally in time-dependent and dose-dependent manners (FIG. 11C and FIG. 11D; test "polymorph HT compound" concentration in brain samples is shown as ng/g brain tissue), mirroring the PK profile seen in the plasma in the same animals (compare with FIGS. 11A and 11B). The brain PK data also demonstrates that the "E559 polymorph" can readily cross the blood-brain barrier in both male and female mice.

Figure 12:
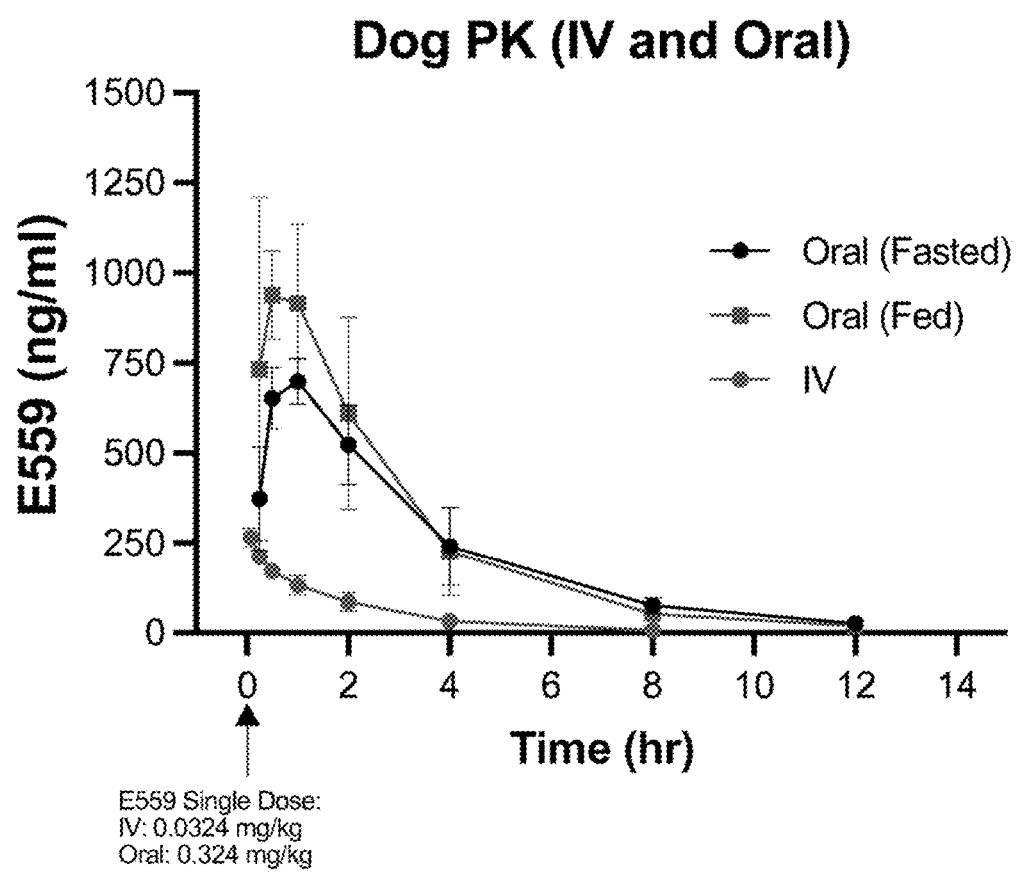
FIG. 12 is a graph demonstrating that LSD polymorph E559 exhibits good oral bioavailability that is not affected by feeding state as shown by concentration of E559 polymorph measured in plasma samples between fasted and fed dogs.

Example 4: LSD Derivative Polymorph Exhibits Good Oral Bioavailability which is not Affected by Feeding State A single-dose comparative pharmacokinetic (PK) study was conducted in Beagle dogs to assess the oral bioavailability and the effect of food on the "E559 polymorph" (FIG. 12). Four male dogs were used in 3 test groups in a cross-over design with at least 3 days washout period between each test group (Groups 1, 2 and 3). In Group 1, four male dogs received a single intravenous (IV) dose of 0.0324 mg/kg of the "polymorph E559". In Group 2 the same four dogs received a single oral dose of 0.324 mg/kg of the "polymorph E559" in fasted state. In Group 3 the same four dogs received a single oral dose of 0.324 mg/kg of the "E559 polymorph" in the fed state (same oral dose amount as in Group 2). Blood samples were collected from all dogs at pre-dose and 0.08, 0.25, 0.5, 1, 2, 4, 8, and 24 hours post dose to measure the "E559 polymorph" levels by LC-MS/MS method conducted as described in Example 3.

As shown in FIG. 12 the "E559 polymorph" exhibited a good oral bioavailability with no differences in the mean absolute and relative oral bioavailability between fasted and fed dogs (concentration in plasma samples is shown as ng/mL of plasma). Data are represented as group means±standard deviation.

Example 5: LSD Derivative Polymorph Blocks Hallucinogenic Effects of Psychedelic Compounds The "E559 polymorph" was studied for its effect to block the hallucinogenic (HTR) response of a psychedelic 2,5-

Figure 13A:
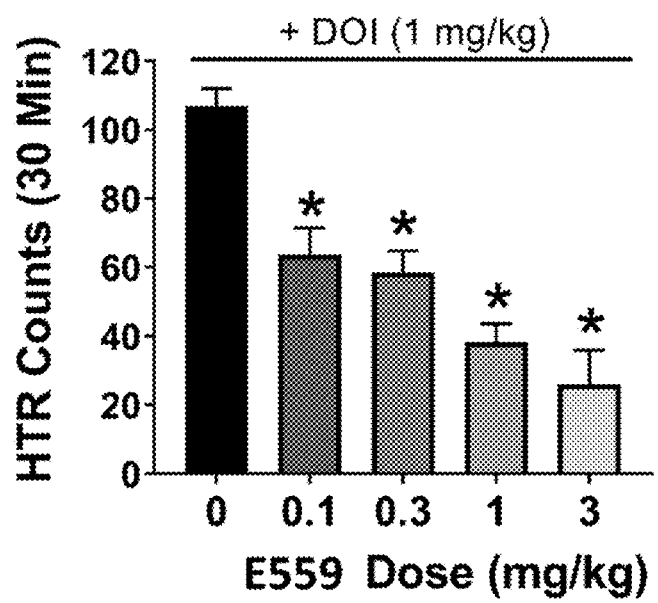
FIGS. 13A and 13B demonstrate LSD polymorph E559 blocks hallucinogenic effects of psychedelic compound 2,5-Dimethoxy-4-iodoamphetamine (DOI) in the mouse HTR model. Pre-treatment of mice with the "E559 polymorph" significantly attenuated the ability of DOI to induce the HTR in mice (FIG. 13A).

Dimethoxy-4-iodoamphetamine (DOI) in the mouse HTR model. DOI is a serotonergic hallucinogenic compound used commonly as a positive control in HTR model [Halberstadt et al., *Psychopharmacology* (Berl). 2013 June; 227(4):727-39]. An HTR study was performed as described in Example 2 as follows: Five groups of mice (n=6-7 per group, 31 total) were either treated with vehicle (saline) or with the "E559 polymorph" at 0.1, 0.3, 1, or 3 mg/kg. Ten minutes later, all of the mice were injected with DOI (1 mg/kg) and then HTR activity was assessed for 30 min. As shown in FIG. 13A, pre-treatment of mice with the "E559 polymorph" significantly attenuated the ability of DOI to induce the HTR in mice. All doses of the "E559 polymorph" were effective in blocking the response to DOI in a dose-dependent manner. The data are represented as group means±standard deviation and asterisks indicate statistical significances (*p<0.0001) compared to the vehicle (saline) control (0 mg/kg in FIG. 13A).

Figure 13B:
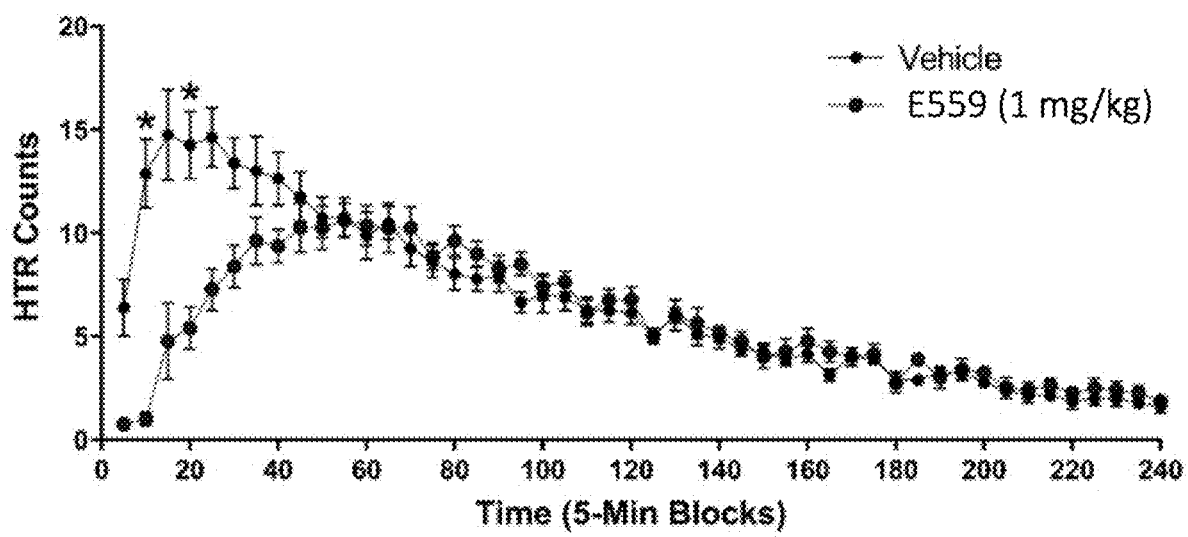

The time course of the blockade of the DOI induced HTR by the "E559 polymorph" was examined. An HTR study was performed as described in Example 2 as follows: Two groups of mice (n=6 per group) were either treated with vehicle or with the "E559 polymorph" at 1 mg/kg. Ten minutes later, all of the mice were injected with DOI (1 mg/kg) and then HTR activity was assessed for 30 min. As shown in FIG. 13B, pre-treatment of mice with the "E559 polymorph" almost completely blocked the DOI induced HTR during the first 10 minutes, and this blockage was gradually reduced until after 40-60 minutes, the blockage was no longer detected. The data are represented as group means±standard deviation and asterisks indicate statistical significances (*p<0.0001) compared to the vehicle (saline) control (0 mg/kg in FIG. 13B). The time course of the blockade of the DOI induced HTR by the "E559 polymorph" mirrors the time course of the pharmacokinetics of the "E559 polymorph" in the mouse brain tissue (shown in Example 3).

Example 6: LSD Derivative Polymorph is a 5HT2A Agonist

Neuro-receptor binding and functional effects of the "E559 polymorph" was examined by analyzing binding affinity [Ki (nM)], functional agonist activity [EC50 (nM)], and functional antagonist activity [IC50 (nM)] against a panel of key receptors in neurophysiological disorders. Binding and functional assays were performed at "E559 polymorph" concentrations of 0.0003, 0.003, 0.01, 0.03, 0.1, 0.3, 1, and 10 µM. In binding assays, cell membrane homogenates, expressing each receptor target, were incubated with the corresponding radio-ligand in absence or presence of several concentration of the "E559 polymorph" compound. The measurement of binding affinity of the "E559 polymorph" is represented in TABLE XIII by Ki (nM) which was calculated as percent inhibition of the binding of a radioactively labeled reference ligand at each receptor. In functional assays the HEK-293 cells expressing each receptor target were suspended in buffer and distribute in microplates and incubated for 30 minutes at room temperature or 37° C. in the presence of buffer alone (basal control), the reference agonist or antagonist, or the "E559 polymorph. Following incubation, the cells were lysed and the appropriate fluorescent probe (Ca2+ flux, cAMP, or IP1) were added for 60 minutes to measure the fluorescence transfer at the appropriate wavelength using a microplate reader. The cellular agonist effect (EC50) was calculated as a percent of control response to a known reference agonist and the cellular antagonist effect (IC50) was calculated as percent inhibition of control reference agonist response for each receptor.

As shown in TABLE XII the "E559 polymorph" is a 5-HT2A receptor agonist, which is novel and surprising since the "E559 polymorph" is non-hallucinogenic (see Example 2) and hallucinations by serotonergic compounds are believed to be mediated by 5-HT2A agonism (Halberstadt et al., Behav Brain Res. 2015, 277: 99-120).

In this screen (TABLE XII), in addition to 5-HT2A, the "E559 polymorph" exhibits potent agonist activity at the 5-HT1B and alpha1A receptors. The "E559 polymorph" exhibits antagonist activity at the 5-HT2B receptor. The "E559 polymorph" receptor functional profile is assessed in further detail in Examples 7 and 8. These results reveal that the "E559 polymorph" is a CNS active drug with pharmacological and therapeutic potential in various neuropsychological/neuropsychiatric/neurological disorders.

TABLE XII

| Target Receptor | Species | Binding Ki (nM) | Functional (Agonist) Assay | EC50 (nM) | Funcational (Antagonist Assay | IC50 (nM) |
|---|---|---|---|---|---|---|
| Serotonin 1A receptor (5-HT1AR) | human | 9.3 | Ca2+ flux | 3000 | Ca2+ flux | >10,000 |
| Serotonin 1B receptor (5-HT1BR) | human | 77 | cAMP | 6.69 | cAMP | >10,000 |
| Serotonin 1A receptor (5-HT2AR) | human | 2.2 | IP1 | 11 | IP1 | 24.9 |
| Serotonin 2B receptor (5-HT2BR) | human | 7 | IP1 | >10,000 | IP1 | 97 |
| Serotonin 2C receptor (5-HT2CR) | human | 19 | IP1 | >10,000 | IP1 | 1100 |
| Serotonin 7 receptor (5-HT7R) | human | 3.81 | cAMP | >10,000 | cAMP | 240 |
| Alpha 1A adrenergic receptor | human | 59 | Ca2+ flux | 51 | Ca2+ flux | >10,000 |
| Alpha 2A adrenergic receptor | human | 10.3 | Ca2+ flux | >10,000 | Ca2+ flux | 260 |
| Alpha 2B adrenergic receptor | human | 27 | cAMP | >10,000 | cAMP | 3600 |
| Alpha 2C adrenergic receptor | human | 27 | cAMP | 730 | cAMP | >10,000 |
| Beta 1 adrenergic receptor | human | 109 | cAMP | >10,000 | cAMP | 870 |
| Beta 2 adrenergic receptor | human | 88 | cAMP | >10,000 | cAMP | 360 |
| D1 dopamine receptor | human | 25 | cAMP | >10,000 | cAMP | 820 |
| D2S dopamine receptor | human | 2.1 | cAMP | >10,000 | cAMP | >10,000 |

Example 7: LSD Derivative Polymorph is not a 5-HT2B Agonist and has a Safer Cardiovascular Profile Compared to LSD 5-HT2B receptor agonism, when seen with a drug, is a cardiac safety liability as it has been reported to cause cardiac valvulopathy in humans (Cavero et al., *Journal of Pharmacological and Toxicological Methods* 69, 2014, p150-161). LSD is known to be a 5-HT2B agonist (Horvath et al., *Mov. Disord.*, 2004, 19:656-662). The "E559 polymorph" was examined to determine its binding and functional effects on the 5HT2B receptor. Surprisingly and in marked contrast to LSD which is a 5-HT2B agonist, the "E559 polymorph" is found to bind to the 5-HT2B receptor (TABLE XII—Ki column), but lacks agonist activity at the 5-HT2B receptor (TABLE XII—Functional Agonist column), and in fact the "E559 polymorph" is found to be a 5-HT2B antagonist (TABLE XII—Functional Antagonist column).

The activity of the "E559 polymorph" at the 5-HT2B receptor was further assessed by 5-HT2B-mediated Gq dissociation (FIG. 14A), 5-HT2B-mediated 0-arrestin2 recruitment (FIG. 14B) and 5-HT2B Gq-mediated calcium flux assessments (FIG. 14C) using bioluminescence resonance energy transfer (BRET) assay in HEK293T cells FIG. 14A to C, 5-HT refers to serotonin). These assays were performed as described in Example 8. In 5-HT2B antagonist assays, the "E559 polymorph" antagonism was measured by its ability to block 5-HT2B receptor activation by 5-HT.

As shown in FIGS. 14A, 14B and 14C, LSD shows potent agonism of the 5-HT2B receptor as seen by all three functional assessments, while the "E559 polymorph" does not show the agonism seen with LSD. The "E559 polymorph" antagonism was observed in blocking 5-HT-mediated activation of the 5-HT2B receptor in all three assays (comparison of 5-HT versus 2-Br-LSD+5-HT curves respectively in FIGS. 14A, 14B and 14C).

The human ether-related-to-go (hERG) channel, is a potassium channel whose inhibition is related to cardiac arrhythmias (Abbott et al., Cell, 1999, V97(2); p175-187). The effect of the "E559 polymorph" on the hERG channel was performed in a cell-based hERG antagonist assay. In brief, CHO-K1 cells were stably transfected with human hERG cDNA and allowed to achieve whole cell configuration in culture. Cells were held at −80 mV and a 500 ms pulse to −40 mV is delivered to measure the leaking current, which is subtracted from the tail current on-line. Then the cell is depolarized to +40 mV for 500 ms and then to −80 mV over a 100 ms ramp to elicit the hERG tail current. This paradigm is delivered once every 8 s to monitor the current amplitude. The assay is conducted at room temperature. The "E559 polymorph" is then applied to cells from low to high concentrations (0.0003, 0.003, 0.01, 0.03, 0.1, 0.3, 1, 10, 30, and 100 µM) sequentially for 5 minutes. Astermizole is used at multiple concentrations as a reference compound to calculate the percent inhibition of hERG channel by the "polymorph E559".

As shown in FIG. 14D, the "E559 polymorph" produced only weak blockade of channel activity at very high concentrations (EC50=31.6 µM), indicating that the "E559 polymorph" exhibits low risk of causing cardiac arrhythmias in humans.

Together the data presented in this example predict that surprisingly the "E559 polymorph" has a significantly safer cardiovascular toxicity profile compared to LSD.

Figure 15:
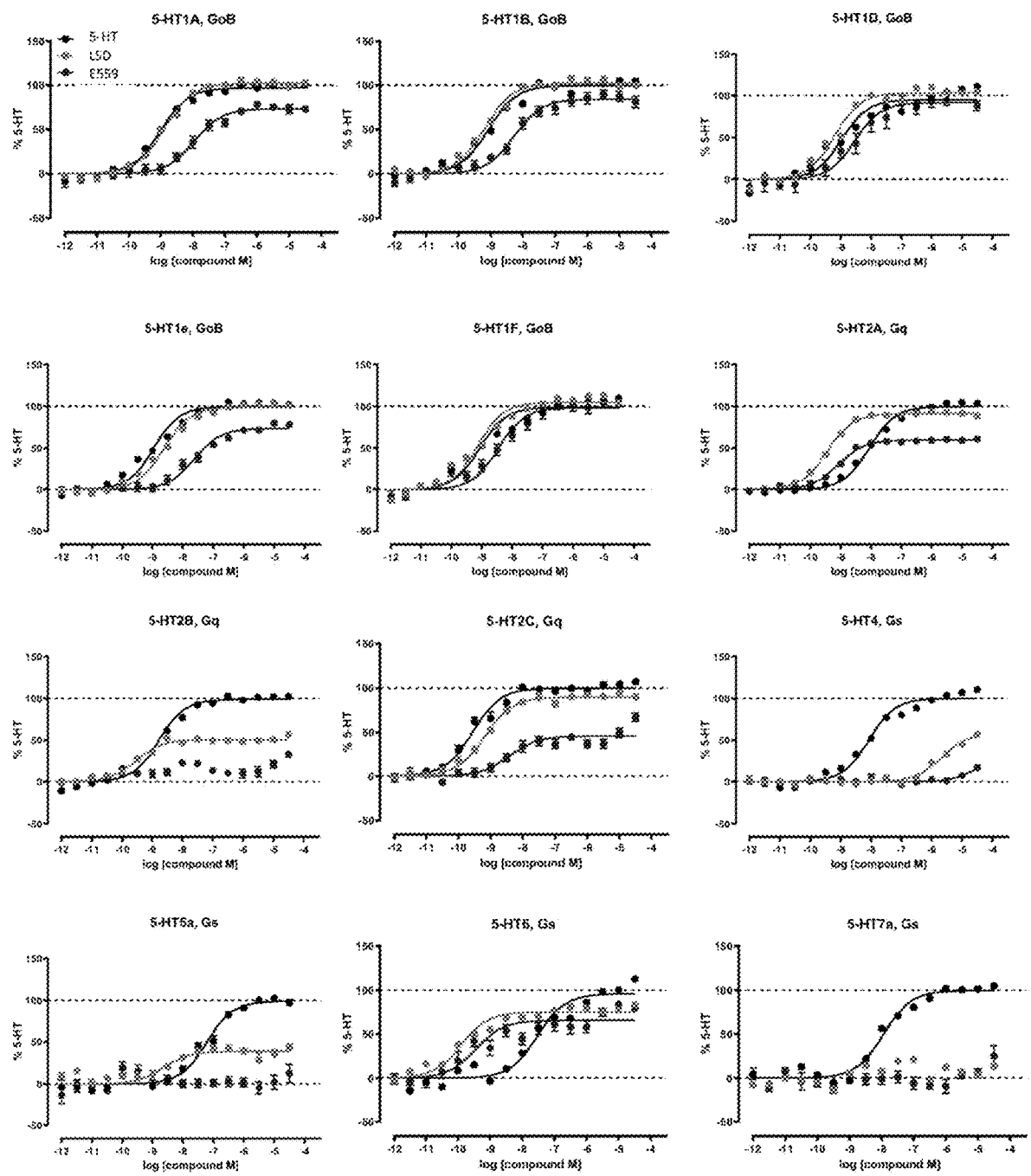
FIG. 15 are graphs demonstrating polymorph E559 activity at CNS receptors/targets: 5-HT1A, 5-HT1B, 5-HT1D, 5-HT1e, 5-HT1F, 5-HT2A, 5-HT2B, 5-HT2C, 5-HT4, 5-HT5A, 5-HT6 and 5-HT7A, and compared to activity of serotonin (5-HT) and LSD.

Example 8: LSD Derivative Polymorph Exhibits Activity at Key CNS Receptors/Targets The data shown in this example demonstrates an in depth pharmacological profile of the "E559 polymorph" conducted in parallel to LSD across 12 human serotonin (5-HT) receptors and 21 members of non-5-HT aminergic GPCRs (including D1-D5 dopamine; α1A/1B, α2A, B, C and β1/2-adrenergic, H1-H4 histamine, and M1-M5 muscarinic subtypes) using BRET-based G protein dissociation assay (FIG. 15, FIG. 17A, and TABLE XIII). In addition, secondary messengers assay including G protein-mediated cAMP inhibition (Gi/o) and accumulation (Gs), Gq-calcium flux (FIG. 16A/B), and (3-arrestin2 recruitment BRET (FIG. 17B) assays were performed across select 5-HT or dopamine receptors. Assays in this Example were conducted as previously described (Cameron et al., *Nature*, 2021, 589, p474-479). In brief, 48 hours before assays, HEK293T or Gq-KO or Gs-KO HEK293T cells were transfected using a reverse transfection method in a 1:1:1:1 ratio of target receptor:Gα-Rluc8: Beta:GFP$^2$-γ constructs. Human isoforms of 5-HT receptors were expressed in mammalian cell system by using receptor constructs in pCDNA vectors. Stably-expressing 5-HT2A/2B/2C receptor Flp-In 293 T-Rex Tetracycline inducible system were used for calcium flux assays. In cAMP accumulation/inhibition assays, HEK293T cells were co-transfected in 1:1 ratio with codon-optimized Tango pcDNA3.1 library with V2tail/TEV/tTA encoding regions deleted to yield "de-Tango" constructs. For β-Arrestin2 recruitment assays, cells were transfected a 1:15 ratio of 5-HT-Rluc8:GFP$^2$-fused human β-Arrestin2. On the day of the assay, drug dilutions of all test compounds were performed in McCorvy buffer [1×HBSS, 20 mM HEPES, pH 7.4, supplemented with 0.3% BSA fatty acid free (GoldBio), and 0.03% ascorbic acid] and treated cells were incubated at 37° C. in a humidified incubator for 60 minutes or specified time point. Before reading of plates in a FLIPR TETRA system (Molecular Devices), 5 µM coelenterazine were added to the plates. Immediately after, plates were read at 400 nm Rluc8 and 510 nm GFP$^2$ emission filters for 0.8 second per well using a PheraStarFSX (BMB Lab Tech). The BRET ratios of 510/400 luminescence were calculated per well and were plotted as a function of drug concentration using Graphpad Prism 5 or 9 (Graphpad Software Inc., San Diego, CA). Data were analyzed using nonlinear regression "log(agonist) vs. response" to yield Emax and EC$_{50}$ parameter estimates. Data were normalized to % positive control (reference ligand for each receptor) stimulation, for which a concentration-response curve was present on every plate. The data are shown as a percentage of the reference ligand-induced maximal response, and as group means±standard deviation.

A. 5-HT1 Receptor Family

The detailed functional activity profile of the "E559 polymorph" was compared to LSD at the following 5-HT1 receptor subtypes: 5-HT1A, 1B, 1D, 1E, and 1F.

Figure 16A:
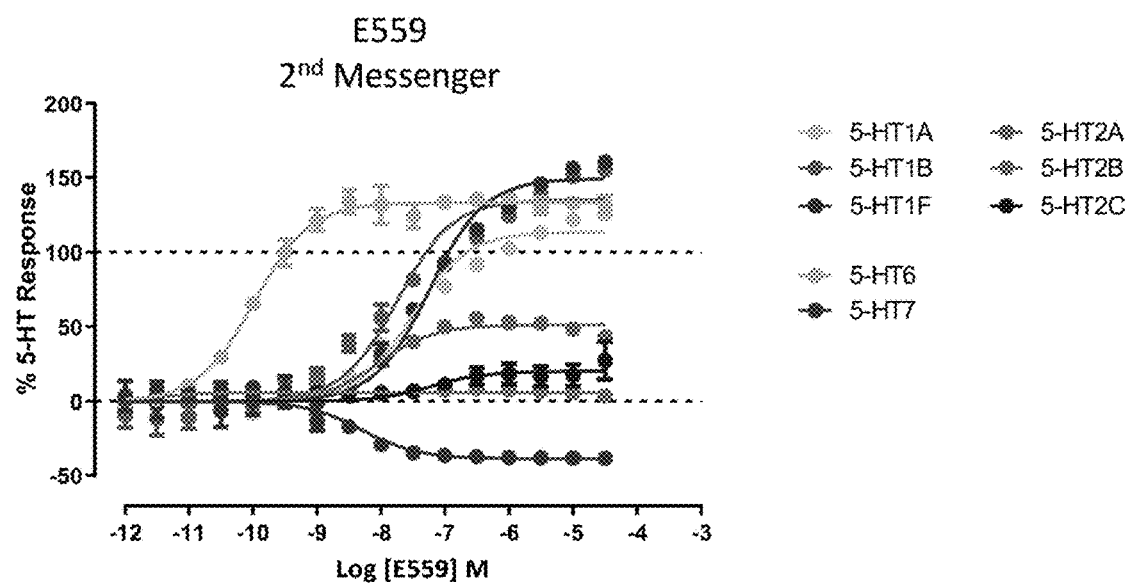
FIGS. 16A/B are graphs demonstrating polymorph E559 activity on secondary messenger activity downstream of each target receptor: 5-HT1A, 5-HT1B, 5-HT1F, 5-HT2A, 5-HT2B, 5-HT2C, 5-HT6 and 5-HT7.
Figure 17A:
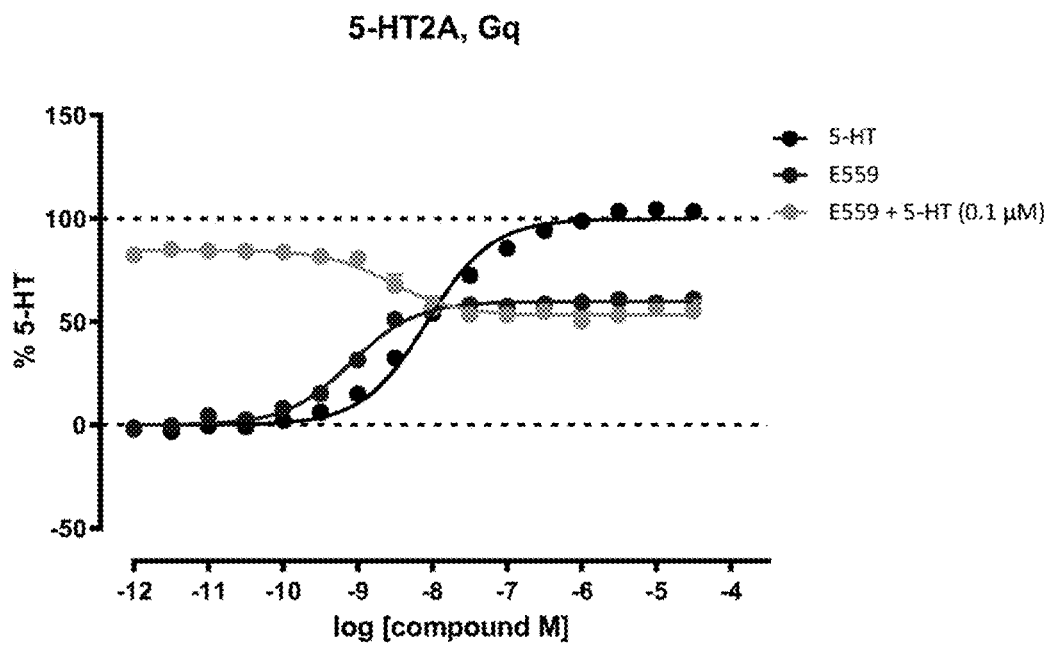
FIG. 17A is a graph showing polymorph E559 antagonizes the 5-HT-mediated activation of 5-HT2A receptor as assessed by Gq dissociation assay.
Figure 17B:
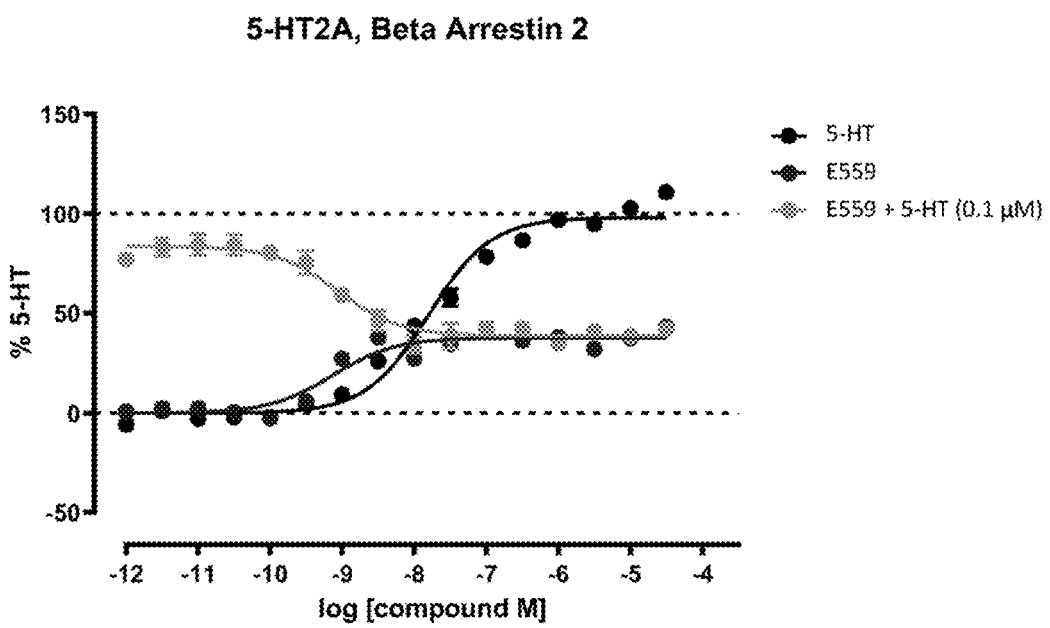
FIG. 17B is a graph showing polymorph E559 antagonizes the 5-HT-mediated activation of β-arrestin2 recruitment BRET assay at 5-HT2A receptor.

As shown in FIG. 15 and FIG. 16A/B, the "E559 polymorph" is a moderate to potent agonist across all the 5-HT1 receptor subtypes with slight decrease in Emax (maximal drug effect) relative to LSD. The "E559 polymorph" exhibits the greatest potency (agonism) at 5-HT1F and 5-HT1D receptors (FIG. 15 and FIG. 16A/B).

B. 5-HT2 Receptor Family

The detailed functional activity profile of the "E559 polymorph" was compared to LSD at the following 5-HT2 receptor subtypes: 5-HT2A, 5-HT2B, and 5-HT2C. Agonism at the 5-HT2A receptor is understood to be the main pathway for hallucinogenic effects of serotonergic psychedelics and for many of the potential therapeutic outcomes of such compounds (Preller et al., *Current Biology*, 2017, 27(3), p451-457).

Figure 16B:
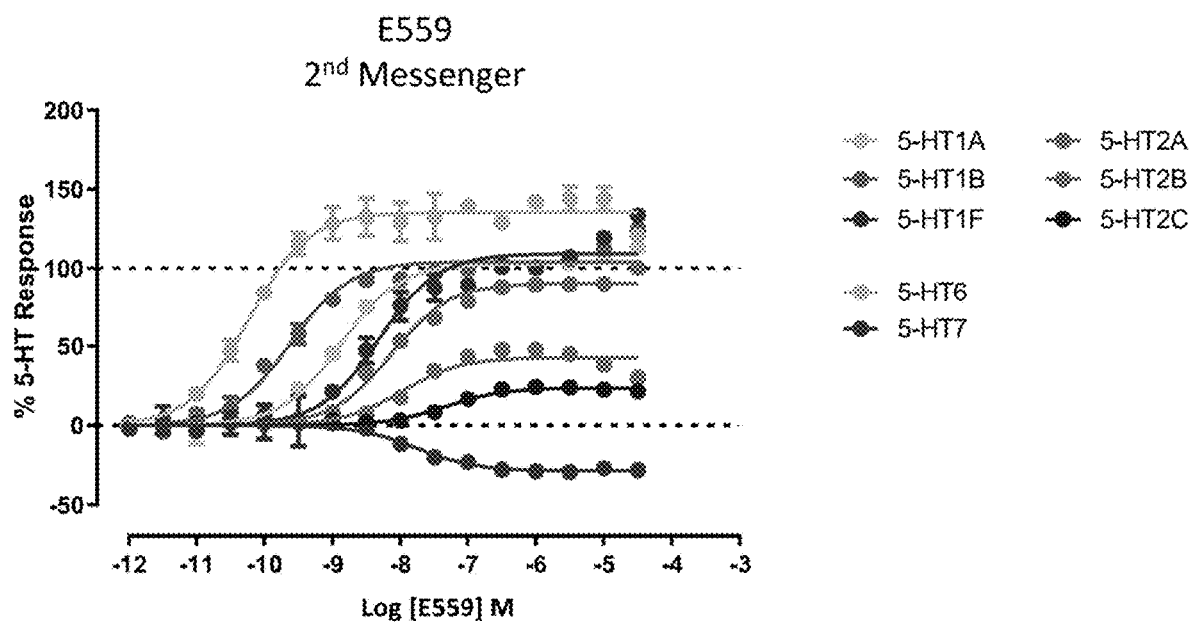

As shown in FIG. 15 and FIG. 16A/B, the "E559 polymorph" is a potent partial agonist of 5-HT2A, whereas LSD is a potent almost full 5-HT2A agonist. The binding of the "E559 polymorph" to the ligand pocket of 5-HT2A, is very similar to that of the parent ligand 5-HT, as shown by the competition (antagonist) experiments where the "E559 polymorph" antagonizes the 5-HT activation as assessed by Gq dissociation (FIG. 17A) and β-arrestin2 recruitment (FIG. 17B) assays. As also exemplified in Example 2 and Example 6, the "E559 polymorph" is unexpectedly a 5-HT2A agonist while not exhibiting hallucinogenic properties. The "E559 polymorph" is further differentiated from LSD in the degree of 5-HT2A agonism (FIG. 15 and FIG. 16)

The detailed functional profile at the 5-HT2B receptor confirms the conclusions drawn in Example 7, that in contrast to LSD which is an agonist of 5-HT2B, the "E559 polymorph" is inactive as an agonist at the 5-HT2B receptor (FIG. 15 and FIG. 16A/B), and therefore does not carry the cardiac safety concerns associated with 5-HT2B agonist compounds (Cavero et al., *Journal of Pharmacological and Toxicological Methods* 69, 2014, p150-161).

The detailed functional profile at the 5-HT2C receptor, shows that the "E559 polymorph" is moderately different in its effect on 5-HT2C compared to LSD. As shown in FIG. 15 and FIG. 16A/B, LSD is an almost full agonist at 5-HT2C, while the "E559 polymorph" exhibits partial agonism at 5-HT2C.

C. Other 5-HT Receptors

The detailed functional activity profile of the "E559 polymorph" was compared to LSD at the following other 5-HT receptors: 5-HT4, 5-HT5A, 5-HT6 and 5-HT7A.

At the 5-HT4 receptor, "E559 polymorph" is similar to LSD in that both lack potent agonist activity at 5-HT4 receptor in G protein dissociation assay (FIG. 15).

At the 5-HT5A receptor, LSD acts as a partial agonist, whereas in sharp contrast, the "E559 polymorph" antagonizes this receptor subtype (FIG. 15).

At the 5-HT6 receptor, the "E559 polymorph" similar to LSD acts as a very potent partial agonist in both G protein dissociation (FIG. 15) and cAMP accumulation second messenger (FIG. 16A/B) assays.

At the 5-HT7 receptor, the "E559 polymorph" and LSD are similar and both act as potent antagonist and inverse agonists as confirmed by G protein dissociation (FIG. 15) and cAMP accumulation second messenger assays (FIG. 16A/B), although the "E559 polymorph" exhibits significantly greater inverse agonism than LSD at this receptor.

D. Alpha Receptor Family

The detailed functional activity profile of the "E559 polymorph" was compared to LSD at the following adrenergic receptors: α1A, α1B, α2A, α2B, α2C, β1 and β2.

At the α1A, α1B, β1 and β2 adrenergic receptors, the "E559 polymorph" like LSD is an antagonist, but the degree of "E559 polymorph" antagonism is greater than seen with LSD (TABLE XIII).

At the α2C adrenergic receptor, the "E559 polymorph" like LSD is a partial agonist, but LSD is a more potent partial agonist than the "E559 polymorph" (TABLE XIII).

At the α2A and α2B adrenergic receptors, the "E559 polymorph" activity surprisingly differs markedly from that of LSD. At both these receptors, LSD acts as a partial agonist, while the "E559 polymorph" acts an antagonist at both receptors (TABLE XIII).

E. Dopamine Receptor Family

The detailed functional activity profile of the "E559 polymorph" was compared to LSD at the following dopamine receptors: D1, D2, D3, D4, and D5 receptors.

At the D1 receptor, the "E559 polymorph" activity surprisingly differs markedly from that of LSD. LSD acts a partial agonist, while the "polymorph HT compound" acts an antagonist at this receptor (TABLE XIII).

At the D2 receptor, the "E559 polymorph" like LSD is a potent agonist, but the potency of the "E559 polymorph" agonism is slightly higher than seen with LSD (FIG. 16A/B and TABLE XIII).

At the D3 receptor, the "E559 polymorph" like LSD is a partial agonist, but the degree of the "polymorph HT compound" partial agonism is significantly lower than seen with LSD (TABLE XIII).

At the D4 receptor, the "E559 polymorph" has similar potent agonism activity like LSD (FIG. 16A/B and TABLE XIII).

At the D5 receptor, the "E559 polymorph" is an agonist with activity higher than LSD based on EC50 values (TABLE XIII).

F. Muscarinic Acetylcholine Receptor Family

The detailed functional activity profile of the "E559 polymorph" was compared to LSD at the following muscarinic receptors: M1, M2, M3, M4, and M5 receptors. At all muscarinic receptors tested, both LSD and the "E559 polymorph" exhibited weak or no activity in both agonist and antagonist modes of action. (TABLE XIII).

G. Histaminergic Receptor Family

The detailed functional activity profile of the "E559 polymorph" was compared to LSD at the following histaminergic receptors: H1, H2, H3, and H4 receptors. At the H1, H3, and H4 receptors, the "E559 polymorph" like LSD exhibited weak or no agonism (TABLE XIII). At the H2 receptor, the "E559 polymorph" differs slightly from LSD, by showing partial agonistic activity that was slightly greater than LSD's activity (TABLE XIII).

TABLE XIII

| Receptor | Reference Ligand | | LSD | | E559 | | Antagonist Data |
|---|---|---|---|---|---|---|---|
| | EC50, nM | Emax | EC50, nM | Emax | EC50, nM | Emax | KB, nM |
| D1 | 295.1 | 100 | 107.6 | 41.3 | 0.12 | NA | 32.95 |
| D2 | 4.92 | 100 | 2.17 | 86.0 | 0.35 | 77.4 | ND |
| D3 | 0.35 | 100 | 7.57 | 74.5 | 2.84 | 31.8 | 7.13 |
| D4 | 3.52 | 100 | 4.03 | 91.9 | 1.22 | 673 | ND |
| D5 | 75.5 | 100 | 165.6 | 70.7 | 3.75 | 15.6 | 25.06 |
| ADRa1A | 25.7 | 100 | 38.5 | 24.8 | 25.00 | NA | 56.87 |
| ADRa1B | 65.6 | 100 | NA | NA | NA | NA | 55.88 |
| ADRa2A | 1.91 | 100 | 19.4 | 64.7 | 282.49 | NA | 11.93 |
| ADRa2B | 4.26 | 100 | 11.8 | 61.8 | NA | NA | 79.24 |

TABLE XIII-continued

| Receptor | Reference Ligand EC50, nM | Emax | LSD EC50, nM | Emax | E559 EC50, nM | Emax | Antagonist Data KB, nM |
|---|---|---|---|---|---|---|---|
| ADRa2C | 0.49 | 100 | 0.56 | 80.2 | 10.35 | 40.5 | 15.99 |
| ADRb1 | 55.8 | 100 | NA | NA | >10,000 | NA | 95.24 |
| ADRb2 | 39.26 | 100 | NA | NA | 4.26 | NA | 17.59 |
| H1 | 102.1 | 100 | 0.28 | 15.5 | 152.1 | NA | 983.25 |
| H2 | 1288.2 | 100 | >10,000 | 21.2 | 295.8 | 28.77 | 5187.44 |
| H3 | 4.56 | 100 | 0.00 | 18.6 | NA | NA | ND |
| H4 | 32.1 | 100 | 0.09 | 15.0 | 0.0 | 17.4 | ND |
| CHRM1 | 619.4 | 100 | 211.35 | NA | 2.96 | NA | ND |
| CHRM2 | 12.02 | 100 | >10,000 | NA | 214.29 | NA | ND |
| CHRM3 | 550.8 | 100 | NA | NA | NA | NA | ND |
| CHRM4 | 111.7 | 100 | 453.9 | NA | 0.04 | 15.56 | ND |
| CHRM5 | 374.1 | 100 | >10,000 | NA | 5821.03 | NA | ND |

NA = No Activity;
ND = Not Determined

Example 9: LSD Derivative Polymorph Activity at CNS Receptors is Stereochemistry Dependent The functional agonist activity [EC50 (nM), Emax], and functional antagonist activity [IC50 (nM)] of the 5R:8S stereoisomer of the "E559 polymorph" (5R:8S E558) was compared with the "E559 polymorph" (a 5R:8R stereoisomer) at selected serotonin receptors. The assays were performed as described in Example 6.

Figure 18A:
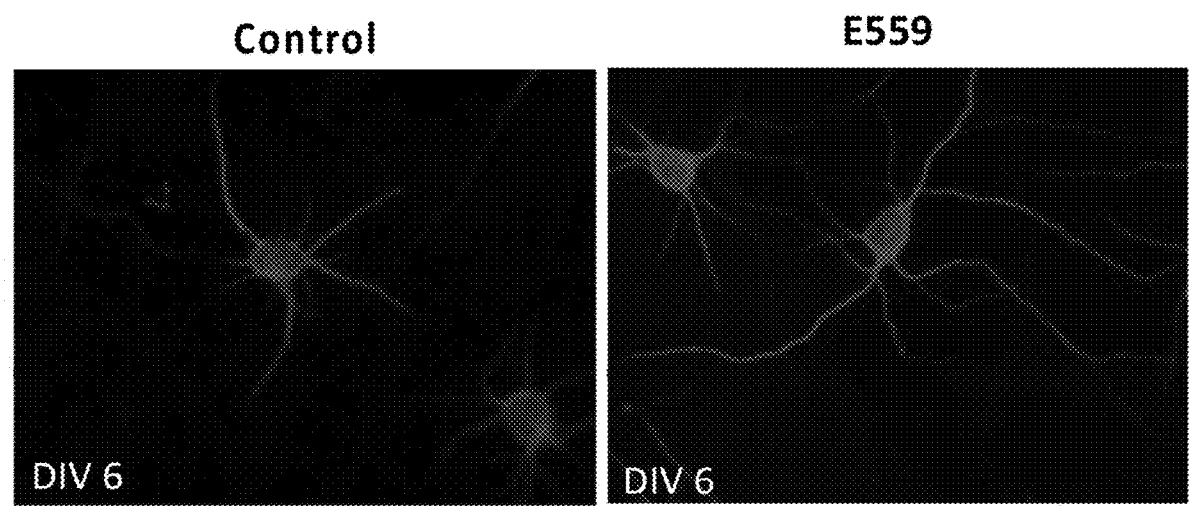
FIG. 18A shows images of MAP2 stained rat cortical neurons treated with vehicle (no drug control) or with the E559 polymorph on day in vitro 6 (DIV6)
Figure 18B:
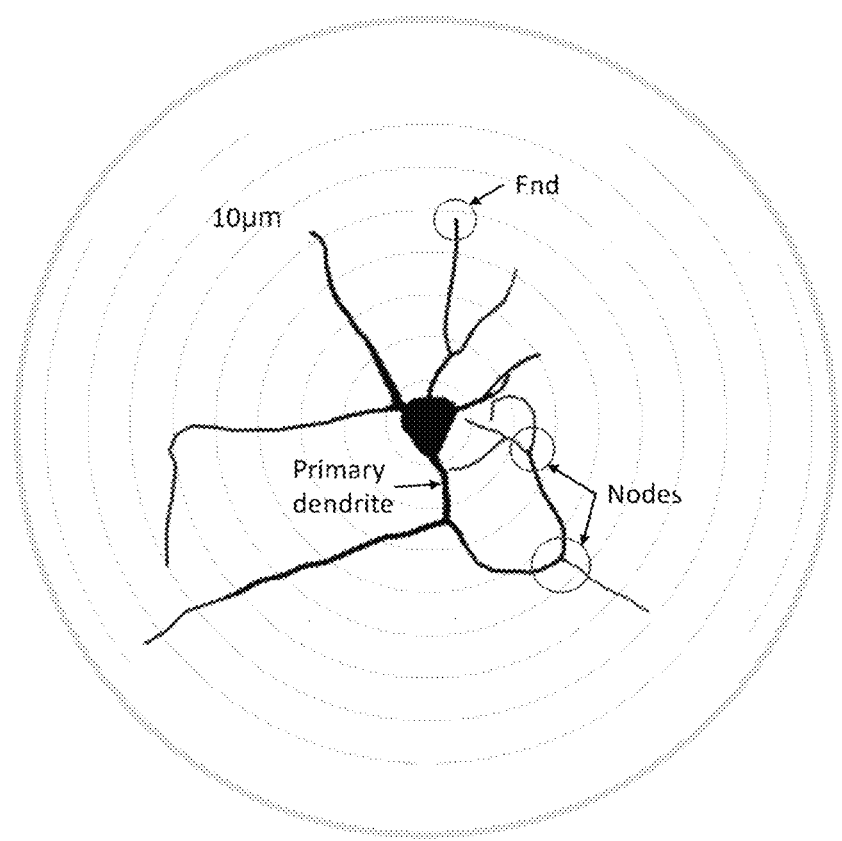
FIG. 18B shows the schematics of Sholl analysis which generates measures of neuron arbor complexity by assessing (A) number of times neuron processes are crossed, (B) total length of neurons and (C) number of nodes and end points.

As shown in TABLE XIV, compared with the "E559 polymorph" the 5R:8S E558 shows a significantly decreased serotoninergic receptor functional activity (based on EC50 and Emax) at the serotonin receptors tested (both agonist and antagonist modes). These novel results reveal that the stereochemistry of the "E559 polymorph" plays a critical role in its serotoninergic receptor activity, and different stereoisomers will be expected to exhibit different pharmacological profile and activities. Differential pharmacological profiles may be selected for various treatments.

embryonic cortical neurons. Briefly, cultured primary cortical neurons (rat) were treated at day in vitro (DIV) 3 for 3 hours with increasing concentrations (1, 10 and 100 nM, 1 and 10 mM) of the "E559 polymorph" and morphological changes in dendritic arbor complexity (dendritogenesis) were assessed at DIV6 by immunofluorescent staining of fixed neurons with microtubule-associated protein 2 (MAP2, a microtubule marker), F-actin (cytoskeletal marker), and phalloidin (actin filament marker) followed by fluorescent microscopy and Sholl analysis of neurons' images. FIG. 18B shows the schematics of the Sholl analysis. The spine density assessments (spinogenesis) were made on DIV 18. The cell viability assessments were made on DIV 6 by using the Neurite Outgrowth Staining Kit which includes fluorescent probes for dead and live neuronal cells. Ketamine was used as a comparator and positive control. Ketamine is known to induce dendritogenesis and its effects on synaptic plasticity are believed to mediate its antidepressant effects (Aguilar-Valles et al., *Nature*, 2021, 590, p315-319). Rep-

TABLE XIV

| Targets | | | | Functional Assay (agonist) | | | | Funcational Assay (antagonist) | | | |
|---|---|---|---|---|---|---|---|---|---|---|---|
| Receptor | Species | Ligand | Assay | 2-Br-LSD EC50 (nM) | 2-Br-LSD Emax | Iso-2-Br-LSD EC30 (nM) | Iso-2-Br-LSD Emax | Ligand | Assay | 2-Br-LSD IC50 (nM) | Iso-2-Br-LSD IC50 (nM) |
| 5-HT1B | Human | 5-HT | cAMP | 6.96 | 100 | >10000 | NA | ND | ND | ND | ND |
| 5-HT1E | Human | 5-HT | Arrestin | >10000 | 8.7 | >10000 | NA | ND | ND | ND | ND |
| 5-HT1F | Human | 5-HT | cAMP | 13.77 | 92.6 | 3115 | 66.9 | ND | ND | ND | ND |
| 5-HT2A | Human | 5-HT | IP1 | 11 | 99 | 200.00 | 55.0 | 5-HT | IP1 | 24.9 | >10000 |
| 5-HT2B | Human | 5-HT | IP1 | >10000 | 0 | >10000 | NA | 5-HT | IP1 | 97 | >10000 |
| 5-HT6 | Human | 5-HT | cAMP | 0.5 | 80.1 | 99.00 | 71.0 | ND | ND | ND | ND |

NA: No activity;
ND: Not Determined

Example 10: LSD Derivative Polymorph is a Potent Promoter of Neural Plasticity The ability of the "E559 polymorph" to induce neural plasticity was evaluated in vitro. In vitro dendritogenesis and spinogenesis assays were conducted using primary rat resentative images of MAP2 stained rat cortical neurons treated with vehicle (no drug control) or with "E559 polymorph" is shown in FIG. 18A.

FIG. 19A shows representative Sholl tracings of neurons treated with the vehicle (control) or increasing concentration of the "E559 polymorph". FIG. 19B displays the total number of Sholl radii crossings by MAP2-positive neurites following treatment with vehicle (control), "E559 polymorph" or ketamine. FIG. 19C shows the total number of dendritic arbor length from neurons in FIG. 19A and FIG. 19B. FIG. 19D exhibits representative fluorescent images of dendritic spines in cortical neurons treatment with vehicle (control), the "E559 polymorph" or ketamine. FIG. 19E shows total number of spines per 10 μm section (see FIG. 18B) on the longest apical dendrite that was scored from the first branch point. FIG. 19F shows the ratio of living to dead neuronal cells in randomly selected 40× objective fields of view in cell viability assay. Horizontal lines in all figure panels represent the means±standard error of the mean (S.E.M.).

The "E559 polymorph" significantly induced neuronal plasticity in vitro in a dose dependent manner in all parameters of neuronal plasticity assessed, and the increase in neuronal plasticity was detectable at the compound concentrations as low as 1 nM and reached statistical significance at concentrations as low as 1 μM (FIGS. 19B, 19C and 19E). The compound performed significantly better than the positive control drug ketamine (tested at the very high concentration of 10 mM) in most parameters of neuronal plasticity. Briefly, the "E559 polymorph" significantly increased the number of total dendrites crossing the Sholl radii, reaching a maximal effect with the top two concentrations (1 and 10 mM) (FIG. 19B; Control vs 1 μM 2-Br-LSD *$p=0.0113$, Control vs 10 μM 2-Br-LSD *$p=0.0193$, and Control vs ketamine $p=0.0096$). The total length of the dendritic arbor was also increased in the "E559 polymorph" treated neurons compared to controls at 1 and 10 μM (FIG. 19C; Control vs 1 μM 2-Br-LSD $p=0.0019$, Control vs 10 μM 2-Br-LSD $p=0.003$, and Control vs ketamine $p=0.0096$). The "E559 polymorph" also increased the spine density after 3-hour incubation at 1 and 10 μM concentrations (FIG. 19D and FIG. 19E, Control vs 1 μM 2-Br-LSD * $p=0.0322$, Control vs 10 μM 2-Br-LSD *$p<0.0001$, and Control vs ketamine *$p<0.0001$). The effect of the "E559 polymorph" on the viability of cultured primary rat neurons was tested and no cytotoxic activity was observed at all tested concentrations (FIG. 19F).

Example 11: LSD Derivative Polymorph Induced Neuroplasticity Involves the 5-HT2A Receptor (In Vitro)

The 5-HT2A receptor plays a key role in the function of serotonergic psychedelics and their derivatives (Jaster, et al., *Psychopharmacology*, 2022, 239, p1665-1677.). We have demonstrated that the "E559 polymorph" induces neuroplasticity in dendritogenesis and spinogenesis assays (see Example 10). The in vitro dendritogenesis assay was repeated in the presence or absence of a selective 5-HT2A antagonist volinanserin. In brief, FIG. 20A represents tracings of the cortical neurons (DIV 3) treated with volinanserin (Vol) at 0.1, 0.5 or 1 mM) followed by either vehicle or "E559 polymorph" (1 μM). Sholl radii are spaced 10 μm. FIG. 20B shows the total number of Sholl crossings for neurons treated in FIG. 20A. FIG. 20C represents the total dendritic arbour length for neurons treated in FIG. 20A. In FIGS. 20B and 20C, violin plots represent the distribution of individual cells (n=15/treatment), while dots represent the averages per independent experiment (n=5/treatment). In this study primary cortical neurons (rats) were treated with volinanserin (0.1-1 μM), a selected 5-HT2A receptor antagonist, prior to the administration of the "polymorph HT compound" (1 μM 2-Br-LSD).

As shown in FIG. 20, volinanserin alone (labelled as Vehicle) did not change any parameters linked to dendritic arbor complexity (marker of neuroplasticity). However, pretreatment with volinanserin at every concentration tested blocked the effect of the "E559 polymorph" (1 μM) on dendritic arbor complexity to levels seen in control neurons, as observed by Sholl intersection analysis (FIG. 20B; control—no Vol, no 2-Br-LSD-, vs Vol and 2-Br-LSD *$p<0.0001$). Volinanserin also blocked the increase in total dendrite length induced by the "E559 polymorph" (FIG. 20C; control—no Vol, no "E559 polymorph"—, vs Vol and "E559 polymorph" *$p<0.0001$).

The data in this Example indicate that the 5-HT2A receptor plays a role in the "E559 polymorph's" neuroplasticity promoting activity.

Example 12: LSD Derivative Polymorph Repeated Dosing does not Induce Tolerance

Tolerance (also referred to as tachyphylaxis) or cross-tolerance, commonly observed with psychedelic drugs or 5-HT receptor agonists, can limit the therapeutic efficacy of repeated drug administration or combination therapy with other CNS active drugs (Douglas et al., *Journal of Pharmacology and Experimental Therapeutics*, 2014, 351(3) p485-491). Repeated administration of LSD, as with most other psychedelic drugs, leads to a decline in responsiveness or tolerance. Studies have shown that 3 days off LSD was sufficient for patients to fully recover from somatic and mental tolerance (Buchbom et al., *Neuropathology of Drug Addictions and Substance Misuse*, Chapter 79, Academic Press, 2016, p846-858). β-Arrestin recruitment via 5-HT receptors is responsible for receptor internalization and downregulation, two mechanisms involved in induction of tolerance (Reiter et al., *Annu Rev Pharmacol Toxicol*. 2012; 52:p179-97). Assessment of β-Arrestin recruitment via 5-HT receptors is therefore a good surrogate to predict tolerance induction.

As shown in FIG. 21A, the "E559 polymorph" is a weak recruiter of β-Arrestin2 using the BRET-based β-arrestin2 recruitment assay (described in Example 8) at the 5-HT2A receptor. The comparators tested were LSD, DOI and the parent ligand 5-HT. In contrast to the "E559 polymorph", LSD, DOI and 5-HT are strong recruiters of β-Arrestin2. The data are shown as a percentage of the 5-HT-induced maximal response, and as group means±standard deviation.

Figure 21B:
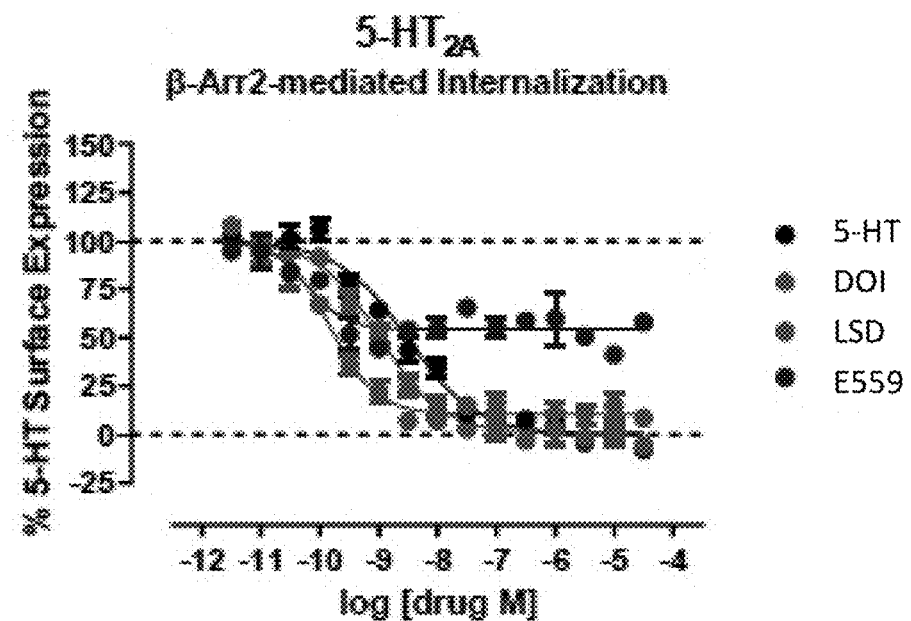

To assess the ability of the "E559 polymorph" to induce β-arrestin-mediated 5-HT2A receptor internalization in vitro, the loss of surface expression of 5-HT2A receptor was measured using a NanoBit N-terminal HiBit-fused 5-HT2A construct cloned in HEK293T cells (1:15 ratio 5-HT2A:β-arrestin2). In brief, cells were treated with serial dilution of test compounds for 1 hour or a specified time point. Approximately 15 minutes before to reading, LgBit and coelenterazine (5 μM) were added to cell plates and read on a PheraStar FSX or Mithras LB940 plate readers at 485 nm at 37° C. for time-capture quantification of receptor internalization or loss of surface expression. Luminescence was plotted as a function of drug concentration using Graphpad Prism 5 or 9 (Graphpad Software Inc., San Diego, CA). As shown in FIG. 21B, single 1 hour treatment with the "E559 polymorph" only exhibits weak internalization of the 5-HT2A receptor, which contrasts with the potent internalization seen with LSD, DOI and 5-HT. The data are shown as a percentage of the 5-HT-induced maximal response, and as group means±standard deviation.

To determine if repeated dosing of the "E559 polymorph" can induce tolerance in vivo, HTR experiment described in Examples 2 and 5 was repeated where mice received IP injections of vehicle, DOI (10 mg/kg/day), or the "E559 polymorph" (3 mg/kg/day; once daily for 7 consecutive days) and were then challenged with DOI (1 mg/kg) 24 hours later. Data shown in FIG. 22 are group means±standard deviation for the entire 60 minutes test session. Asterisks indicate statistical significances compared to the Vehicle control (Vehicle was saline). As seen in FIG. 22, while repeated treatment with DOI induced a significant degree of tachyphylaxis/tolerance as shown by reduced HTR count (FIG. 22, vehicle vs DOI *p<0.001), no tolerance was observed in the mice treated repeatedly with the "E559 polymorph". That repeated dosing of the "E559 polymorph" does not induce tolerance as known to occur with LSD is a surprising result. This should allow dosing frequency of the "polymorph HT compound" at short intervals including once daily or even multiple times in a day, dosing frequencies not possible with other tolerance-inducing 5-HT receptor agonists such as LSD.

Example 13: LSD Derivative Polymorph Exhibits Anti-Depressant/Anxiolytic Activity in a Chronic Stressed Animal Model The "polymorph HT compound" (from Example 1) was tested for its anti-depression/anxiety activity in the chronic variable stress (CVS) mouse model as assessed by a self-grooming splash test and an open field test (OFT) [Strekalova et al., *Psychopharmacology* (Berl). 2022, 239(3):663-693; Willner, P. *Neurobiol Stress,* 2017, 6:78-93]. In brief, $C_{57}BL/6J$ mice were subjected to a CVS protocol, consisting of 2 stressors per day for 35 days. Naive mice (not exposed to CVS) are used as a control for CVS-induced depression activity. Following the 35 days CVS, mice were treated with the "E559 polymorph" (FIG. 23) via intraperitoneal injection (IP) as follows: single dose after the last day of CVS (3 mg/kg) or 4 doses (1 mg/kg) applied every 48 hours starting on day 28 of CVS. Saline was used as the vehicle control. The splash test and OFT were performed as previously described in (Aguilar-Valles et al., *Nature,* 2021, 590, p315-319). In brief, FIG. 23A shows the study design as described above. FIG. 23B represents distance travelled in the open field by female mice treated with E559 polymorph. FIG. 23C represents time spend in the center of the open field of mice in FIG. 23B. FIG. 23D shows time spent self-grooming in the splash test by female mice treated as described in FIG. 23A. Horizontal lines represent the mean±standard error of the mean (S.E.M.) and asterisks indicate statistical significances.

As shown in FIG. 23C, CVS induced a 55.95±19.3 second decrease in the time that mice spent exploring the center of the open field (Naïve-saline vs CVS-saline *p=0.0069), without changing total distance travelled (FIG. 23B). In the CVS group treated with the "E559 polymorph" repeat dose of 1 mg/kg, this CVS induced time decrease in exploration of the arena center was fully reversed to the levels seen in the control (Naïve-Saline) group (FIG. 23C; CVS-saline vs CVS-E559 polymorph 4×1 mg/kg p=0.0044) without affecting locomotion (FIG. 23B). Treatment with the "E559 polymorph" single dose of 3 mg/kg partially restored the effect of CVS, as this group spent an amount of time in the center of the open field intermediate between the CVS-saline and Naïve-Saline groups (FIG. 25C). As shown in FIG. 23**D the CVS mice spent significantly less time grooming in a splash test (Naïve-saline vs CVS-saline *p=0.0282), a measure of self-care behavior and depressive-like behavior. The "E559 polymorph" partially reversed this CVS-induced effect by increasing the grooming time in "E559 polymorph-treated CVS mice to levels intermediate between the naive-saline and CVS-saline groups (FIG. 23D).

The same cohort of CVS mice was tested 28 days after the last "E559 polymorph" treatment. The effect of CVS in reducing the time in center in OFT remained reversed (at levels similar to the acute effect of the "E559 polymorph") 28 days after the last "E559 polymorph" treatment, supporting the long-term anti-depressant and anxiolytic effects of the "E559 polymorph" (FIG. 24A; CVS-saline vs CVS-E559 polymorph 4×1 mg/kg p=0.0052). FIG. 24B represent time spent self-grooming in the splash test by female mice 28 days after the last "E559 polymorph" treatment as indicated in FIG. 23**A.

Example 14: LSD Derivative Polymorph Exhibits Anti-Depressant/Anxiolytic Activity in Acute Stress Animal Model The ""E559 polymorph" demonstrated anti-depression and anti-anxiety activity in a non-stressed mouse model as assessed by two behavioural tests that have been used to screen for anti-depressant and anxiolytic treatments: the forced swim test (FST) and open field test (OFT) (Strekalova et al., *Psychopharmacology* (Berl). 2022, 39(3):663-693). In brief, stress naive mice were treated (IP injection) with either saline (control) or single dose of the "E559 polymorph" at 0.3, 1, or 3 mg/kg dose levels and were evaluated 24 hours (OFT) and 25 hours (FST) after treatment. The OFT was performed described in Example 13. The FST was performed as previously described in (Aguilar-Valles et al., *Nature,* 2021, 590, p315-319). Briefly FST was performed 24-hour post treatment by placing the mice (one by one) in a 4-liter wide-mouthed flask of 35° C. water. Mice activities were recorded for 6 minutes and assessed for total time the animal remains immobile, a sign of depressive-like behavior. FIG. 25A depicts the study design where female/male mice (n=10/group/sex) were treated by IP injection with the "E559 polymorph" or vehicle (saline) followed by open field and force swim test 24 hours post treatment. FIGS. 25B and 25E represent the total distance travelled in the open field test 24 hours after vehicle or the "E559 polymorph" in female and male mice, respectively. FIGS. 25C and 25F represent the time in the center of the open field by female and male mice, respectively. FIGS. 25D and 25G represent the immobility time during the last 4 minutes of the forced swim test in female and male mice, respectively. Horizontal lines represent the mean±standard error of the mean (S.E.M.) and asterisks indicate statistical significances.

In the OFT, female mice showed increased exploration of the arena center after treatment at the 1 and 3 mg/kg "E559 polymorph" (FIG. 25C; vehicle (0 mg/kg) vs 1 mg/kg 2-Br-LSD ***p=0.0001, vehicle vs 3 mg/kg 2-Br-LSD*p=0.0459), with a maximal effect (an increase of 88.18±18.89 second) at the 1 mg/kg dose. The increased exploration of the stressogenic area of the open field by the "E559 polymorph" was not evident in male mice (FIG. 25F).

In the FST, a decrease in immobility by 35.18±10.03 second was seen in females at the 1 mg/kg "E559 polymorph" dose (FIG. 25D; vehicle vs 1 mg/kg E559 polymorph p=0.0069). A similar effect was observed in males at all the concentrations assayed (FIG. 25**G; vehicle vs 0.3 mg/kg E559 polymorph *p=0.0464, vehicle vs 1 mg/kg E559 polymorph **p=0.0056, vehicle vs 3 mg/kg E559 polymorph **p=0.0014). Decreases in immobility by 0.3, 1 and 3 mg/kg doses in males (20.89 8.249; 27.27±8.226; and 31.36±8.226 s, respectively) were comparable to that induced by the 1 mg/kg "E559 polymorph" dose in females.

Following testing in the FST, brains were collected for spine density analysis in the prefrontal cortex region (~26 hour after treatment; FIG. 25H). A significant increase in the average spine density was observed following the "E559 polymorph" treatment, in both sexes, as compared to controls (FIG. 25I Female mice: vehicle vs 1 mg/kg E559 polymorph *p=0.0447 and FIG. 25I Male mice: vehicle vs 1 mg/kg E559 polymorph **p=0.0028).

The data in this Example demonstrate that the "E559 polymorph" can reduce depression- and anxiety-like behaviour in mice in acute stress environment and this effect correlates with promotion of neuroplasticity in the prefrontal cortex region of the brain.

Example 15: LSD Derivative Polymorph Anti-Depressant/Anxiolytic Effects Involves the 5-HT2A Receptor (In Vivo)

Figures 26A, 26B:
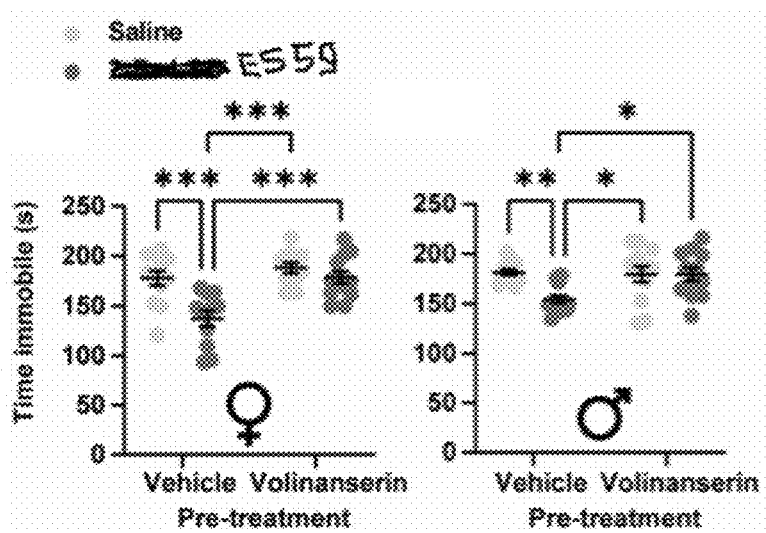
Figures 26C, 26D:
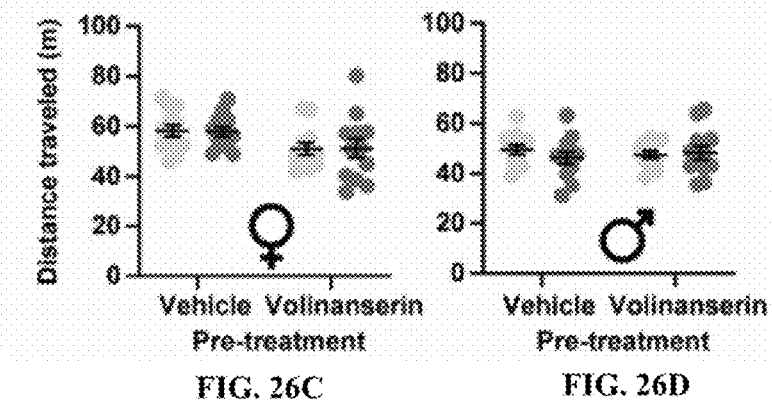

The 5-HT2A receptor plays a key role in the function of many serotonergic psychedelics and their derivatives (Jaster et al., *Psychopharmacology*, 2022, 239, p1665-1677.). We have demonstrated an antidepressant and anxiolytic properties of the "E559 polymorph" in mouse depression/anxiety models in vivo (see Examples 13 and 14). To further investigate the role of the 5-HT2A receptor in the "E559 polymorph" effects in these in vivo models, the open field test and forced swim test in mice was repeated as described in Example 14, with and without volinanserin, a selective 5-HT2A antagonist, treatment. Briefly, volnanserin (0.125 mg/kg) was administered (IP injection) 1 hour prior to the administration of the "E559 polymorph" (1 mg/kg, IP) to stress-naïve mice, and forced swim test was performed 24 hours later as described in Example 14. In brief, FIG. 26A represents immobility time in the forced swim test of female mice (n=12/group) pre-treated with vehicle or volinanserin, followed by either vehicle (saline) or "E559 polymorph" (1 mg/kg). FIG. 26B shows male mice treated as in FIG. 26A and measured for immobility in the FST (n=12/group). FIG. 26C represents distance travelled in the open field Measured 24 hours after treatment (as in FIG. 26A) in female mice (n=12). FIG. 26D shows distance travelled in the open field measured 24 hours after treatment (as in FIG. 26C) in male mice (n=12). Horizontal lines in FIG. 26 represent the mean±standard error of the mean (S.E.M.) and asterisks indicate statistical significances.

As shown in FIG. 26, volinanserin pre-treatment blocked the decrease in immobility induced by the "E559 polymorph" in the FST in both female (FIG. 26A; vehicle and E559 polymorph vs Vol and E559 polymorph ***p=0.0006) and male mice (FIG. 26B; vehicle and E559 polymorph vs Vol and E559 polymorph *p=0.0187). Neither volinanserin or a combination of volinanserin and the "E559 polymorph" affected locomotion in the OFT in female or male mice (FIG. 26C and FIG. 26D). These data indicate that 5-HT2A receptor plays a role in the "E559 polymorph" anti-depressant and anxiolytic effects in vivo.

Example 16: LSD Derivative Polymorph Attenuates Neuropathic Pain in Spared Nerve Injury Model To evaluate the function the "E559 polymorph" in neuropathic pain, mechanical allodynia test was evaluated by von Frey filament in rat spared nerve injury (SNI) model before and after before and after treatment with the "E559 polymorph". The SNI model and von Frey filament testing were conducted as previously described (Decosterd & Woolf. *Pain,* 2000, v87, p149-158). Briefly, Animals with a pain threshold of <15 g, assessed using the Von Frey mechanical allodynia testing, were randomly placed in experimental groups. Each rat group consisted of 10 male rats. On day 7 post-surgery treatment was initiated. Treatment was with either the "E559 polymorph", vehicle only (saline) as a negative control, or gabapentin as a positive control.

FIG. 27 shows pain response assessment results after single dose treatment of the "E559 polymorph" on day 7 post-surgery. The pain response (Von Frey testing) was evaluated on day 0 pre-surgery (labelled as Baseline in FIG. 27), on day 6 post-surgery (labelled as Day 6 Pre grouping in FIG. 27), and at 2, 4, 6, and 24 hours after a single oral dose of either vehicle, or the "E559 polymorph" at 0.3, 1, 3, or 10 mg/kg (labelled as BETR-001 in FIG. 27), or gabapentin at 150 mg/kg. The data are shown as group means±standard deviation and asterisks indicate statistical significances. Single dose treatment of the "E559 polymorph" demonstrated significant dose-dependent inhibition of neuropathic pain, compared to baseline and vehicle, at 2 and 4 hours post administration (FIG. 27; Vehicle vs 3 mg/kg BETR-001 *p<0.05, Vehicle vs 10 mg/kg BETR-001 4 hr p<0.01, Vehicle vs 10 mg/kg BETR-001 2 hr *p<0.001, Vehicle vs Gabapentin ****p<0.0001).

FIG. 28 shows pain response assessment results after multiple dose treatments of the "E559 polymorph" starting on day 7 post-surgery. Rat groups were treated (via oral administration) with either vehicle, or the "E559 polymorph" at 20 mg/kg (labelled as BETR-001 in FIG. 28), or gabapentin at 150 mg/kg. Treatment was given on days 7, 9, 11, 13 and 15 post-surgery. The pain response (Von Frey testing) was evaluated on day 0 pre-surgery (labelled as Baseline in FIG. 28), on day 6 post-surgery (labelled as Day 6 Pre grouping in FIG. 28), and at 2 hours post-treatment given on days 7, 11, and 15 post-surgery. Repeated dosing of the "E559 polymorph" enhanced the inhibition effect on mechanism allodynia to levels comparable to the gabapentin positive control (FIG. 28, Vehicle vs BETR-001 day 7, 11, and 15 and Vehicle vs Gabapentin days 7, 11, and 15 ****p<0.0001). The data are represented as group means±standard deviation and asterisks indicate statistical significances.

These findings demonstrate that the "E559 polymorph" exhibits potent analgesic activity in a neuropathic pain model in both single and repeated administration.

The above disclosure generally describes the present invention. Although specific terms have been employed herein, such terms are intended in a descriptive sense and not for purposes of limitation.

Patent applications, patents, and publications are cited herein to assist in understanding the embodiments described. All such references cited herein are incorporated herein by reference in their entirety and for all purposes to the same extent as if each individual publication or patent or patent application was specifically and individually indicated to be incorporated by reference in its entirety for all purposes. To the extent publications and patents or patent applications incorporated by reference contradict the disclosure contained in the specification, the specification is intended to supersede and/or take precedence over any such contradictory material.

Although specific embodiments of the invention have been described herein in detail, it will be understood by those skilled in the art that variations may be made thereto without departing from the spirit of the invention or the scope of the appended claims.

It will be understood that certain of the above-described structures, functions, and operations of the above-described embodiments are not necessary to practice the present invention and are included in the description simply for completeness of an exemplary embodiment or embodiments. In addition, it will be understood that specific structures, functions, and operations set forth in the above-described referenced patents and publications can be practiced in conjunction with the present invention, but they are not essential to its practice. It is therefore to be understood that the invention may be practiced otherwise than as specifically described without actually departing from the spirit and scope of the present invention as defined by the appended claims.

What is claimed is:

1. A substantially pure crystalline form of a compound selected from:

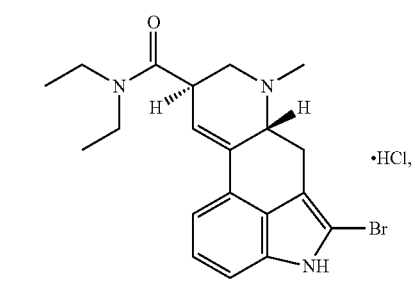
•HCl,

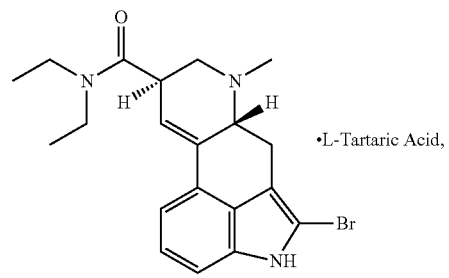
•L-Tartaric Acid,

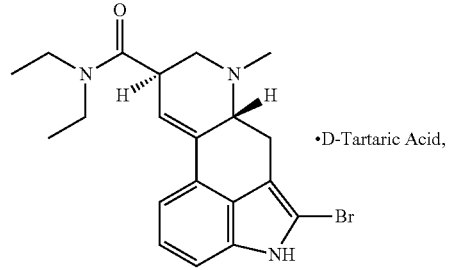
•D-Tartaric Acid,

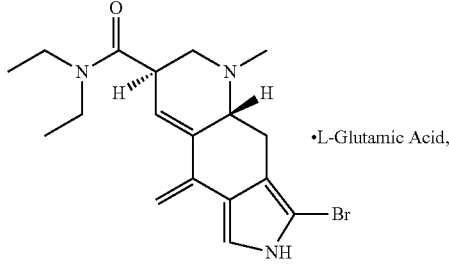
•L-Glutamic Acid,

-continued

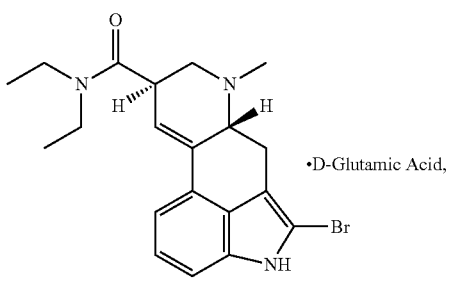
•D-Glutamic Acid,

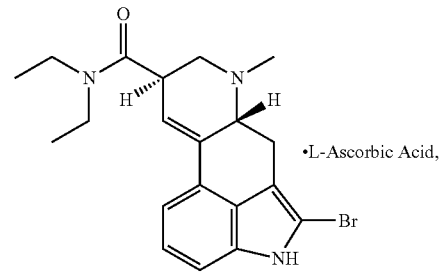
•L-Ascorbic Acid,

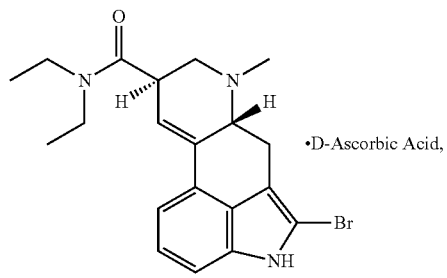
•D-Ascorbic Acid,

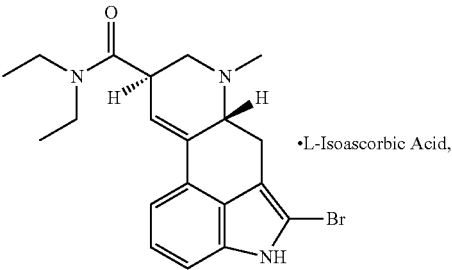
•L-Isoascorbic Acid,

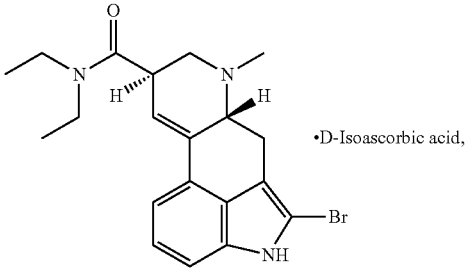
•D-Isoascorbic acid,

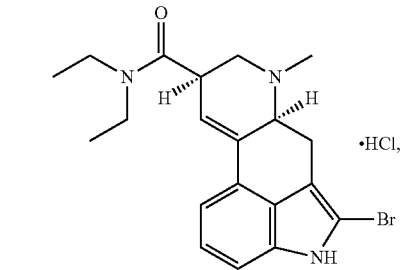
•HCl,

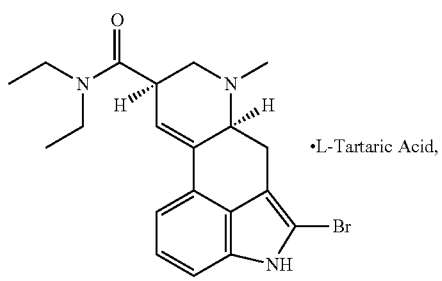
•L-Tartaric Acid,
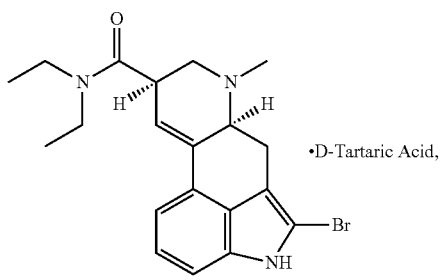
•D-Tartaric Acid,
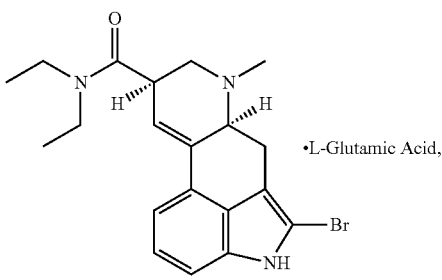
•L-Glutamic Acid,
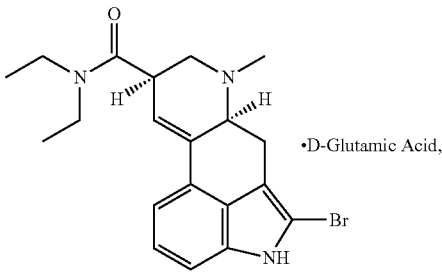
•D-Glutamic Acid,
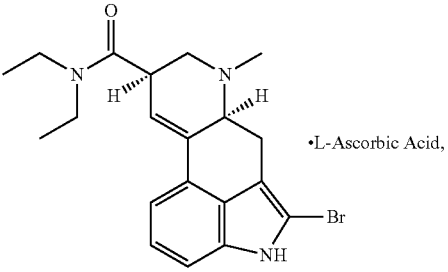
•L-Ascorbic Acid,
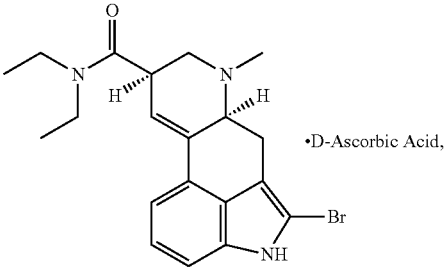
•D-Ascorbic Acid,
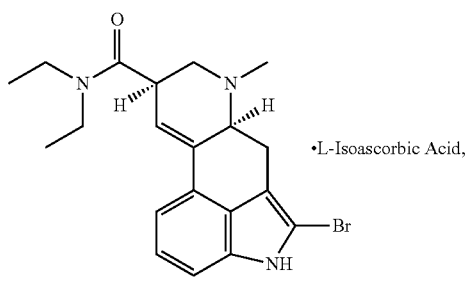
•L-Isoascorbic Acid,
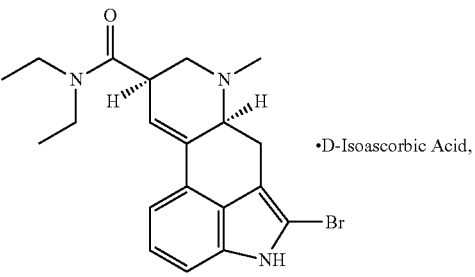
•D-Isoascorbic Acid,
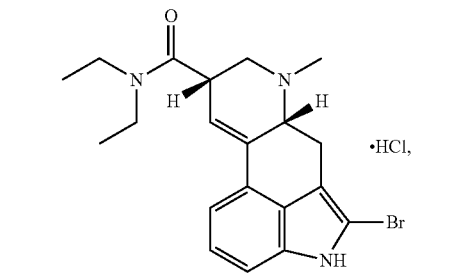
•HCl,
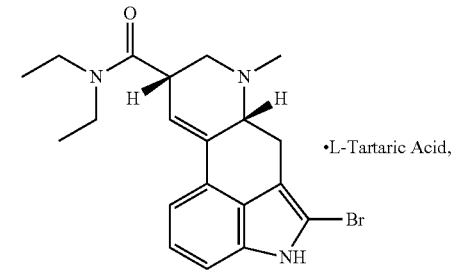
•L-Tartaric Acid,
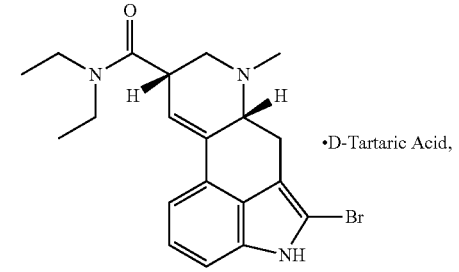
•D-Tartaric Acid,
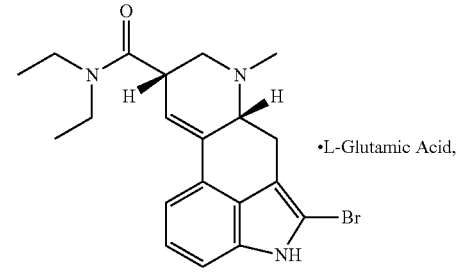
•L-Glutamic Acid,

- D-Glutamic Acid,
- L-Ascorbic Acid,
- D-Ascorbic Acid,
- L-Isoascorbic Acid,
- D-Isoascorbic Acid,
- HCl,
- L-Tartaric Acid,
- D-Tartaric Acid,
- L-Glutamic Acid,
- D-Glutamic Acid,
- L-Ascorbic Acid,
- D-Ascorbic Acid, -continued

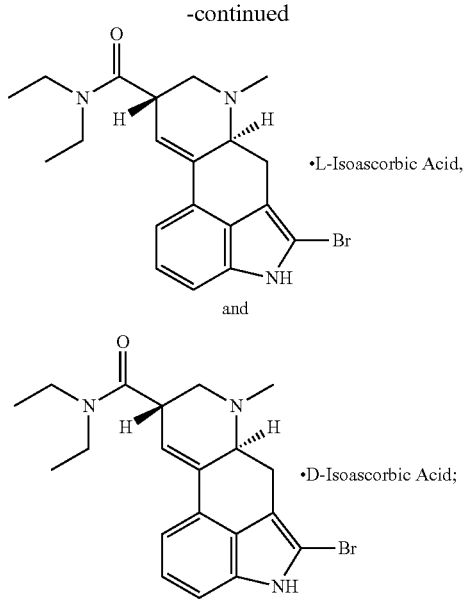

•L-Isoascorbic Acid, and

•D-Isoascorbic Acid;

wherein the compound has a Powder X-ray Diffraction (PXRD) pattern comprising a peak at 10.3°±0.2° (2θ).

2. The substantially pure crystalline form of the compound of claim 1, wherein stereocenters of the compound are 5R and 8R.

3. The substantially pure crystalline form of the compound of claim 1, wherein stereocenters of the compound are 5R and 8S.

4. The substantially pure crystalline form of the compound of claim 1, wherein the compound is 2-bromo-LSD tartrate salt.

5. The substantially pure crystalline form of the compound of claim 4, wherein the compound is (5R, 8R) 2-bromo-LSD hemi-D-tartrate salt.

6. The substantially pure crystalline form of the compound of claim 1, wherein the compound is a substantially pure polymorph of (5R, 8R) 2-bromo-LSD hemi-D-tartrate salt.

7. The substantially pure crystalline form of the compound of claim 6, wherein the PXRD pattern of the compound further comprises peaks at 4.7°±0.2° (2θ), 9.4°±0.2° (2θ), and 20.1°=0.2° (2θ).

8. The substantially pure crystalline form of the compound of claim 7, wherein the compound has an optical rotation of about 0.30° to about 0.40°.

9. The substantially pure crystalline form of the compound of claim 6, wherein the compound is substantially non-hallucinogenic.

10. The substantially pure crystalline form of the compound of claim 9, wherein the compound promotes neural plasticity in neurons.

11. The substantially pure crystalline form of the compound of claim 9, wherein the compound exhibits one or more of:
  i) does not induce tolerance to the compound in a subject;
  ii) is a moderate to potent pan-agonist across 5-HT1 receptor subtypes;
  iiii) is a potent 5-HT6 receptor partial agonist;
  iv) is a partial agonist at 5-HT2A and 5-HT1A receptor subtypes;
  v) is not an agonist or is an antagonist if 5-HT2B receptor; and
  vi) exhibits agonism at D2-like receptors.

12. A composition comprising one or more of the substantially pure crystalline form of the compound(s) of claim 1.

13. A formulation comprising the composition of claim 12 and a pharmaceutically acceptable carrier, diluent or excipient.

14. The substantially pure crystalline form of the compound of claim 1, wherein the compound is at least 98% pure.

15. The substantially pure crystalline form of the compound of claim 1, wherein the compound is at least 99% pure.

16. The substantially pure crystalline form of the compound of claim 1, wherein the compound is 100% pure.

17. A substantially pure crystalline form of a compound selected from:

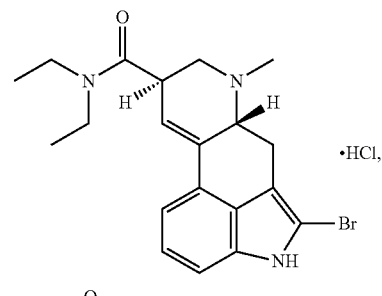

•HCl,

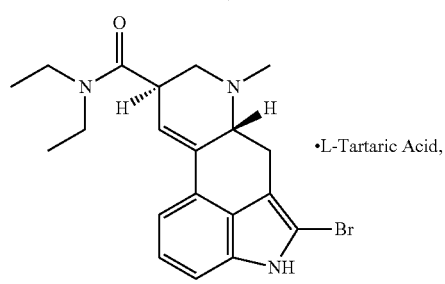

•L-Tartaric Acid,

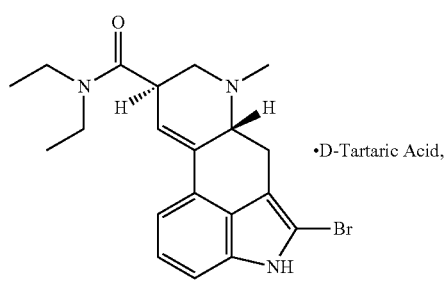

•D-Tartaric Acid,

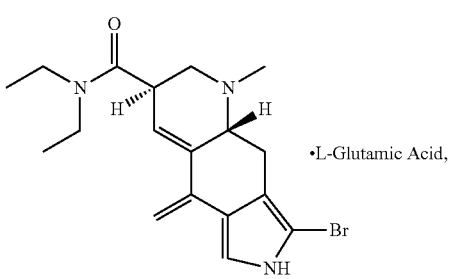

•L-Glutamic Acid,

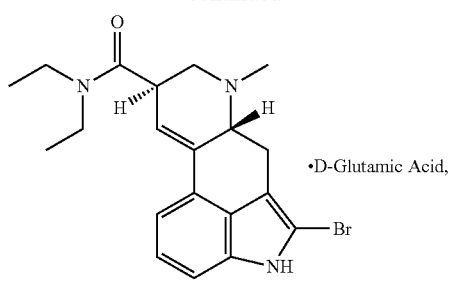
•D-Glutamic Acid,
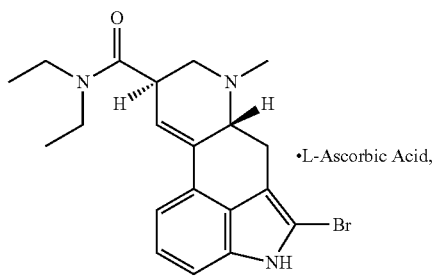
•L-Ascorbic Acid,
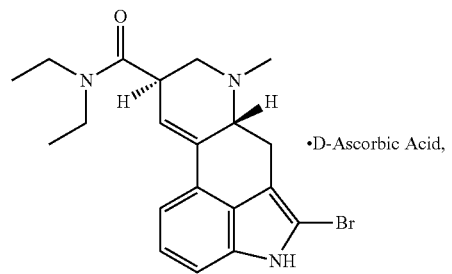
•D-Ascorbic Acid,
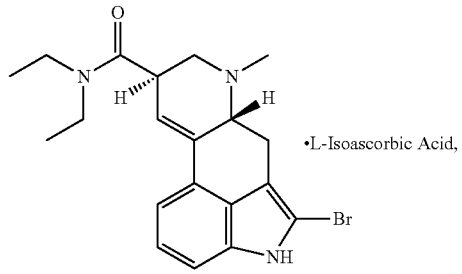
•L-Isoascorbic Acid,
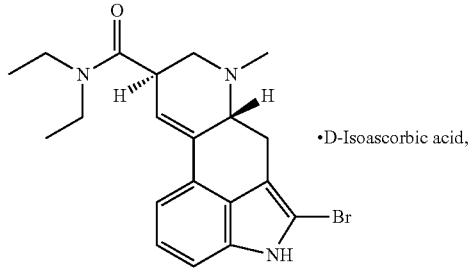
•D-Isoascorbic acid,
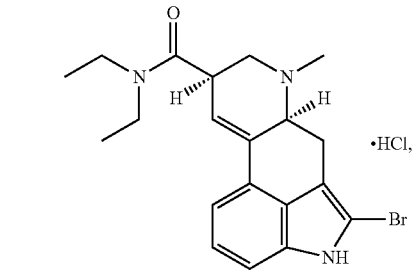
•HCl,
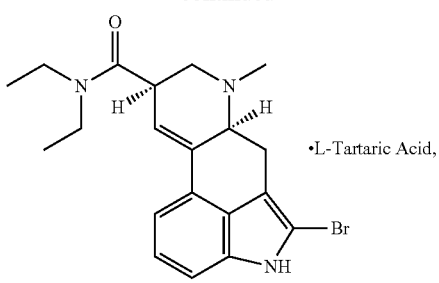
•L-Tartaric Acid,
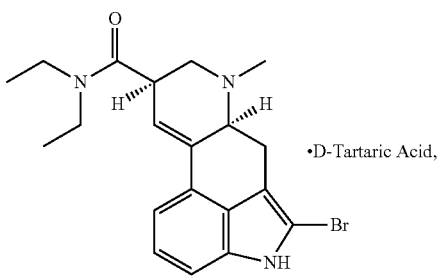
•D-Tartaric Acid,
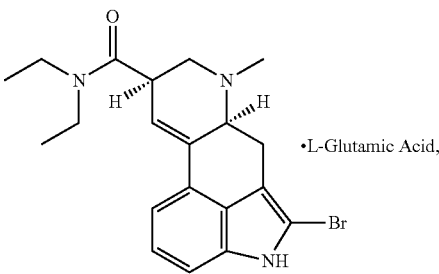
•L-Glutamic Acid,
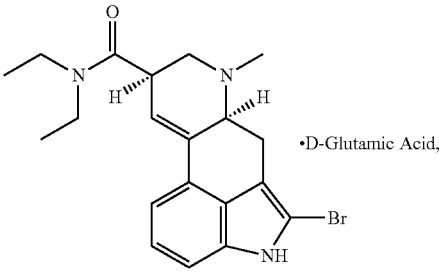
•D-Glutamic Acid,
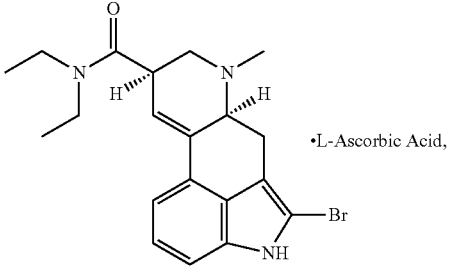
•L-Ascorbic Acid,
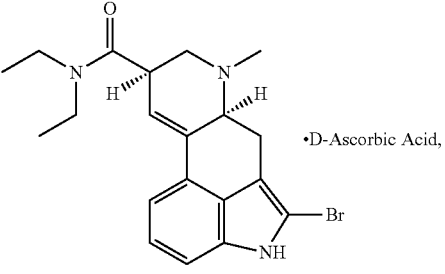
•D-Ascorbic Acid, -continued
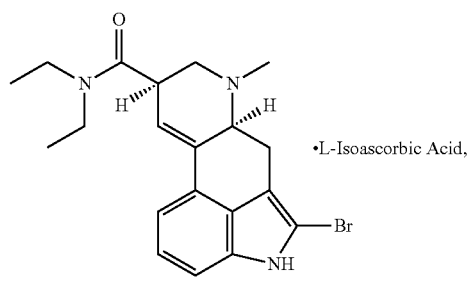
•L-Isoascorbic Acid,
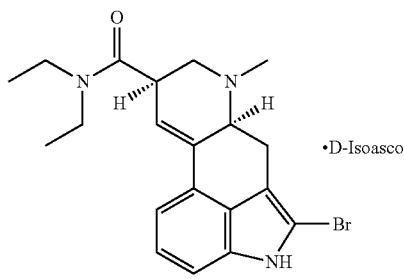
•D-Isoascorbic Acid,
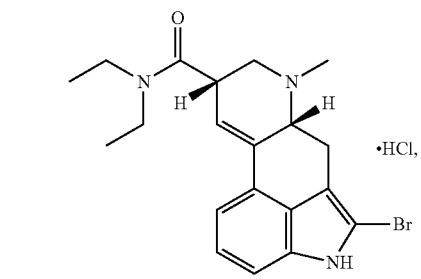
•HCl,
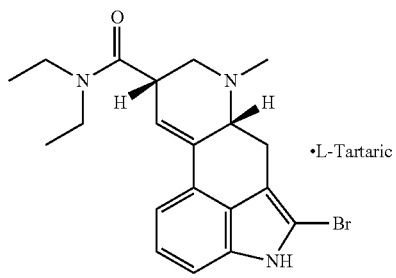
•L-Tartaric Acid,
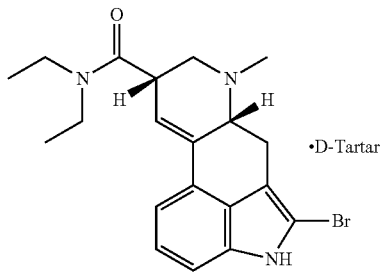
•D-Tartaric Acid,
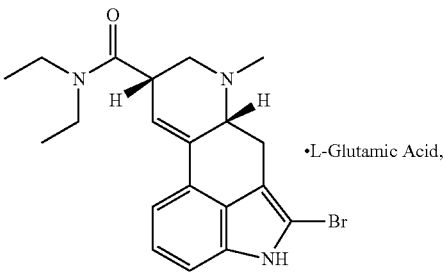
•L-Glutamic Acid,
-continued
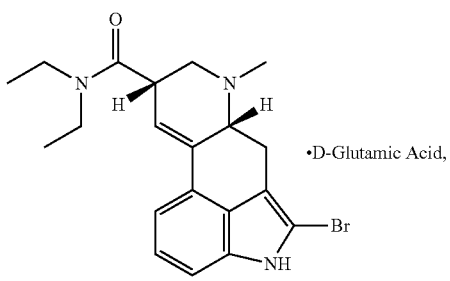
•D-Glutamic Acid,
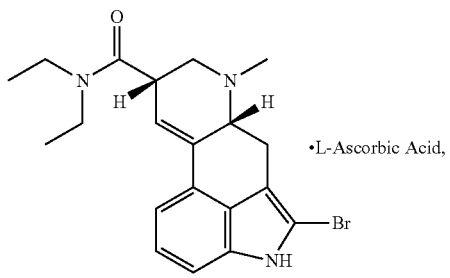
•L-Ascorbic Acid,
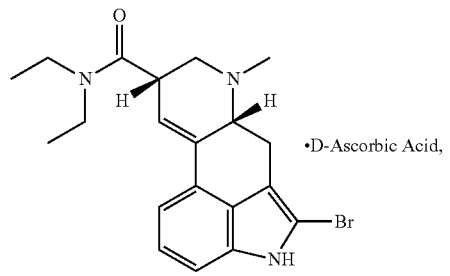
•D-Ascorbic Acid,
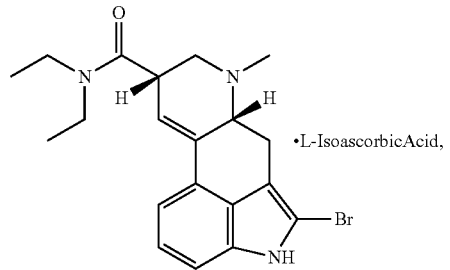
•L-Isoascorbic Acid,
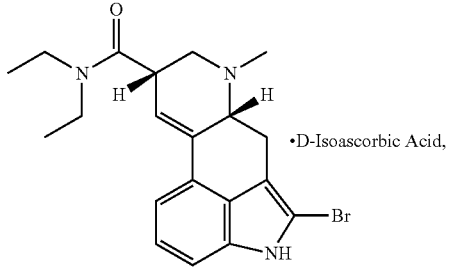
•D-Isoascorbic Acid,
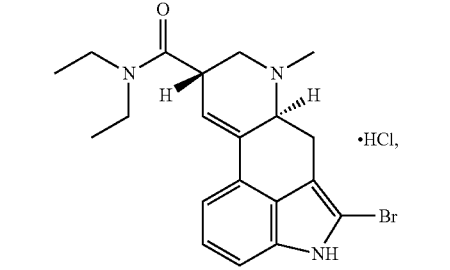
•HCl, -continued

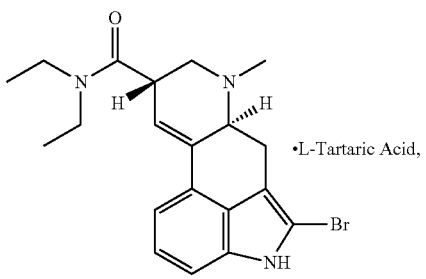
•L-Tartaric Acid,

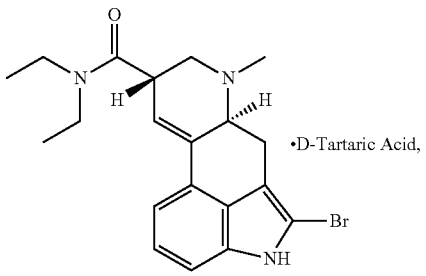
•D-Tartaric Acid,

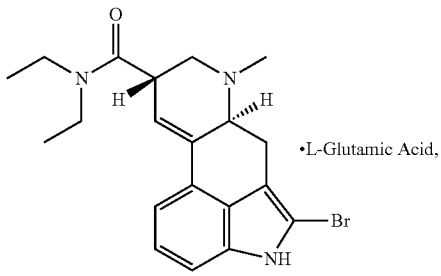
•L-Glutamic Acid,

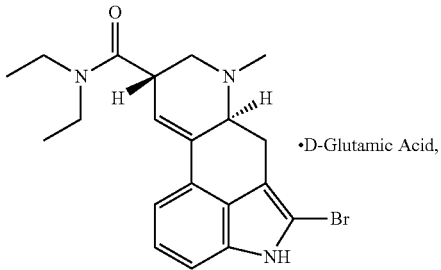
•D-Glutamic Acid,

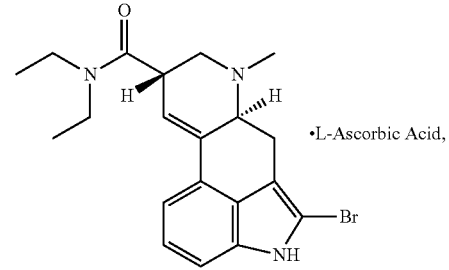
•L-Ascorbic Acid,

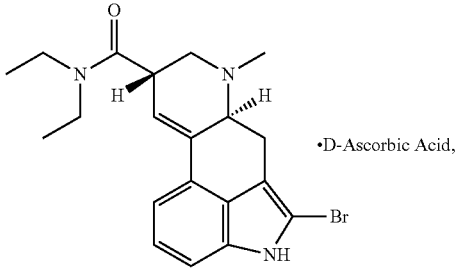
•D-Ascorbic Acid,

-continued

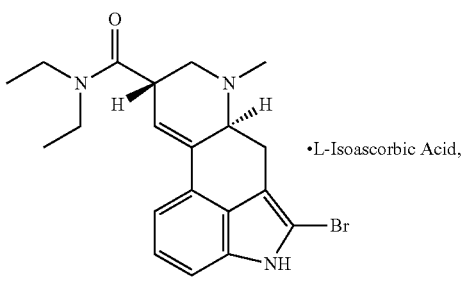
•L-Isoascorbic Acid, and

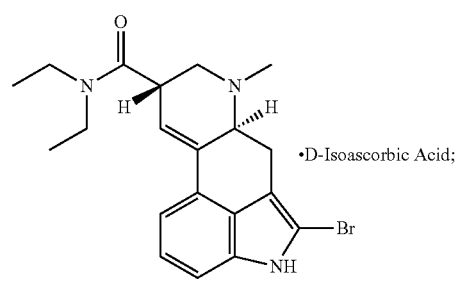
•D-Isoascorbic Acid;

wherein the compound has a Powder X-ray Diffraction (PXRD) pattern comprising a peak at 10.3°±0.2° (2θ) and another peak at one or more of 4.7°±0.2° (2θ), 9.4°±0.2° (2θ), and 20.1°±0.2° (2θ).

18. A substantially pure crystalline form of a compound selected from:

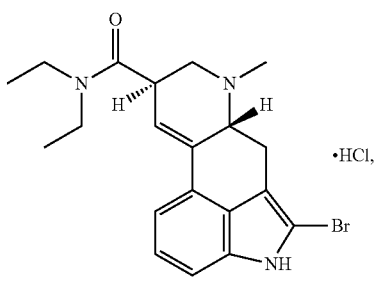
•HCl,

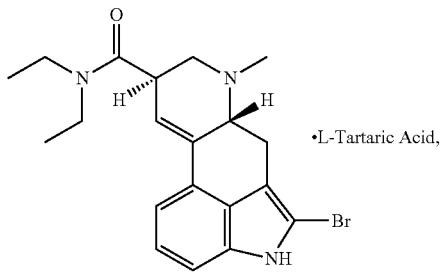
•L-Tartaric Acid,

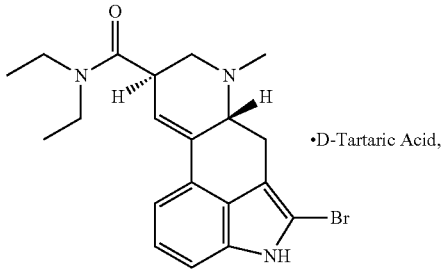
•D-Tartaric Acid,

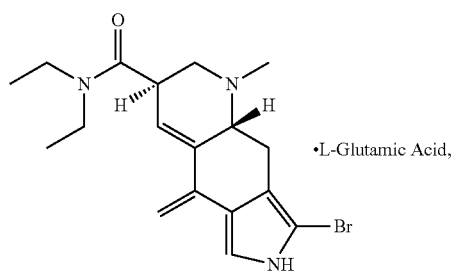
•L-Glutamic Acid,
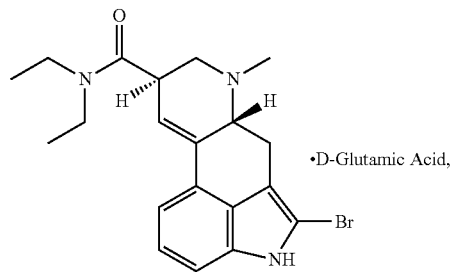
•D-Glutamic Acid,
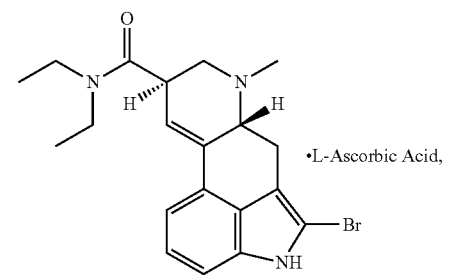
•L-Ascorbic Acid,
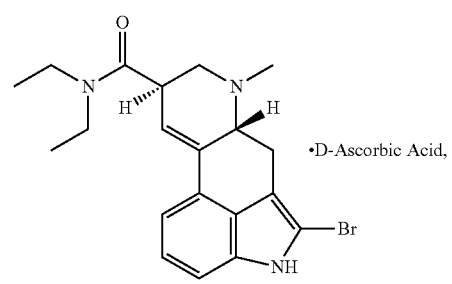
•D-Ascorbic Acid,
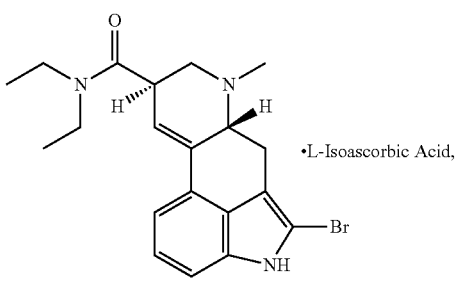
•L-Isoascorbic Acid,
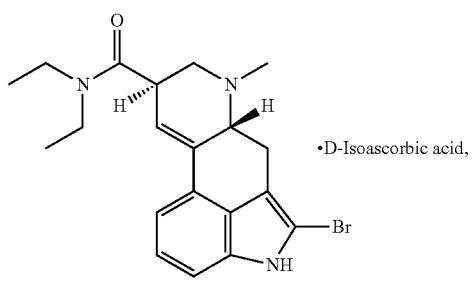
•D-Isoascorbic acid,
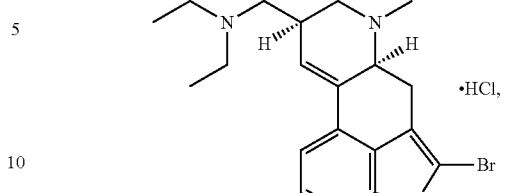
•HCl,
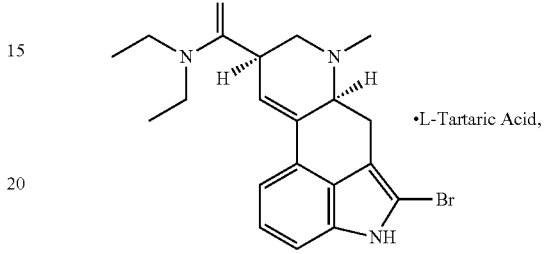
•L-Tartaric Acid,
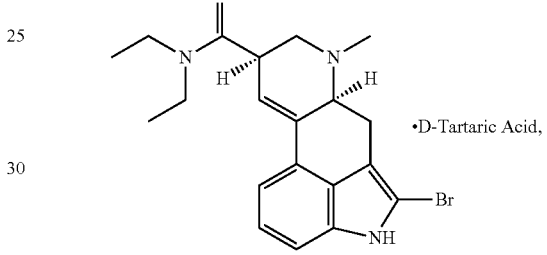
•D-Tartaric Acid,
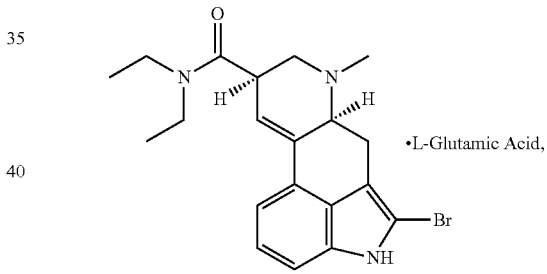
•L-Glutamic Acid,
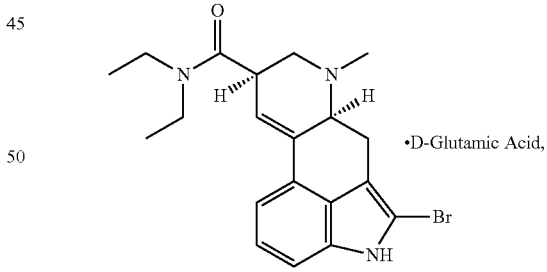
•D-Glutamic Acid,
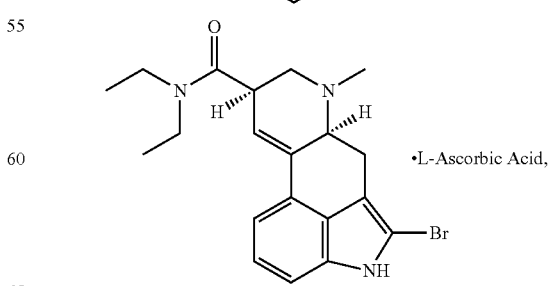
•L-Ascorbic Acid, 167
-continued
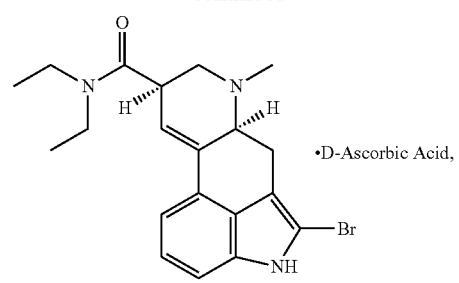
•D-Ascorbic Acid,
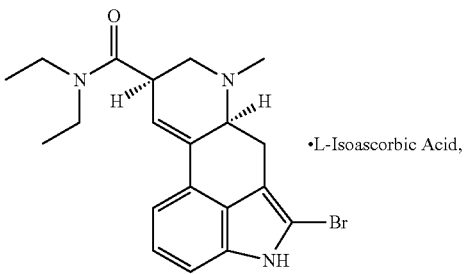
•L-Isoascorbic Acid,
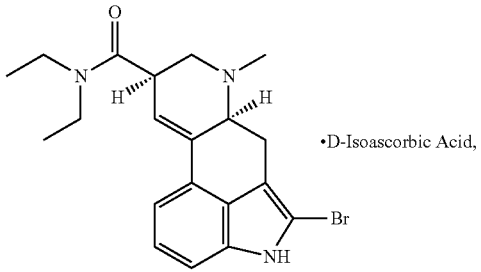
•D-Isoascorbic Acid,
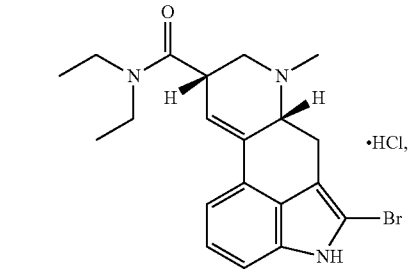
•HCl,
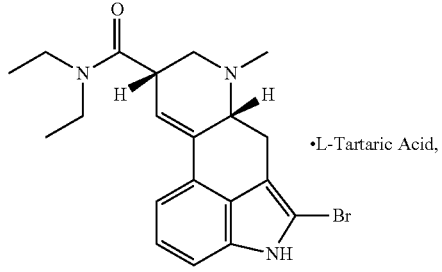
•L-Tartaric Acid,
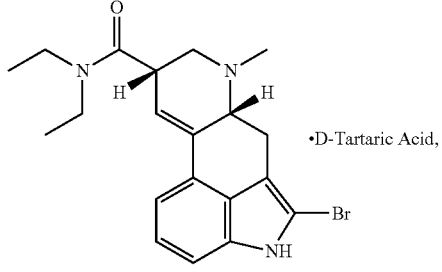
•D-Tartaric Acid,
168
-continued
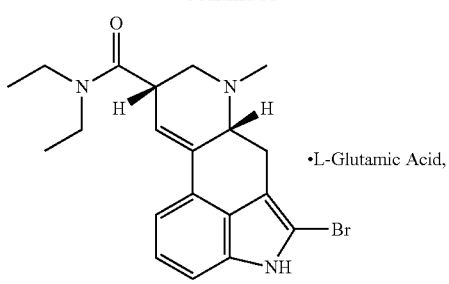
•L-Glutamic Acid,
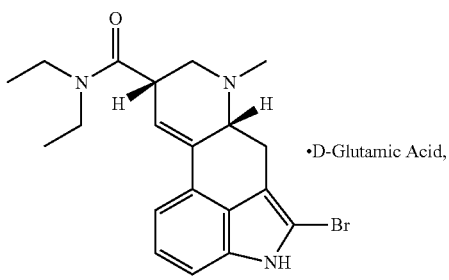
•D-Glutamic Acid,
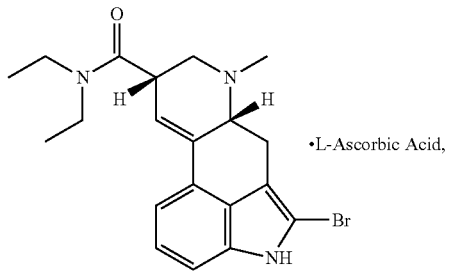
•L-Ascorbic Acid,
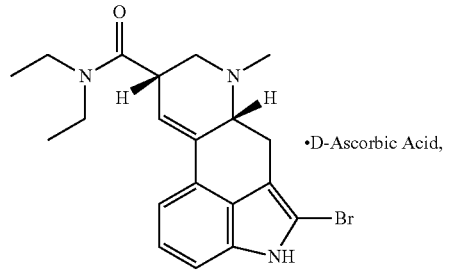
•D-Ascorbic Acid,
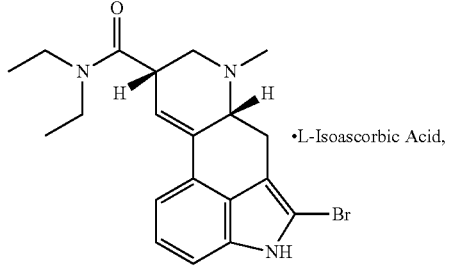
•L-Isoascorbic Acid,
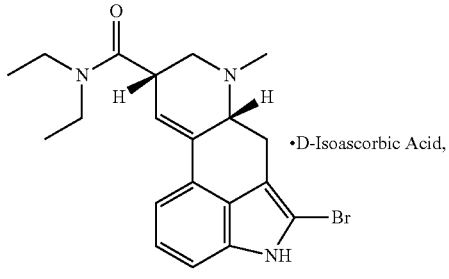
•D-Isoascorbic Acid, -continued

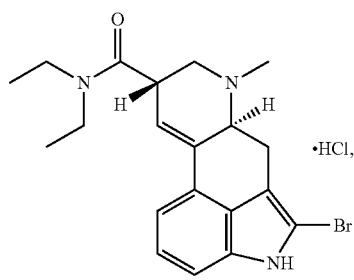
•HCl,

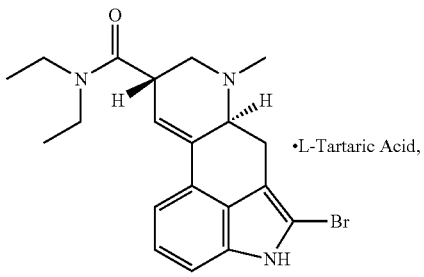
•L-Tartaric Acid,

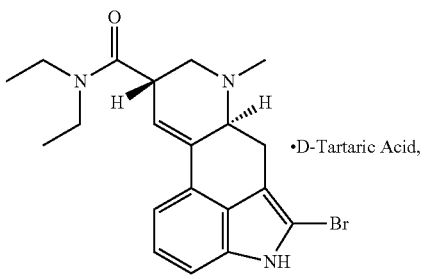
•D-Tartaric Acid,

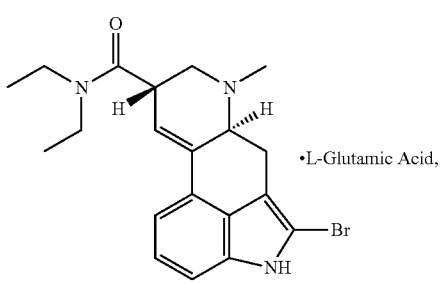
•L-Glutamic Acid,

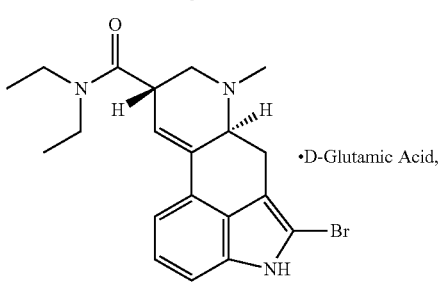
•D-Glutamic Acid,

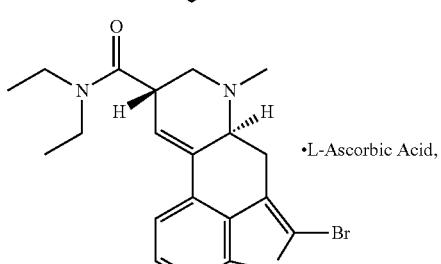
•L-Ascorbic Acid,

-continued

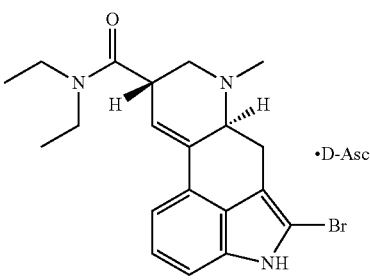
•D-Ascorbic Acid,

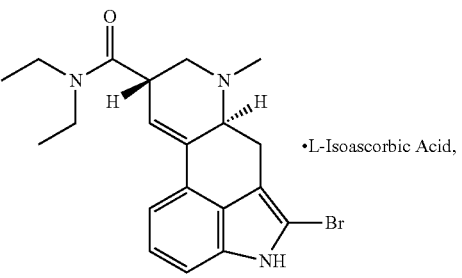
•L-Isoascorbic Acid, and

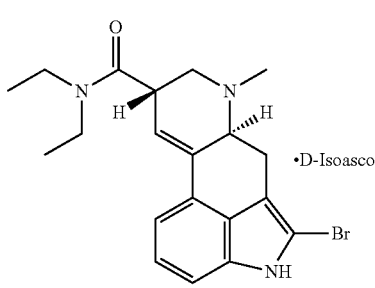
•D-Isoascorbic Acid;

wherein the compound has a peak at 10.3°±0.2° (2θ) and d value of about 8.6 Å, optionally, another peak at one or more of 4.7°±0.2° (2θ) and d value of about 18.8 Å, and 9.4°±0.2° (2θ) and d value of about 9.4 Å.

19. A substantially pure crystalline form of a compound selected from:

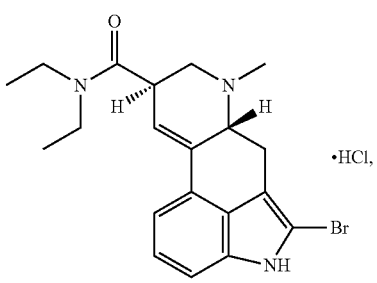
•HCl,

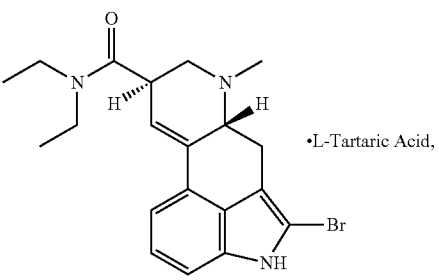
•L-Tartaric Acid,

-continued
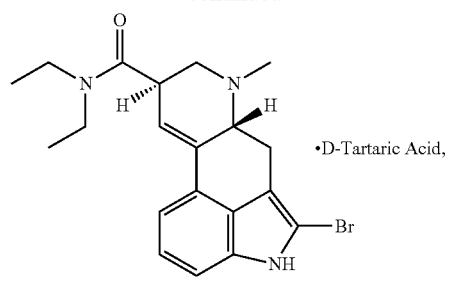 •D-Tartaric Acid,
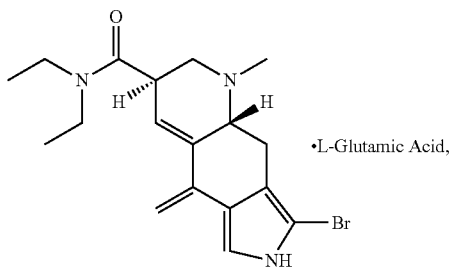 •L-Glutamic Acid,
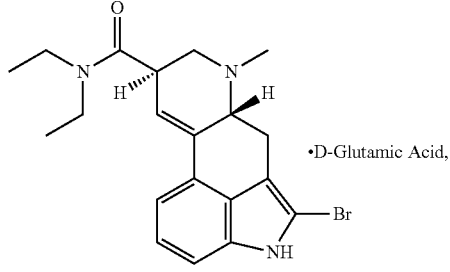 •D-Glutamic Acid,
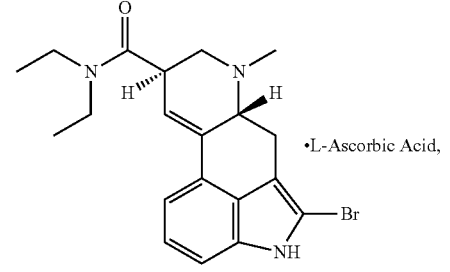 •L-Ascorbic Acid,
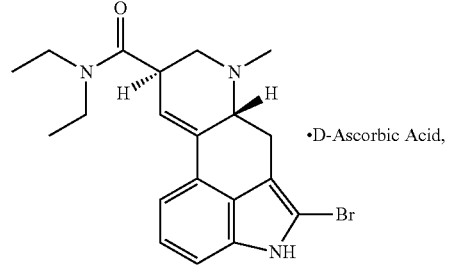 •D-Ascorbic Acid,
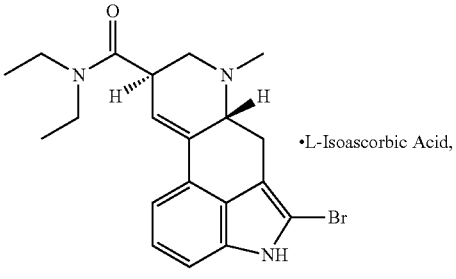 •L-Isoascorbic Acid,
-continued
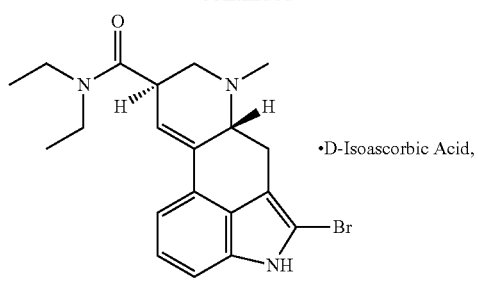 •D-Isoascorbic Acid,
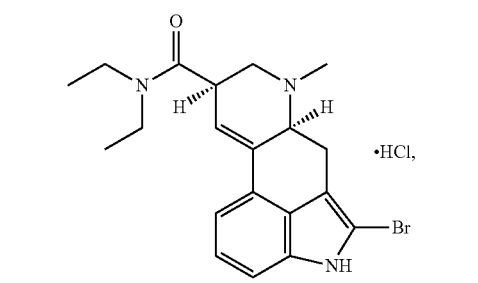 •HCl,
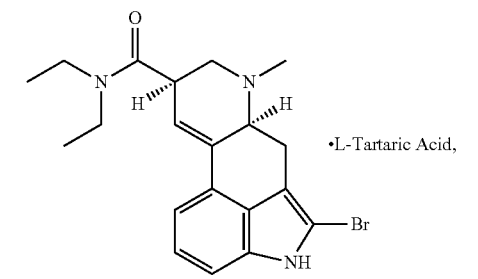 •L-Tartaric Acid,
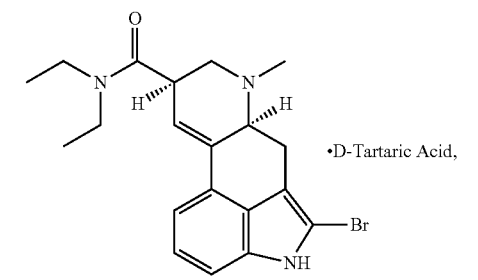 •D-Tartaric Acid,
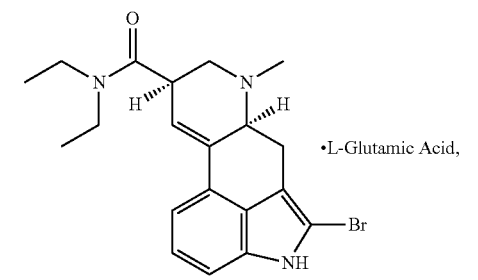 •L-Glutamic Acid,
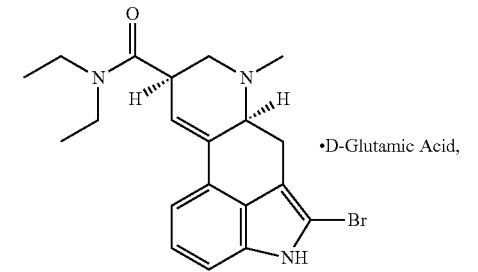 •D-Glutamic Acid, -continued
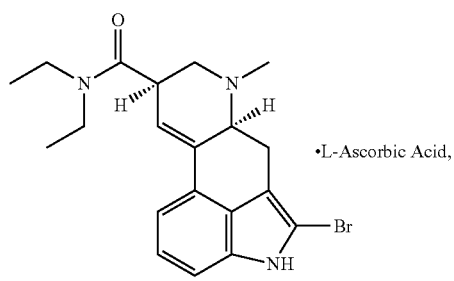
•L-Ascorbic Acid,
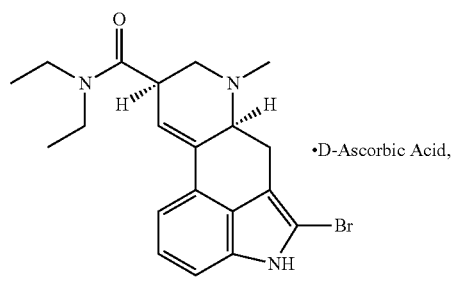
•D-Ascorbic Acid,
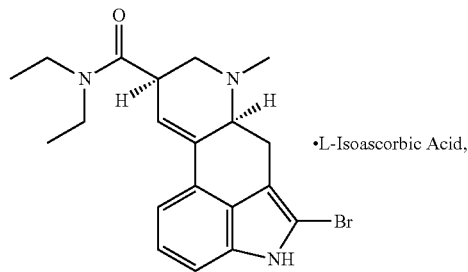
•L-Isoascorbic Acid,
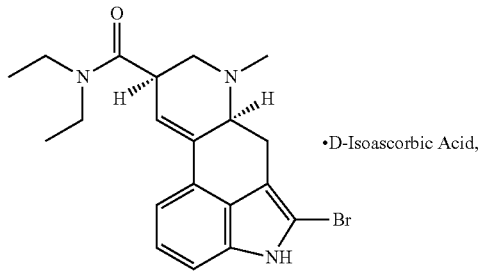
•D-Isoascorbic Acid,
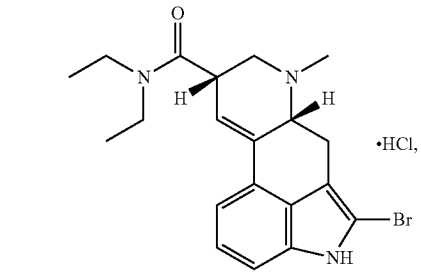
•HCl,
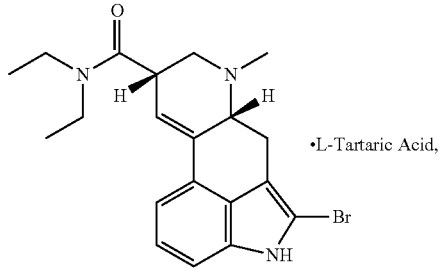
•L-Tartaric Acid,
-continued
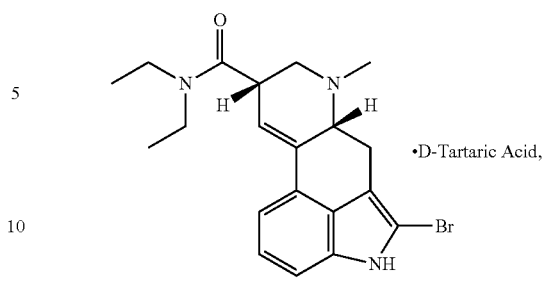
•D-Tartaric Acid,
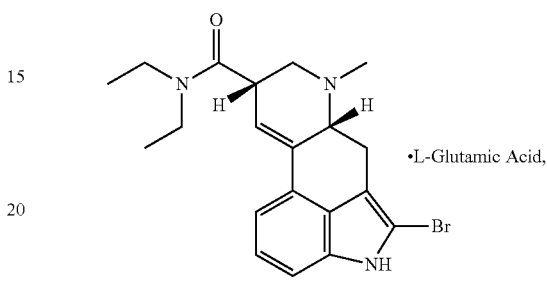
•L-Glutamic Acid,
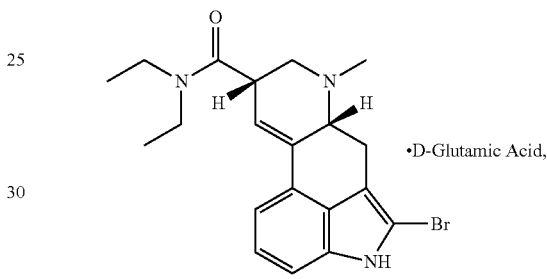
•D-Glutamic Acid,
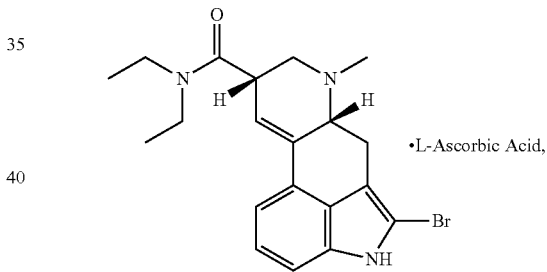
•L-Ascorbic Acid,
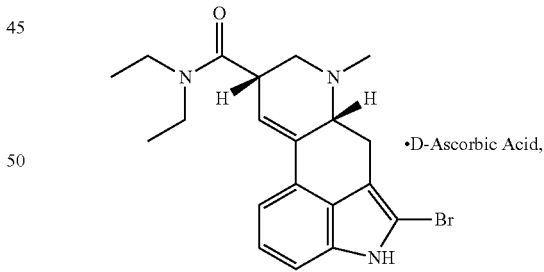
•D-Ascorbic Acid,
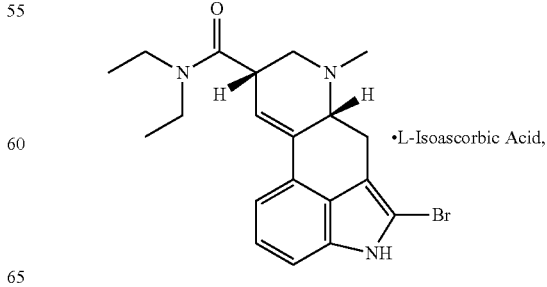
•L-Isoascorbic Acid, 175
-continued
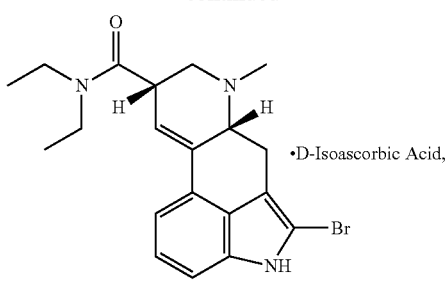
·D-Isoascorbic Acid,
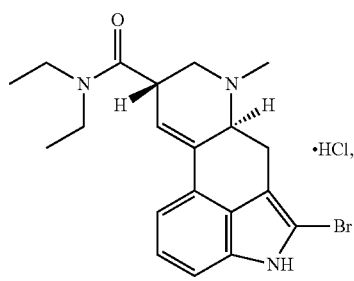
·HCl,
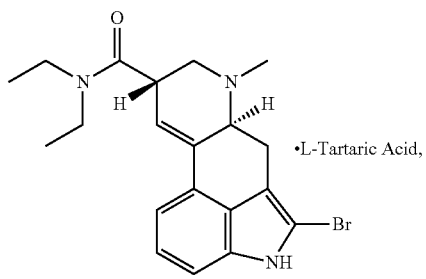
·L-Tartaric Acid,
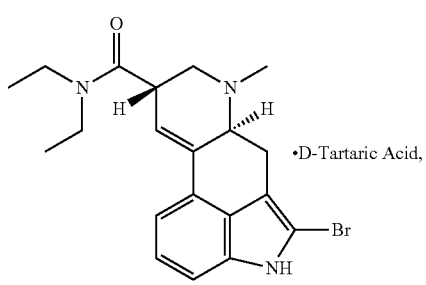
·D-Tartaric Acid,
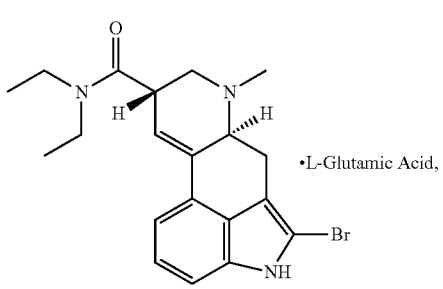
·L-Glutamic Acid,
176
-continued
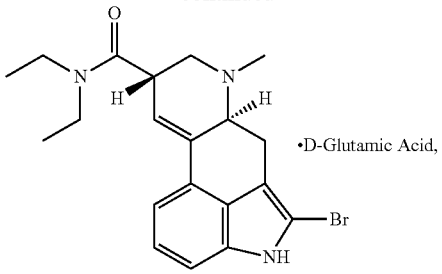
·D-Glutamic Acid,
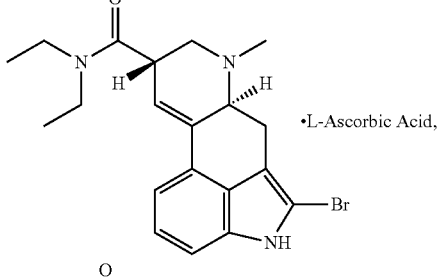
·L-Ascorbic Acid,
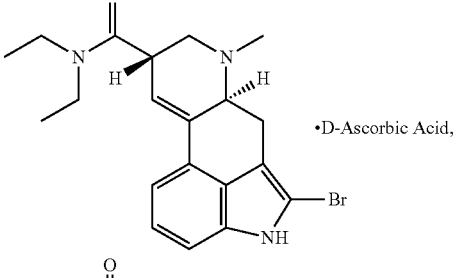
·D-Ascorbic Acid,
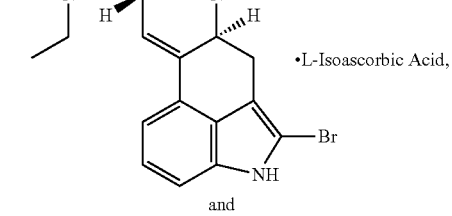
·L-Isoascorbic Acid,
and
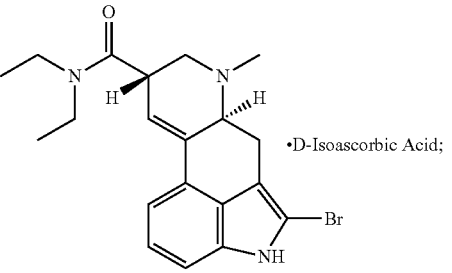
·D-Isoascorbic Acid;
wherein the compound comprising a Powder X-ray Diffraction (PXRD) pattern comprising one or more peaks at 10.3°±0.2° (2θ), 4.7°±0.2° (2θ), 9.4°±0.2° (2θ), and 20.1°±0.2° (2θ).
* * * * *